US012295939B2

(12) United States Patent
Thatcher et al.

(10) Patent No.: US 12,295,939 B2
(45) Date of Patent: May 13, 2025

(54) SUBSTITUTED BENZOTHIOPHENE ANALOGS AS SELECTIVE ESTROGEN RECEPTOR DEGRADERS

(71) Applicant: The Board of Trustees of the University of Illinois, Urbana, IL (US)

(72) Inventors: Gregory R Thatcher, Tucson, AZ (US); Rui Xiong, Chicago, IL (US); Jiong Zhao, Chicago, IL (US); Yunlong Lu, Chicago, IL (US); Lauren Gutgesell, Chicago, IL (US); Carlo Ivan Rosales, Chicago, IL (US); Yangfeng Li, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 18/364,621

(22) Filed: Aug. 3, 2023

(65) Prior Publication Data

US 2023/0381137 A1    Nov. 30, 2023

Related U.S. Application Data

(62) Division of application No. 16/967,188, filed as application No. PCT/US2019/016793 on Feb. 6, 2019, now Pat. No. 11,759,450.

(60) Provisional application No. 62/657,046, filed on Apr. 13, 2018, provisional application No. 62/626,785, filed on Feb. 6, 2018.

(51) Int. Cl.
*A61K 31/397* (2006.01)
*A61K 31/138* (2006.01)
*A61K 31/167* (2006.01)
*A61K 31/277* (2006.01)
*A61K 31/4025* (2006.01)
*A61K 31/4196* (2006.01)
*A61K 31/4535* (2006.01)
*A61K 31/565* (2006.01)
*A61K 31/566* (2006.01)
*A61K 31/573* (2006.01)
*A61K 38/09* (2006.01)
*A61K 39/395* (2006.01)
*A61K 45/06* (2006.01)
*C07D 409/12* (2006.01)

(52) U.S. Cl.
CPC .......... *A61K 31/397* (2013.01); *A61K 31/138* (2013.01); *A61K 31/167* (2013.01); *A61K 31/277* (2013.01); *A61K 31/4025* (2013.01); *A61K 31/4196* (2013.01); *A61K 31/4535* (2013.01); *A61K 31/565* (2013.01); *A61K 31/566* (2013.01); *A61K 31/573* (2013.01); *A61K 38/09* (2013.01); *A61K 39/3955* (2013.01); *A61K 45/06* (2013.01); *C07D 409/12* (2013.01); *C07B 2200/05* (2013.01)

(58) Field of Classification Search
CPC .. A61K 31/397; A61K 31/167; A61K 31/138; C07D 409/12
See application file for complete search history.

(56) References Cited

U.S. PATENT DOCUMENTS

| 5,728,724 A | 3/1998 | Bryant et al. |
| 9,540,361 B2 | 1/2017 | Dijcks et al. |
| 2018/0230123 A1 | 8/2018 | Strum |

FOREIGN PATENT DOCUMENTS

| CN | 107406424 A | 11/2017 |
| CN | 110461853 A | 11/2019 |
| EP | 0759434 A1 | 2/1997 |
| WO | 20120084711 A1 | 6/2012 |
| WO | 2014066692 A1 | 5/2014 |
| WO | 2014130310 A1 | 8/2014 |
| WO | 2017100715 A1 | 6/2017 |
| WO | 2017140669 A1 | 8/2017 |
| WO | 2018148576 A1 | 8/2018 |
| WO | 2020037251 A1 | 2/2020 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802). (Year: 1995).*
Chinese Office Action dated Aug. 15, 2023 in co-pending Chinese Patent Application No. 2019800244558.
Chinese Office Action for Appln. No. 201980024455.8 mailed Feb. 8, 2023.
Grese T A et al: 11 Structure-Activity Relationships of Selective Estrogen Receptor Modulators: Modifications to the 2-Arylbenzothiophene Core of Raloxifene 11 , Journal of Medicinal Chemistry, American Chemical Society, vol. 40, No. 2, Jan. 17, 1997 (Jan. 17, 1997), pp. 146-167, XP002050782, ISSN: 0022-2623, DOI: 10.1021/JM9606352 * the whole document* * example 13(1); tables 1, 2, 3 *.

(Continued)

*Primary Examiner* — Marcos L Sznaidman
(74) *Attorney, Agent, or Firm* — Thomas| Horstemeyer, LLP

(57) ABSTRACT

In one aspect, the disclosure relates to relates to substituted benzothiophene analogs which are useful as selective degraders of estrogen receptor, methods of making same, pharmaceutical compositions comprising same, and methods of treating one or more clinical conditions associated with estrogen receptor, such as a cancer, including breast cancer, or osteoporosis. This abstract is intended as a scanning tool for purposes of searching in the particular art and is not intended to be limiting of the present disclosure.

15 Claims, No Drawings

(56) References Cited

OTHER PUBLICATIONS

Extended European search report for Application 19751111.6-1110 mailed Sep. 30, 2021.
PubChem-CID-123708684, Create Date Jan. 25, 2017 (Jan. 25, 2017), p. 2, Fig.
Grese, Structure-Activity Relationships of Selective Estrogen Receptor Modulators: Modifications to the 2-Arylbenzothiophene Core of Raloxifene, J Med Chem, vol. 40, p. 146-167, 1997.
International Search Report issued for PCT/US2019/016793, mailed Jun. 14, 2019.

* cited by examiner

SUBSTITUTED BENZOTHIOPHENE ANALOGS AS SELECTIVE ESTROGEN RECEPTOR DEGRADERS

CROSS-REFERENCE TO RELATED APPLICATIONS

This application is a divisional application of U.S. nonprovisional application Ser. No. 16/967,133, filed on Aug. 4, 2020, which is a national phase application under 35 USC 371 of international application no. PCT/US2019/016793, filed on Feb. 6, 2019, which claims the benefit of U.S. provisional application No. 62/626,785, filed on Feb. 6, 2018, and U.S. provisional application No. 62/657,046, filed on Apr. 13, 2018, each of which is incorporated herein by reference in its entirety.

STATEMENT REGARDING FEDERALLY SPONSORED RESEARCH

This disclosure was made with U.S. Government support under grant number 1R01CA18801701A1 awarded by the National Institute of Health. The U.S. government has certain rights in the disclosure.

BACKGROUND

The estrogen receptor ("ER") is a ligand-activated transcriptional regulatory protein that mediates induction of a variety of biological effects through its interaction with endogenous estrogens. Endogenous estrogens include 17β-estradiol and estrones. ER has been found to have two isoforms, ER-α and ER-β. Estrogens and estrogen receptors are implicated in a number of diseases or conditions, such as bone cancer, breast cancer, colorectal cancer, endometrial cancer, prostate cancer, ovarian cancer, uterine cancer, cervical cancer, lung cancer, as well as others diseases or conditions. For example, about 70% of patients who suffer from breast cancer express ER and/or progesterone receptors, indicating that the growth of this tumor cells is hormone-dependent, and the growth of other tumors such as ovarian cancer and endometrial cancer is also dependent on ERα.

The treatment of these diseases can be done by inhibiting ER signaling through a variety of ways, including antagonism the binding of ligand to ER, antagonism or downregulation of ERα, blocking estrogen synthesis, and the like. At the same time the ERα and ER3 are expressed in the endocrine tumors such as adrenal cortical tumors, pancreatic cancer, prostate cancer and thyroid cancer, gastrointestinal system tumors such as colon cancer, esophageal cancer, liver cancer and pancreatic cancer, and lung cancer. Although the above-mentioned treatment has played a role in ER-positive cancer patients, it also leads to drug resistance.

Although considerable advances have been made in targeting the estrogen signaling axis for the treatment of breast cancer and osteoporosis, there remains a need for compounds that are potent, efficacious, and selective degraders of the estrogen receptor, and also effective in the treatment of clinical conditions and disorders, e.g. breast cancer, which are associated with the estrogen receptor. These needs and other needs are satisfied by the present disclosure.

SUMMARY

In accordance with the purpose(s) of the disclosure, as embodied and broadly described herein, the disclosure, in one aspect, relates to substituted benzothiophene analogs which are useful as selective degraders of estrogen receptor, methods of making same, pharmaceutical compositions comprising same, and methods of treating one or more clinical conditions associated with estrogen receptor, such as a cancer, including breast cancer, or osteoporosis.

Disclosed are compounds having a structure represented by a formula:

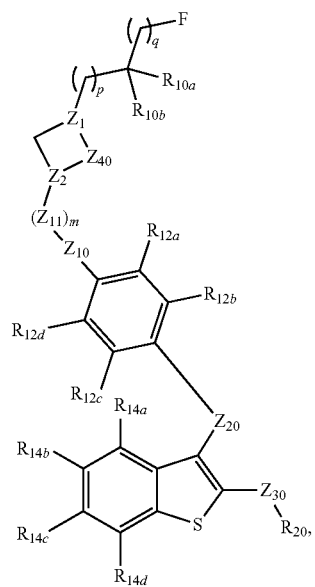

wherein m is selected from 0 and 1; wherein n is selected from 1, 2, and 3; wherein p is selected from 0, 1, and 2; wherein q is selected from 0, 1, and 2; wherein each of $Z_1$ and $Z_2$ is independently selected from —CH— or —N—; provided $Z_1$ and $Z_2$ are not simultaneously —CH— or —N—; and provided when $Z_1$ is —CH— and m is 1, that p and q are not both 0; wherein $Z_{10}$ is selected from —O—, —CH$_2$—, —S—, —NR$_{17}$—, —CHF—, and —CF$_2$—; wherein $Z_{11}$ is, when present, —CH$_2$CH$_2$—; wherein $Z_{20}$ is selected from —O—, —CH$_2$—, —S—, —NR$_{18}$—, —CHF—, and —CF$_2$—; wherein $Z_{30}$ is selected from —C(O)—, —CF$_2$—, cyclopropyl, —CH$_2$—, and —CHF—; wherein $Z_{40}$ is —(CH$_2$)$_n$—; wherein each of $R_{10a}$ and $R_{10b}$ are independently selected from hydrogen, deuterium, halogen, and $C_1$-$C_3$ methyl; wherein each of $R_{12a}$, $R_{12b}$, $R_{12c}$, and $R_{12d}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, $C_1$-$C_6$ alkyl, $C_1$-$C_6$ haloalkyl, $C_3$-$C_8$ cycloalkyl, —O($C_1$-$C_6$ alkyl), —O($C_1$-$C_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N($C_1$-$C_6$ alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, $C_1$-$C_6$ alkenyl, $C_1$-$C_6$ alkynyl, aryl, —($C_1$-$C_6$ alkyl)aryl, aryloxy, heteroaryl, and —($C_1$-$C_6$ alkyl)heteroaryl; wherein three of $R_{14a}$, $R_{14b}$, $R_{14c}$, and $R_{14d}$ are independently selected from hydrogen, hydroxyl, thiol, nitroso, —SF$_5$, —OR$_{15}$, —SR$_{15}$, —N(R$_{15}$)$_2$, —CN, —NO$_2$, halogen, $C_1$-$C_6$ alkyl, $C_1$-$C_6$ haloalkyl, $C_3$-$C_8$ cycloalkyl, —O($C_1$-$C_6$ alkyl), —O($C_1$-$C_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(C$_1$-C$_6$ alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; and wherein one of R$_{14a}$, R$_{14b}$, R$_{14c}$, and R$_{14d}$ is selected from hydrogen, hydroxyl, sulfhydryl, halogen, amino, aminoalkyl, —O(C$_1$-C$_6$ alkyl), —S(C$_1$-C$_6$ alkyl), aryloxy, —OC(O)(C$_1$-C$_6$ alkyl), —OC(S)(C$_1$-C$_6$ alkyl), —OC(O)C$_6$H$_5$, —OC(S)C$_6$H$_5$, —OC(O)aryl, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, OC(S)OC$_6$H$_5$, and —OSO$_2$(C$_2$-C$_6$ alkyl); wherein each occurrence of R$_{15}$ is independently selected from hydrogen, C$_1$-C$_6$ alkyl, C$_1$-C$_6$ alkenyl, C$_1$-C$_6$ alkynyl, C$_3$-C$_8$ cycloalkyl, aryl, —(C$_1$-C$_6$ alkyl)aryl, heteroaryl, and —(C$_1$-C$_6$ alkyl)heteroaryl; wherein each occurrence of R$_{16}$ is independently selected from —N(R$_{15}$)$_2$, —SR$_{15}$, —OR$_{15}$; wherein each of R$_{17}$ and R$_{18}$ is independently selected from hydrogen, —C(O)R$_{15}$, —C(S)R$_{15}$, —C(O)R$_{16}$, —C(S)R$_{16}$, C$_1$-C$_6$ alkyl, C$_1$-C$_6$ alkenyl, C$_1$-C$_6$ alkynyl, C$_3$-C$_8$ cycloalkyl, aryl, and heteroaryl; wherein R$_{20}$ is selected from aryl, heteroaryl, thiophenyl, C$_3$-C$_8$ cycloalkyl, and bicyclic heterocyclyl, and wherein R$_{20}$ is substituted with 0, 1, 2, 3, or 4 groups independently selected from halogen, —SF$_5$, —CN, —NO$_2$, —OR$_{15}$, —SR$_{15}$, —N(R$_{15}$)$_2$, hydroxyl, thiol, nitroso, C$_1$-C$_6$ alkyl, C$_1$-C$_6$ haloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; or a pharmaceutically acceptable salt thereof.

Also disclosed are compounds having a structure represented by a formula:

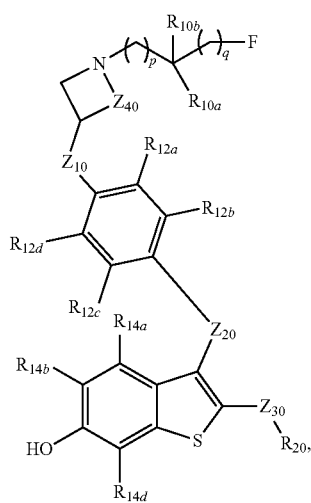

wherein p is selected from 0, 1, and 2; wherein q is selected from 0, 1, and 2; wherein Z$_{10}$ is selected from —O—, —CH$_2$—, —S—, —NR$_{17}$—, —CHF—, and —CF$_2$—; wherein Z$_{20}$ is selected from —O—, —CH$_2$—, —S—, —NR$_{18}$—, —CHF—, and —CF$_2$—; wherein Z$_{30}$ is selected from —C(O)—, —CF$_2$—, cyclopropyl, —CH$_2$—, and —CHF—; wherein Z$_{40}$ is —(CH$_2$)$_n$— and wherein n is 1, 2, 3, or 4; wherein each of R$_{10a}$ and R$_{10b}$ are independently selected from hydrogen, deuterium, halogen, and C$_1$-C$_3$ methyl; wherein each occurrence of R$_{12}$ and R$_{14}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_8$ cycloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(C$_1$-C$_6$ alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; wherein each occurrence of R$_{15}$ is independently selected from hydrogen, C$_1$-C$_6$ alkyl, C$_1$-C$_6$ alkenyl, C$_1$-C$_6$ alkynyl, C$_3$-C$_8$ cycloalkyl, aryl, —(C$_1$-C$_6$ alkyl)aryl, heteroaryl, and —(C$_1$-C$_6$ alkyl)heteroaryl; wherein each occurrence of R$_{16}$ is independently selected from —N(R$_{15}$)$_2$, —SR$_{15}$, —OR$_{15}$; wherein each of R$_{17}$ and R$_{18}$ is independently selected from hydrogen, —C(O)R$_{15}$, —C(S)R$_{15}$, —C(O)R$_{16}$, —C(S)R$_{16}$, C$_1$-C$_6$ alkyl, C$_1$-C$_6$ alkenyl, C$_1$-C$_6$ alkynyl, C$_3$-C$_8$ cycloalkyl, aryl, and heteroaryl; wherein R$_{20}$ is selected from aryl, heteroaryl, thiophenyl, C$_3$-C$_8$ cycloalkyl, and bicyclic heterocyclyl, and wherein R$_{20}$ is substituted with 0, 1, 2, 3, or 4 groups independently selected from halogen, —SF$_5$, —CN, —NO$_2$, —OR$_{15}$, —SR$_{15}$, —N(R$_{15}$)$_2$, hydroxyl, thiol, nitroso, C$_1$-C$_6$ alkyl, C$_1$-C$_6$ haloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; or a pharmaceutically acceptable salt thereof.

Also disclosed are compounds having a structure represented by a formula:

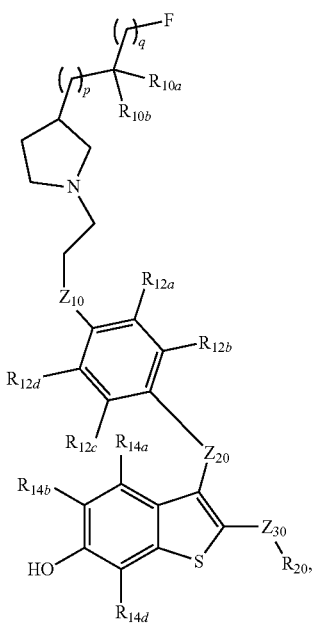

wherein p is selected from 0, 1, and 2; wherein q is selected from 0, 1, and 2; wherein $Z_{10}$ is selected from —O—, —$CH_2$—, —S—, —$NR_{17}$—, —CHF—, and —$CF_2$—; wherein $Z_{20}$ is selected from —O—, —$CH_2$—, —S—, —$NR_{18}$—, —CHF—, and —$CF_2$—; wherein $Z_{30}$ is selected from —C(O)—, —$CF_2$—, cyclopropyl, —$CH_2$—, and —CHF—; wherein each of $R_{10a}$ and $R_{10b}$ are independently selected from hydrogen, deuterium, halogen, and $C_1$-$C_3$ methyl; wherein each occurrence of $R_{12}$ and $R_{14}$ is independently selected from hydrogen, hydroxyl, thiol, nitroso, —$SF_5$, —$OR_{15}$, —$SR_{15}$, —$N(R_{15})_2$, —CN, —$NO_2$, halogen, $C_1$-$C_6$ alkyl, $C_1$-$C_6$ haloalkyl, $C_3$-$C_8$ cycloalkyl, —O($C_1$-$C_6$ alkyl), —O($C_1$-$C_6$ haloalkyl), —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(C_1$-$C_6$ alkyl)$SO_2OR_{15}$, —N(alkyl)$SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, $C_1$-$C_6$ alkenyl, $C_1$-$C_6$ alkynyl, aryl, —($C_1$-$C_6$ alkyl)aryl, aryloxy, heteroaryl, and —($C_1$-$C_6$ alkyl)heteroaryl; wherein each occurrence of $R_{15}$ is independently selected from hydrogen, $C_1$-$C_6$ alkyl, $C_1$-$C_6$ alkenyl, $C_1$-$C_6$ alkynyl, $C_3$-$C_8$ cycloalkyl, aryl, —($C_1$-$C_6$ alkyl)aryl, heteroaryl, and —($C_1$-$C_6$ alkyl)heteroaryl; wherein each occurrence of $R_{16}$ is independently selected from —$N(R_{15})_2$, —$SR_{15}$, —$OR_{15}$; wherein each of $R_{17}$ and $R_{18}$ is independently selected from hydrogen, —$C(O)R_{15}$, —$C(S)R_{15}$, —$C(O)R_{16}$, —$C(S)R_{16}$, $C_1$-$C_6$ alkyl, $C_1$-$C_6$ alkenyl, $C_1$-$C_6$ alkynyl, $C_3$-$C_8$ cycloalkyl, aryl, and heteroaryl; wherein $R_{20}$ is selected from aryl, heteroaryl, thiophenyl, $C_3$-$C_8$ cycloalkyl, and bicyclic heterocyclyl, and wherein $R_{20}$ is substituted with 0, 1, 2, 3, or 4 groups independently selected from halogen, —$SF_5$, —CN, —$NO_2$, —$OR_{15}$, —$SR_{15}$, —$N(R_{15})_2$, hydroxyl, thiol, nitroso, $C_1$-$C_6$ alkyl, $C_1$-$C_6$ haloalkyl, —O($C_1$-$C_6$ alkyl), —O($C_1$-$C_6$ haloalkyl), —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —N(alkyl)$SO_2OR_{15}$, —N(alkyl)$SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, $C_1$-$C_6$ alkenyl, $C_1$-$C_6$ alkynyl, aryl, —($C_1$-$C_6$ alkyl)aryl, aryloxy, heteroaryl, and —($C_1$-$C_6$ alkyl)heteroaryl; or a pharmaceutically acceptable salt thereof.

Also disclosed are pharmaceutical compositions comprising a therapeutically effective amount of one or more disclosed compounds, or pharmaceutically acceptable salt thereof, and a pharmaceutically acceptable carrier.

Also disclosed are methods for the treatment of a disorder associated with an estrogen receptor dysfunction or estrogen-related disorder in a mammal comprising the step of administering to the mammal a therapeutically effective amount of at least one disclosed compound or pharmaceutically acceptable salt thereof.

Also disclosed are methods for selective degradation of estrogen receptor in a mammal comprising the step of administering to the mammal a therapeutically effective amount of at least one disclosed compound or pharmaceutically acceptable salt thereof.

Also disclosed are methods for selective degradation of estrogen receptor in at least one cell, comprising the step of contacting the cell with an effective amount of at least one disclosed compound or pharmaceutically acceptable salt thereof.

Also disclosed are uses of a disclosed compound, or a pharmaceutically acceptable salt thereof; a disclosed product of making, or a pharmaceutically acceptable salt thereof; or a disclosed pharmaceutical composition.

Also disclosed are uses of a disclosed compound, or a pharmaceutically acceptable salt thereof, in the manufacture of a medicament for the treatment of an estrogen receptor dysfunction or estrogen-related disorder in a mammal.

Also disclosed are methods for the manufacture of a medicament to degrade the estrogen receptor in a mammal comprising combining at least one disclosed compound, or a pharmaceutically acceptable salt thereof with a pharmaceutically acceptable carrier or diluent.

Also disclosed are kits comprising a disclosed compound, or a pharmaceutically acceptable salt thereof, or a disclosed pharmaceutical composition; and one or more of: (a) at least one agent known to treat an estrogen-associated disorder; and/or (b) instructions for treating an estrogen-associated disorder.

While aspects of the present disclosure can be described and claimed in a particular statutory class, such as the system statutory class, this is for convenience only and one of skill in the art will understand that each aspect of the present disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

DETAILED DESCRIPTION

Many modifications and other aspects disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific aspects disclosed and that modifications and other aspects are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, blood vessel biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a cancer," "a receptor," or "an alkyl group," including, but not limited to, two or more such cancers, estrogen receptors, or alkyl groups, including combinations of cancers, receptors, or alkyl groups, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x' less than y', and 'less than z' Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to y", where 'x' and 'y' are numerical values, includes "about 'x to about'y".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%;

about 0.5% to about 3.2%, and about 0.5% to about 4.4%, and other possible sub-ranges) within the indicated range.

As used herein, "about," "approximately," "substantially," and the like, when used in connection with a numerical variable, can generally refers to the value of the variable and to all values of the variable that are within the experimental error (e.g., within the 95% confidence interval for the mean) or within +/−10% of the indicated value, whichever is greater. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined, in general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer. Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metastatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"Estrogen dependent cancer" or "estrogen receptor positive cancer" as used interchangeably herein refers to a tumor that contains estrogen receptor (ER) positive cells, i.e., cells that have estrogen receptors, and respond to the presence of estrogen with increased proliferation. Estrogen dependent cancers may include breast cancer, ovarian cancer, or endometrial cancer. "Estrogen receptor positive breast cancer" is a type of breast cancer that is sensitive to estrogen.

"Estrogen receptor" or "ER" as used interchangeably herein refers to a receptor that is activated by the hormone estrogen and is a member of the nuclear hormone family of intracellular receptors. There are two different isoforms of estrogen receptor, referred to as a (also referred to as "ERa") and β (also referred to as "ERb"). ERa and ERb genes are encoded by ESR1 and ESR2 gene, respectively. Hormone-activated estrogen receptors form dimers and may form homodimers or heterodimers. Both ERs are widely expressed in different tissue types.

"Estrogen receptor negative breast cancer" or "Estrogen independent breast cancer" as used interchangeably herein refers to a tumor that does not contain estrogen receptor positive cells, i.e., cells that lack estrogen receptors, and does not depend on the presence of estrogen for ongoing proliferation.

"Selective estrogen receptor degraders," "selective estrogen receptor downregulator," or "SERDs" as used interchangeably herein refers to a compound that interacts with an ER and induce a conformational change that results in the degradation or downregulation of the receptor.

A "cancer therapeutic agent" as used herein refers to any compound, e.g., small molecule or peptide/polypeptide, which has been shown to exert a therapeutic effect (i.e., inhibition of proliferation and/or survival) on cancer cells. Typically, the cancer therapeutic agent is a cytotoxic agent or a cytostatic agent.

A "targeted cancer therapeutic agent" as used herein refers to any compound, e.g., small molecule or peptide/polypeptide, or polypeptide or conjugated polypeptide that has been shown to exert a therapeutic effect (i.e., inhibition of proliferation and/or survival) on specific cancer cells or tissues. Typically, the targeted cancer therapeutic agent is an antibody, a polypeptide having an antibody-like domain, or other polypeptide, e.g., enzyme, hormone, growth factor, cytokine, etc., which selectively binds to the surface of a target cell. The antibody, polypeptide having an antibody-like domain, or other polypeptide may be unconjugated or may be conjugated to a cancer therapeutic agent. The targeted cancer therapeutic agent can be a compound that exerts a therapeutic effect on specific cancer cells or tissues.

As used herein "an inhibitor of CDK4/6" and "inhibitor of cyclin D" refer to a compound or composition that inhibits activity of cyclin-dependent kinase 4 and 6 (CDK4/6) to phosphorylate a serine or threonine residue on proteins, or inhibits the interaction of CDK4:6 or cyclin D with other proteins that may be in the signal pathway. CDK4 and CDK6 form a complex with Cyclin D to regulate cell cycle progression from G1 to S phase. CDK 4 as been shown to also interact with the following proteins: retinoblastoma (Rb), CDC37, CDKN1B, CDKN2B, CDKN2C, CEBPA, CCND1, CCND3, DBNL, MyoD, P16, PCNA, and SER- TAD1. CDK6 has been shown to also interact with Cyclin-dependent kinase 6 was shown to interact with retinoblastoma, CDKN2C, PPM1B, Cyclin D3, Cyclin D1 and PPP2CA. It is contemplated that the inhibitor can inhibit the interaction of CDK4 or CDK6 with any of the proteins listed above.

As used herein, the phrase "phosphatidylinositol-3-kinase (PI3K) inhibitor" refers to an agent which is effective to inhibit PI3K activity. A PI3K inhibitor inhibits the activity of the enzyme that phosphorylates the hydroxyl group at the 3-position of inositol ring of inositol phosphatide.

As used herein, the term "BET inhibitor" refers to a compound that binds to BET and inhibits and/or reduces a biological activity of BET. In some embodiments, BET inhibitor substantially or completely inhibits the biological activity of BET, In some embodiments, the biological activity is binding of BET to chromatin (e.g., histones associated with DNA) and/or another acetylated protein. In certain embodiments, a BET inhibitor has an IC50 or binding constant of less about 50 µM, less than about 1 µM, less than about 500 nM, less than about 100 nM, or less than about 10 nM. In some embodiments, the BET inhibitor inhibits one or more of BRD2, BRD3, BRD4, and BRDT.

The term "Bromodomain and Extra Terminal Domain" or "BET" as used herein, refers to any native BET from any vertebrate source, including mammals such as primates (e.g. humans) and rodents (e.g., mice and rats), unless otherwise indicated. The term "BET" refers to members of the BET family, including BRD2, BRD3, BRD4, and BRDT. The term encompasses "full-length," unprocessed BET as well as any form of BET that results from processing in the cell. The term also encompasses naturally occurring variants of BET, e.g., splice variants or allelic variants.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intra-hepatic, intralesional, and intracranial injections or infusion techniques. Administration can be continuous or intermittent. In various aspects, a preparation can be administered therapeutically: that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrhythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "attached" can refer to covalent or non-covalent interaction between two or more molecules. Non-covalent interactions can include ionic bonds, electrostatic interactions, van der Walls forces, dipole-dipole interactions, dipole-induced-dipole interactions, London dispersion forces, hydrogen bonding, halogen bonding, electromagnetic interactions, $\pi$-$\pi$ interactions, cation-$\pi$ interactions, anion-$\pi$ interactions, polar $\pi$-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, associated with an estrogen receptor dysfunction or an estrogen-related disorder. The effect can be therapeutic in terms of a partial or complete cure of a disease, condition, symptom or adverse effect attributed to the disease, disorder, or condition. The term "treatment" as used herein can include any treatment of an estrogen receptor dysfunction or an estrogen-related disorder. in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment, Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration: the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by Increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days, Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable" describes a material that is not biologically or otherwise undesirable, i.e., without causing an unacceptable level of undesirable biological effects or interacting in a deleterious manner.

The term "pharmaceutically acceptable salts" as used herein, means salts of the active principal agents which are prepared with adds or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent, Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or In a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C1-to-C6 alkyl esters and C5-to-C7 cycloalkyl esters, although C1-to-C4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C1-to-C6 alkyl amines and secondary C1-to-C6 dialkyl amines. In the case of secondary amines, the amine can also be in the form of a 5- or 6-membered heterocycle containing one nitrogen atom. Amides derived from ammonia, C1-to-C3 alkyl primary amides and C1-to-C2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g. a "halogenated alkoxy," a particular substituted alkenyl can be, e.g. an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene). —CH$_2$CH—, —CH$_2$C(CH$_3$)$_2$CH$_2$—, and —CH$_2$CH$_2$CH$_2$— are non-limiting examples of alkanediyl groups.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above, "Alkoxy" also includes polymers of alkoxy groups as just described; that is, an alkoxy can be a polyether such as —OA$^1$-OA$^2$ or —O A$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond.

Asymmetric structures such as (A$^1$A$^2$)C=C(A$^3$A$^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "aromatic group" as used herein refers to a ring structure having cyclic clouds of delocalized π electrons above and below the plane of the molecule, where the π clouds contain (4n+2)π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$ where A$^1$ and A$^2$ can be, independently, hydrogen or alkyl, cycloalkyl, alkenyl, cycloalkenyl, alkynyl, cycloalkynyl, aryl, or heteroaryl group as described herein, A specific example of amino is —NH$_2$.

The term "alkylamino" as used herein is represented by the formula —NH(-alkyl) and —N(-alkyl)$_2$, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide." as used herein can be used interchangeably and refer to F, Cl, Br, or 1.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "thiol" as used herein is represented by the formula —SH.

"$R^1$," "$R^2$," "$R^3$," ... "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position, Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

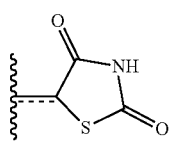

regardless of whether thiazolidinedione is used to prepare the compound. In some aspects the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some aspects, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, monosubstituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture, Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (3) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., AC, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

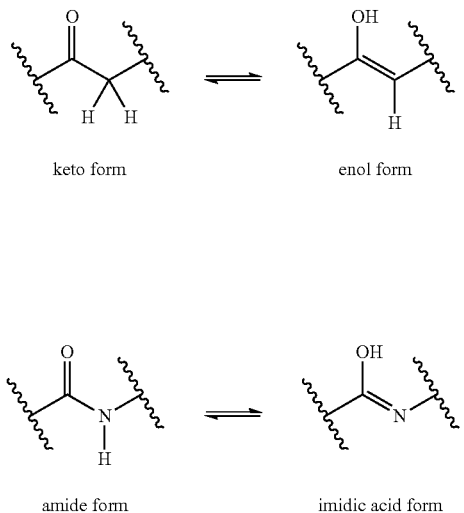

keto form    enol form amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

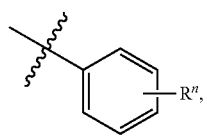

which is understood to be equivalent to a formula:

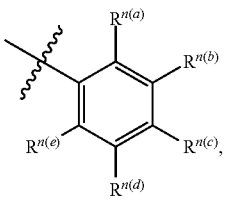

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains. N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule. A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention, Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

As used herein, nomenclature for compounds, including organic compounds, can be given using common names, IUPAC, IUBMB, or CAS recommendations for nomenclature. When one or more stereochemical features are present, Cahn-ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

It is understood, that unless otherwise specified, temperatures referred to herein are based on atmospheric pressure (i.e. one atmosphere).

Described herein are substituted benzothiophene analogs that have therapeutic or clinical utility. Also described herein are methods of synthesizing the disclosed substituted benzothiophene analogs. Also described herein are methods of administering the disclosed substituted benzothiophene analogs to a subject in need thereof. In some aspects, the subject can have an estrogen receptor dysfunction or an estrogen-related disorder. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

B. Compounds

Disclosed are compounds having a structure represented by a formula:

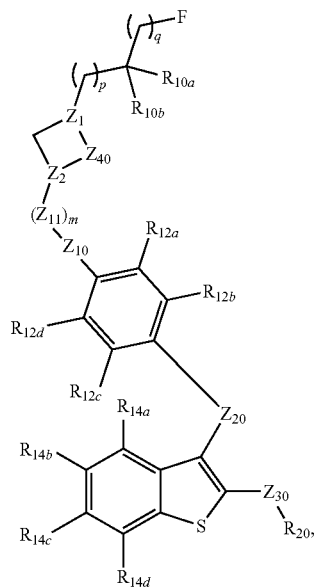

wherein m is selected from 0 and 1; wherein n is selected from 1, 2, and 3; wherein p is selected from 0, 1, and 2; wherein q is selected from 0, 1, and 2; wherein each of $Z_1$ and $Z_2$ is independently selected from —CH— or —N—; provided $Z_1$ and $Z_2$ are not simultaneously —CH— or —N—; and provided when $Z_1$ is —CH— and m is 1, that p and q are not both 0; wherein $Z_{10}$ is selected from —O—, —CH$_2$—, —S—, —NR$_{17}$—, —CHF—, and —CF$_2$—; wherein $Z_{11}$ is, when present, —CH$_2$CH$_2$—; wherein $Z_{20}$ is selected from —O—, —CH$_2$—, —S—, —NR$_{18}$—, —CHF—, and —CF$_2$—; wherein $Z_{30}$ is selected from —C(O)—, —CF$_2$—, cyclopropyl, —CH$_2$—, and —CHF—; wherein $Z_{40}$ is —(CH$_2$)$_n$—; wherein each of $R_{10a}$ and $R_{10b}$ are independently selected from hydrogen, deuterium, halogen, and C1-C3 methyl; wherein each of $R_{12a}$, $R_{12b}$, $R_{12c}$, and $R_{12d}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_8$ cycloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(C$_1$-C$_6$ alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; wherein three of $R_{14a}$, $R_{14b}$, $R_{14c}$, and $R_{14d}$ are independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_8$ cycloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(C$_1$-C$_6$ alkyl)SO$_2$OR$_{15}$, —N(alkyl) SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; and wherein one of $R_{14a}$, $R_{14b}$, $R_{14c}$, and $R_{14d}$ is selected from hydrogen, hydroxyl, sulfhydryl, halogen, amino, aminoalkyl, —O(C$_1$-C$_6$ alkyl), —S(C$_1$-C$_6$ alkyl), aryloxy, —OC(O)(C$_1$-C$_6$ alkyl), —OC(S)(C$_1$-C$_6$ alkyl), —OC(O)C$_6$H$_5$, —OC(S)C$_6$H$_5$, —OC(O)aryl, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, OC(S)OC$_6$H$_5$, and —OSO$_2$(C$_2$-C$_6$ alkyl); wherein each occurrence of R$_{15}$ is independently selected from hydrogen, C$_1$-C$_6$ alkyl, C$_1$-C$_6$ alkenyl, C$_1$-C$_6$ alkynyl, C$_3$-C$_8$ cycloalkyl, aryl, —(C$_1$-C$_6$ alkyl)aryl, heteroaryl, and —(C$_1$-C$_6$ alkyl)heteroaryl; wherein each occurrence of R$_{16}$ is independently selected from —N(R$_{15}$)$_2$, —SR$_{15}$, —OR$_{15}$; wherein each of R$_{17}$ and R$_{18}$ is independently selected from hydrogen, —C(O)R$_{15}$, —C(S)R$_{15}$, —C(O)R$_{16}$, —C(S)R$_{16}$, C$_1$-C$_6$ alkyl, C$_1$-C$_6$ alkenyl, C$_1$-C$_6$ alkynyl, C$_3$-C$_8$ cycloalkyl, aryl, and heteroaryl; wherein R$_{20}$ is selected from aryl, heteroaryl, thiophenyl, C$_3$-C$_8$ cycloalkyl, and bicyclic heterocyclyl, and wherein R$_{20}$ is substituted with 0, 1, 2, 3, or 4 groups independently selected from halogen, —SF$_5$, —CN, —NO$_2$, —OR$_{15}$, —SR$_{15}$, —N(R$_{15}$)$_2$, hydroxyl, thiol, nitroso, C$_1$-C$_6$ alkyl, C$_1$-C$_6$ haloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; or a pharmaceutically acceptable salt thereof.

Also disclosed are compounds having a structure represented by a formula:

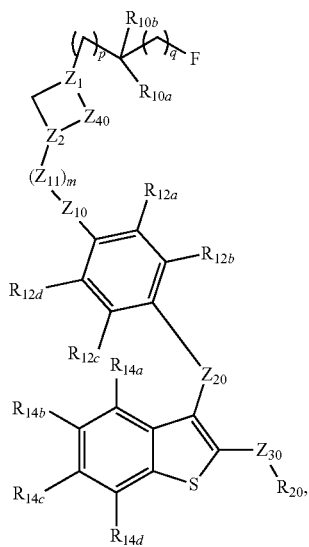

wherein a is selected from 0 and 1; wherein n is selected from 1, 2, and 3; wherein p is selected from 0, 1, and 2; wherein q is selected from 0, 1, and 2; wherein each of Z$_1$ and Z$_2$ is independently selected from —CH— or —N—, provided that Z$_1$ and Z$_2$ are not simultaneously —CH— or —N—; wherein Z$_{10}$ is selected from —O—, —CH$_2$—, —S—, —NR$_{17}$—, —CHF—, and —CF$_2$—; wherein Z$_{11}$ is, when present, —CH$_2$CH$_2$—; wherein Z$_{20}$ is selected from —O—, —CH$_2$—, —S—, —NR$_{18}$—, —CHF—, and —CF$_2$—; wherein Z$_{30}$ is selected from —C(O)—, —CF$_2$—, cyclopropyl, —CH$_2$—, and —CHF—; wherein Z$_{40}$ is —(CH$_2$)$_n$—; wherein each of R$_{10a}$ and R$_{10b}$ are independently selected from hydrogen, deuterium, and C$_1$-C$_3$ methyl; wherein each of R$_{12a}$, R$_{12b}$, R$_{12c}$, and R$_{12d}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_8$ cycloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_1$S, —OSO$_2$R$_{16}$, —NHSO$_2$OR$_1$S, —NHSO$_2$R$_{16}$, —N(C$_1$-C$_6$ alkyl)SO$_2$OR$_1$S, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_1$S, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl, wherein three of R$_{14a}$, R$_{14b}$, R$_{14c}$, and R$_{14d}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_8$ cycloalkyl, —O(C$_1$-C$_6$ alkyl), —O(C$_1$-C$_6$ haloalkyl), —B(OH)$_2$, —B(OR$_1$S)$_2$, —C(O)OR$_{15}$, —C(O)R$_{16}$, —C(S)OR$_{15}$, —C(S)R$_{16}$, —OSO$_2$OR$_1$S, —OSO$_2$R$_{16}$, —NHSO$_2$OR$_1$S, —NHSO$_2$R$_{16}$, —N(C$_1$-C$_6$ alkyl)SO$_2$OR$_1$S, —N(alkyl)SO$_2$R$_{16}$, —OP(O)(OR$_1$S)$_2$, —OP(O)(R$_{16}$)$_2$, —P(O)(OR$_1$S)$_3$, —P(O)(R$_{16}$)$_3$, —P(O)OR$_{15}$, —P(O)R$_{16}$, —SO$_2$R$_{16}$, —SO$_2$OR$_1$S, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl, and wherein one of R$_{14a}$, R$_{14b}$, R$_{14c}$, and R$_{14d}$ is selected from hydroxyl, hydrogen, halogen, —O(C$_1$-C$_6$ alkyl), —S(C$_1$-C$_6$ alkyl), aryloxy, —OC(O)(C$_1$-C$_6$ alkyl), —OC(S)(C$_1$-C$_6$ alkyl), —OC(O)C$_6$H$_5$, —OC(S)C$_6$H$_5$, —OC(O)aryl, —OC(S)aryl, —OC(O)heteroaryl, —OC(S) heteroaryl, —OC(O)O(C$_1$-C$_6$ alkyl), —OC(S)O(C$_1$-C$_6$ alkyl), —OC(O)OC$_6$H$_5$, OC(S)OC$_6$H$_5$, amino, aminoalkyl, —SH, and —OSO$_2$(C$_2$-C$_6$ alkyl); wherein each occurrence of R$_{15}$ is independently selected from hydrogen, C$_1$-C$_6$ alkyl, C$_1$-C$_6$ alkenyl, C$_1$-C$_6$ alkynyl, C$_3$-C$_8$ cycloalkyl, aryl, —(C$_1$-C$_6$ alkyl)aryl, heteroaryl, and —(C$_1$-C$_6$ alkyl)heteroaryl; wherein each occurrence of R$_{16}$ is independently selected from —N(R$_{15}$)$_2$, —SR$_{15}$, —OR$_{15}$; wherein each of R$_{17}$ and R$_{18}$ is independently selected from hydrogen, —C(O)R$_{15}$, —C(S)R$_{15}$, —C(O)R$_{16}$, —C(S)R$_{16}$, C$_1$-C$_6$ alkyl, C$_1$-C$_6$ alkenyl, C$_1$-C$_6$ alkynyl, C$_3$-C$_8$ cycloalkyl, aryl, and heteroaryl; wherein R$_{20}$ is selected from aryl, heteroaryl, thiophenyl, C$_3$-C$_8$ cycloalkyl, and bicyclic heterocyclyl, and wherein R$_{20}$ is substituted with 0, 1, 2, 3, or 4 groups independently selected from halogen, —SF$_5$, —CN, —NO$_2$, —OR$_{15}$, —SR$_{15}$, —N(R$_{15}$)$_2$, hydroxyl, thiol, nitroso, C$_1$-C$_6$ alkyl, C$_1$-C$_6$ haloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_1$S, —OSO$_2$R$_{16}$, —NHSO$_2$OR$_1$S, —NHSO$_2$R$_{16}$, —N(alkyl)SO$_2$OR$_1$S, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_1$S, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; or a pharmaceutically acceptable salt thereof; provided that the compound is not a structure represented by a formula:

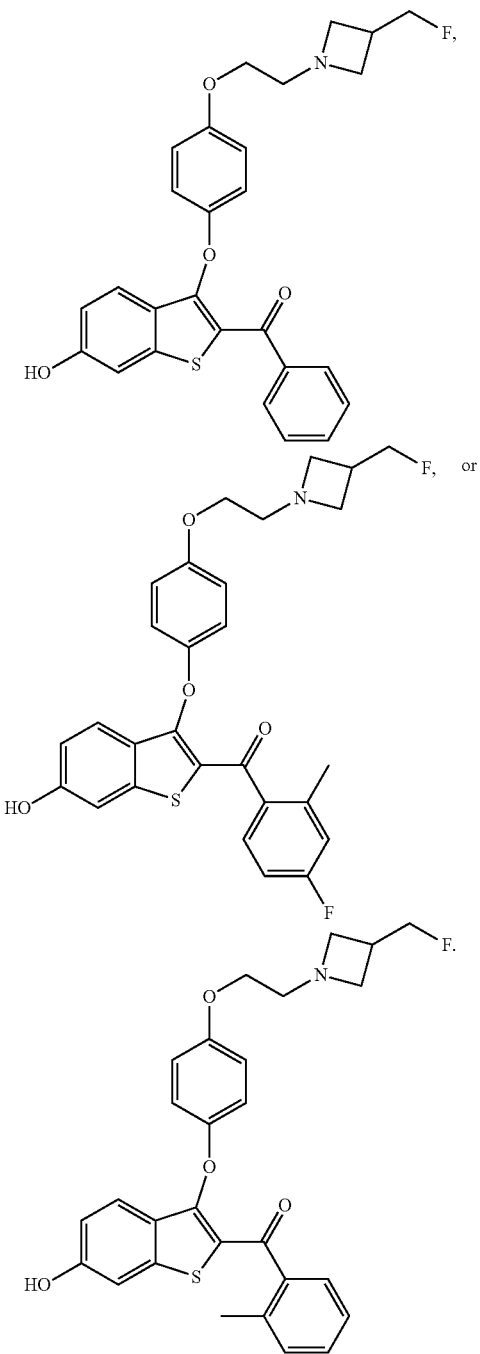

In various aspects, $Z_1$ is —CH—; $Z_2$ is —N—; and m is 0. In a further aspect, $Z_1$ is —CH—; $Z_2$ is —N—; m is 1; and p and q are not both 0. In a still further aspect, $Z_1$ is —N—; and $Z_2$ is —CH—.

In various aspects, $Z_{10}$ is selected from —O—, —CH$_2$—, —S—, and —NR$_{17}$—. In a further aspect, $Z_{10}$ is selected from —O—, —CH$_2$—, —S—, and —NH—. In a still further aspect, $Z_{10}$ is selected from —O— and —NH—.

In various aspects, m is 0; and $Z_{11}$ is not present. In a further aspect, m is 1; and $Z_{11}$ is —CH$_2$CH$_2$—.

In various aspects, $Z_{20}$ is selected from —O—, —CH$_2$—, —S—, and —NR$_{17}$—. In a further aspect, $Z_{20}$ is selected from —O—, —CH$_2$—, —S—, and —NH—. In a still further aspect, $Z_{20}$ is selected from —O— and —NH—.

In various aspects, $Z_{30}$ is —C(O)—.

In various aspects, $Z_{40}$ is selected from —(CH$_2$)—, —(CH$_2$)$_2$—, and —(CH$_2$)$_3$—.

In various aspects, each of $R_{12a}$, $R_{12b}$, $R_{12c}$, and $R_{12d}$ is independently selected from fluoro, chloro, —SF$_5$, —CN, —NO$_2$, —OCH$_3$, —SCH$_3$, —N(CH$_3$)$_2$, —NHCH$_3$, hydroxyl, thiol, C$_1$-C$_3$ alkyl, C$_1$-C$_3$ fluoroalkyl, —O(C$_1$-C$_3$ alkyl), —O(C$_1$-C$_3$ fluoroalkyl), —B(OH)$_2$, —B(OCH$_3$)$_2$, —C(O)OCH$_3$, —C(O)OH, —C(O)NH$_2$, —C(S)OCH$_3$, —C(S)OH, —C(S)NH$_2$, —OSO$_2$OCH$_3$, —OSO$_2$OH, —OSO$_2$OH, —NHSO$_2$OH, —NHSO$_2$OCH, —NHSO$_2$R$_{16}$, —N(CH$_3$)SO$_2$OCH$_3$, —N(CH$_3$)SO$_2$OH, —N(CH$_3$)SO$_2$NH$_2$, —OP(O)(OCH$_3$)$_2$, —OP(O)(OH)$_2$, —P(O)(OCH$_3$)$_3$, —P(O)(OH)$_3$, —P(O)OCH$_3$, —P(O)OH, —SO$_2$NH$_2$, —SO$_2$OH, and —SO$_2$OCH$_3$. In a further aspect, each of $R_{12a}$, $R_{12b}$, $R_{12c}$, and $R_{12d}$ is independently selected from fluoro, chloro, —SF$_5$, —CN, —NO$_2$, —OCH$_3$, —SCH$_3$, —N(CH$_3$)$_2$, —NHCH$_3$, hydroxyl, thiol, methyl, fluoromethyl, difluoromethyl, —OCH$_3$, —OCH$_2$F, —B(OH)$_2$, —B(OCH$_3$)$_2$, —C(O)OCH$_3$, —C(O)OH, —C(O)NH$_2$, —C(S)OCH$_3$, —C(S)OH, —C(S)NH$_2$, —OSO$_2$OCH$_3$, —OSO$_2$OH, —OSO$_2$OH, —NHSO$_2$OH, —NHSO$_2$OCH$_3$, —NHSO$_2$R$_{16}$, —N(CH$_3$)SO$_2$OCH$_3$, —N(CH$_3$)SO$_2$OH, —N(CH$_3$)SO$_2$NH$_2$, —OP(O)(OCH$_3$)$_2$, —OP(O)(OH)$_2$, —P(O)(OCH$_3$)$_3$, —P(O)(OH)$_3$, —P(O)OCH$_3$, —P(O)OH, —SO$_2$NH$_2$, —SO$_2$OH, and —SO$_2$OCH$_3$. In a still further aspect, each of $R_{12a}$, $R_{12b}$, $R_{12c}$, and $R_{12d}$ is independently selected from fluoro, chloro, —SF$_5$, —CN, —NO$_2$, —OCH$_3$, —SCH$_3$, —N(CH$_3$)$_2$, —NHCH$_3$, hydroxyl, thiol, methyl, fluoromethyl, difluoromethyl, —OCH$_3$, and —OCH$_2$F. In a yet further aspect, each of $R_{12a}$, $R_{12b}$, $R_{12c}$, and $R_{12d}$ is independently selected from fluoro, chloro, hydroxyl, methyl, and fluoromethyl.

In various aspects, each of $R_{14a}$, $R_{14b}$, and $R_{14d}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_6$ cycloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{15}$, —C(S)OR$_{15}$, —C(S)R$_{16}$, —OSO$_2$OR$_{15}$, —OSO$_2$OR$_{16}$, —NHSO$_2$OR$_{15}$, —NHSO$_2$R$_{16}$, —N(C$_1$-C$_6$ alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$alkyl)aryl, aryloxy, heteroaryl, and —(C$_1$-C$_6$ alkyl)heteroaryl. In a further aspect, each of $R_{14a}$, $R_{14b}$, and $R_{14d}$ is independently selected from fluoro, chloro, —SF$_5$, —CN, —NO$_2$, —OCH$_3$, —SCH$_3$, —N(CH$_3$)$_2$, —NHCH$_3$, hydroxyl, thiol, C$_1$-C$_3$ alkyl, C$_1$-C$_3$ fluoroalkyl, —O(C$_1$-C$_3$ alkyl), —O(C$_1$-C$_3$ fluoroalkyl), —B(OH)$_2$, —B(OCH$_3$)$_2$, —C(O)OCH$_3$, —C(O)OH, —C(O)NH$_2$, —C(S)OCH$_3$, —C(S)OH, —C(S)NH$_2$, —OSO$_2$OCH$_3$, —OSO$_2$OH, —OSO$_2$OH, —NHSO$_2$OH, —NHSO$_2$OCH$_3$, —NHSO$_2$R$_{16}$, —N(CH$_3$)SO$_2$OCH$_3$, —N(CH$_3$)SO$_2$OH, —N(CH$_3$)SO$_2$NH$_2$, —OP(O)(OCH$_3$)$_2$, —OP(O)(OH)$_2$, —P(O)(OCH$_3$)$_3$, —P(O)(OH)$_3$, —P(O)OCH$_3$, —P(O)OH, —SO$_2$NH$_2$, —SO$_2$OH, and —SO$_2$OCH$_3$. In a still further aspect, each of $R_{14a}$, $R_{14b}$, and $R_{14d}$ is independently selected from fluoro, chloro, —SF$_5$, —CN, —NO$_2$, —OCH$_3$, —SCH$_3$, —N(CH$_3$)$_2$, —NHCH$_3$, hydroxyl, thiol, methyl, fluoromethyl, difluoromethyl, —OCH$_3$, —OCH$_2$F, —B(OH)$_2$, —B(OCH$_3$)$_2$, —C(O)OCH$_3$, —C(O)OH, —C(O)NH$_2$, —C(S)OCH$_3$, —C(S)OH, —C(S)NH$_2$, —OSO$_2$OCH$_3$, —OSO$_2$OH, —OSO$_2$OH, —NHSO$_2$OH, —NHSO$_2$OCH$_3$, —NHSO$_2$R$_{16}$, —N(CH$_3$)SO$_2$OCH$_3$, —N(CH$_3$)SO$_2$OH, —N(CH$_3$)SO$_2$NH$_2$, —OP(O)(OCH$_3$)$_2$, —OP(O)(OH)$_2$, —P(O)(OCH$_3$)$_3$, —P(O)(OH)$_3$, —P(O)

$OCH_3$, $-P(O)OH$, $-SO_2NH_2$, $-SO_2OH$, and $-SO_2OCH_3$. In a yet further aspect, each of $R_{14a}$, $R_{14b}$, and $R_{14d}$ is independently selected from fluoro, chloro, $-SF_5$, $-CN$, $-NO_2$, $-OCH_3$, $-SCH_3$, $-N(CH_3)_2$, $-NHCH_3$, hydroxyl, thiol, methyl, fluoromethyl, difluoromethyl, $-OCH_3$, and $-OCH_2F$. In an even further aspect, each of $R_{14a}$, $R_{14b}$, and $R_{14d}$ is independently selected from fluoro, chloro, hydroxyl, methyl, and fluoromethyl.

In various aspects, $R_{14c}$ is selected from hydrogen, hydroxyl, sulfhydryl, halogen, amino, aminoalkyl, $-O(C_1-C_6$ alkyl), $-S(C_1-C_6$ alkyl), aryloxy, $-OC(O)(C_1-C_6$ alkyl), $-OC(S)(C_1-C_6$ alkyl), $-OC(O)C_6H_5$, $-OC(S)C_6H_5$, $-OC(O)$aryl, $-OC(S)$aryl, $-OC(O)$heteroaryl, $-OC(S)$heteroaryl, $-OC(O)O(C_1-C_6$ alkyl), $-OC(S)O(C_1-C_6$ alkyl), $-OC(O)OC_6H_5$, $OC(S)OC_6H_5$, and $-OSO_2(C_2-C_6$ alkyl). In a still further aspect, $R_{14c}$ is selected from hydrogen, hydroxyl, sulfhydryl, halogen, $-NH_2$, $-NHCH_3$, $-NHCH_2CH_3$, $-NH(CH_2)_2CH_3$, $-NHCH(CH_3)_2$, $-NH(CH_2)_3CH_3$, $-NH(CH_2)_4CH_3$, $-N(CH_3)_2$, $-N(CH_3)CH_2CH_3$, $-N(CH_3)(CH_2)_2CH_3$, $-N(CH_3)CH(CH_3)_2$, $-N(CH_2CH_3)_2$, $-N(CH_2CH_3)((CH_2)_2CH_3)$, $-N(CH_2CH_3)(CH(CH_3)_2)$, $-OCH_3$, $-OCH_2CH_3$, $-O(CH_2)_2CH_3$, $-OCH(CH_3)_2$, $-OCH(CH_2CH_3)(CH_3)$, $-SCH_3$, $-SCH_2CH_3$, $-S(CH_2)_2CH_3$, $-SCH(CH_3)_2$, $-SCH(CH_2CH_3)(CH_3)$, $-OC(O)CH_3$, $-OC(O)CH_2CH_3$, $-OC(O)(CH_2)_2CH_3$, $-OC(O)CH(CH_3)_2$, $-OC(O)(CH_2)_3CH_3$, $-OC(O)(CH_2)_4CH_3$, $-OC(S)CH_3$, $-OC(S)CH_2CH_3$, $-OC(S)(CH_2)_2CH_3$, $-OC(S)CH(CH_3)_2$, $-OC(S)(CH_2)_3CH_3$, $-OC(S)(CH_2)_4CH_3$, $-OC(O)C_6H_5$, $-OC(S)C_6H_5$, $-OC(O)OCH_3$, $-OC(O)OCH_2CH_3$, $-OC(O)O(CH_2)_2CH_3$, $-OC(O)OCH(CH_3)_2$, $-OC(O)O(CH_2)_3CH_3$, $-OC(O)O(CH_2)_4CH_3$, $-OC(S)OCH_3$, $-OC(S)OCH_2CH_3$, $-OC(S)O(CH_2)_2CH_3$, $-OC(S)OCH(CH_3)_2$, $-OC(S)O(CH_2)_3CH_3$, $-OC(S)O(CH_2)_4CH_3$, $-OC(O)OC_6H_5$, $OC(S)OC_6H_5$, $-OSO_2CH_3$, $-OSO_2CH_2CH_3$, $-OSO_2(CH_2)_2CH_3$, $-OSO_2CH(CH_3)_2$, $-OSO_2(CH_2)_3CH_3$, and $-OSO_2(CH_2)_4CH_3$. In a yet further aspect, $R_{14c}$ is selected from hydrogen, hydroxyl, sulfhydryl, $-F$, $-Cl$, $-NH_2$, $-NHCH_3$, $-NHCH_2CH_3$, $-N(CH_3)_2$, $-N(CH_3)CH_2CH_3$, $-N(CH_2CH_3)_2$, $-OCH_3$, $-OCH_2CH_3$, $-SCH_3$, $-SCH_2CH_3$, $-OC(O)CH_3$, $-OC(O)CH_2CH_3$, $-OC(S)CH_3$, $-OC(S)CH_2CH_3$, $-OC(O)C_6H_5$, $-OC(S)C_6H_5$, $-OC(O)OCH_3$, $-OC(O)OCH_2CH_3$, $-OC(S)OCH_3$, $-OC(S)OCH_2CH_3$, $-OC(O)OC_6H_5$, $-OC(S)OC_6H_5$, $-SO_2CH_3$, and $-OSO_2CH_2CH_3$. In an even further aspect, $R_{14c}$ is selected from hydrogen, hydroxyl, sulfhydryl, $-F$, $-NH_2$, $-NHCH_3$, $-N(CH_3)_2$, $-OCH_3$, $-SCH_3$, $-OC(O)CH_3$, $-OC(S)CH_3$, $-OC(O)OCH_3$, $-OC(S)OCH_3$, and $-OSO_2CH_3$. In a still further aspect, $R_{14c}$ is selected from hydrogen, hydroxyl, sulfhydryl, $-F$, and $-NH_2$. In a yet further aspect, $R_{14c}$ is selected from hydroxyl, sulfhydryl, $-F$, and $-NH_2$. In an even further aspect, $R_{14c}$ is hydroxyl. In a still further aspect, $R_{14c}$ is sulfhydryl. In a yet further aspect, $R_{14c}$, is $-F$. In an even further aspect, $R_{14c}$ is $-NH_2$.

In various aspects, each occurrence of $R_{15}$ is independently selected from hydrogen, methyl, ethyl, propyl, isopropyl, cyclopropyl, cyclobutyl, cyclopentyl, cyclohexyl, phenyl, benzyl, pyridinyl, and pyrimidinyl. In a further aspect, in each occurrence of $R_{15}$ is independently selected from hydrogen, methyl, ethyl, propyl, isopropyl, cyclopropyl, cyclobutyl, cyclopentyl, and cyclohexyl. In a still further aspect, each occurrence of $R_{15}$ is independently selected from hydrogen, methyl, and ethyl.

In various aspects, each occurrence of $R_{16}$ is independently selected from $-NH_2$, $-NHCH_3$, $-NHCH_2CH_3$, $-NH(CH_2)_2CH_3$, $-NHCH(CH_3)_2$, $-NH(CH_2)_3CH_3$, $-NH(CH_2)_4CH_3$, $-N(CH_3)_2$, $-N(CH_3)CH_2CH_3$, $-N(CH_3)(CH_2)_2CH_3$, $-N(CH_3)CH(CH_3)_2$, $-N(CH_2CH_3)_2$, $-N(CH_2CH_3)((CH_2)_2CH_3)$, $-N(CH_2CH_3)(CH(CH_3)_2)$, $-OH$, $-OCH_3$, $-OCH_2CH_3$, $-O(CH_2)_2CH_3$, $-OCH(CH_3)_2$, $-OCH(CH_2CH_3)(CH_3)$, $-SH$, $-SCH_3$, $-SCH_2CH_3$, $-S(CH_2)_2CH_3$, $-SCH(CH_3)_2$, and $-SCH(CH_2CH_3)(CH_3)$. In a still further aspect, each occurrence of $R_{16}$ is independently selected from $-NH_2$, $-NHCH_3$, $-NHCH_2CH_3$, $-N(CH_3)_2$, $-N(CH_3)CH_2CH_3$, $-N(CH_2CH_3)_2$, $-OH$, $-OCH_3$, $-OCH_2CH_3$, $-SH$, $-SCH_3$, and $-SCH_2CH_3$. In a yet further aspect, each occurrence of $R_{16}$ is independently selected from $-NH_2$, $-NHCH_3$, $-N(CH_3)_2$, $-OH$, $-OCH_3$, $-SH$, and $-SCH_3$.

In various aspects, $R_{17}$ is selected from hydrogen, methyl, ethyl, propyl, isopropyl, cyclopropyl, cyclobutyl, cyclopentyl, cyclohexyl, phenyl, benzyl, $-C(O)OH$, $-C(O)OCH_3$, $-C(O)ONH_2$. $-C(S)OH$, $-C(S)OCH_3$, $-C(S)ONH_2$, pyridinyl, and pyrimidinyl. In a further aspect, $R_{17}$ is selected from hydrogen, methyl, ethyl, propyl, isopropyl, cyclopropyl, cyclobutyl, cyclopentyl, and cyclohexyl. In a still further aspect, $R_{17}$ is selected from hydrogen, methyl, and ethyl.

In various aspects, $R_{18}$ is selected from hydrogen, methyl, ethyl, propyl, isopropyl, cyclopropyl, cyclobutyl, cyclopentyl, cyclohexyl, phenyl, benzyl, $-C(O)OH$, $-C(O)OCH_3$, $-C(O)ONH_2$, $-C(S)OH$, $-C(S)OCH_3$, $-C(S)ONH_2$, pyridinyl, and pyrimidinyl. In a further aspect, $R_{18}$ is selected from hydrogen, methyl, ethyl, propyl, isopropyl, cyclopropyl, cyclobutyl, cyclopentyl, and cyclohexyl. In a still further aspect, $R_{18}$ is selected from hydrogen, methyl, and ethyl.

In various aspects, $R_{20}$ is phenyl; and wherein $R_{20}$ is substituted with 1, 2, or 3 groups independently selected from fluoro, chloro, $-SF_5$, $-CN$, $-NO_2$, $-OCH_3$, $-SCH_3$, $-N(CH_3)_2$, $-NHCH_3$, hydroxyl, thiol, $C_1-C_3$ alkyl, $C_1-C_3$ fluoroalkyl, $-O(C_1-C_3$ alkyl), $-O(C_1-C_3$ fluoroalkyl), $-B(OH)_2$, $-B(OCH_3)_2$, $-C(O)OCH_3$, $-C(O)OH$, $-C(O)NH_2$. $-C(S)OCH_3$, $-C(S)OH$, $-C(S)NH_2$, $-OSO_2OCH_3$, $-OSO_2OH$, $-OSO_2OH$, $-NHSO_2OH$, $-NHSO_2OCH_3$, $-NHSO_2R_{16}$, $-N(CH_3)SO_2OCH_3$, $-N(CH_3)SO_2OH$, $-N(CH_3)SO_2NH_2$, $-OP(O)(OCH_3)_2$, $-OP(O)(OH)_2$, $-P(O)(OCH_3)_3$, $-P(O)(OH)_3$, $-P(O)OCH_3$, $-P(O)OH$, $-SO_2NH_2$, $-SO_2OH$, and $-SO_2OCH_3$. In a further aspect, $R_{20}$ is phenyl; and wherein $R_{20}$ is substituted with 1, 2, or 3 groups independently selected from fluoro, chloro, $-SF_5$, $-CN$, $-NO_2$, $-OCH_3$, $-SCH_3$, $-N(CH_3)_2$, $-NHCH_3$, hydroxyl, thiol, methyl, fluoromethyl, difluoromethyl, $-OCH_3$, $-OCH_2F$, $-B(OH)_2$, $-B(OCH_3)_2$, $-OC(O)OCH_3$, $-C(O)OH$, $-C(O)NH_2$, $-C(S)OCH_3$, $-C(S)OH$, $-C(S)NH_2$, $-OSO_2OCH_3$, $-OSO_2OH$, $-OSO_2OH$, $-NHSO_2OH$, $-NHSO_2OCH_3$, $-NHSO_2R_{16}$, $-N(CH_3)SO_2OCH_3$, $-N(CH_3)SO_2OH$, $-N(CH_3)SO_2NH_2$, $-OP(O)(OCH_3)_2$, $-OP(O)(OH)_2$, $-P(O)(OCH_3)_3$, $-P(O)(OH)_3$, $-P(O)OCH_3$, $-P(O)OH$, $-SO_2NH_2$, $-SO_2OH$, and $-SO_2OCH_3$. In a still further aspect, $R_{20}$ is phenyl; and wherein $R_{20}$ is substituted with 1, 2, or 3 groups independently selected from fluoro, chloro, $-SF_5$, $-CN$, $-NO_2$, $-OCH_3$, $-SCH_3$, $-N(CH_3)_2$, $-NHCH_3$, hydroxyl, thiol, methyl, fluoromethyl, difluoromethyl, $-OCH_3$, and $-OCH_2F$. In an even further aspect, $R_{20}$ is phenyl; and wherein $R_{20}$ is substituted with 1, 2, or 3 groups independently selected from fluoro, chloro, hydroxyl, methyl, and fluoromethyl.

In various aspects, also disclosed are compounds having a structure represented by a formula:

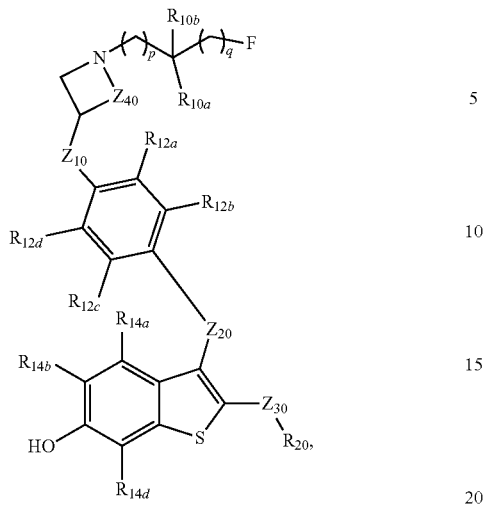

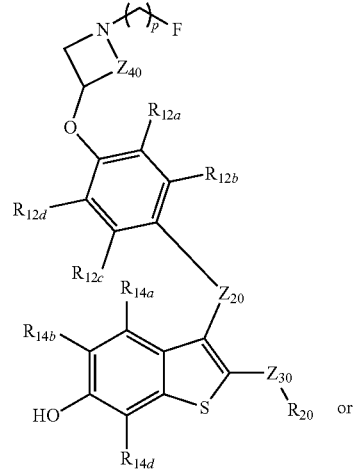

wherein p is selected from 0, 1, and 2; wherein q is selected from 0, 1, and 2; wherein $Z_{10}$ is selected from —O—, —CH$_2$—, —S—, —NR$_{17}$—, —CHF—, and —CF$_2$—; wherein $Z_{20}$ is selected from —O—, —CH$_2$—, —S—, —NR$_{18}$—, —CHF—, and —CF$_2$—; wherein $Z_{30}$ is selected from —C(O)—, —CF$_2$—, cyclopropyl, —CH$_2$—, and —CHF—; wherein $Z_{40}$ is —(CH$_2$)$_n$— and wherein n is 1, 2, 3, or 4; wherein each of $R_{10a}$ and $R_{10b}$ are independently selected from hydrogen, deuterium, halogen, and C1-C3 methyl; wherein each occurrence of $R_{12}$ and $R_{14}$ is independently selected from hydrogen, hydroxyl, thiol, nitroso, —SF$_5$, —OR$_{15}$, —SR$_{15}$, —N(R$_{15}$)$_2$, —CN, —NO$_2$, halogen, C$_1$-C$_6$ alkyl, C$_1$-C$_6$ haloalkyl, C$_3$-C$_8$ cycloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(C$_1$-C$_6$ alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; wherein each occurrence of $R_{15}$ is independently selected from hydrogen, C$_1$-C$_6$ alkyl, C$_1$-C$_6$ alkenyl, C$_1$-C$_6$ alkynyl, C$_3$-C$_8$ cycloalkyl, aryl, —(C$_1$-C$_6$ alkyl)aryl, heteroaryl, and —(C$_1$-C$_6$ alkyl)heteroaryl; wherein each occurrence of $R_{16}$ is independently selected from —N(R$_{15}$)$_2$, —SR$_{15}$, —OR$_{15}$; wherein each of $R_{17}$ and $R_{18}$ is independently selected from hydrogen, —C(O)R$_{15}$, —C(S)R$_{15}$, —C(O)R$_{16}$, —C(S)R$_{16}$, C$_1$-C$_6$ alkyl, C$_1$-C$_6$ alkenyl, C$_1$-C$_6$ alkynyl, C$_3$-C$_8$ cycloalkyl, aryl, and heteroaryl; wherein $R_{20}$ is selected from aryl, heteroaryl, thiophenyl, C$_3$-C$_8$ cycloalkyl, and bicyclic heterocyclyl, and wherein $R_{20}$ is substituted with 0, 1, 2, 3, or 4 groups independently selected from halogen, —SF$_5$, —CN, —NO$_2$, —OR$_{15}$, —SR$_{15}$, —N(R$_{15}$)$_2$, hydroxyl, thiol, nitroso, C$_1$-C$_6$ alkyl, C$_1$-C$_6$ haloalkyl, —O(C$_1$-C$_6$ alkyl), —O(C$_1$-C$_6$ haloalkyl), —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, C$_1$-C$_6$ alkenyl, C$_1$-C$_6$ alkynyl, aryl, —(C$_1$-C$_6$ alkyl)aryl, aryloxy, heteroaryl, and —(C$_1$-C$_6$ alkyl)heteroaryl; or a pharmaceutically acceptable salt thereof.

In various aspects, also disclosed are compounds having a structure represented by a formula:

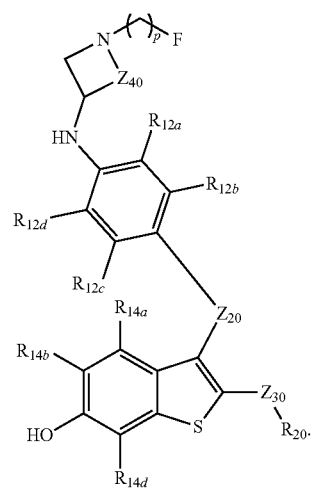

In various aspects, also disclosed are compounds having a structure represented by a formula:

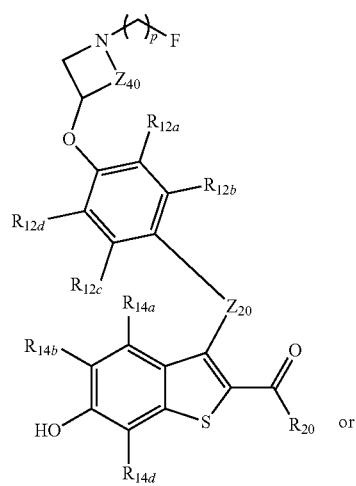

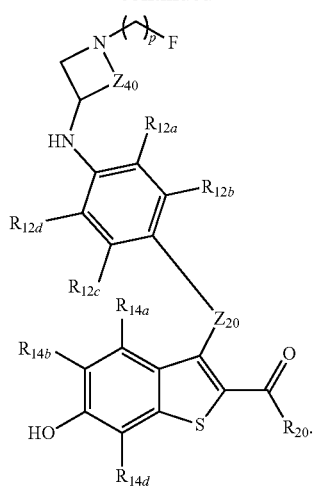
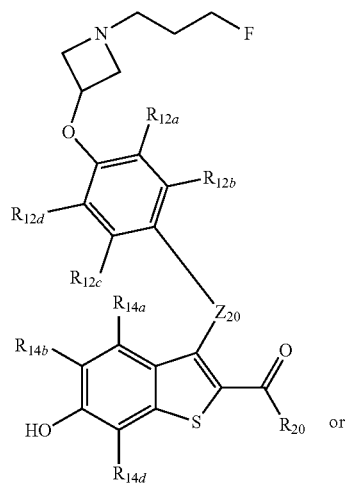
In various aspects, also disclosed are compounds having a structure represented by a formula:
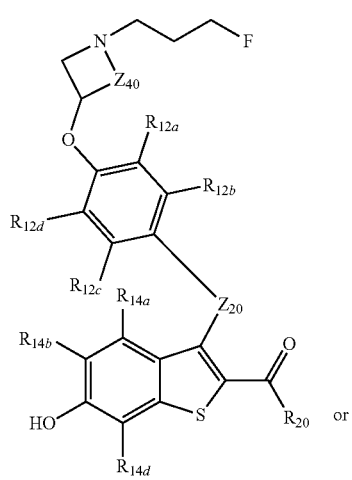
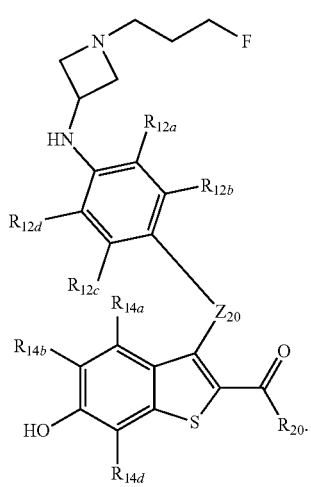
In various aspects, also disclosed are compounds having a structure represented by a formula:
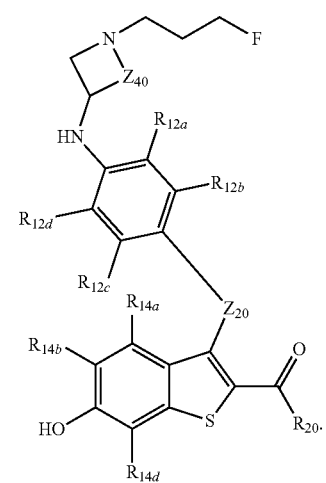
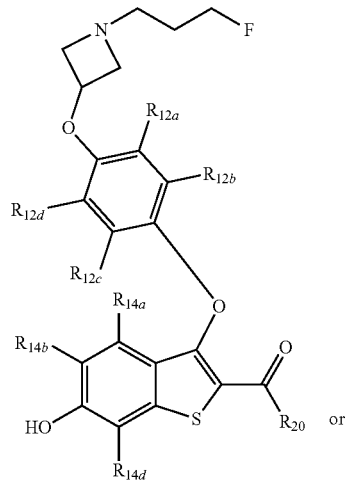
In various aspects, also disclosed are compounds having a structure represented by a formula:

-continued

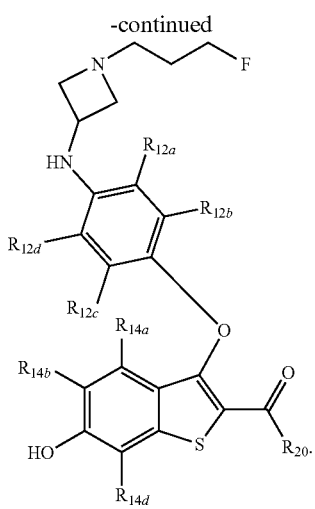

In various aspects, also disclosed are compounds having a structure represented by a formula:

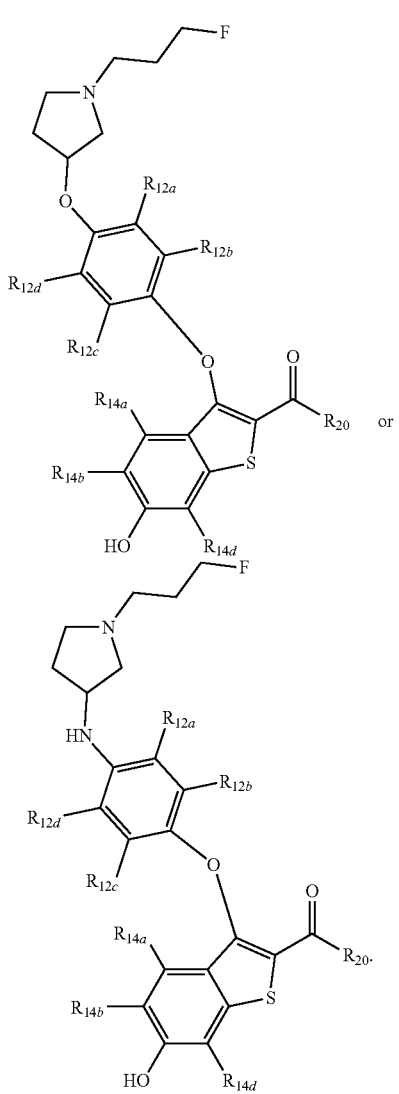

or

In various aspects, also disclosed are compounds having a structure represented by a formula:

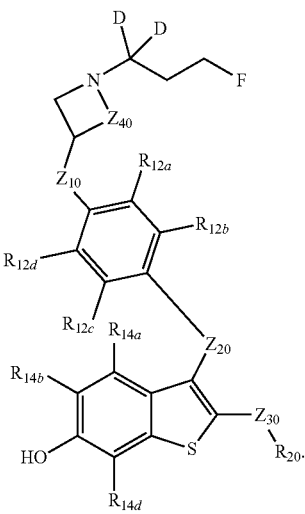

In various aspects, also disclosed are compounds having a structure represented by a formula:

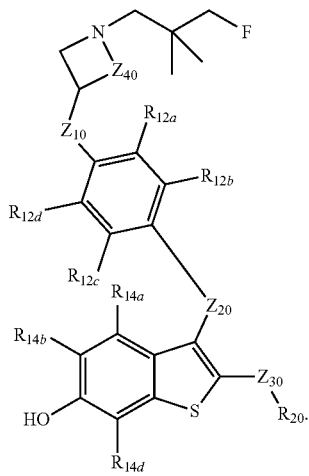

In various aspects, also disclosed are compounds having a structure represented by a formula:

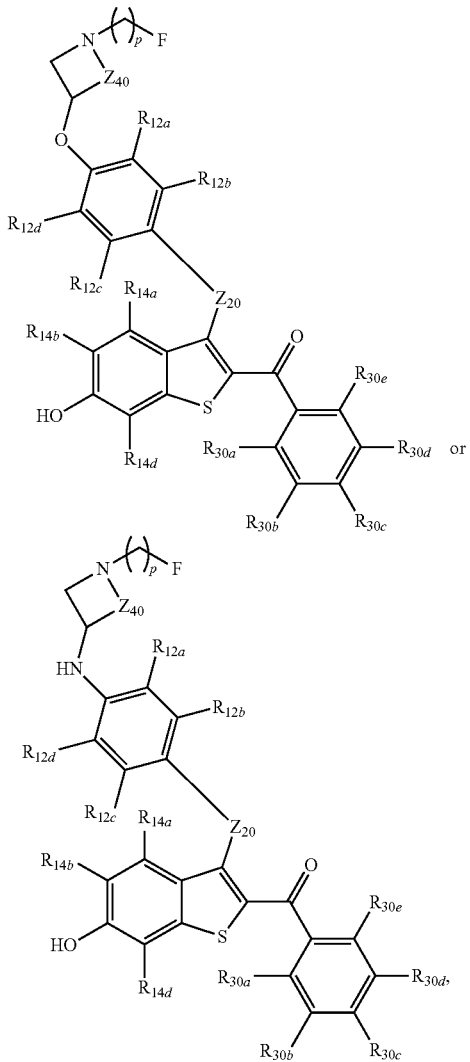

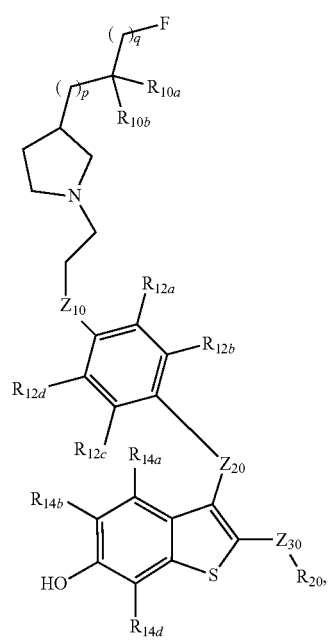

wherein each of $R_{30a}$, $R_{30b}$, $R_{30c}$, $R_{30d}$, and $R_{30e}$, is independently selected from hydrogen, fluoro, chloro, —$SF_5$, —CN, —$NO_2$, —$OCH_3$, —$SCH_3$, —$N(CH_3)_2$, —$NHCH_3$, hydroxyl, thiol, $C_1$-$C_3$ alkyl, $C_1$-$C_3$ fluoroalkyl, —O($C_1$-$C_3$ alkyl), —O($C_1$-$C_3$ fluoroalkyl), —$B(OH)_2$, —$B(OCH_3)_2$, —$C(O)OCH_3$, —C(O)OH, —$C(O)NH_2$, —$C(S)OCH_3$, —C(S)OH, —$C(S)NH_2$, —$OSO_2OCH_3$, —$OSO_2OH$, —$OSO_2OH$, —$NHSO_2OH$, —$NHSO_2OCH_3$, —$NHSO_2R_{16}$, —$N(CH_3)SO_2OCH_3$, —$N(CH_3)SO_2OH$, —$N(CH_3)SO_2NH_2$, —$OP(O)(OCH_3)_2$, —$OP(O)(OH)_2$, —$P(O)(OCH_3)_3$, —$P(O)(OH)_3$, —$P(O)OCH_3$, —P(O)OH, —$SO_2NH_2$, —$SO_2OH$, and —$SO_2OCH_3$. In a further aspect, each of $R_{30a}$, $R_{30b}$, $R_{30c}$, $R_{30d}$, and $R_{30e}$, is independently selected from hydrogen, fluoro, chloro, —$SF_5$, —CN, —$NO_2$, —$OCH_3$, —$SCH_3$, —$N(CH_3)_2$, —$NHCH_3$, hydroxyl, thiol, methyl, fluoromethyl, difluoromethyl, —$OCH_3$, —$OCH_2F$, —$B(OH)_2$, —$B(OCH_3)_2$, —C(O)OCH$_3$, —C(O)OH, —$C(O)NH_2$, —$C(S)OCH_3$, —C(S)OH, —$C(S)NH_2$, —$OSO_2OCH_3$, —$OSO_2OH$, —$OSO_2OH$, —$NHSO_2OH$, —$NHSO_2OCH_3$, —$NHSO_2R_{16}$, —$N(CH_3)SO_2OCH_3$, —$N(CH_3)SO_2OH$, —$N(CH_3)SO_2NH_2$, —OP(O)(OCH$_3)_2$, —$OP(O)(OH)_2$, —$P(O)(OCH_3)_3$, —$P(O)(OH)_3$, —$P(O)OCH_3$, —P(O)OH, —$SO_2NH_2$, —$SO_2OH$, and —$SO_2OCH_3$. In a still further aspect, each of $R_{30a}$, $R_{30b}$, $R_{30c}$, $R_{30d}$, and $R_{30e}$, is independently selected from hydrogen, fluoro, chloro, —$SF_5$, —CN, —$NO_2$, —$OCH_3$, —$SCH_3$, —$N(CH_3)_2$, —$NHCH_3$, hydroxyl, thiol, methyl, fluoromethyl, difluoromethyl, —$OCH_3$, and —$OCH_2F$. In a yet further aspect, each of $R_{30a}$, $R_{30b}$, $R_{30c}$, $R_{30d}$, and $R_{30e}$, is independently selected from hydrogen, fluoro, chloro, hydroxyl, methyl, and fluoromethyl. In an even further aspect, at least one of $R_{30a}$, $R_{30b}$, $R_{30c}$, $R_{30d}$, and $R_{30e}$ is hydrogen. In a still further aspect, at least two of $R_{30a}$, $R_{30b}$, $R_{30c}$, $R_{30d}$, and $R_{30e}$ are hydrogen. In a yet further aspect, at least three of $R_{30a}$, $R_{30b}$, $R_{30c}$, $R_{30d}$, and $R_{30e}$ are hydrogen. In an even further aspect, at least four of $R_{30a}$, $R_{30b}$, $R_{30c}$, $R_{30d}$, and $R_{30e}$ are hydrogen.

In various aspects, also disclosed are compounds having a structure represented by a formula:

wherein p is selected from 0, 1, and 2; wherein q is selected from 0, 1, and 2; wherein $Z_{10}$ is selected from —O—, —$CH_2$—, —S—, —$NR_{17}$—, —CHF—, and —$CF_2$—; wherein $Z_{20}$ is selected from —O—, —$CH_2$—, —S—, —$NR_{18}$—, —CHF—, and —$CF_2$—; wherein $Z_{30}$ is selected from —C(O)—, —$CF_2$—, cyclopropyl, —$CH_2$—, and —CHF—; wherein each of $R_{10a}$ and $R_{10b}$ are independently selected from hydrogen, deuterium, halogen, and $C_1$-$C_3$ methyl; wherein each occurrence of $R_{12}$ and $R_{14}$ is independently selected from hydrogen, hydroxyl, thiol, nitroso, —$SF_5$, —$OR_{15}$, —$SR_{15}$, —$N(R_{15})_2$, —CN, —$NO_2$, halogen, $C_1$-$C_6$ alkyl, $C_1$-$C_6$ haloalkyl, $C_3$-$C_8$ cycloalkyl, —O($C_1$-$C_6$ alkyl), —O($C_1$-$C_6$ haloalkyl), —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(C_1$-$C_6$ alkyl)$SO_2OR_{15}$, —N(alkyl)$SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, $C_1$-$C_6$ alkenyl, $C_1$-$C_6$ alkynyl, aryl, —($C_1$-$C_6$ alkyl)aryl, aryloxy, heteroaryl, and —($C_1$-$C_6$ alkyl)heteroaryl; wherein each occurrence of $R_{15}$ is independently selected from hydrogen, $C_1$-$C_6$ alkyl, $C_1$-$C_6$ alkenyl, $C_1$-$C_6$ alkynyl, $C_3$-$C_8$ cycloalkyl, aryl, —($C_1$-$C_6$ alkyl)aryl, heteroaryl, and —($C_1$-$C_6$ alkyl)heteroaryl; wherein each occurrence of $R_{16}$ is independently selected from —$N(R_{15})_2$, —$SR_{15}$, —$OR_{15}$; wherein each of $R_{17}$ and $R_{18}$ is independently selected from hydrogen, —$C(O)R_{15}$, —$C(S)R_{15}$, —$C(O)R_{16}$, —$C(S)R_{16}$, $C_1$-$C_6$ alkyl, $C_1$-$C_6$ alkenyl, $C_1$-$C_6$ alkynyl, $C_3$-$C_8$ cycloalkyl, aryl, and heteroaryl; wherein $R_{20}$ is selected from aryl, heteroaryl, thiophenyl, $C_3$-$C_8$ cycloalkyl, and bicyclic heterocyclyl, and wherein $R_{20}$ is substituted with 0, 1, 2, 3, or 4 groups independently selected from halogen, —$SF_5$, —CN, —$NO_2$, —$OR_{15}$, —$SR_{15}$, —$N(R_{15})_2$, hydroxyl, thiol, nitroso, $C_1$-$C_6$ alkyl, $C_1$-$C_6$ haloalkyl, —O($C_1$-$C_6$ alkyl), —O($C_1$-$C_6$ haloalkyl), —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(alkyl)SO_2OR_{15}$, —$N(alkyl)SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, $C_1$-$C_6$ alkenyl, $C_1$-$C_6$ alkynyl, aryl, —($C_1$-$C_6$ alkyl)aryl, aryloxy, heteroaryl, and —($C_1$-$C_6$ alkyl)heteroaryl; or a pharmaceutically acceptable salt thereof.

In various aspects, also disclosed are compounds having a structure represented by a formula:

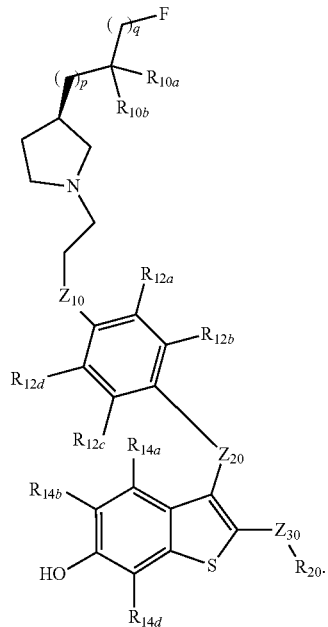

In various aspects, also disclosed are compounds having a structure represented by a formula:

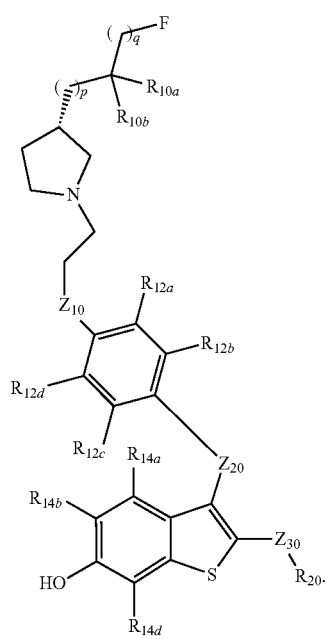

In various aspects, also disclosed are compounds having a structure represented by a formula:

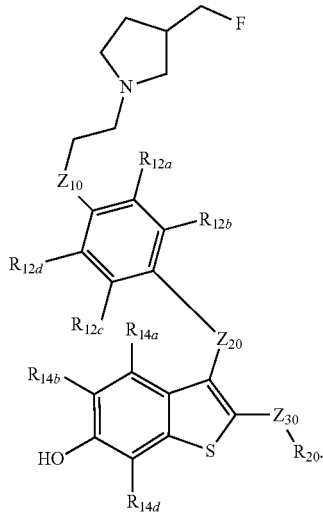

In various aspects, also disclosed are compounds having a structure represented by a formula:

In various aspects, also disclosed are compounds having a structure represented by a formula:

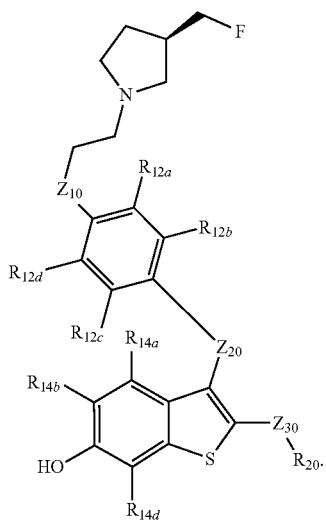
In various aspects, also disclosed are compounds having a structure represented by a formula:
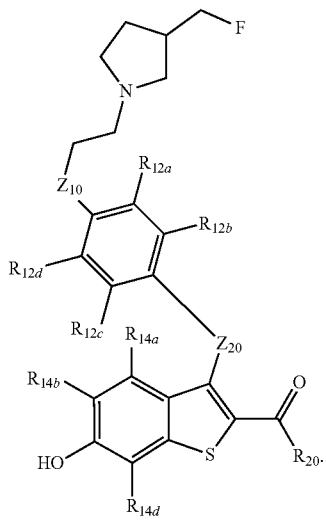
In various aspects, also disclosed are compounds having a structure represented by a formula:
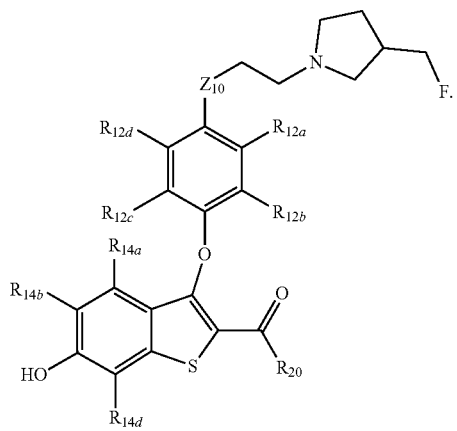
In various aspects, also disclosed are compounds having a structure represented by a formula:
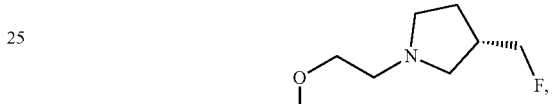
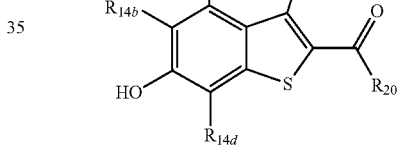
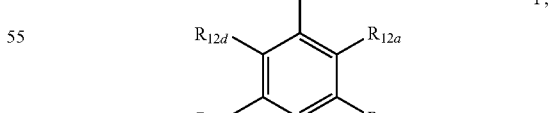
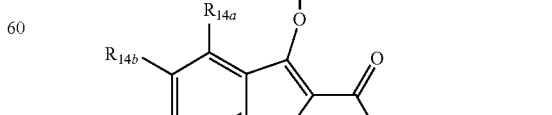

-continued

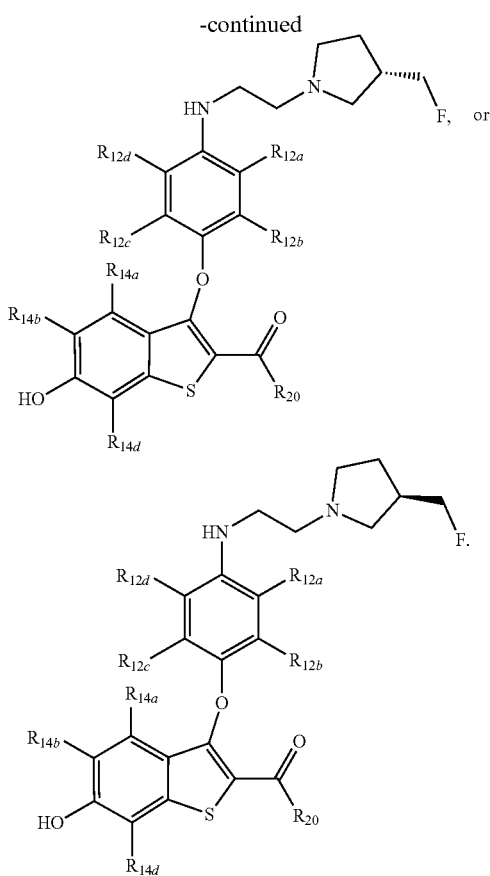

In various aspects, also disclosed are compounds having a structure represented by a formula:

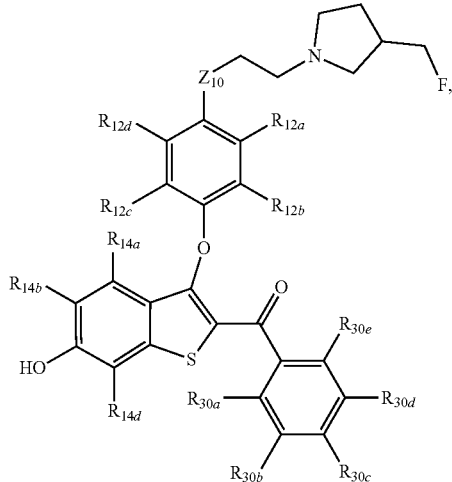

wherein each of $R_{30a}$, $R_{30b}$, $R_{30c}$, $R_{30d}$, and $R_{30e}$, is independently selected from hydrogen, fluoro, chloro, —SF$_5$, —CN, —NO$_2$, —OCH$_3$, —SCH$_3$, —N(CH$_3$)$_2$, —NHCH$_3$, hydroxyl, thiol, C$_1$-C$_3$ alkyl, C$_1$-C$_3$ fluoroalkyl, —O(C$_1$-C$_3$ alkyl), —O(C$_1$-C$_3$ fluoroalkyl), —B(OH)$_2$, —B(OCH$_3$)$_2$, —C(O)OCH$_3$, —C(O)OH, —C(O)NH$_2$, —C(S)OCH$_3$, —C(S)OH, —C(S)NH$_2$, —OSO$_2$OCH$_3$, —OSO$_2$OH, —OSO$_2$OH, —NHSO$_2$OH, —NHSO$_2$OCH$_3$, —NHSO$_2$R$_{16}$, —N(CH$_3$)SO$_2$OCH$_3$, —N(CH$_3$)SO$_2$OH, —N(CH$_3$)SO$_2$NH$_2$, —OP(O)(OCH$_3$)$_2$, —OP(O)(OH)$_2$, —P(O)(OCH$_3$)$_3$, —P(O)(OH)$_3$, —P(O)OCH$_3$, —P(O)OH, —SO$_2$NH$_2$, —SO$_2$OH, and —SO$_2$OCH$_3$. In a further aspect, each of $R_{30a}$, $R_{30b}$, $R_{30c}$, $R_{30d}$, and $R_{30e}$, is independently selected from hydrogen, fluoro, chloro, —SF$_5$, —CN, —NO$_2$, —OCH$_3$, —SCH$_3$, —N(CH$_3$)$_2$, —NHCH$_3$, hydroxyl, thiol, methyl, fluoromethyl, difluoromethyl, —OCH$_3$, —OCH$_2$F, —B(OH)$_2$, —B(OCH$_3$)$_2$, —C(O)OCH$_3$, —C(O)OH, —C(O)NH$_2$, —C(S)OCH$_3$, —C(S)OH, —C(S)NH$_2$, —OSO$_2$OCH$_3$, —OSO$_2$OH, —OSO$_2$OH, —NHSO$_2$OH, —NHSO$_2$OCH$_3$, —NHSO$_2$R$_{16}$, —N(CH$_3$)SO$_2$OCH$_3$, —N(CH$_3$)SO$_2$OH, —N(CH$_3$)SO$_2$NH$_2$, —OP(O)(OCH$_3$)$_2$, —OP(O)(OH)$_2$, —P(O)(OCH$_3$)$_3$, —P(O)OCH$_3$, —P(O)OH, —SO$_2$NH$_2$, —SO$_2$OH, and —SO$_2$OCH$_3$. In a still further aspect, each of $R_{30a}$, $R_{30b}$, $R_{30c}$, $R_{30d}$, and $R_{30e}$, is independently selected from hydrogen, fluoro, chloro, —SF$_5$, —CN, —NO$_2$, —OCH$_3$, —SCH$_3$, —N(CH$_3$)$_2$, —NHCH$_3$, hydroxyl, thiol, methyl, fluoromethyl, difluoromethyl, —OCH$_3$, and —OCH$_2$F. In a yet further aspect, each of $R_{30a}$, $R_{30b}$, $R_{30c}$, $R_{30d}$, and $R_{30e}$, is independently selected from hydrogen, fluoro, chloro, hydroxyl, methyl, and fluoromethyl.

In various aspects, also disclosed are compounds having a structure represented by a formula:

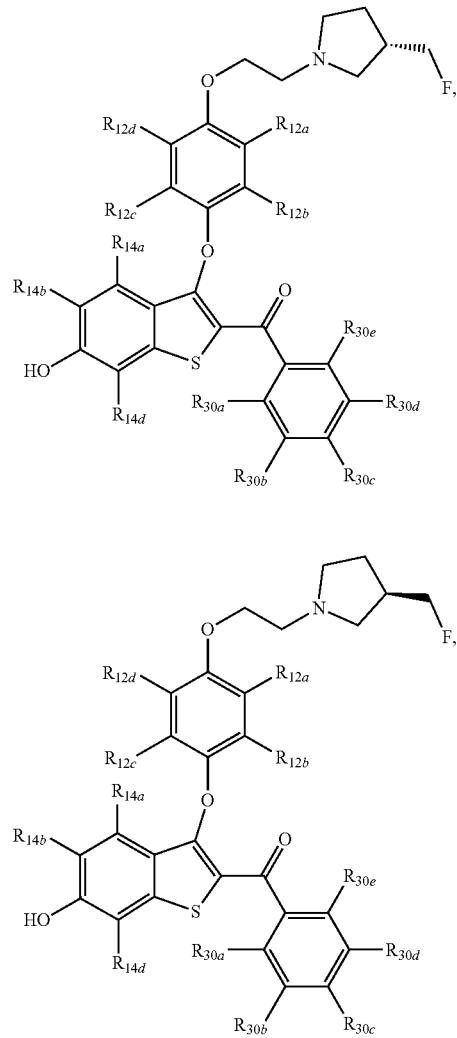

-continued

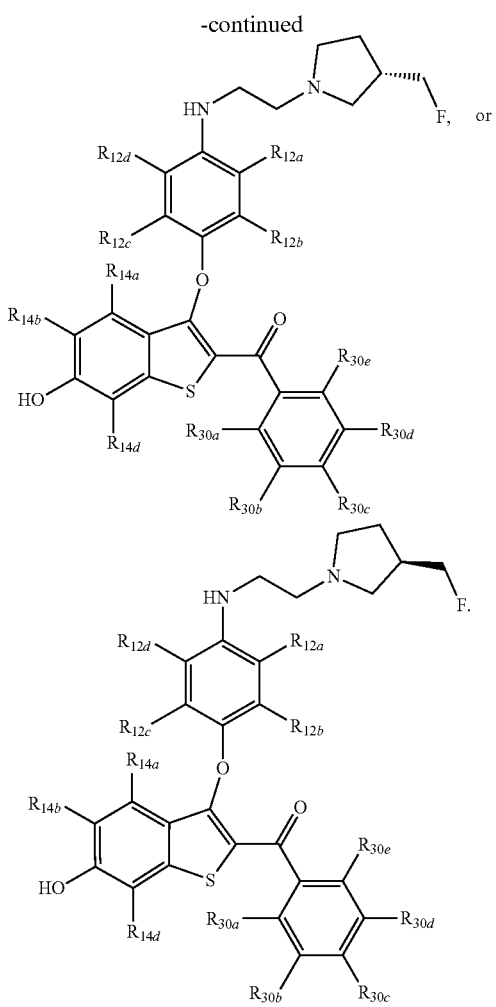

In a further aspect, at least one of $R_{30a}$, $R_{30b}$, $R_{30c}$, $R_{30d}$, and $R_{30e}$ is hydrogen. In a still further aspect, at least two of $R_{30a}$, $R_{30b}$, $R_{30c}$, $R_{30d}$, and $R_{30e}$ are hydrogen. In a yet further aspect, at least three of $R_{30a}$, $R_{30b}$, $R_{30c}$, $R_{30d}$, and $R_{30e}$ are hydrogen. In an even further aspect, at least four of $R_{30a}$, $R_{30b}$, $R_{30c}$, $R_{30d}$, and $R_{30e}$ are hydrogen.

In various aspects, it is contemplated herein that the disclosed compounds further comprise their biosteric equivalents. The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are: (i) Burger A, *Relation of chemical structure and biological activity*; in Medicinal Chemistry Third ed., Burger A, ed.; Wiley-Interscience; New York, 1970, 64-60; (ii) Burger, A.; "Isosterism and bioisosterism in drug design"; *Prog. Drug Res.* 1991, 37, 287-371; (iii) Burger A, "Isosterism and bioanalogy in drug design", *Med. Chem. Res.* 1994, 4, 89-92; (iv) Clark P D, Ferguson A M. Cramer R D. "Bioisosterism and molecular diversity", *Perspect. Drug Discovery Des.* 1998, 9/10/11, 213-224; (v) Koyanagi T, Haga T, "Bioisosterism in agrochemicals", *ACS Symp. Ser.* 1995, 584, 15-24; (vi) Kubinyi H, "Molecular similarities. Part 1. Chemical structure and biological activity". *Pharm. Unserer Zeit* 1998, 27, 92-106; (vii) Lipinski C A.; "Bioisosterism in drug design"; *Annu. Rep. Med. Chem.* 1986, 21, 283-91; (viii) Patani G A, LaVoie E J, "Bioisosterism: A rational approach in drug design", *Chem. Rev.* (Washington, D.C.) 1996, 96, 3147-3176; (ix) Soskic V, Joksimovic J. "Bioisosteric approach in the design of new dopaminergic/serotonergic ligands", *Curr Med. Chem.* 1998, 5, 493-512 (x) Thornber C W, "Isosterism and molecular modification in drug design". *Chem. Soc. Rev.* 1979, 8, 563-80.

In further aspects, bioisosteres are atoms, ions, or molecules in which the peripheral layers of electrons can be considered substantially identical. The term bioisostere is usually used to mean a portion of an overall molecule, as opposed to the entire molecule itself, Bioisosteric replacement involves using one bioisostere to replace another with the expectation of maintaining or slightly modifying the biological activity of the first bioisostere. The bioisosteres in this case are thus atoms or groups of atoms having similar size, shape and electron density. Preferred bioisosteres of esters, amides or carboxylic acids are compounds containing two sites for hydrogen bond acceptance. In one aspect, the ester, amide or carboxylic acid bioisostere is a 5-membered monocyclic heteroaryl ring, such as an optionally substituted 1H-imidazolyl, an optionally substituted oxazolyl, 1H-tetrazolyl, [1,2,4]triazolyl, or an optionally substituted [1,2,4]oxadiazolyl.

In various aspects, it is contemplated herein that the disclosed compounds further comprise their isotopically-labelled or isotopically-substituted variants, i.e., compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

In various aspects, the disclosed compounds can be in the form of a co-crystal. The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O. et. al., The Royal Society of Chemistry, 1889-1896, 2004. Preferred co-crystals include p-toluene-sulfonic acid and benzenesulfonic acid.

The term "pharmaceutically acceptable co-crystal" means one that is compatible with the other ingredients of the formulation and not deleterious to the recipient thereof.

In a further aspect, the disclosed compounds can be isolated as solvates and, in particular, as hydrates of a disclosed compound, which can be obtained, for example, by crystallization from a solvent or from aqueous solution. In this connection, one, two, three or any arbitrary number of solvate or water molecules can combine with the compounds according to the invention to form solvates and hydrates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. In a further aspect, salts further include, but are not limited to, the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e. 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

In various aspects, the present disclosure pertains to compounds or a pharmaceutically acceptable salt thereof of Formula I:

Formula I

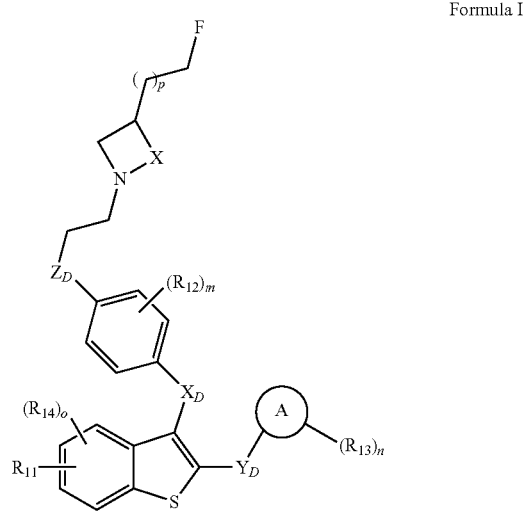

such that m is 0, 1, 2, 3, or 4; n is 0, 1, 2, 3, or 4; o is 0, 1, 2, or 3; p is 0, 1, 2, or 3; $X_D$ is selected from —O—, —CH$_2$—, —S—, —NR$_{17}$, —CHF—, —CF$_2$—, and cycloalkyl; $Y_D$ is selected from —C(O)—, —CF$_2$—, cyclopropyl, —CH$_2$—, and —CHF—; $Z_D$ is selected from O—, —CH$_2$—, —S—, —NR$_{17}$, —CHF—, —CF$_2$—, Ring A is phenyl, heteroaryl, thiophenyl, 5- or 6-membered monocyclic heteroaryl, cycloalkyl or 7-, 8-, 9- or 10-membered bicyclic heterocyclyl; $R_{11}$ is selected from hydroxyl, hydrogen, halogen, —O(C$_1$-C$_6$ alkyl), —S(C$_1$-C$_6$ alkyl), aryloxy, —OC(O)(C$_1$-C$_6$ alkyl), —OC(S)(C$_1$-C$_6$ alkyl), —OC(O)C$_6$H$_6$, —OC(S)C$_6$H$_6$, —OC(O)aryl, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, OC(S)OC$_6$H$_5$, amino, aminoalkyl, —SH, and —OSO$_2$(C$_2$-C$_6$ alkyl); $R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$ fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula II:

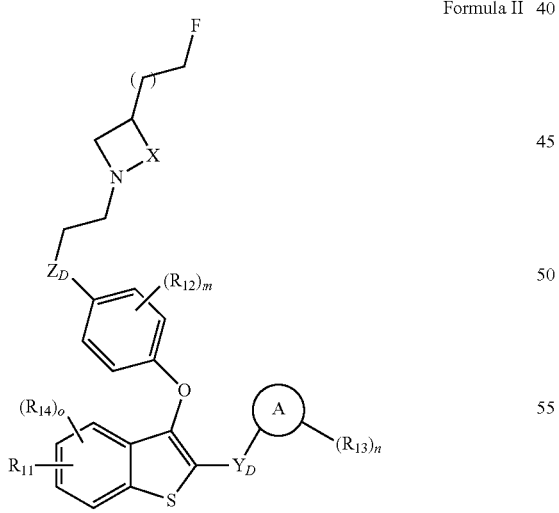

Formula II such that m is 0, 1, 2, 3, or 4; n is 0, 1, 2, 3, or 4; o is 0, 1, 2, or 3; p is 0, 1, 2, or 3; $X_D$ is selected from —O—, —CH$_2$—, —S—, —NR$_{17}$, —CHF—, —CF$_2$—, and cycloalkyl; $Y_D$ is selected from —C(O)—, —CF$_2$—, cyclopropyl, —CH$_2$—, and —CHF—; $Z_D$ is selected from O—, —CH$_2$—, —S—, —NR$_{17}$, —CHF—, —CF$_2$—, Ring A is phenyl, heteroaryl, thiophenyl, 5- or 6-membered monocyclic heteroaryl, cycloalkyl or 7-, 8-, 9- or 10-membered bicyclic heterocyclyl; $R_{11}$ is selected from hydroxyl, hydrogen, halogen, —O(C$_1$-C$_6$ alkyl), —S(C$_1$-C$_6$ alkyl), aryloxy, —OC(O)(C$_1$-C$_6$ alkyl), —OC(S)(C$_1$-C$_6$ alkyl), —OC(O)C$_6$H$_5$, —OC(S)C$_6$H$_5$, —OC(O)aryl, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, OC(S)OC$_6$H$_5$, amino, aminoalkyl, —SH, and —OSO$_2$(C$_2$-C$_6$ alkyl); $R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula III:

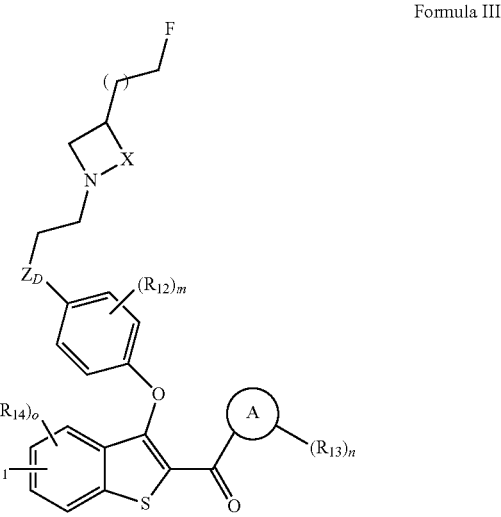

Formula III such that m is 0, 1, 2, 3, or 4; n is 0, 1, 2, 3, or 4; o is 0, 1, 2, or 3; p is 0, 1, 2, or 3; $X_D$ is selected from —O—, —CH$_2$—, —S—, —NR$_{17}$, —CHF—, —CF$_2$—, and cycloalkyl; $Y_D$ is selected from —C(O)—, —CF$_2$—, cyclopropyl, —CH$_2$—, and —CHF—; $Z_D$ is selected from O—, —CH$_2$—, —S—, —NR$_{17}$, —CHF—, —CF$_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{11}$ is selected from hydroxyl, hydrogen, halogen, —O(C$_1$-C$_6$ alkyl), —S(C$_1$-C$_6$ alkyl), aryloxy, —OC(O)(C$_1$-C$_6$ alkyl), —OC(S)(C$_1$-C$_6$ alkyl), —OC(O)C$_6$H$_5$, —OC(S)C$_6$H$_5$, —OC(O)aryl, —OC(S)aryl, —OC(O)heteroaryl, —OC(S)heteroaryl, —OC(O)O(C$_1$-C$_6$ alkyl), —OC(S)O(C$_1$-C$_6$ alkyl), —OC(O)OC$_6$H$_5$, OC(S)

$OC_6H_5$, amino, aminoalkyl, —SH, and —$OSO_2(C_2$-$C_6$ alkyl); $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —$O(C_1$-$C_6$ alkyl), —$O(C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(alkyl)SO_2OR_{15}$, —$N(alkyl)SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula IV:

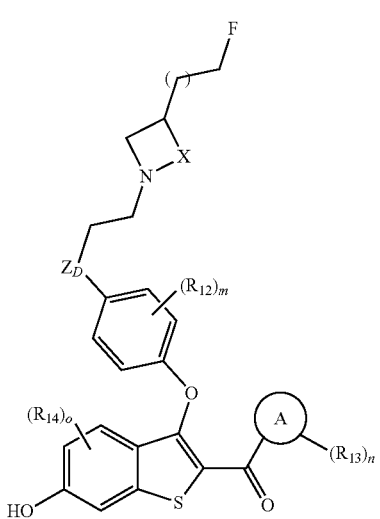

Formula IV such that m is 0, 1, 2, 3, or 4; n is 0, 1, 2, 3, or 4; o is 0, 1, 2, or 3; p is 0, 1, 2, 3, or 4; $X_D$ is selected from —O—, —$CH_2$—, —S—, —$NR_{17}$, —CHF—, —$CF_2$—, and cycloalkyl; $Y_D$ is selected from —C(O)—, —$CF_2$—, cyclopropyl, —$CH_2$—, and —CHF—; $Z_D$ is selected from O—, —$CH_2$—, —S—, —$NR_{17}$, —CHF—, —$CF_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —$O(C_1$-$C_6$ alkyl), —$O(C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(alkyl)SO_2OR_{15}$, —$N(alkyl)SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula V:

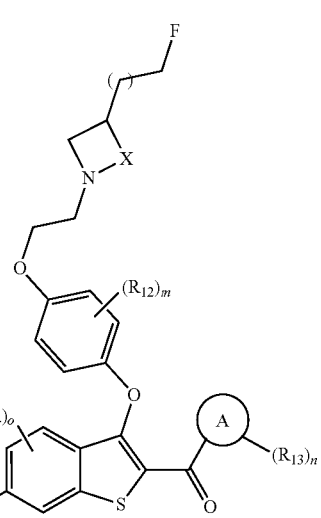

Formula V such that m is 0, 1, 2, 3, or 4; n is 0, 1, 2, 3, or 4; o is 0, 1, 2, or 3; p is 0, 1, 2, 3, or 4; $X_D$ is selected from —O—, —$CH_2$—, —S—, —$NR_{17}$, —CHF—, —$CF_2$—, and cycloalkyl; $Y_D$ is selected from —C(O)—, —$CF_2$—, cyclopropyl, —$CH_2$—, and —CHF—; $Z_D$ is selected from O—, —$CH_2$—, —S—, —$NR_{17}$, —CHF—, —$CF_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —$O(C_1$-$C_6$ alkyl), —$O(C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(alkyl)SO_2OR_{15}$, —$N(alkyl)SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula VI:

Formula VI

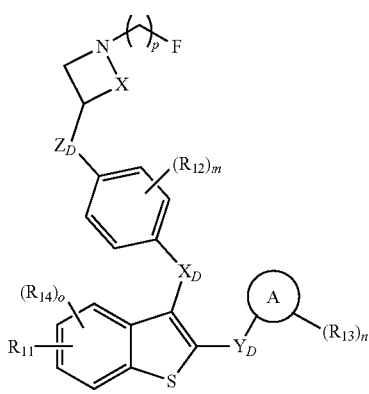

such that m is 0, 1, 2, 3, or 4; n is 0, 1, 2, 3, or 4; o is 0, 1, 2, or 3; p is 0, 1, 2, 3, or 4; $X_D$ is selected from —O—, —$CH_2$—, —S—, —$NR_{17}$, —CHF—, —$CF_2$—, and cycloalkyl; $Y_D$ is selected from —C(O)—, —$CF_2$—, cyclopropyl, —$CH_2$—, and —CHF—; $Z_D$ is selected from O—, —$CH_2$—, —S—, —$NR_{17}$, —CHF—, —$CF_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(alkyl)SO_2OR_{15}$, —$N(alkyl)SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula VII:

Formula VII

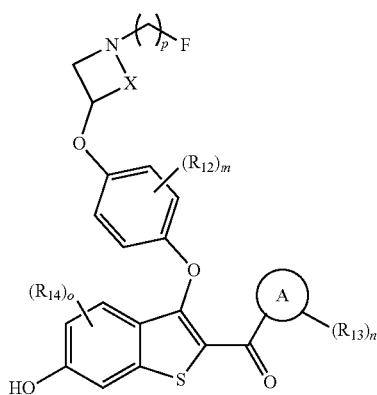

such that m is 0, 1, 2, 3, or 4; n is 0, 1, 2, 3, or 4; o is 0, 1, 2, or 3; p is 0, 1, 2, 3, or 4; $X_D$ is selected from —O—, —$CH_2$—, —S—, —$NR_{17}$, —CHF—, —$CF_2$—, and cycloalkyl; $Y_D$ is selected from —C(O)—, —$CF_2$—, cyclopropyl, —$CH_2$—, and —CHF—; $Z_D$ is selected from O—, —$CH_2$—, —S—, —$NR_{17}$, —CHF—, —$CF_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —$N(alkyl)SO_2OR_{15}$, —$N(alkyl)SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula VIII:

Formula VIII

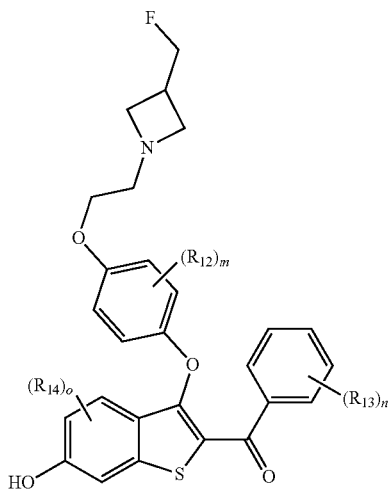

such that m is 0, 1, 2, 3, or 4; n is 0, 1, 2, 3, or 4; o is 0, 1, 2, or 3; p is 0, 1, 2, 3, or 4; $X_D$ is selected from —O—, —$CH_2$—, —S—, —$NR_{17}$, —CHF—, —$CF_2$—, and cycloalkyl; $Y_D$ is selected from —C(O)—, —$CF_2$—, cyclopropyl, —$CH_2$—, and —CHF—; $Z_D$ is selected from O—, —$CH_2$—, —S—, —$NR_{17}$, —CHF—, —$CF_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —O($C_1$-$C_6$ alkyl), —O($C_1$-$C_6$fluoroalkyl), —$SF_5$, —$B(OH)_2$, —$B(OR_{15})_2$, —$C(O)OR_{15}$, —$C(O)R_{16}$, —$C(S)$ OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; R$_{15}$ is independently selected at each occurrence from hydrogen, alkyl, alkenyl, alkynyl, cycloalkyl, aryl, arylalkyl, heteroaryl, and heteroarylalkyl; R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula IX:

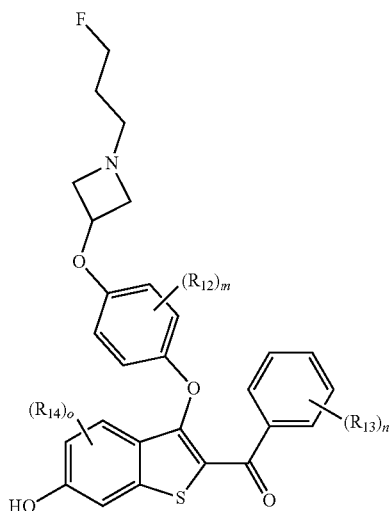

Formula IX such that m is 0, 1, 2, 3, or 4; n is 0, 1, 2, 3, or 4; o is 0, 1, 2, or 3; p is 0, 1, 2, 3, or 4; X$_D$ is selected from —O—, —CH$_2$—, —S—, —NR$_{17}$, —CHF—, —CF$_2$—, and cycloalkyl; Y$_D$ is selected from —C(O)—, —CF$_2$—, cyclopropyl, —CH$_2$—, and —CHF—; Z$_D$ is selected from O—, —CH$_2$—, —S—, —NR$_{17}$, —CHF—, —CF$_2$—; Ring A is phenyl, heteroaryl, thiophenyl, 5- or 6-membered monocyclic heteroaryl, cycloalkyl or 7-, 8-, 9- or 10-membered bicyclic heterocyclyl; R$_{12}$, R$_{13}$, and R$_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; R$_{15}$ is independently selected at each occurrence from hydrogen, alkyl, alkenyl, alkynyl, cycloalkyl, aryl, arylalkyl, heteroaryl, and heteroarylalkyl; R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula X:

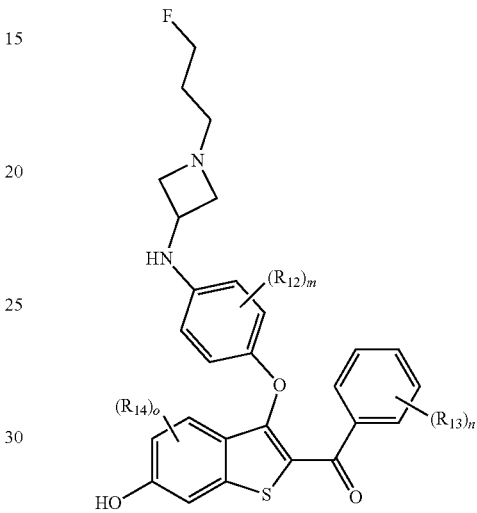

Formula X such that m is 0, 1, 2, 3, or 4; n is 0, 1, 2, 3, or 4; o is 0, 1, 2, or 3; p is 0, 1, 2, 3, or 4; X$_D$ is selected from —O—, —CH$_2$—, —S—, —NR$_{17}$, —CHF—, —CF$_2$—, and cycloalkyl; Y$_D$ is selected from —C(O)—, —CF$_2$—, cyclopropyl, —CH$_2$—, and —CHF—; Z$_D$ is selected from O—, —CH$_2$—, —S—, —NR$_{17}$, —CHF—, —CF$_2$—; Ring A is phenyl, heteroaryl, thiophenyl, 5- or 6-membered monocyclic heteroaryl, cycloalkyl or 7-, 8-, 9- or 10-membered bicyclic heterocyclyl; R$_{12}$, R$_{13}$, and R$_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; R$_{15}$ is independently selected at each occurrence from hydrogen, alkyl, alkenyl, alkynyl, cycloalkyl, aryl, arylalkyl, heteroaryl, and heteroarylalkyl; R$_{16}$ is independently selected at each occurrence from —N(R$_{15}$)$_2$, —SR$_{15}$, —OR$_{15}$; and R$_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula XI:

Formula XI

Formula XII

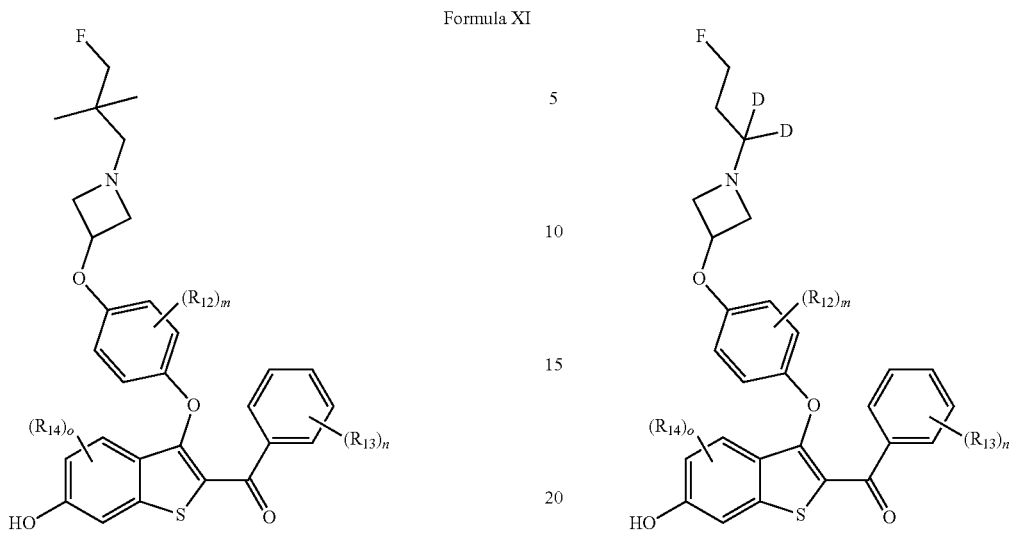

such that m is 0, 1, 2, 3, or 4; n is 0, 1, 2, 3, or 4; o is 0, 1, 2, or 3; p is 0, 1, 2, 3, or 4; $X_D$ is selected from —O—, —CH$_2$—, —S—, —NR$_{17}$, —CHF—, —CF$_2$—, and cycloalkyl; $Y_D$ is selected from —C(O)—, —CF$_2$—, cyclopropyl, —CH$_2$—, and —CHF—; $Z_D$ is selected from O—, —CH$_2$—, —S—, —NR$_{17}$, —CHF—, —CF$_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula XII:

such that m is 0, 1, 2, 3, or 4; n is 0, 1, 2, 3, or 4; o is 0, 1, 2, or 3; p is 0, 1, 2, 3, or 4; $X_D$ is selected from —O—, —CH$_2$—, —S—, —NR$_{17}$, —CHF—, —CF$_2$—, and cycloalkyl; $Y_D$ is selected from —C(O)—, —CF$_2$—, cyclopropyl, —CH$_2$—, and —CHF—; $Z_D$ is selected from O—, —CH$_2$—, —S—, —NR$_{17}$, —CHF—, —CF$_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —OR$_{15}$, —SR$_{15}$, —N(R$_{15}$)$_2$, hydrogen, aryl, heteroaryl, halogen, —CN, —NO$_2$, haloalkyl, cycloalkyl, thiol, nitroso, C$_1$-C$_6$alkyl, hydroxyl, —O(C$_1$-C$_6$ alkyl), —O(C$_1$-C$_6$fluoroalkyl), —SF$_5$, —B(OH)$_2$, —B(OR$_{15}$)$_2$, —C(O)OR$_{15}$, —C(O)R$_{16}$, —C(S)OR$_{15}$, —C(S)R$_{16}$, —OSO$_2$OR$_{15}$, —OSO$_2$R$_{16}$, —NHSO$_2$OR$_{15}$, —NHSO$_2$R$_{16}$, —N(alkyl)SO$_2$OR$_{15}$, —N(alkyl)SO$_2$R$_{16}$, —OP(O)(OR$_{15}$)$_2$, —OP(O)(R$_{16}$)$_2$, —P(O)(OR$_{15}$)$_3$, —P(O)(R$_{16}$)$_3$, —P(O)OR$_{15}$, —P(O)R$_{16}$, —SO$_2$R$_{16}$, —SO$_2$OR$_{15}$, alkyne, alkene, arylalkyl, aryloxy, heteroarylalkyl, and C$_1$-C$_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —N(R$_{15}$)$_2$, —SR$_{15}$, —OR$_{15}$; and $R_{17}$ is independently selected at each occurrence from hydrogen, alkyl, alkenyl, alkynyl, cycloalkyl, aryl, —C(O)R$_{15}$, —C(S)R$_{15}$, —C(O)R$_{16}$, —C(S)R$_{16}$, and heteroaryl.

In various aspects, the present disclosure pertains to compounds or a pharmaceutically acceptable salt thereof of Formula XIII:

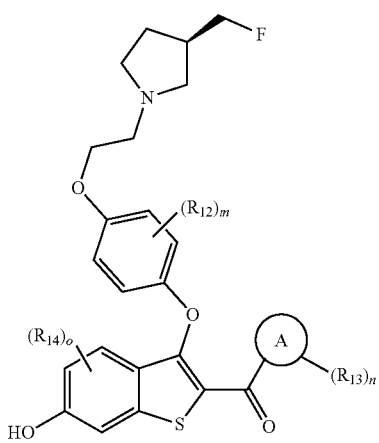

such that m is 0, 1, 2, 3, or 4; n is 0, 1, 2, 3, or 4; o is 0, 1, 2, or 3; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —$O(C_1$-$C_6$ alkyl), —$O(C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —N(alkyl)$SO_2OR_{15}$, —N(alkyl)$SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula XIV:

Formula XIV

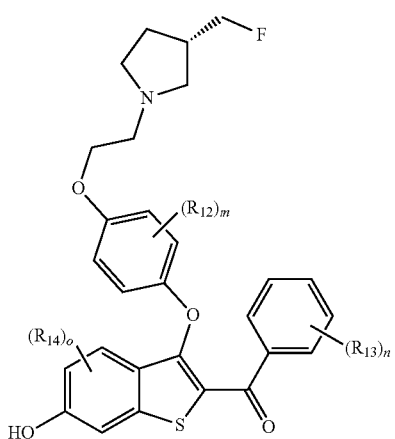

such that m is 0, 1, 2, 3, or 4; n is 0, 1, 2, 3, or 4; o is 0, 1, 2, or 3; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —$O(C_1$-$C_6$ alkyl), —$O(C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —N(alkyl)$SO_2OR_{15}$, —N(alkyl)$SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from —$N(R_{15})_2$, —$SR_{15}$, —$OR_{15}$; and $R_{17}$ is independently selected at each occurrence from hydrogen, alkyl, alkenyl, alkynyl, cycloalkyl, aryl, —$C(O)R_{15}$, —$C(S)R_{15}$, —$C(O)R_{16}$, —$C(S)R_{16}$, and heteroaryl.

In various aspects, the present disclosure pertains to compounds or a pharmaceutically acceptable salt thereof of Formula XV:

Formula XV

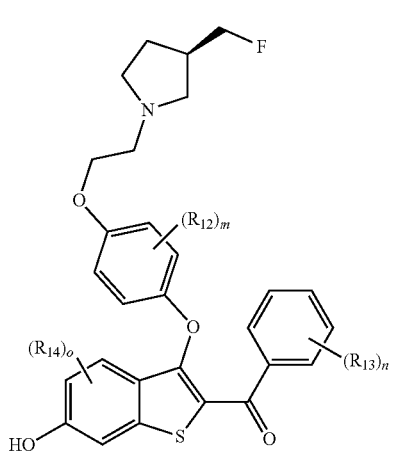

such that m is 0, 1, 2, 3, or 4; n is 0, 1, 2, 3, or 4; o is 0, 1, 2, or 3; p is 0, 1, 2, 3, or 4; $X_D$ is selected from —O—, —$CH_2$—, —S—, —$NR_{17}$, —CHF—, —$CF_2$—, and cycloalkyl; $Y_D$ is selected from —C(O)—, —$CF_2$—, cyclopropyl, —$CH_2$—, and —CHF—; $Z_D$ is selected from O—, —$CH_2$—, —S—, —$NR_{17}$, —CHF—, —$CF_2$—; Ring A is phenyl, heteroaryl, thiophenyl, 5- or 6-membered monocyclic heteroaryl, cycloalkyl or 7-, 8-, 9- or 10-membered bicyclic heterocyclyl; $R_{12}$, $R_{13}$, and $R_{14}$ are independently selected at each occurrence from —$OR_{15}$, —$SR_{15}$, —$N(R_{15})_2$, hydrogen, aryl, heteroaryl, halogen, —CN, —$NO_2$, haloalkyl, cycloalkyl, thiol, nitroso, $C_1$-$C_6$alkyl, hydroxyl, —$O(C_1$-$C_6$ alkyl), —$O(C_1$-$C_6$fluoroalkyl), —$SF_5$, —$B(OH)_2$, —$B(OR_{15})_2$, —$C(O)OR_{15}$, —$C(O)R_{16}$, —$C(S)OR_{15}$, —$C(S)R_{16}$, —$OSO_2OR_{15}$, —$OSO_2R_{16}$, —$NHSO_2OR_{15}$, —$NHSO_2R_{16}$, —N(alkyl)$SO_2OR_{15}$, —N(alkyl)$SO_2R_{16}$, —$OP(O)(OR_{15})_2$, —$OP(O)(R_{16})_2$, —$P(O)(OR_{15})_3$, —$P(O)(R_{16})_3$, —$P(O)OR_{15}$, —$P(O)R_{16}$, —$SO_2R_{16}$, —$SO_2OR_{15}$, alkyne, alkene, arylalkyl, aryloxy, heteroarylalkyl, and $C_1$-$C_6$fluoroalkyl; $R_{15}$ is independently selected at each occurrence from hydrogen, alkyl, alkenyl, alkynyl, cycloalkyl, aryl, arylalkyl, heteroaryl, and heteroarylalkyl; $R_{16}$ is independently selected at each occurrence from $-N(R_{15})_2$, $-SR_{15}$, $-OR_{15}$; and $R_{17}$ is independently selected at each occurrence from hydrogen, alkyl, alkenyl, alkynyl, cycloalkyl, aryl, $-C(O)R_{15}$, $-C(S)R_{15}$, $-C(O)R_{16}$, $-C(S)R_{16}$, and heteroaryl.
In various aspects, a disclosed compound can be present as:
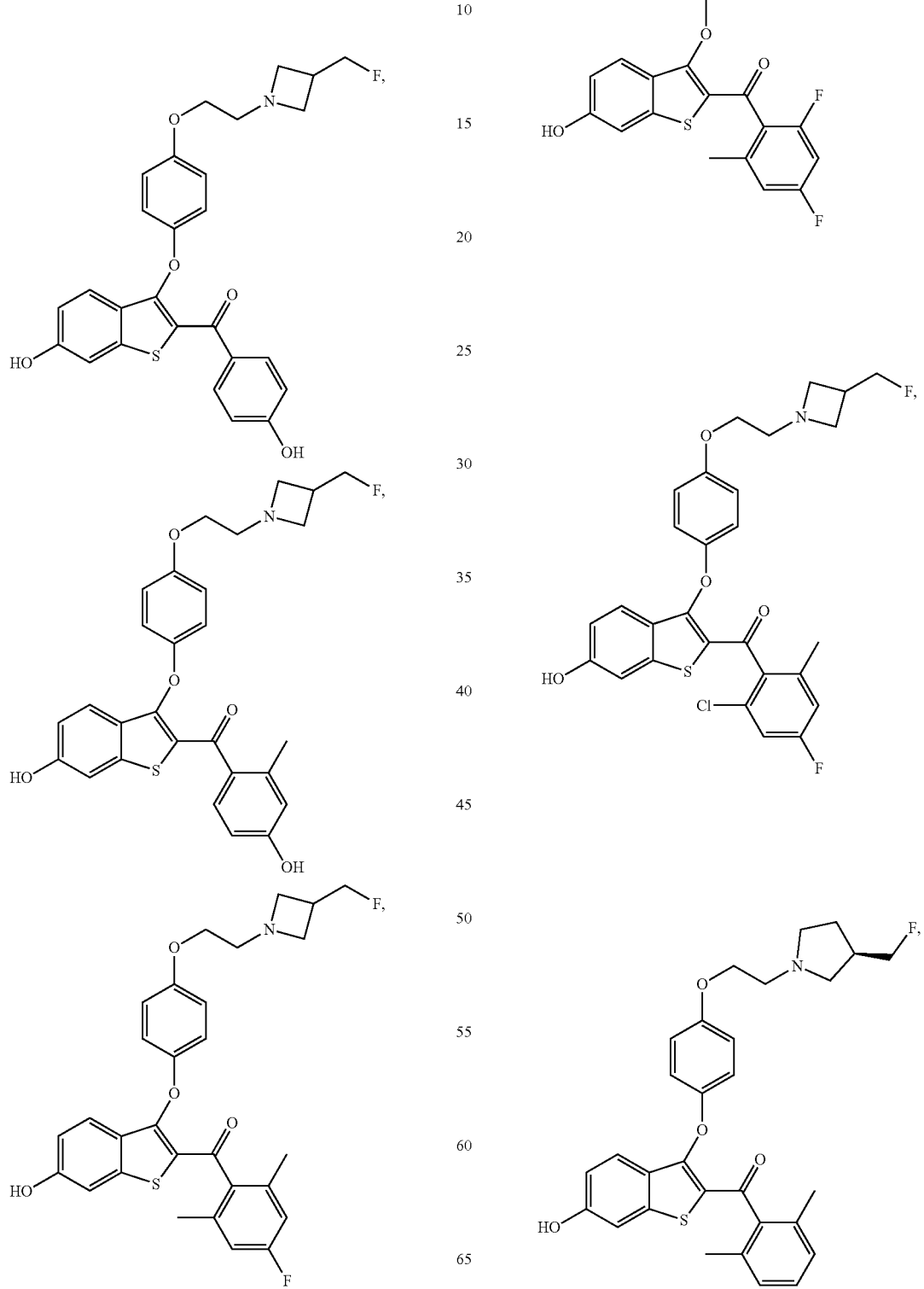

67
-continued
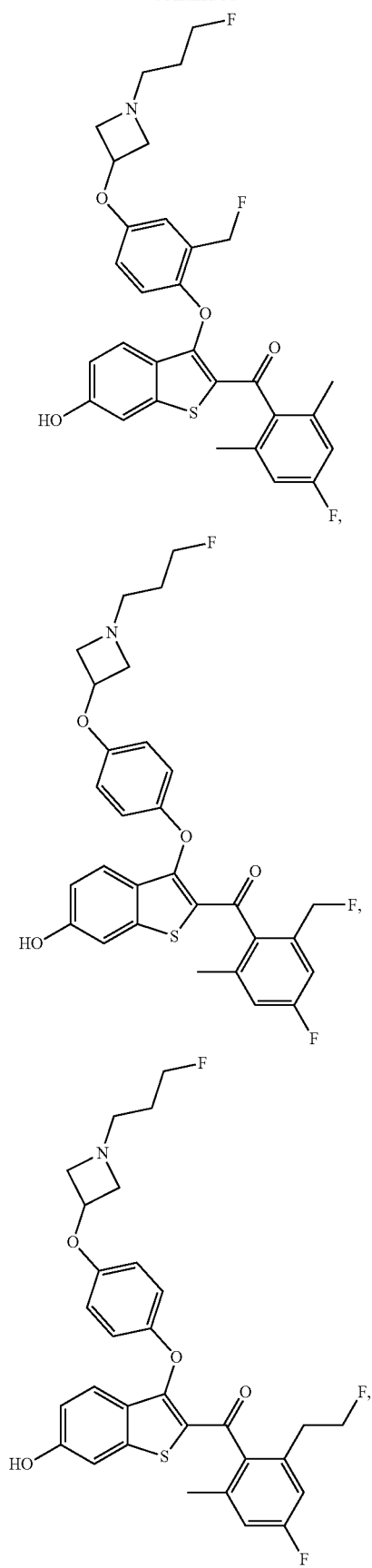
68
-continued
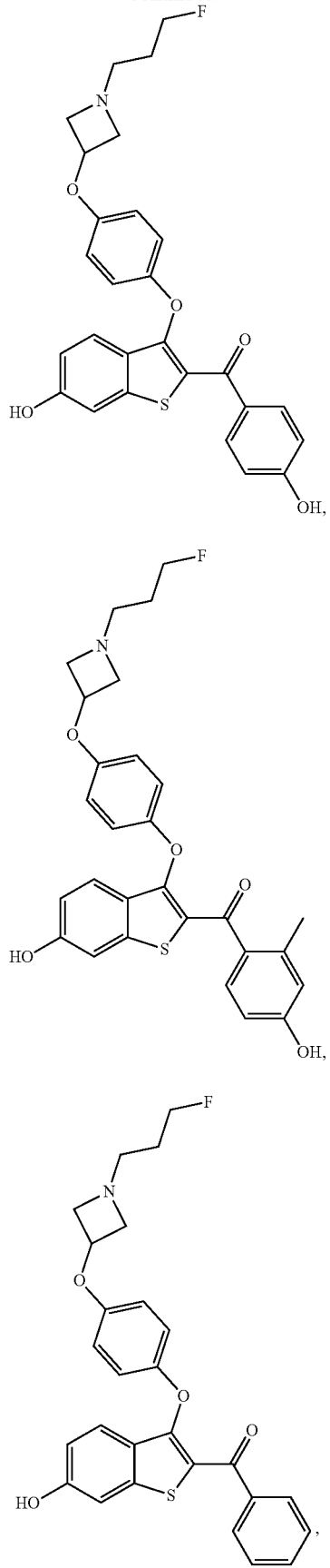

69
-continued
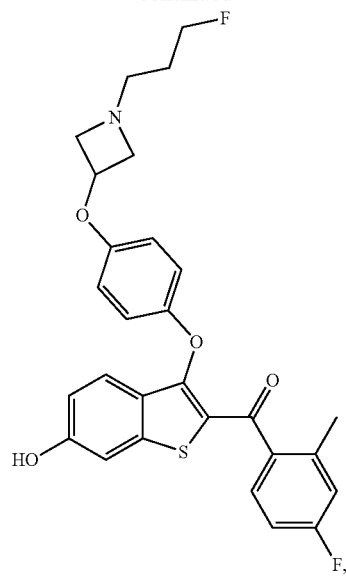
70
-continued
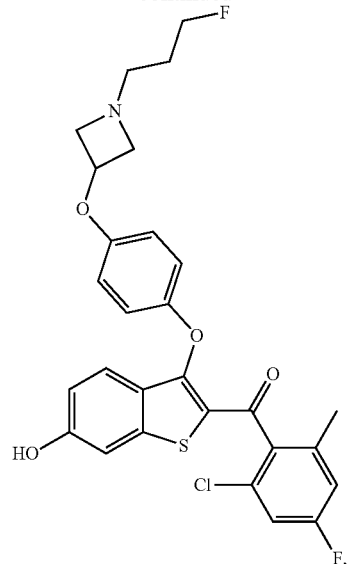
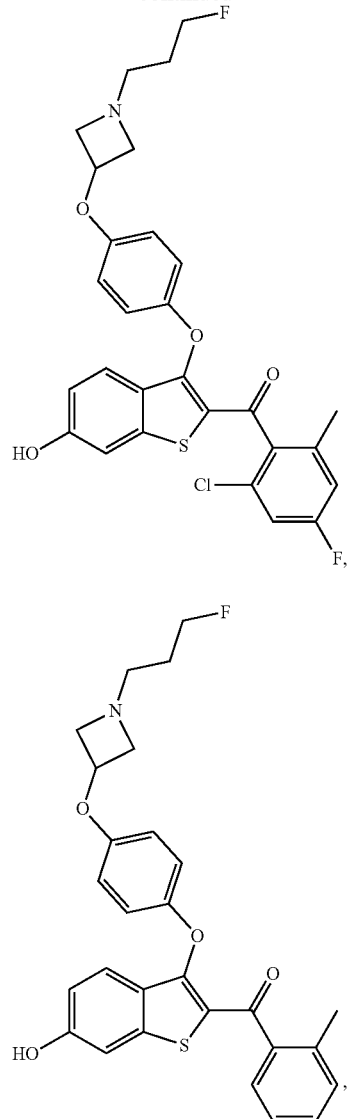
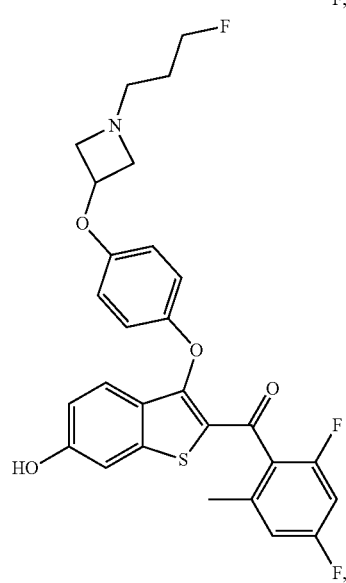
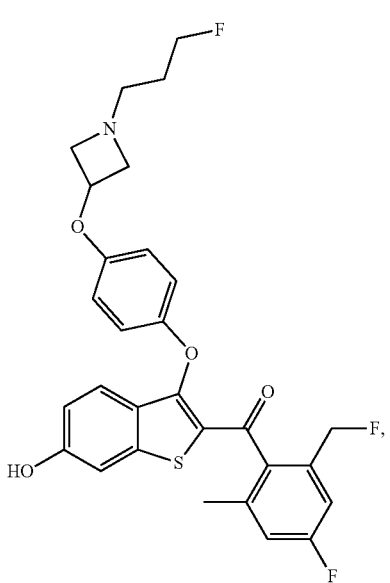

71
-continued
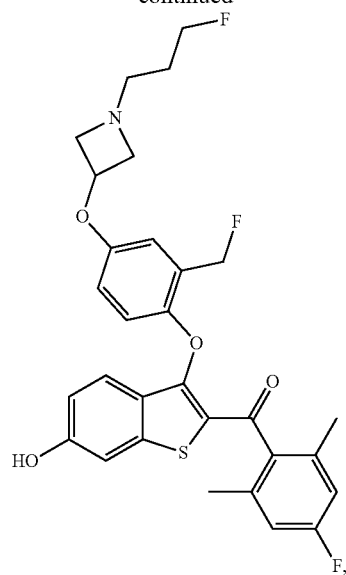
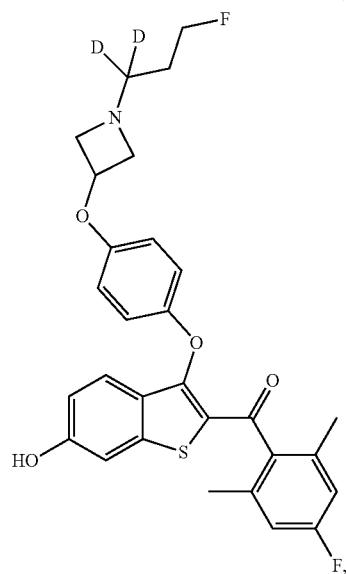
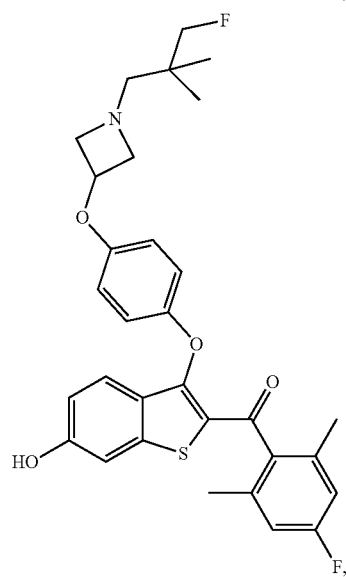
72
-continued
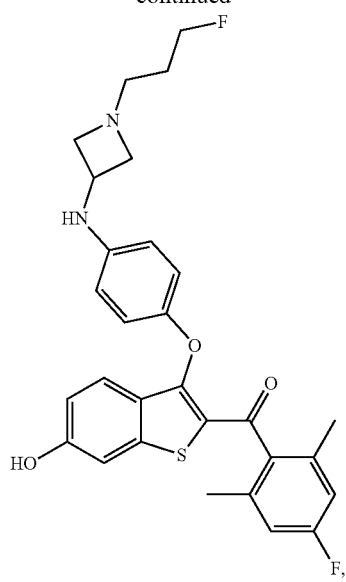
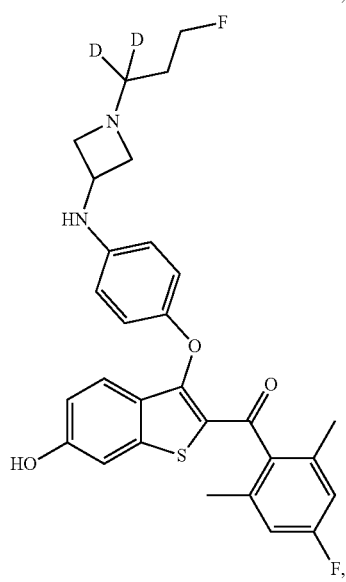
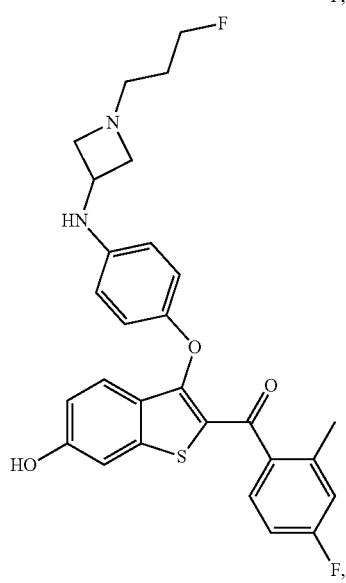

73
-continued
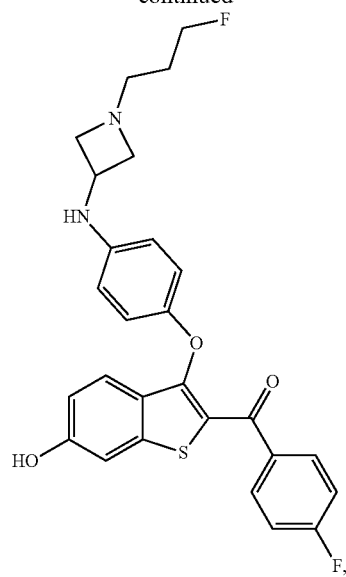
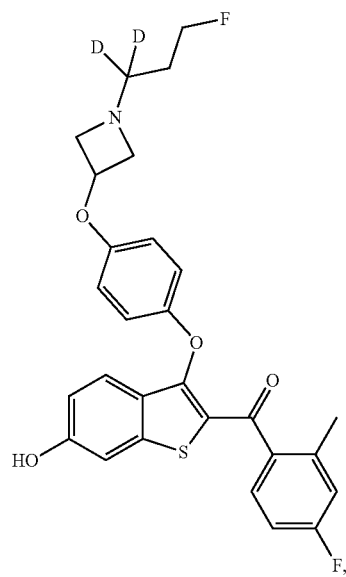
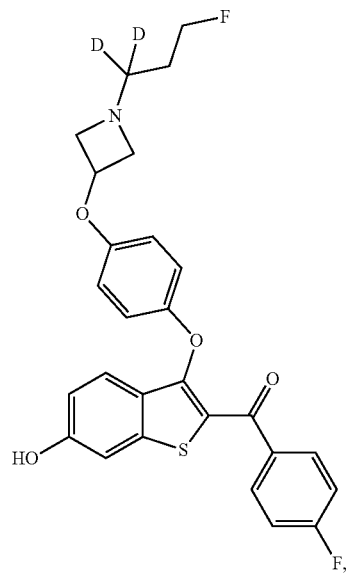
74
-continued
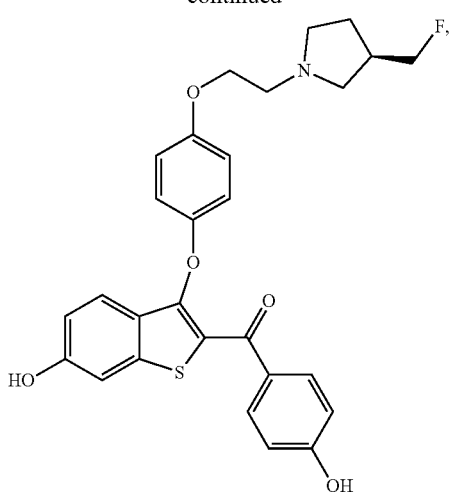
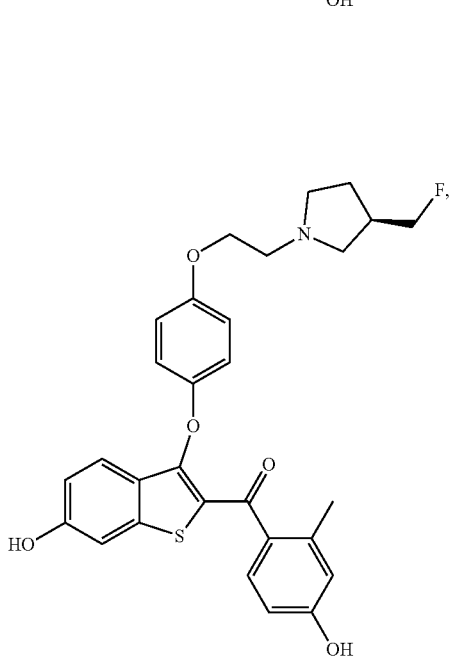
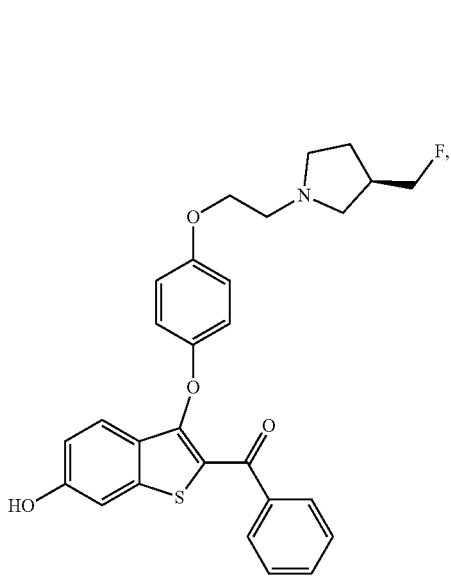

75
-continued
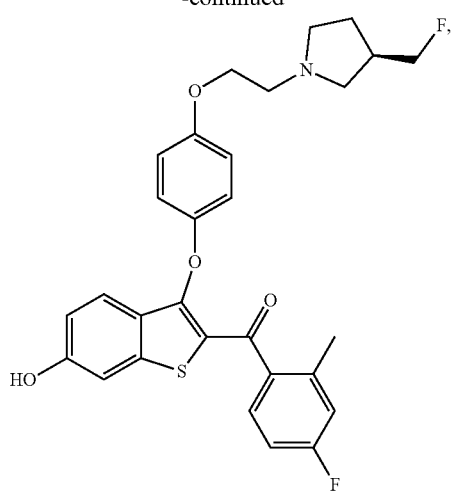
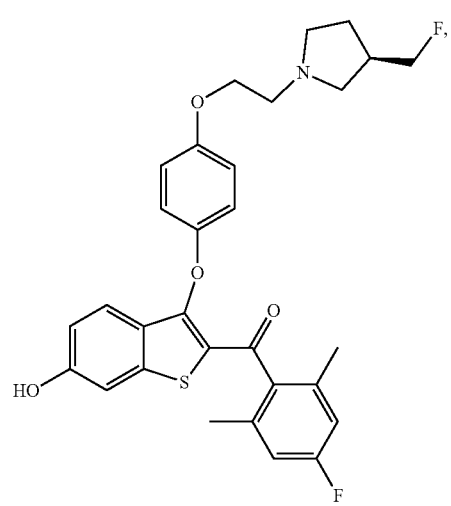
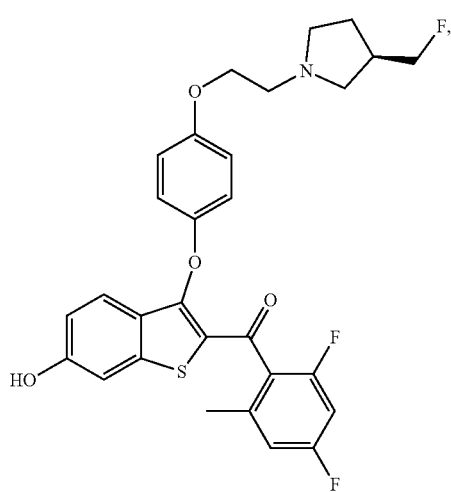
76
-continued
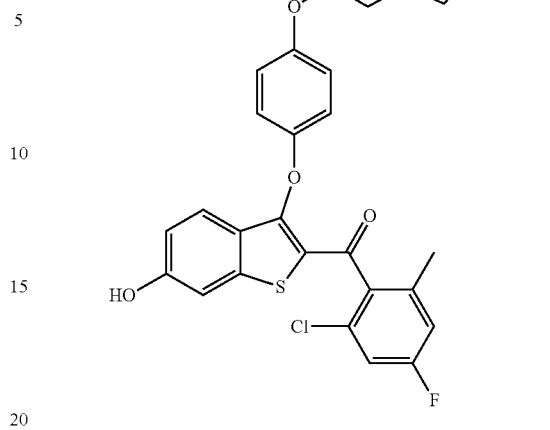
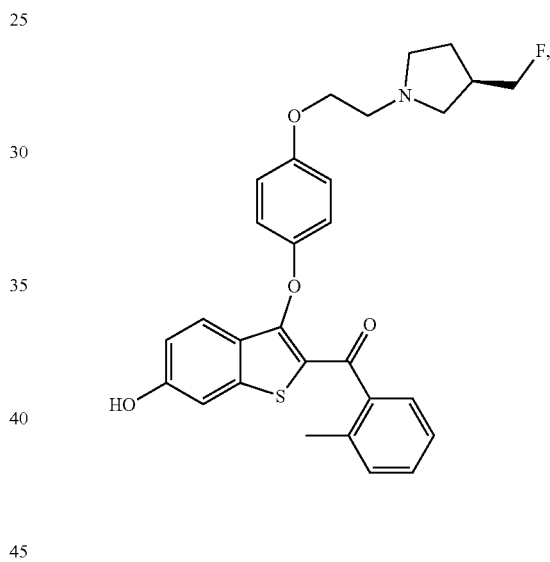
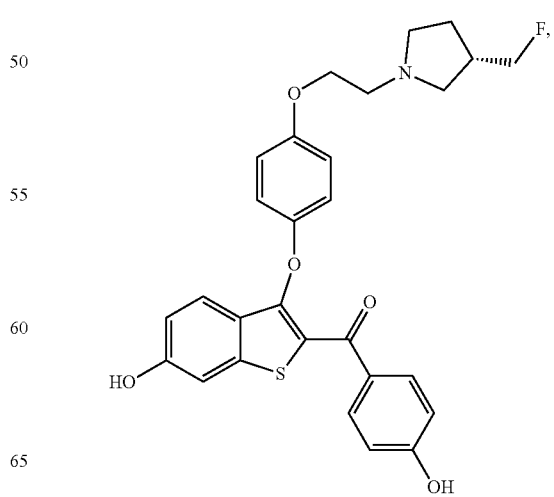

77
-continued
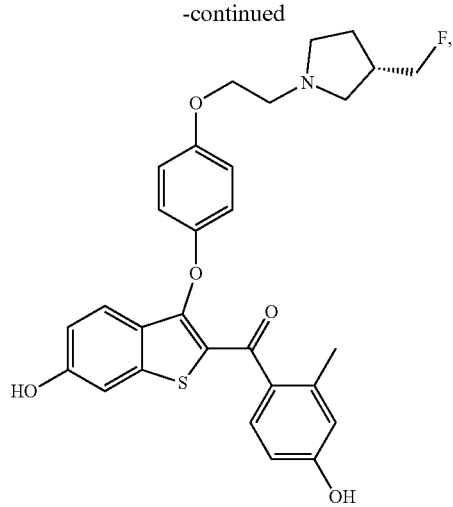
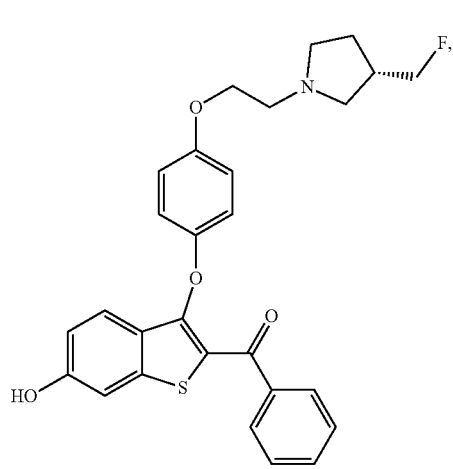
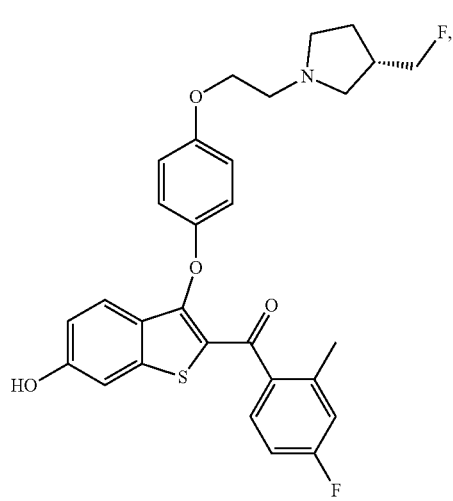
78
-continued
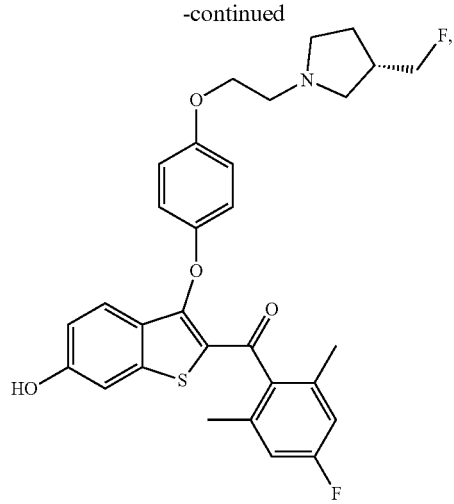
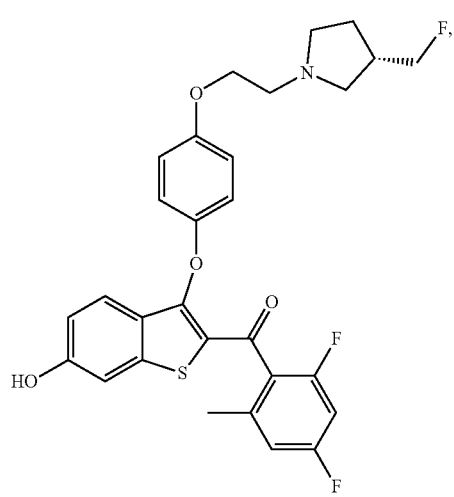
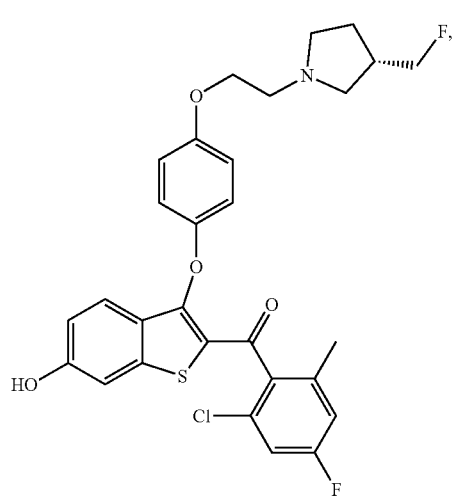

79
-continued
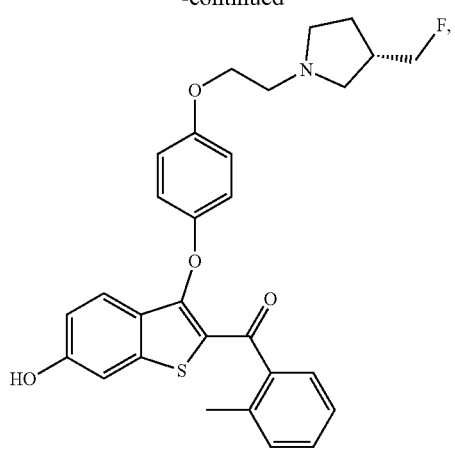
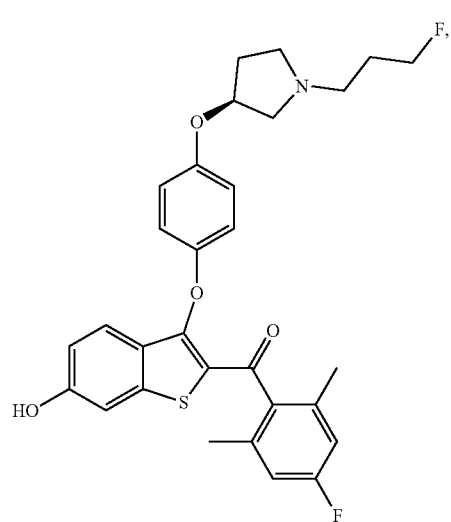
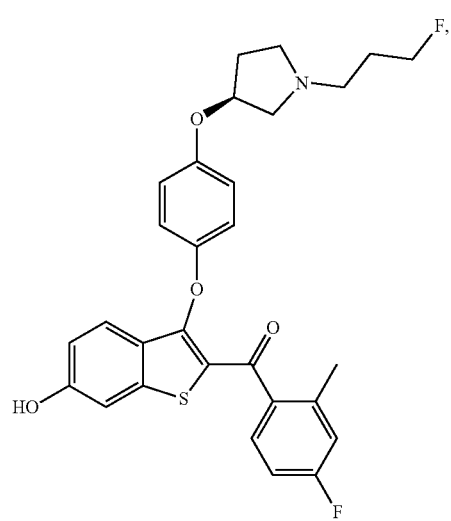
80
-continued
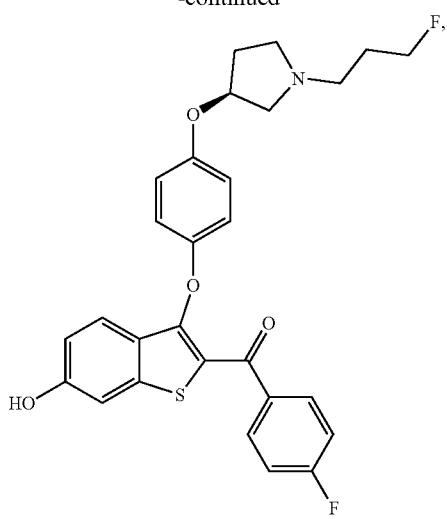
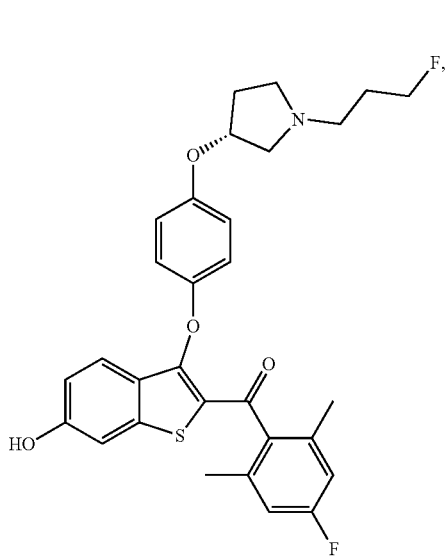
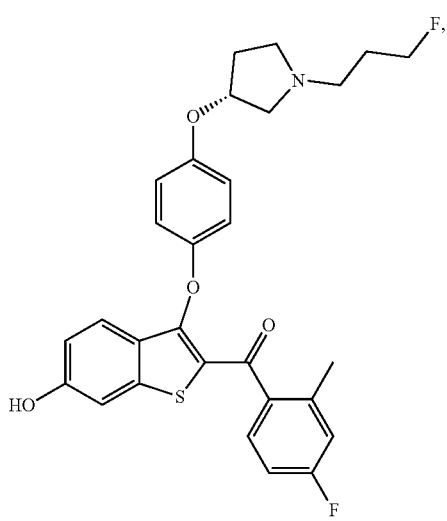

| 81 | 82 |
|---|---|
| -continued | -continued |
| 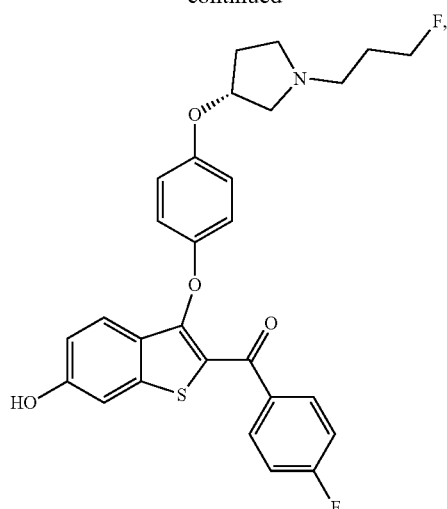 | 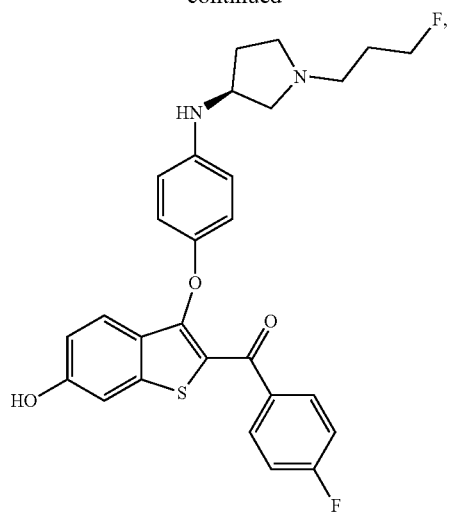 |
| 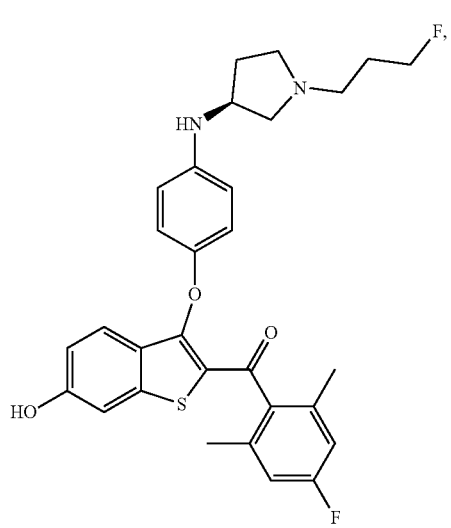 | 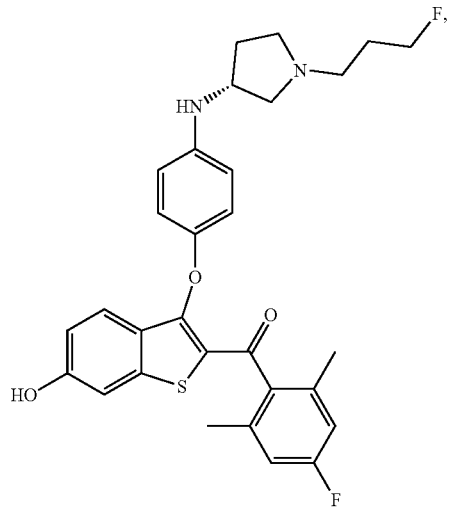 |
| 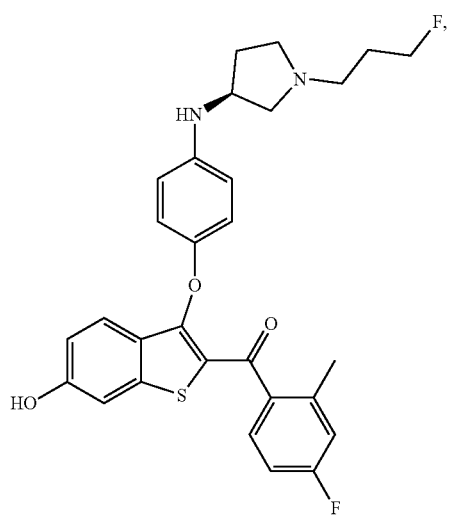 | 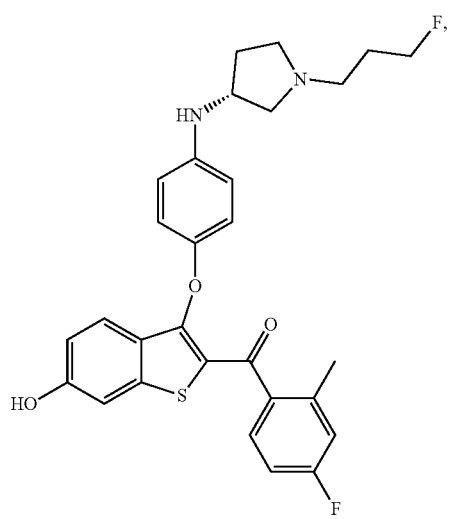 |

83
-continued
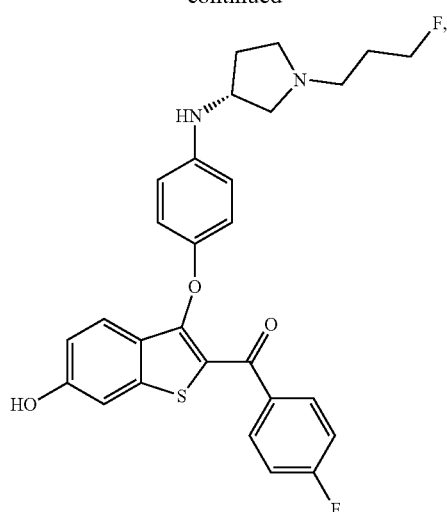
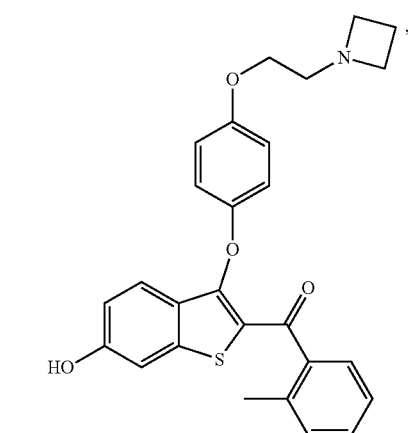
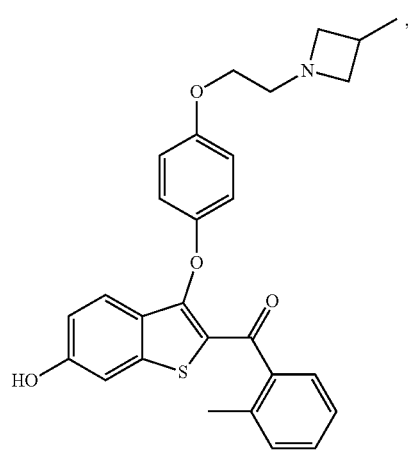
84
-continued
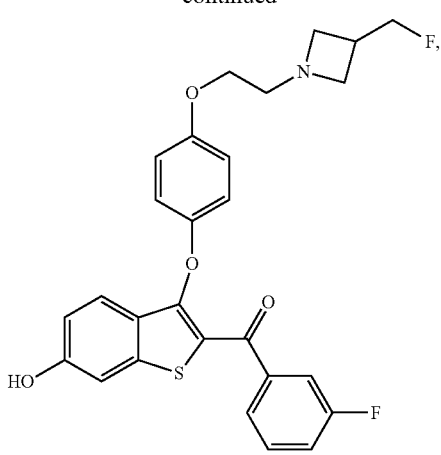
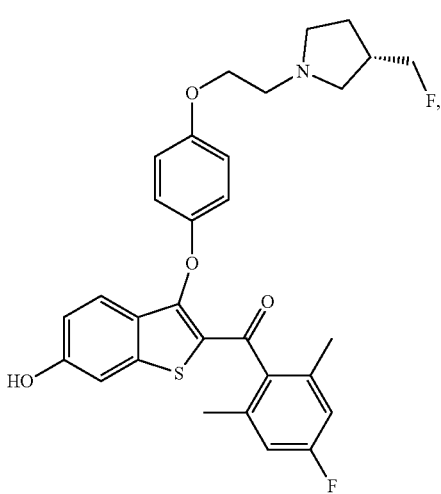
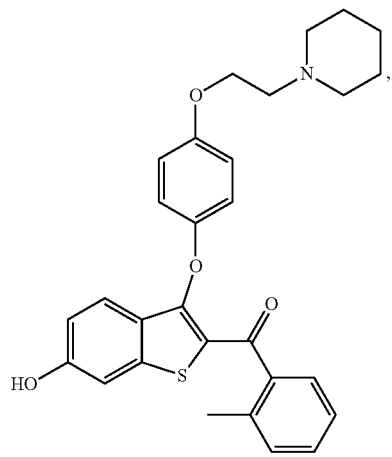

-continued

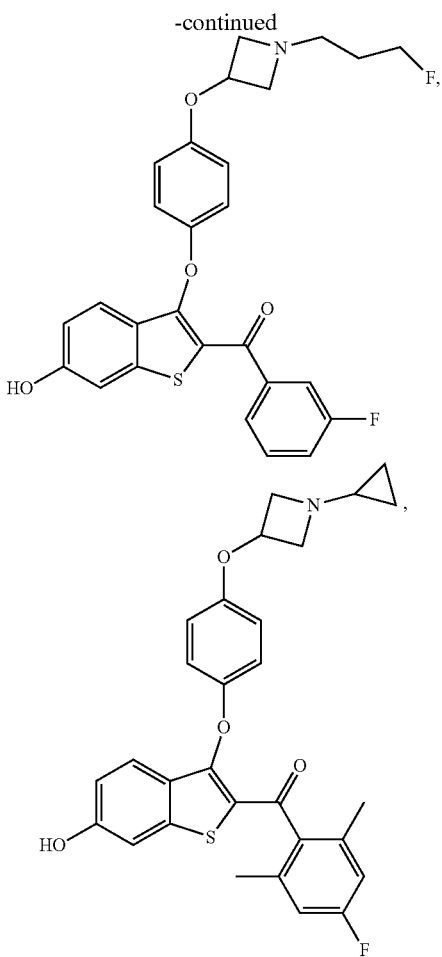

or a subgroup thereof.

C. Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with an basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like, in a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oi-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term "unit dosage form," as used herein, refers to physically discrete units suitable as unitary dosages, each unit containing a predetermined quantity of active ingredient calculated to produce the desired therapeutic effect in association with the required pharmaceutical carrier. That is, a "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979): Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones. Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1939); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert &. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{16}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_1$-$C_{12}$-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example EudragitR RS), copolymerizates of acrylic and methacrylic acid esters and trimethyl ammonium methacrylate (for example EudragitR RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl tributyl, triethyl-citrate); glycerol and glycerol esters (glycerol diacetate, -triacetate, acetylated monoglycerides, castor oil); phthalic acid esters (dibutyl-, diamyl-, diethyl, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm, Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate". J, Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example *arachis* oil, olive oil, sesame oil or coconut oil, or in a mineral oil such as liquid paraffin, Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1.2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride), Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ $\alpha$-, $\beta$- or $\gamma$-cyclodextrins or their derivatives, in particular hydroxyalkyl substituted cyclodextrins, e.g. 2-hydroxypropyl-$\beta$-cyclodextrin or sulfobutyl-$\beta$-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure suitable injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe.

The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution, Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g. as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present invention may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum, Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition, Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base, Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems, Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application, Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present invention include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present invention therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present invention include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration, Such notice, for example, may include labeling approved by the US. Food and Drug Administration for prescription drugs or of an approved product insert. Compositions comprising the topical composition of the invention formulated in a pharmaceutically acceptable carrier may also be prepared, placed in an appropriate container, and labeled for treatment of an indicated condition.

Another patch system configuration which can be used by the present invention is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present invention is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways, Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking: as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require of degradation of estrogen receptor, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for degrading estrogen receptor (e.g. treatment of an estrogen receptor dysfunction or an estrogen-related disorder) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a second therapeutic agent, e.g., a chemotherapeutic agent. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

D. Methods of Using the Compounds

In various aspects, the present disclosure provides methods of treatment comprising administration of a therapeutically effective amount of a disclosed compound or pharmaceutical composition as disclosed herein above to a subject in need thereof. In a further aspect, disclosed are methods for the treatment of an estrogen-associated disorder in a mammal comprising the step of administering to the mammal a therapeutically effective amount of at least one disclosed compound, or a pharmaceutically acceptable salt thereof, or a disclosed pharmaceutical composition.

In a further aspect, the mammal is a human. In a still further aspect, the mammal has been diagnosed with a need for treatment of the disorder prior to the administering step. In a yet further aspect, the method further comprises the step of identifying a mammal in need of treatment of the disorder.

The disclosed methods can be generally used to treat a disease in which downregulation or degradation of estrogen receptor would have a beneficial clinical effect. For example, diseases associated an estrogen receptor disorder or dysfunction include, but are not limited to, osteoporosis, bone demineralization, reduced bone mass, density, or growth, osteoarthritis, acceleration of bone fracture repair and healing, acceleration of healing in joint replacement, periodontal disease, acceleration of tooth repair or growth, Paget's disease, osteochondrodysplasias, muscle wasting, the maintenance and enhancement of muscle strength and function, frailty or age-related functional decline ("ARFD"), sarcopenia, chronic fatigue syndrome, chronic myalgia, acute fatigue syndrome, acceleration of wound healing, maintenance of sensory function, chronic liver disease, AIDS, weightlessness, burn and trauma recovery, thrombocytopenia, short bowel syndrome, irritable bowel syndrome, inflammatory bowel disease, Crohn's disease and ulcerative colitis, obesity, eating disorders including anorexia associated with cachexia or aging, hypercortisolism and Cushing's syndrome, cardiovascular disease or cardiac dysfunction, congestive heart failure, high blood pressure, breast cancer, malignant tumore cells containing the androgen receptor including breast, brain, skin, ovary, bladder, lymphatic, liver, kidney, uterine, pancreas, endometrium, lung, colon, and prostate, prostatic hyperplasia, hirsutism, acne, seborrhea, androgenic alopecia, anemia, hyperpilosity, adenomas and neoplasis of the prostate, hyperinsulinemia, insulin resistance, diabetes, syndrome X, dyslipidemia, urinary incontinence, artherosclerosis, libido enhancement, sexual dysfunction, depression, depressive symptoms, nervousness, irritability, stress, reduced mental energy and low self-esteem, improvement of cognitive function, endometriosis, polycystic ovary syndrome, counteracting preeclampsia, premenstrual syndrome, contraception, uterine fibroid disease, and/or aortic smooth muscle cell proliferation, vaginal dryness, pruritis, dyspareunia, dysuria, frequent urination, urinary tract infections, hypercholesterolemia, hyperlipidemia, peripheral vascular disease, restenosis, vasospasm, vascular wall damage due to immune responses, Alzheimer's disease, bone disease, aging, inflammation, rheumatoid arthritis, respiratory disease, emphysema, reperfusion injury, viral hepatitis, tuberculosis, psoriasis, systemic lupus erythematosus, amyotrophic lateral sclerosis, stroke, CNS trauma, dementia, neurodegeneration, breast pain and dysmenorrhea, menopausal or postmenopausal disorders, vasomotor symptoms, urogenital or vulvar vaginal atrophy, atrophic vaginitis, female sexual dysfunction, for enhancing libido, for the treatment of hypoactive sexual disorder, sexual arousal disorder, for increasing the frequency and intensity of orgasms, vaginismus, osteopenia, endometriosis, BPH (benign prostatic hypertrophy), dysmenorrhea, autoimmune diseases, Hashimoto's thyroiditis, SLE (systemic lupus erythematosus), myasthenia gravis, or reperfusion damage of ischemic myocardium. In a particular aspect, the disclosed methods of treatment relate to menopausal or postmenopausal disorders, vasomotor symptoms, urogenital or vulvar vaginal atrophy, atrophic vaginitis, endometriosis, female sexual dysfunction, breast cancer, depressive symptoms, diabetes, bone demineralization, or osteoporosis.

In various aspects, the estrogen-associated disorder treated in the disclosed method is a cancer. In a further aspect, the cancer is selected from breast cancer, ovarian cancer, endometrial cancer, prostate cancer, and lung cancer. In some aspects, the cancer is selected from breast cancer, ovarian cancer, and endometrial cancer. In a particular aspect, the cancer is breast cancer. The breast cancer can be a hormone receptor positive metastatic breast cancer. In some instances, the breast cancer is tamoxifen resistant, aromatase inhibitor resistant, CDK4/6 inhibitor resistant breast cancer, or a combination thereof. In some cases, in the breast cancer is a triple negative breast cancer.

In various aspects, the disclosed methods described can be used to treat an estrogen receptor positive cancer of the brain. In some aspects, the cancer may include subtypes of brain tumors that may express ER, such as Breast Cancer Brain Metastases (BCBM), Astrocytoma, Chondrosarcoma, Craniopharyngioma, Gliobiastoma, Glioma, Hemangioma, Medulloblastoma, Meningioma, Neurofibroma, Neuronal and Mixed Neuronal-Glial Tumors, Oligoastrocytoma, Pituitary Tumor, PNET-(primitive neuroectodermal tumor), Schwannomak, or Leptomeningeal metastases. In some aspects, the cancer may be other cancers such as Atypical Teratoid Rhabdoid Tumor (ATRT), Choroid Plexus Carcinoma, Ependymoma, Germ Cell Tumor, Juvenile Pilocytic Astrocytoma, Oligodendroglioma, or Pineal Tumor.

In various aspects, the disclosed methods can be used to treat a cancer that is resistant to an estrogen receptor modulator. The resistance to the estrogen receptor modulator may be acquired. The estrogen receptor modulator may be a selective estrogen receptor modulator (SERM). The SERM may be tamoxifen, idoxifene, raloxifene or ICI 182,780. The cancer may be breast, endometrial or ovarian cancer. The cancer may be tamoxifen resistant breast cancer.

In various aspects, the estrogen-associated disorder treated in the disclosed method is bone loss. In a particular instance, the estrogen-associated disorder treated in the disclosed method the estrogen-associated disorder is osteoporosis.

In various aspects, the disclosed method can further comprise co-administering a hormone therapy agent. The hormone therapy agent can be selected from bicalutamide, flutamide, fulvestrant, leuprolide acetate, megestrol acetate, tamoxifen, raloxifene, anastrozole, exemestane, letrozole, and combinations thereof.

In various aspects, can include a combination treatment of a disclosed compound with other drugs and/or other conventional cancer therapies, such as hormone therapy. For example, the disclosed methods can further include administering an effective amount of at least one compound of a cyclin-dependent kinase 4 and 6 inhibitor (CDK4/6 inhibitor), an antiestrogen, a ligand of retinoic acid or retinoic X receptor, an antiprogestin, an antiandrogen, vitamin D or metabolite thereof, a farnesyl transferase inhibitor, a PPARα or gamma agonist and a MAP kinase inhibitor.

In various aspects, the disclosed methods can further comprise administering a disclosed compound or a disclosed pharmaceutical composition with a conventional cancer therapy. Conventional cancer therapies may include surgery, radiation therapy, chemotherapy, hormone therapy, and targeted therapy, Examples of surgery include open craniotomy with maximal excision, which may be followed by radiation therapy. Examples of radiation therapy include whole-brain irradiation, fractionated radiotherapy, and radiosurgery, such as stereotactic radiosurgery, e.g., Gamma Knife radiosurgery. Examples of chemotherapy include anthracyclines, such as doxorubicin (Adriamycin, Doxil), epirubicin (Ellence), and daunorubicin (Cerubidine, DaunoXome), capecitabine (Xeloda), carboplatin (Paraplatin), cisplatin, cyclophosphamide (Cytoxan), eribulin (Halaven), fluorouracil (also called 5-fluorouracil or 5-FU; Adrucil), gemcitabine (Gemzar), ixabepilone (Ixempra), methotrexate (Amethopterin, Mexate, Folex), mitoxantrone (Novantrone), mutamycin (Mitomycin), taxanes, such as paclitaxel (Taxol, Abraxane), and docetaxel (Taxotere), thiotepa (Thioplex), vincristine (Oncovin, Vincasar PES, Vincrex), and vinorelbine (Navelbine). Examples of targeted therapy include trastuzumab (Herceptin), lapatinib (Tykerb), bevacizumab (Avastin), pertuzumab (Perjeta), and everolimus (Afinitor).

In various aspects, the disclosed methods can further comprise administering a disclosed compound or a disclosed pharmaceutical composition with endocrine therapy, also known as hormonal therapy, hormone therapy, and hormone treatment, is a treatment that adds, blocks, or removes hormones. For example, hormones may be given to adjust low hormone levels. Synthetic hormones or other drugs may be given to block the body's natural hormones to slow or stop the growth of certain cancers (such as prostate and breast cancer). Endocrine therapy may also include surgery to remove the gland that makes a certain hormones. Examples of hormone therapy include selective estrogen receptor modulators (SERMs), such as tamoxifen, raloxifene, endoxifene, toremifene, lasofoxifene, pipendoxifene, bazedoxifene, and ospemifene, aromatase inhibitors, such anastrozole, letrozole, exemestane, formestane, fadrozole, aminoglutethimide, and testolactone, a HER2 intervention drug, such as a HER2 inhibitor, such as Herceptin (trastuzumab), pertuzumab, and lapatinib, and estrogen-receptor downregulators, such as fulvestrant (ICI 182,780).

In various aspects, the disclosed method can further comprise co-administering a therapeutic antibody that binds PD-1, PD-L1, EGFR, VEGF, HER2, or combinations of such antibodies. The therapeutic antibody can be selected from panitumumab, bevacizumab, cetuximab, trastuzumab, and combinations thereof.

In various aspects, the disclosed compound can be utilized in combination with an antibody that binds PD-1. Non-limiting examples of such antibodies include pembrolizumab, nivolumab, cemiplimab, pidilizumab, AMP-224 (GlaxoSmithKline), AMP-514 (GlaxoSmithKline), PDR001 (Novartis), cemiplimab (Regeneron/Sanofi), or combinations thereof.

In various aspects, the disclosed compound can be utilized in combination with an antibody that binds PD-L1. Non-limiting examples of such antibodies include atezolizumab, avelumab, durvalumab, BMS-936559 (Bristol-Myers Squibb), CK-301 (Checkpoint Therapeutics), or combinations thereof.

In various aspects, the disclosed method can further comprise co-administering a therapeutic agent selected from the group consisting of a chemotherapeutic agent, a radioisotope, an anti-hormonal agent, a cytotoxic agent, an immunotherapeutic agent, and a combination thereof. Example as of a suitable chemotherapeutic agents are folate antagonists, purine antagonists, pyrimidine antagonists. DNA alkylating agents, DNA cross-linking drugs, antibiotics, platinum complexes, proteosome inhibitors, mitotic spindle poisons, topoisomerase inhibitors, and tyrosine kinase inhibitors.

In various aspects, the chemotherapeutic agent is selected from the group consisting of cyclosphosphamide, busulfan, improsulfan, piposulfan, benzodopa, carboquone, meturedopa, uredopa, altretamine, triethylenemelamine, trietylenephosphoramide, triethiylenethiophosphoramide, trimethylolomelamine, bullatacin, bullatacinone, delta-9-tetrahydrocannabinol, beta-lapachone, lapachol, colchicine or a colchicine derivative, betulinic acid, topotecan, irinotecan, acetylcamptothecin, scopolectin, 9-aminocamptothecin, bryostatin, callystatin, CC-1065, adozelesin, carzelesin, bizelesin, podophyllotoxin, podophyllinic acid, teniposide, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, calicheamicin, calicheamicin gammaII, calicheamicin omegaII, dynemicin, dynemicin A, esperamicin, aclacinomysins, actinomycin, authramycin, azaserine, bleomycin, cactinomycin, carabicin, caminomycin, carzinophilin, chromomycinis, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, doxorubicin HCl liposome injection, liposomal doxorubicin TLC D-99, peglylated liposomal doxorubicin, deoxydoxorubicin, epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, gemcitabine, tegafur, capecitabine, epothilone, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, razoxane, rhizoxin, sizofiran, spirogermanium, tenuazonic acid, triaziquone, 2,2',2"-trichlorotriethylamine, T-2 toxin, verracurin A, roridin A and anguidine, urethane, dacarbazine, mannomustine, mitobronitol, mitolactol, pipobroman, gacytosine, arabinoside, thiotepa, paclitaxel, docetaxel, chloranbucil, 6-thioguanine, mercaptopurine, methotrexate, cisplatin, oxaliplatin, carboplatin, vinblastine, vincristine, vindesine, vinorelbine, etoposide (VP-16), ifosfamide, mitoxantrone, leucovovin, novantrone, edatrexate, daunomycin, aminopterin, ibandronate, RFS 2000, difluoromethylomithine (DMFO), retinoic acid, bexarotene, clodronate), etidronate, NE-58095, zoledronic acid/zoledronate, alendronate, pamidronate), tiludronate, risedronate, troxacitabine, or combinations thereof.

Further non-limiting examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; *vinca* alkaloids; epipodophyllotoxins; antibiotics such as the enediyne antibiotics (e.g., calicheamicin, especially calicheamicin gammaII and calicheamicin omegaII; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,22"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irinotecan; and combinations of any of the foregoing.

In various aspects, the disclosed method can further comprise co-administering a radioactive isotope. Examples of suitable radioactive isotopes are $At^{211}$, $I^{131}$, $I^{125}$, $Y^{90}$, $Re^{186}$, $Re^{188}$, $Sm^{153}$, $Bi^{212}$, $P^{32}$, $Pb^{212}$, radioactive isotopes of Lu, and combinations thereof.

In various aspects, the disclosed method can further comprise co-administering an anti-hormonal agent. Examples of suitable anti-hormonal agentas are amoxifen, 4-hydroxytamoxifen, toremifene, idoxifene, droloxifene, raloxifene, trioxifene, keoxifene, fulvestrant, formestane, exemestane, anastrazole, letrozole, aminoglutethimide, vorozole, megestrol acetate, fadrozole, leuprolide, goserelin, buserelin, tripterelin, megestrol acetate, medroxyprogesterone acetate, diethylstilbestrol, premarin, fluoxymesterone, fenretinide; onapristone, flutamide, nilutamide and bicalutamide, pharmaceutically acceptable salts thereof, and combinations thereof.

In various aspects, a CDK4/6 inhibitor can be selected from palbociclib, ribociclib, and abemaciclib, or combinations thereof. Further examples of suitable examples of CDK4/6 inhibitors include, but are not limited to, abemaciclib (LY2835219), palbociclib (PD0332991), LEE-011 (ribociclib), LY2835219 (abemaciclib), G1T28-1, SHR6390, or P276-00, or a derivative of any one of palbociclib, LEE-011, G1T28-1, SHR6390, or P276-00. In certain embodiments, the CDK416 inhibitor may be derived from pyridopyrimidine, pyrrolopyrimidine or indolocarbazole compounds. Further non-limiting examples of inhibitors of CDK4/6 include P-276-00 (a selective inhibitor of CDK4-cyclin D1, under development by Nicholas Piramal for the treatment of cancer); GW-491619 (a CDK4 inhibitor, under development by GlaxoSmithKline for the treatment of cancer): NU-6027 (a cyclin dependent kinase (CDK) inhibitor under investigation by AstraZeneca for use in cancer); AG-12275 (a selective CDK4 inhibitor under investigation by Pfizer for the treatment of cancer); AG-12236 (a broad-spectrum CDK4 inhibitor under investigation by Pfizer for the treatment of cancer); PD-0166285 (a cyclin A-mediated inhibitor of CDK4 under investigation by Pfizer for the treatment of cancer); PD-0332991 (a highly-specific CDK416 inhibitor, under development by Pfizer for the treatment of cancer); Alvocidib (flavopiridol; HMR-1275, an inhibitor of Cdk4 under development by Sanofi-Aventis as an anticancer agent). Additional CDK416 inhibitors are described in WO 03/062236. Exemplary CDK4 inhibitors are described and can be prepared based on the descriptions found in U.S. Pat. No. 6,689,864, PCT Patent Publication No. WO08/007123, PCT Patent Publication No. WO07/140222, PCT Patent Publication No. WO06/106046, PCT Patent Publication No. WO03/062236, PCT Patent Publication No. WO05/005426, PCT Patent Publication No. WO99/21845; PCT Patent Publication No. WO06/097449, PCT Patent Publication No. WO06/097460, PCT Patent Publication No. WO99/02162, and PCT Patent Publication No. WO/9950251. For a discussion of standard CDK4 assays, see D. W. Fry et al., J. Biol. Chem. (2001) 16617-16623. Assays for CDK6 inhibitors is similar to that described substituting expressed CDK6 protein. Other specific CDK inhibitors are described in EP1250353, WO02/96888, WO031076437, WO03/76436, WO03/76434, and WO01/64368.

As used herein, a "molecularly targeted agent" is a substance that interferes with the function of a single molecule or group of molecules, preferably those that are involved in tumor growth and progression, when administered to a subject. Non-limiting examples of molecularly targeted agent of the present invention include signal transduction inhibitors, modulators of gene expression and other cellular functions, immune system modulators, antibody-drug conjugates (ADCs), and combinations thereof.

The molecularly targeted agent may be selected from epidermal growth factor receptor family inhibitors (EGFRi), mammalian target of rapamycin (mTor) inhibitors, immune checkpoint inhibitors, anaplastic lymphoma kinase (ALK) inhibitors, B-cell lymphoma-2 (BCL-2) inhibitors, B-Raf inhibitors, cyclin-dependent kinase inhibitors (CDKi), ERK inhibitors, histone deacetylase inhibitors (HDACi), heat shock protein-90 inhibitors (HSP90i), Janus kinase inhibitors, mitogen activated protein kinase (MAPK) inhibitors, MEK inhibitors, poly ADP ribose polymerase (PARP)

inhibitors, phosphoinositide 3-kinase inhibitors (PI3Ki), Ras inhibitors, and combinations thereof.

The molecularly targeted agent may be selected from ado-trastuzumab emtansine, alemtuzumab, cetuximab, ipilimumab, ofatumumab, panitumumab, pertuzumab, rituximab, tositumomab, 131I-tositumomab, trastuzumab, brentuximab vedotin, denileukin diftitox, ibritumomab tiuxetan, axitinib, bortezomib, bosutinib, cabozantinib, crizotinib, carfilzomib, dasatinib, erlotinib, gefitinib, imatinib mesylate, lapatinib, nilotinib, pazopanib, ponatinib, regorafenib, ruxolitinib, sorafenib, sunitinib, tofacitinib, vandetanib, vemurafenib, alitretinoin, bexarotene, everolimus, romidepsin, temsirolimus, tretinoin, vorinostat, and pharmaceutically acceptable salts thereof or combinations thereof. The molecularly targeted agent may include an antibody or an antibody moiety.

In various aspects, the disclosed compound can be utilized in combination with an EGFR inhibitor such as erlotinib, gefitinib, lapatinib, canetinib, pelitinib, neratinib, (R,E)-N-(7-chloro-1-(1-(4-(dimethylamino)but-2-enoyl) azepan-3-yl)-1H-benzo[d]imidazol-2-yl)-2-methylisonicotinamide, Trastuzumab, Margetuximab, panitumumab, matuzumab, Necitumumab, pertuzumab, nimotuzumab, zalutumumab, Necitumumab, cetuximab, icotinib, afatinib, and pharmaceutically acceptable salt thereof. The molecularly targeted agent may be an anti-EGFR family antibody or a complex including the anti-EGFR family antibody. The anti-EGFR family antibody may be an anti-HER1 antibody, an anti-HER2 antibody, or an anti-HER4 antibody.

In various aspects, the disclosed compound can be utilized in combination with a mitotic inhibitor such as a microtubule-destabilizing agent, a microtubule-stabilizing agent, or a combination thereof. The mitotic inhibitor may be taxane, vinca alkaloid, epothilone, or a combination thereof. The mitotic inhibitor may also be selected from BT-062, HMN-214, eribulin mesylate, vindesine, EC-1069, EC-1456, EC-531, vintafolide, 2-methoxyestradiol, GTx-230, trastuzumab emtansine, crolibulin, D1302A-maytansinoid conjugates IMGN-529, lorvotuzumab mertansine, SAR-3419. IMP-588858. IMP-03138, topotecan/vincristine combinations, BPH-8, fosbretabulin tromethamine, estramustine phosphate sodium, vincristine, vinflunine, vinorelbine, RX-21101, cabazitaxel, STA-9584, vinblastine, epothilone A, patupilone, ixabepilone, Epothilone D, paclitaxel, docetaxel, DJ-927, discodermolide, eleutherobin, and pharmaceutically acceptable salts thereof or combinations thereof.

In various aspects, the disclosed compound can be utilized in combination with an alkylating agent. As used herein, an "alkylating agent" is a substance that adds one or more alkyl groups to a nucleic acid. Exemplary alkylating agents can be selected from the group consisting of nitrogen mustards, nitrosoureas, alkyl sulfonates, triazines, ethylenimines, and combinations thereof. Non-limiting examples of nitrogen mustards include mechlorethamine, chlorambucil, cyclophosphamide, bendamustine, ifosfamide, melphalan, melphalan flufenamide, and pharmaceutically acceptable salts thereof. Non-limiting examples of nitrosoureas include streptozocin, carmustine, lomustine, and pharmaceutically acceptable salts thereof. Non-limiting examples of alkyl sulfonates include busulfan and pharmaceutically acceptable salts thereof. Non-limiting examples of triazines include dacarbazine, temozolomide, and pharmaceutically acceptable salts thereof. Non-limiting examples of ethylenimines include thiotepa, altretamine, and pharmaceutically acceptable salts thereof. Other alkylating agents include ProLindac, Ac-225 BC-8, ALF-2111, trofosfamide, MDX-1203, thioureidobutyronitrile, mitobronitol, mitolactol, nimustine, glufosfamide, HuMax-TAC and PBD ADC combinations, BP-C1, treosulfan, nifurtimox, improsulfan tosilate, ranimustine, ND-01, HH-1, 22P1G cells and ifosfamide combinations, estramustine phosphate, prednimustine, lurbinectedin, trabectedin, altreatamine, SGN-CD33A, fotemustine, nedaplatin, heptaplatin, apaziquone, SG-2000, TLK-58747, laromustine, procarbazine, and pharmaceutically acceptable salts thereof.

In various aspects, the disclosed compound can be utilized in combination with a platinum-based antineoplastic drug including, but not limited to, cisplatin, carboplatin, dicycloplatin, eptaplatin, lobaplatin, miriplatin, nedaplatin, oxaliplatin, picoplatin, satraplatin, or combinations thereof.

In various aspects, the disclosed compound can be utilized in combination with an mTor inhibitor. The term "mTOR inhibitors (mTOR inhibitor)" as used herein is used for purposes of a material to inhibit the mTOR signaling pathway of the conventional anticancer agents or immunosuppressive agents. The mTOR inhibitor may be rapamycin, temsirolimus, everolimus, ridaforolimus, MLN4924, XL388, GDC-0349, AZD2014, AZD8055, GSK105965, MLN0128 Ridaforlimus and the like.

In various aspects, the disclosed compound can be utilized in combination with a VEGF inhibitor. "VEGF inhibitor" as used herein is any substance that decreases signaling by the VEGF-VEGFR pathway. VEGF inhibitors can be, to name just a few examples, small molecules, peptides, polypeptides, proteins, including more specifically antibodies, including anti-VEGF antibodies, anti-VEGFR antibodies, intrabodies, maxibodies, minibodies, diabodies, Fc fusion proteins such as peptibodies, receptibodies, soluble VEGF receptor proteins and fragments, and a variety of others. Many VEGF inhibitors work by binding to VEGF or to a VEGF receptor. Others work more indirectly by binding to factors that bind to VEGF or to a VEGF receptor or to other components of the VEGF signaling pathway, Still other VEGF inhibitors act by altering regulatory posttranslational modifications that modulate VEGF pathway signaling. VEGF inhibitors in accordance with the invention also may act through more indirect mechanisms. Whatever the mechanism involved, as used herein, a VEGF inhibitor decreases the effective activity of the VEGF signaling pathway in a given circumstance over what it would be in the same circumstance in the absence of the inhibitor.

Non-limiting examples of VEGF inhibitors include: (a) 4TBPPAPC or a closely related compound described in U.S. 2003/0125339 or U.S. Pat. No. 6,995,162 which is herein incorporated by reference in its entirety, particularly in parts disclosing 4TBPPAPC and closely related VEGF inhibitors; (b) AMG 706 or a closely related substituted alkylamine derivative described in U.S. 2003/0125339 or U.S. 2003/0225106 or U.S. Pat. No. 6,995,162 or U.S. Pat. No. 6,878,714 each of which is herein incorporated by reference in its entirety, particularly in parts disclosing AMG 706 and these closely related VEGF inhibitors; (c) Avastin™ or a closely related non-naturally occurring humanized monoclonal antibody that binds to VEGF, is a VEGF inhibitor, and is at least 90% identical in sequence to Avastin™; (d) Nexavar® or a closely related substituted omega-carboxyaryl diphenyl urea or derivative thereof described in WO00/42012, WO00/41693, U.S. 2005/0033030A1, U.S. 2003/0125359A1, U.S. 2002/0165394A1, U.S. 2001/003447A1. U.S. 2001/0016659A1, and U.S. 2002/013774A1 which are herein incorporated by reference in their entirety, particularly in parts disclosing these VEGF inhibitors; (e) PTK/ZK or a closely related anilinophthalazine or derivative thereof that binds to and inhibits the activity of multiple receptor tyrosine kinases including binding to the protein kinase domain and inhibition of VEGFR1 and VEGFR2; (f) Sutent® or a closely related derivative of (5-[5-fluoro-2-oxo-1,2-dihydroindol-(3Z)-ylidenemethyl]-2,4-dimethyl-1H-pyrrole-3-carboxylic acid [2-diethylaminoethyl]amide) that is a VEGF inhibitor; and (g) VEGFinhibitors as described in U.S. 2006/0241115, including those of Formula IV therein.

Further examples of VEGF inhibitors are the following: (a) 4TBPPAPC, as described in U.S. 2003/0125339 or U.S. Pat. No. 6,995,162 which is herein incorporated by reference in its entirety, particularly in parts disclosing 4TBPPAPC; (b) AMG 706, as described in U.S. 2003/0125339 or U.S. Pat. No. 6,995,162 or U.S. Pat. No. 6,878,714 which is herein incorporated by reference in its entirety, particularly in parts disclosing AMG 706; (c) Avastin™; (d) Nexavar®, as described in WO0/42012, WO00/41698, U.S. 2005/0038080A1, U.S. 2003/0125359A1, U.S. 2002/0165394A1, U.S. 2001/003447A1, U.S. 2001/0016659A1, and U.S. 2002/013774A1 which are herein incorporated by reference in their entirety, particularly in parts disclosing Nexavar®; (e) PTK/ZK; (f) Sutent®, and (g) VEGF inhibitors of Formula IV as described in U.S. 2006/0241115.

In some aspects, the VEGF inhibitor is pegaptanib. In one aspect, the VEGF inhibitor is bevacizumab. In one aspect, the VEGF inhibitor is ranibizumab. In one aspect, the VEGF inhibitor is lapatinib. In one aspect, the VEGF inhibitor is sorafenib. In one aspect, the VEGFinhibitor is sunitinib. In one aspect, the VEGF inhibitor is axitinib. In one aspect, the VEGF inhibitor is pazopanib. In one aspect, the VEGFinhibitor is aflibercept.

In various aspects, the disclosed compound can be utilized in combination with an aromatase inhibitor. By "aromatase inhibitor" it is meant non-steroidal and steroidal compounds that inhibit the enzyme aromatase thereby preventing the conversion of androgens to estrogens, preferably those which inhibit aromatase activity in vitro with an $IC_{50}$ value of less than $10^{-5}$ M as well as their pharmaceutically acceptable salts. Exemplary aromatase inhibitors for use in the methods herein described include without limitation anastrozole, letrozole, exemestane, vorozole, formestane, fadrozole, aminoglutethimide, testolactone, 4-hydroxyandrostenedione, 1,4,6-androstatrien-3,17-dione and 4-androstene-3,6,17-trione.

In various aspects, the disclosed compound can be utilized in combination with a PI3K inhibitor, in certain aspects, the PI3K inhibitor interacts with the P isoform of PI3K Exemplary PI3K inhibitors include LY294002 and biologically active derivatives thereof, LY292223, LY293696, LY293684, LY293646 (Vlahos et al. J. Biol. Chem. 269:5241-5243 (1994), wortmannin (Sigma-Aldrich), PX-866, a wortmannin derivative in Phase I clinical trials (Oncothyreon) ZSTK474 (Zenyaku Kogyo Co.), SF1126 (Semaphore Pharmaceuticals), BEZ235 (Novartis) VQD-002 (VioQuest Pharmaceuticals) KRX-0401 (Keryx Biopharmaceuticals) GSK690693 (GlaxoSmithKine), XL147 (Exelixis) and siRNA and shRNA molecules which specifically hybridize with PI3K beta encoding mRNA and interfere with intracellular production thereof. In a further aspect, the PI3K inhibitor is a prodrug of LY294002 or ZSTK474 comprising a prostate specific antigen cleavable linker which is activated at the site of the prostate cancer cell. This prodrug can be administered in combination with a toxin comprising a cancer targeting moiety such as an antibody, or an immunospecific fragments thereof. In various further aspects, the PI3K inhibitor is IPI-145, GDC-0941, or CAL-101, or pharmaceutically acceptable salts thereof. Further examples of PI3K inhibitors, include, but are not limited to, demethoxyviridin, LY294002, perifosine, PX-866, BAY 30-6946, RP-6503, TGR 1202, SF-1126, INK-1117, BKM-120, XL-147, XL-765, Palomid 529, GSK-1059615, ZSTK-474, PWT-33597, IC-87114, TG100-115, CAL-263, RP-6530, P-103, GNE-477, CUDC-907, and AEZS-136.

In various aspects, the disclosed compound can be utilized in combination with a BET inhibitor. Examples of BET inhibitors include, without limitation. JQ1 ((S)-tert-butyl 2-(4-(4-chlorophenyl)-2,3,9-trimethyl-6H-thieno[3,2-f][1,2,4]triazolo[4,3-a][1,4]diazepin-6-yl)acetate), OTX015 ((6S)-4-(4-chlorophenyl)-N-(4-hydroxyphenyl)-2,3,9-trimethyl-6H-thieno[3,2-f][1,2,4]triazolo[4,3-a][1,4]diazepine-6-acetamide), i-BET-762 ((S)-2-(6-(4-chlorophenyl)-8-methoxy-1-methyl-4H-benzo[f][1,2,4]triazolo[4.3-a][1,4]diazepin-4-yl)-N-ethylacetamide), RVX-208 (2-[4-(2-Hydroxyethoxy)-3,5-dimethylphenyl]-5,7-dimethoxy-4 (3H)-quinazolinone), I-BET-762 (2-[(4S)-6-(4-chlorophenyl)-8-methoxy-1-methyl-4H-[1,2,4]triazolo[4,3-a][1,4]benzodiazepin-4-yl]-N-ethylacetamide), and MS436 ((E)-4-[2-(2-Amino-4-hydroxy-5-methylphenyl)diazenyl]-N-2-pyridinylbenzenesulfonamide). Additional BTK inhibitors include, but are not limited to, (S)-6-amino-9-(1-(but-2-ynoyl)pyrrolidin-3-yl)-7-(4-phenoxyphenyl)-7H-purin-8 (9H)-one ibrutinib (1-[(3R)-3-[4-Amino-3-(4-phenoxyphenyl)-1H-pyrazolo[3,4-d]pyrimidin-1-yl] piperidin-1-yl]prop-2-en-1-one), acalabrutinib, HM71224, CNX-774, RN486, ONO-4059, and CC-292 (speburtinib).

E. Kits

In a further aspect, the present disclosure relates to kits comprising at least one disclosed compound, or a pharmaceutically acceptable salt, hydrate, solvate, or polymorph thereof, or a disclosed pharmaceutical composition and one or more of: (a) at least one agent known to treat an estrogen-associated disorder; and/or (b) instructions for treating an estrogen-associated disorder.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present invention also features such kits further containing instructions for use.

In a further aspect, the present disclosure also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

In various aspects, the at least one disclosed compound and the at least one agent are co-formulated. In other instances, the at least one disclosed compound and the at least one agent are co-packaged.

In various aspects, the estrogen-associated disorder of the disclosed kit can be bone loss. For example, the estrogen-associated disorder is osteoporosis.

In various aspects, the estrogen-associated disorder of the disclosed kit can be a cancer. For example, the cancer can be breast cancer, ovarian cancer, endometrial cancer, prostate cancer, and lung cancer.

In various aspects, the kit instructions comprise instructions to treat a breast cancer. In a further aspect, the kit instructions comprise instructions to treat a primary breast cancer. In a still further aspect, the kit instructions comprise instructions to treat a metastatic cancer, such as metastatic breast cancer.

In various aspects, the kit instructions comprise instructions to treat a hormone receptor positive metastatic breast cancer; a tamoxifen resistant breast cancer; an aromatase inhibitor resistant breast cancer; a CDK4/6 inhibitor resistant breast cancer; a triple negative breast cancer; or combinations thereof.

In various aspects, the kit instructions comprise instructions to administer the compound or the pharmaceutical composition adjunctive to a hormone therapy agent. The hormonal agent can be, for example, but not limited to, bicalutamide, flutamide, fulvestrant, leuprolide acetate, megestrol acetate, tamoxifen, raloxifene, anastrozole, exemestane, letrozole, or combinations thereof.

In various aspects, the kit instructions comprise instructions to administer the compound or the pharmaceutical composition adjunctive to a therapeutic antibody that specifically binds EGFR, VEGF, or HER2. The therapeutic antibody can be, for example, but is not limited to, panitumumab, bevacizumab, cetuximab, trastuzumab, or combinations thereof.

In various aspects, the at least one agent of the kit is selected from the group consisting of a chemotherapeutic agent, a radioisotope, an anti-hormonal agent, a cytotoxic agent, an immunotherapeutic agent, or a combination thereof. Suitable chemotherapeutic agents, include, but are not limited to, folate antagonists, purine antagonists, pyrimidine antagonists, DNA alkylating agents, DNA cross-linking drugs, antibiotics, platinum complexes, proteosome inhibitors, mitotic spindle poisons, topoisomerase inhibitors, and tyrosine kinase inhibitors. Exemplary chemotherapeutic agents that can be used in the kit include, but are not limited to cyclosphosphamide, busulfan, improsulfan, piposulfan, benzodopa, carboquone, meturedopa, uredopa, altretamine, triethylenemelamine, trietylenephosphoramide, triethiylenethiophosphoramide, trimethylolomelamine, bullatacin, bullatacinone, delta-9-tetrahydrocannabinol, beta-lapachone, lapachol, colchicine or a colchicine derivative, betulinic acid, topotecan, irinotecan, acetylcamptothecin, scopolectin, 9-aminocamptothecin, bryostatin, callystatin, CC-1065, adozelesin, carzelesin, bizelesin, podophyllotoxin, podophyllinic acid, teniposide, cryptophycin 1, cryptophycin 3, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimnustine, calicheamicin, calicheamicin gammaII, calicheamicin omegaII, dynemicin, dynemicin A, esperamicin, aclacinomysins, actinomycin, authramycin, azaserine, bleomycin, cactinomycin, carabicin, caminomycin, carzinophilin, chromomycinis, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, doxorubicin HCl liposome injection, liposomal doxorubicin TLC D-99, peglylated liposomal doxorubicin, deoxydoxorubicin, epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, methotrexate, gemcitabine, tegafur, capecitabine, epothilone, 5-fluorouracil (5-FU), denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, razoxane, rhizoxin, sizofiran, spirogermanium, tenuazonic acid, triaziquone, 2,2',2"-trichlorotriethylamine, T-2 toxin, verracurin A, roridin A and anguidine, urethane, dacarbazine, mannomustine, mitobronitol, mitolactol, pipobroman, gacytosine, arabinoside, thiotepa, paclitaxel, docetaxel, chlornabucil, 6-thioguanine, mercaptopurine, methotrexate, cisplatin, oxaliplatin, carboplatin, vinblastine, vincristine, vindesine, vinorelbine, etoposide (VP-16), ifosfamide, mitoxantrone, leucovorin, novantrone, edatrexate, daunomycin, aminopterin, ibandronate, RFS 2000, difluoromethylomithine (DMFO), retinoic acid, bexarotene, clodronate), etidronate, NE-58095, zoledronic acid/zoledronate, alendronate, pamidronate), tiludronate, risedronate, troxacitabine, or combinations thereof.

In various aspects, the at least one agent of the kit is a radioactive isotope. The radioactive isotope can be, but is not limited to, At$^{211}$, I$^{131}$, I$^{125}$, Y$^{90}$, Re$^{186}$, Re$^{188}$, Sm$^{153}$, Bi$^{212}$, P$^{32}$, radioactive isotopes of Lu, or combinations thereof.

In various aspects, the at least one agent of the kit is an anti-hormonal agent. The anti-hormonal agent can be, but is not limited to, amoxifen, 4-hydroxytamoxifen, toremifene, idoxifene, droloxifene, raloxifene, trioxifene, keoxifene, fulvestrant, formestane, exemestane, anastrazole, letrozole, aminoglutethimide, vorozole, megestrol acetate, fadrozole, leuprolide, goserelin, buserelin, tripterelin, megestrol acetate, medroxyprogesterone acetate, diethylstilbestrol, premarin, fluoxymesterone, fenretinide; onapristone, flutamide, nilutamide and bicalutamide, pharmaceutically acceptable salts thereof, or combinations thereof.

F. Research Tools

The disclosed compounds and pharmaceutical compositions have activity as selective estrogen receptor degraders. As such, the disclosed compounds are also useful as research tools. Accordingly, one aspect of the present disclosure relates to a method of using a compound of the invention as a research tool, the method comprising conducting a biological assay using a compound of the invention. Compounds of the invention can also be used to evaluate new chemical compounds. Thus another aspect of the invention relates to a method of evaluating a test compound in a biological assay, comprising: (a) conducting a biological assay with a test compound to provide a first assay value; (b) conducting the biological assay with a compound of the invention to provide a second assay value; wherein step (a) is conducted either before, after or concurrently with step (b); and (c) comparing the first assay value from step (a) with the second assay value from step (b). Exemplary biological assays include for estrogen receptor degradation that can be conducted in vitro or in a cell culture system as known to the skilled artisan. Still another aspect of the invention relates to a method of studying a biological system, e.g., a model animal for a clinical condition such as a xenograft tumor in a rodent model, the method comprising: (a) contacting the biological system or sample with a compound of the invention; and (b) determining the effects caused by the compound on the biological system or sample.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

From the foregoing, it will be seen that aspects herein are well adapted to attain all the ends and objects hereinabove set forth together with other advantages which are obvious and which are inherent to the structure.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only, and is not intended to be limiting. The skilled artisan will recognize many variants and adaptations of the aspects described herein. These variants and adaptations are intended to be included in the teachings of this disclosure and to be encompassed by the claims herein.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

G. Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Exemplary compound synthetic methods are as shown herein below.

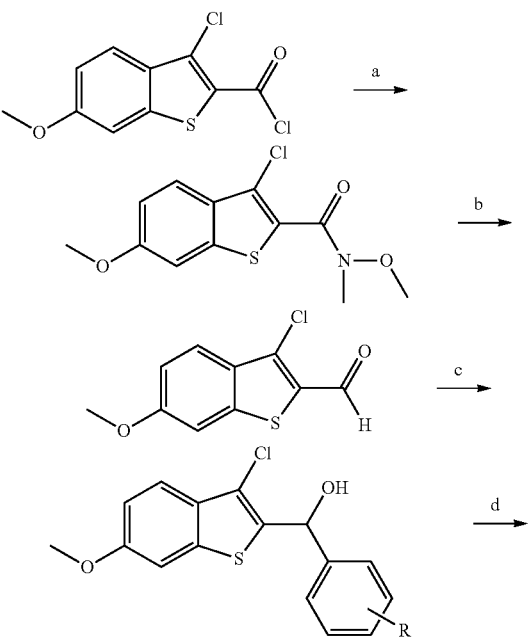

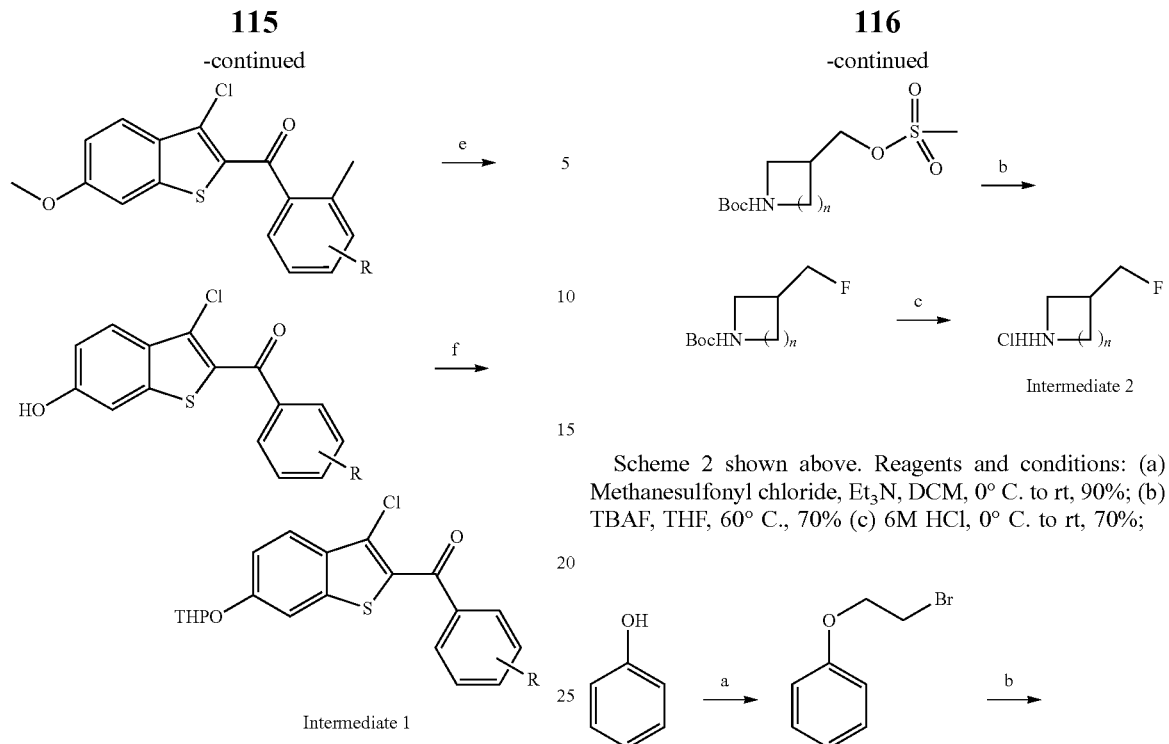
Scheme 1 shown above. Reagents and conditions: (a) N-methoxymethylamine, Et₃N, DCM, rt, 89%; (b) DIBAL, THF, −40° C. to rt, 70% (c) Grignard reagent, THF, 0° C. to rt; (d) PCC, DCM, rt (d) BBr₃, DCM, −78° C. to rt.
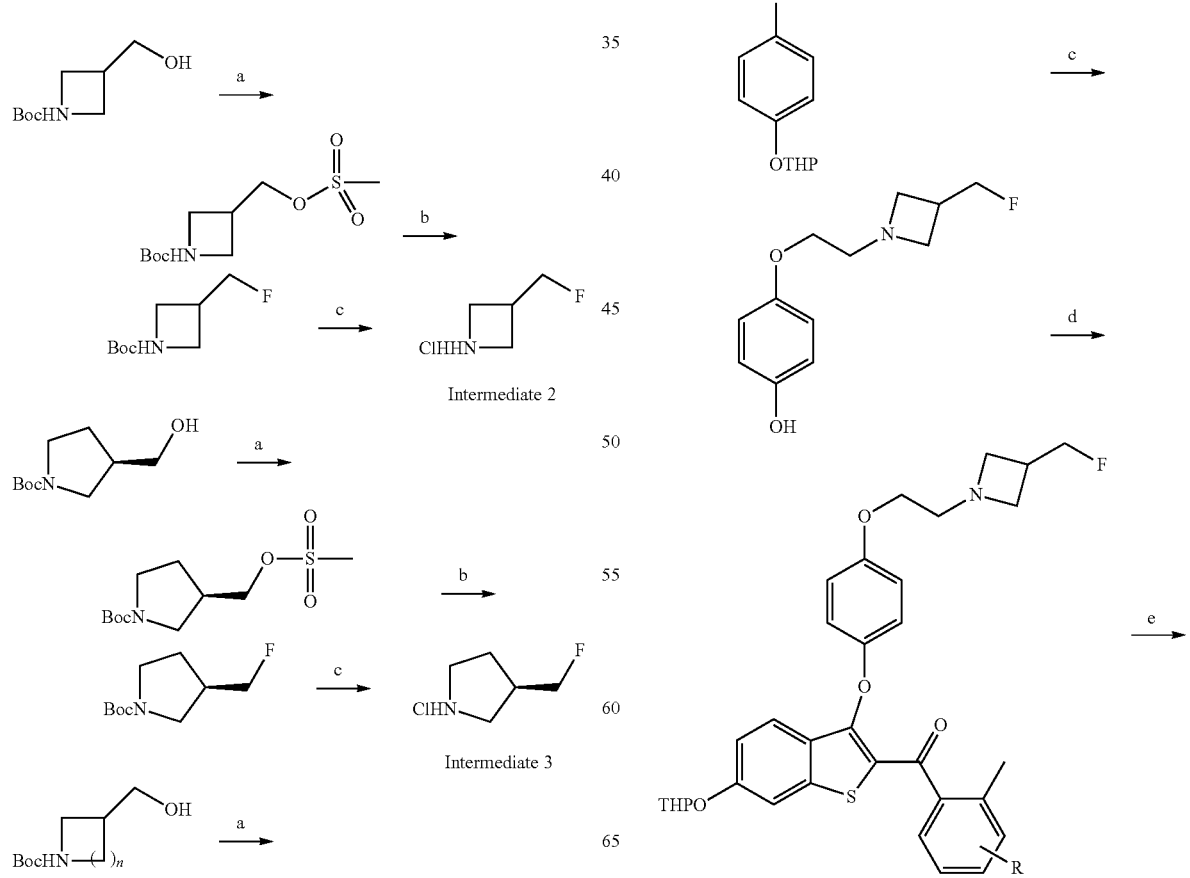
Scheme 2 shown above. Reagents and conditions: (a) Methanesulfonyl chloride, Et₃N, DCM, 0° C. to rt, 90%; (b) TBAF, THF, 60° C., 70% (c) 6M HCl, 0° C. to rt, 70%;

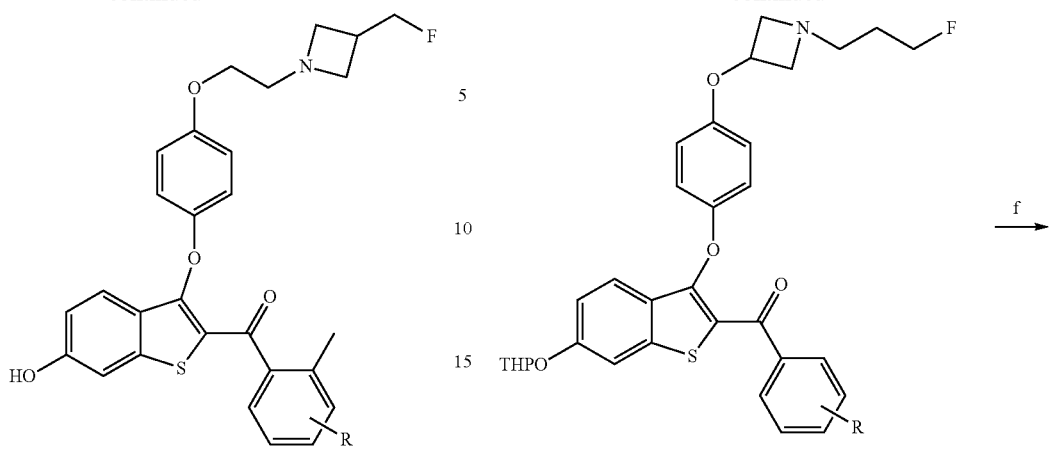

Scheme 3 shown above. Reagents and conditions: (a) 1,2 dibromoethane, NaOH, THF, reflex, 50%; (b) Intermediate 2,3, K$_2$CO$_3$, CH$_3$CN, 60° C. 78% (c) p-Toluenesulfonic acid, MeOH, rt. 82% (d) Intermediate 1, Cs$_2$CO$_3$, DMF, 90° C., 70%; (e) p-Toluenesulfonic acid, MeOH, rt, 78%.

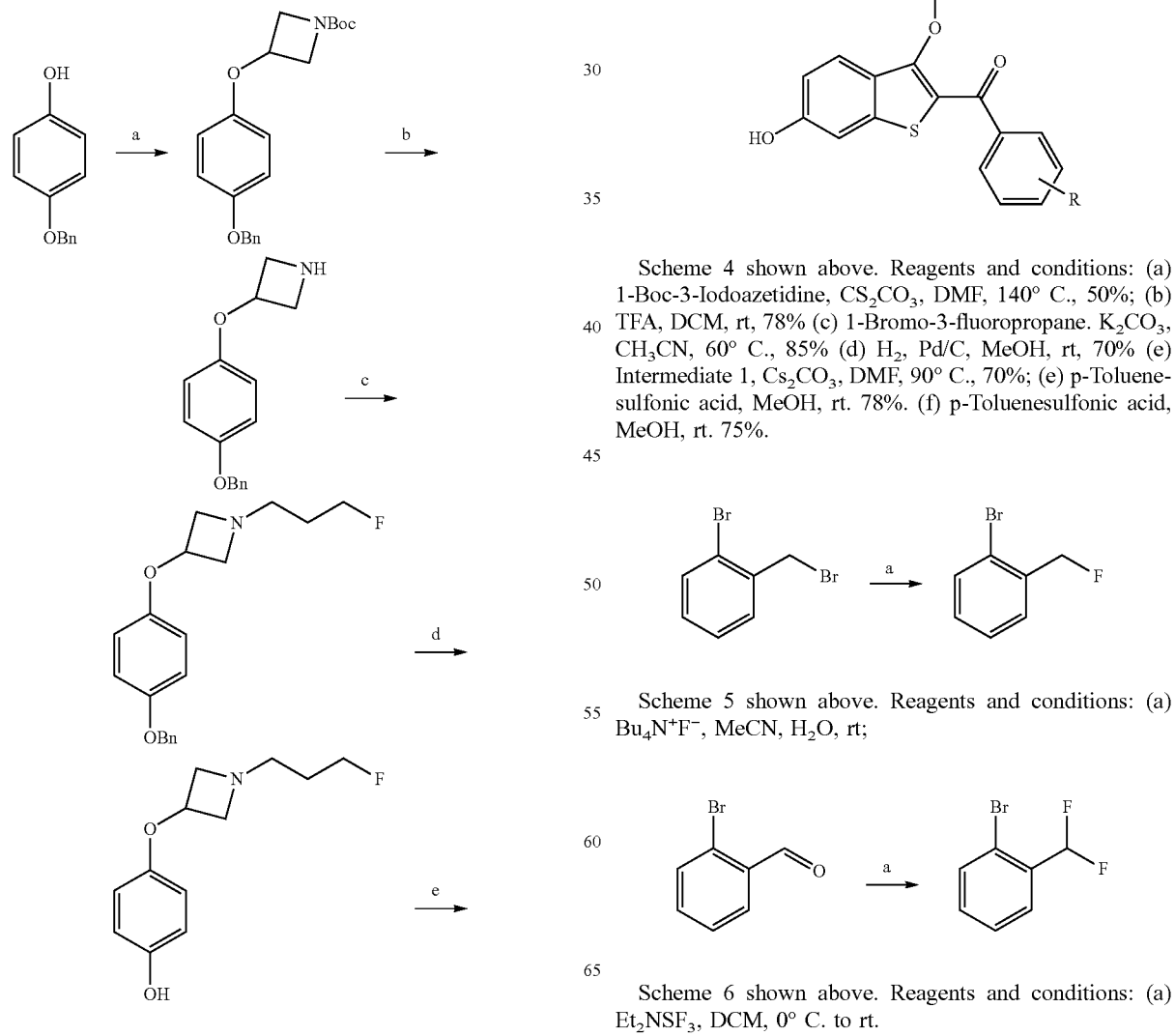

Scheme 4 shown above. Reagents and conditions: (a) 1-Boc-3-Iodoazetidine, CS$_2$CO$_3$, DMF, 140° C., 50%; (b) TFA, DCM, rt, 78% (c) 1-Bromo-3-fluoropropane. K$_2$CO$_3$, CH$_3$CN, 60° C., 85% (d) H$_2$, Pd/C, MeOH, rt, 70% (e) Intermediate 1, Cs$_2$CO$_3$, DMF, 90° C., 70%; (e) p-Toluenesulfonic acid, MeOH, rt. 78%. (f) p-Toluenesulfonic acid, MeOH, rt. 75%.

Scheme 5 shown above. Reagents and conditions: (a) Bu$_4$N$^+$F$^-$, MeCN, H$_2$O, rt;

Scheme 6 shown above. Reagents and conditions: (a) Et$_2$NSF$_3$, DCM, 0° C. to rt.

119
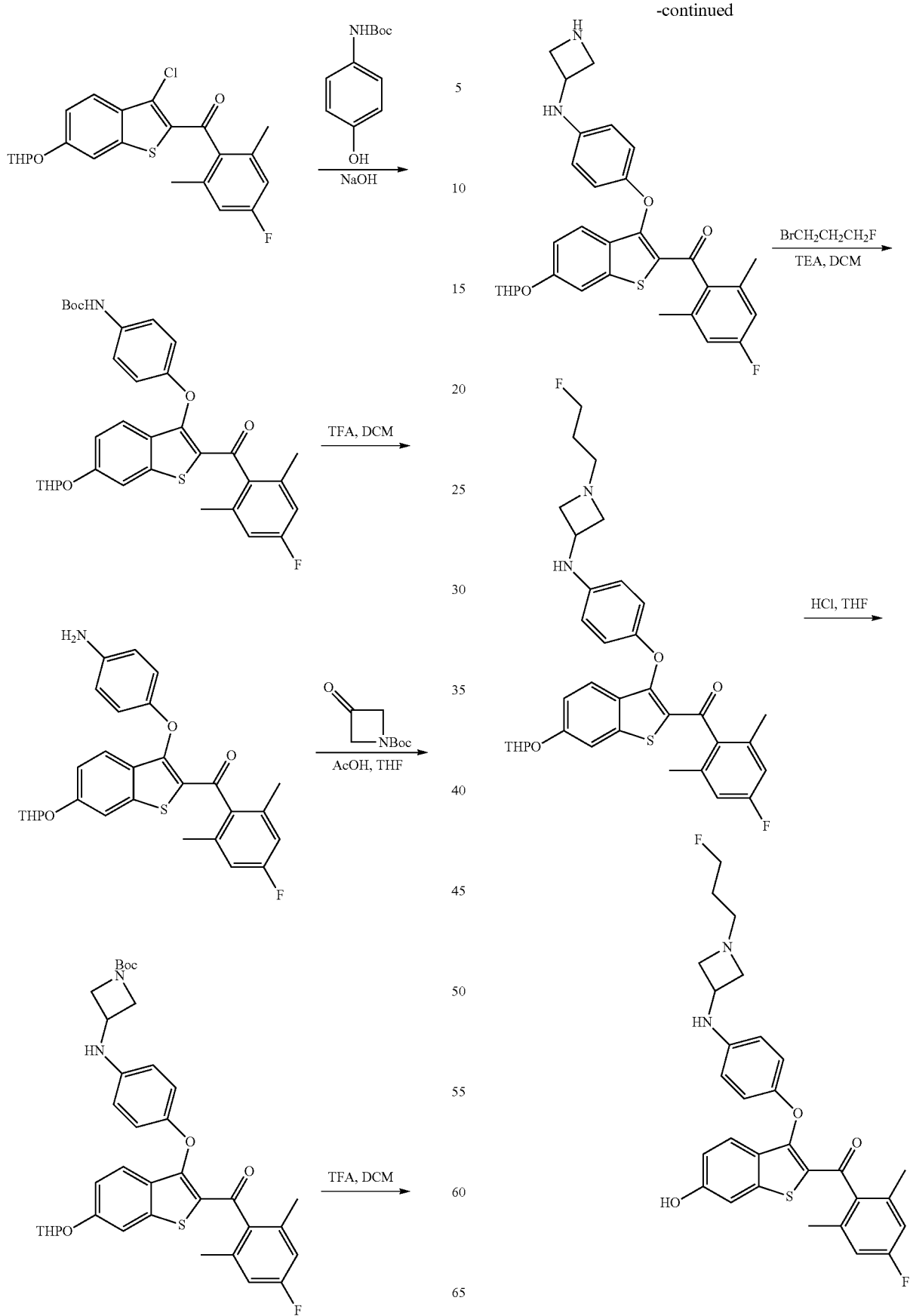
Scheme 7 shown above.

121 122
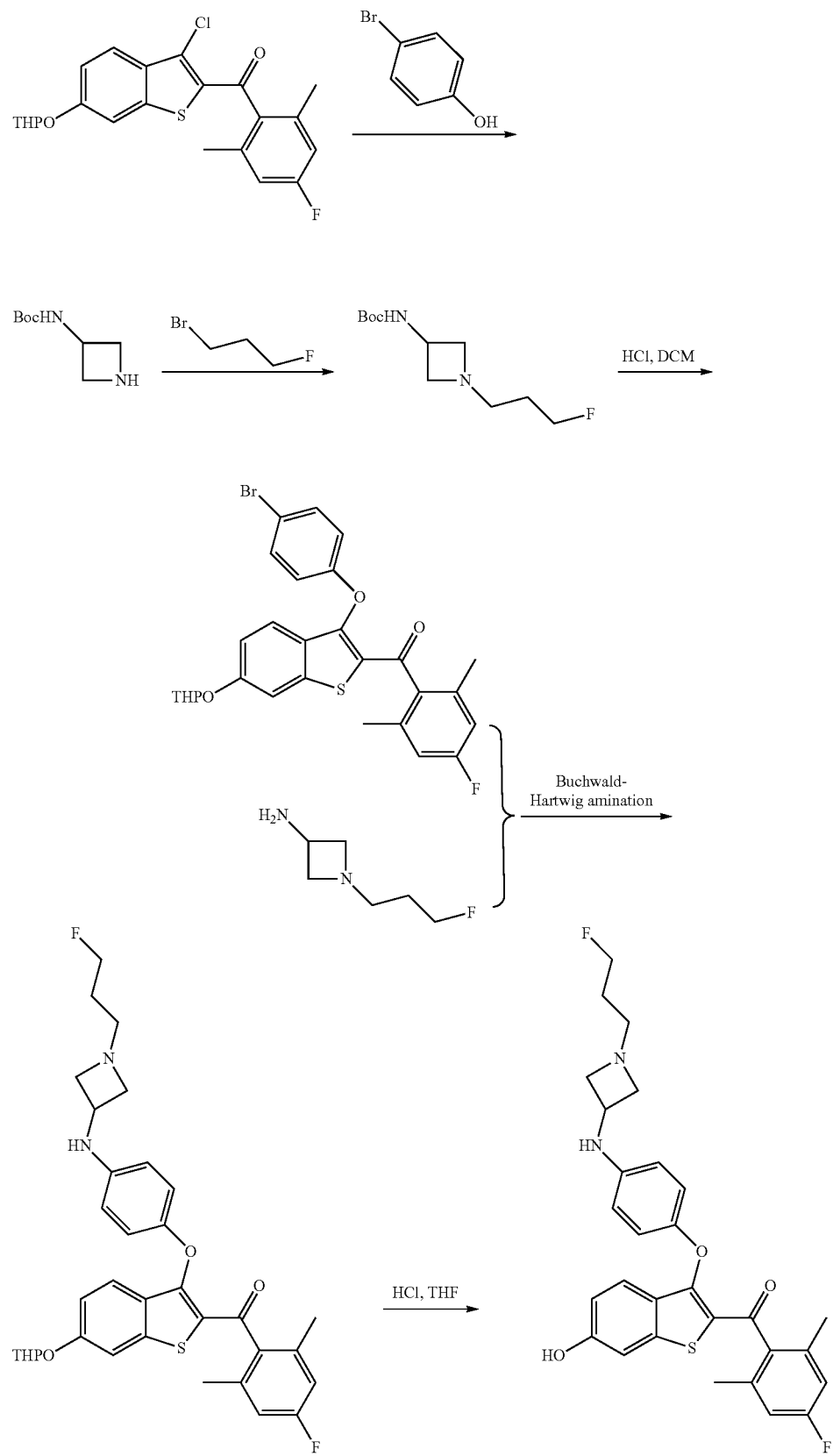
Scheme 3 shown above.

123 124
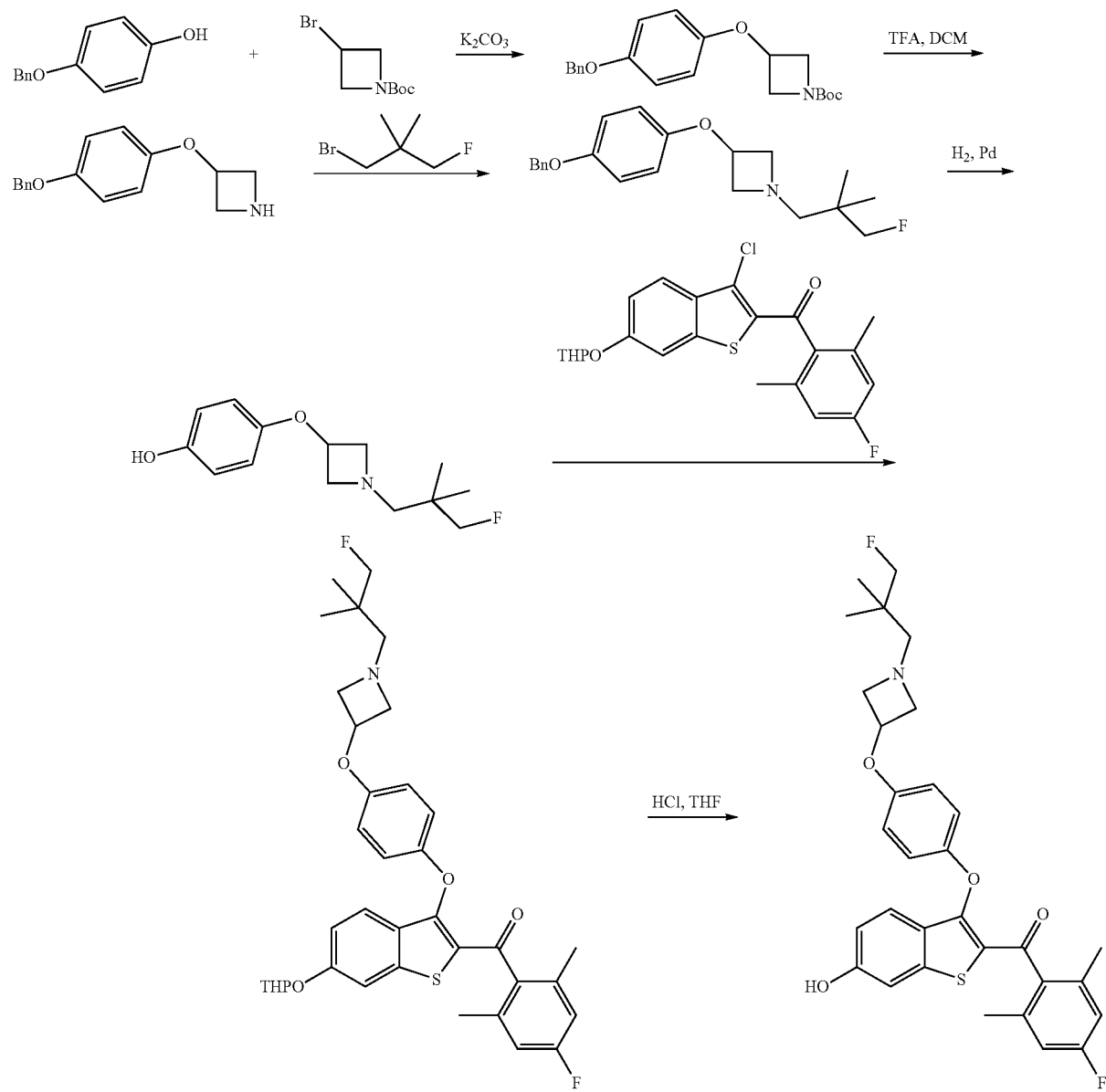
Scheme 9 shown above.
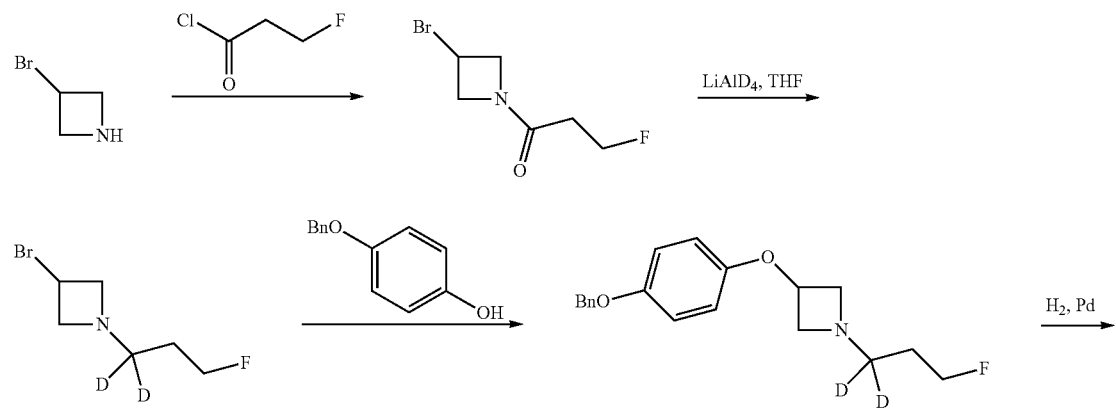

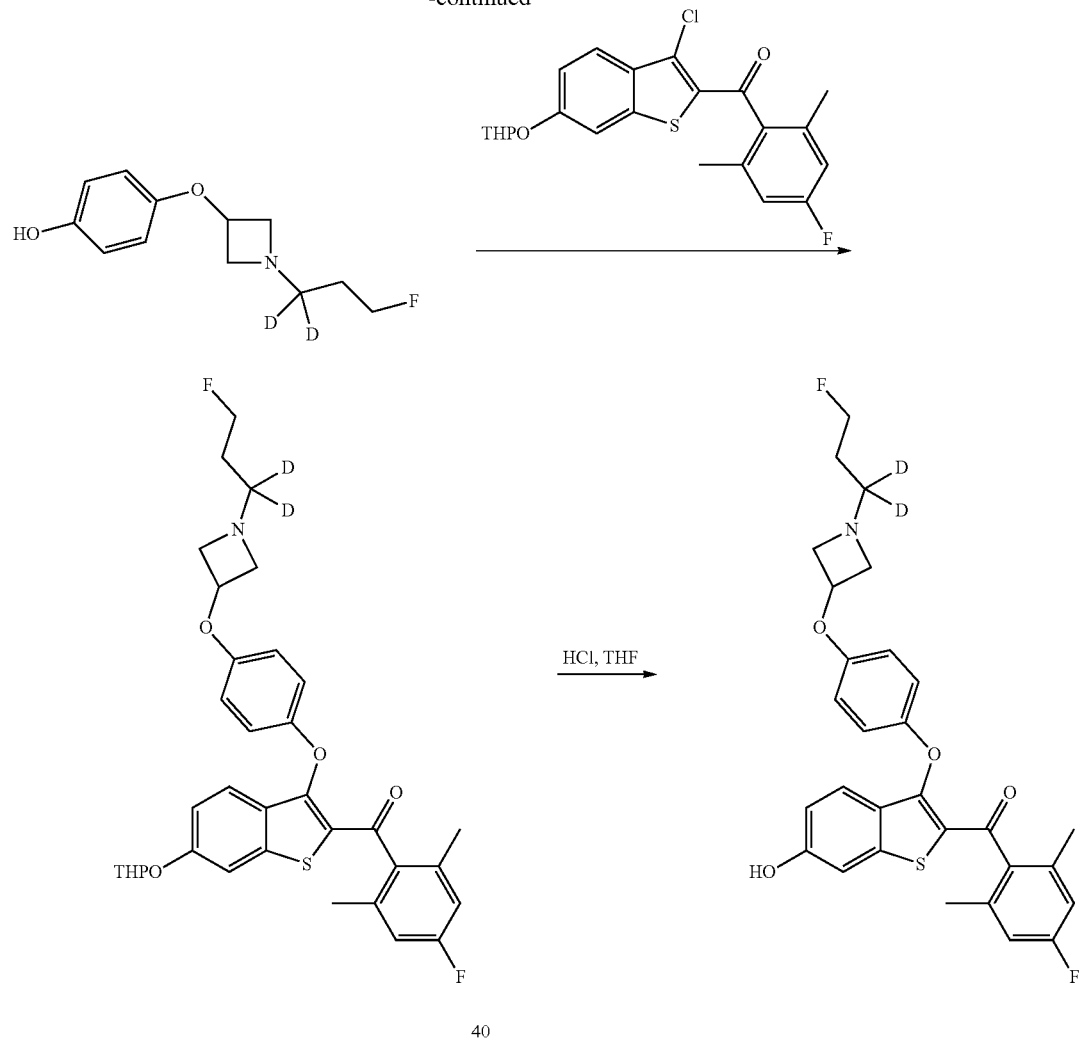

Scheme 10 shown above.

Details regarding the synthesis of intermediates and individual compounds, including chemical characterization is disclosed herein below and in Table 1. In the reactions given below, the name of the compound is given, followed by a reaction scheme, details for the reaction as appropriate (where details are not provided, the reaction was carried out as described in a similar reaction elsewhere herein), and chemical characterization data.

3-chloro-N,6-dimethoxy-N-methylbenzo[b]thiophene-2-carboxamide

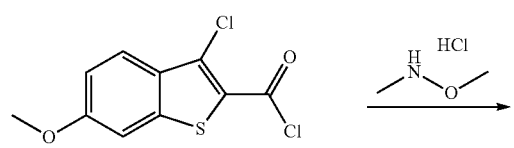

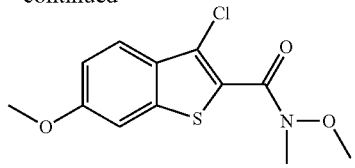

To an over-dried round-bottom flask was dissolved 3-chloro-6-methoxybenzo[b]thiophene-2-carbonyl chloride (2 g, 7.7 mmol) in (15 mL) of anhydrous dichloromethane under argon atmosphere. N,O-Dimethylhydroxylamine hydrochloride (0.83 g, 8.5 mmol) was added in one portion followed by Et$_3$N (5.4 mL, 38.8 mmol) dropwise to the mixture. The reaction was stirred at room temperature and monitored by TLC. Upon completion, the reaction was quenched by water and extracted with ethyl acetate, washed by water, brine and dried over Na$_2$SO$_4$. The organic extracts were evaporated under reduced pressure and purified by flash chromatography (10-30% ethyl acetate in hexanes) to give 1.7 g light yellow solid (yield, 78%), $^1$H NMR (400 MHz, CDCl$_3$) δ 7.80 (d, J=8.9 Hz, 1H), 7.22 (d, J=2.2 Hz, 1H), 7.08 (dd, J=8.9, 2.3 Hz, 1H), 3.88 (s, 2H), 3.72 (s, 2H), 3.38 (s, 2H). $^{13}$C NMR (101 MHz, CDCl$_3$) δ 161.45, 159.31, 139.78, 129.81, 124.47, 123.58, 122.66, 115.53, 103.71, 61.47, 55.29, 33.16.

3-chloro-6-methoxybenzo[b]thiophene-2-carbaldehyde

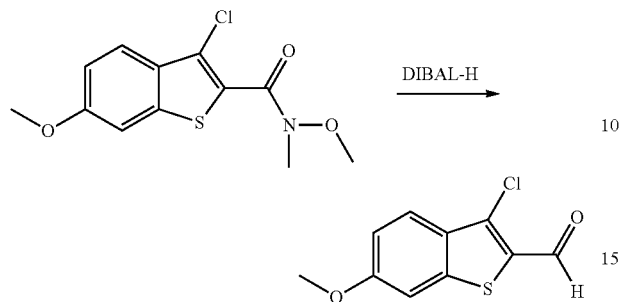

To a solution of anhydrous THF (10 mL) was dissolved (1 g, 3.9 mmol) 3-chloro-N,6-dimethoxy-N-methylbenzo[b]thiophene-2-carboxamide. The reaction mixture was stirred at −78° C. for 0.5 hr. Diisobutylaluminium hydride (3.85 mL, 4.29 mmol) was dropwise slowly to the reaction mixture and then stirred at room temperature until the starting material was consumed completely. Upon completion, the reaction was quenched by potassium sodium tartrate solution at 0° C. and stirred at room temperature until most of the amorphous precipitation was dissolved. The reaction was extracted by ethyl acetate, washed by water, brine and dried over $Na_2SO_4$. The organic extracts were evaporated under reduced pressure and purified by flash chromatography (10-30% ethyl acetate in hexanes) to give 0.5 g white solid (yield, 64%). $^1$H NMR (400 MHz, $CDCl_3$) δ 10.27 (s, 1H). 7.90 (d, J=9.0 Hz, 1H), 7.15 (dd, J=9.0, 2.2 Hz, 1H), 3.95 (s, 3H). $^{13}$C NMR (101 MHz, $CDCl_3$) δ 182.88, 161.39, 141.85, 132.85, 131.05, 130.45, 124.79, 117.07, 104.83, 55.83.

(3-chloro-6-methoxybenzo[b]thiophen-2-yl)(o-tolyl)methanol

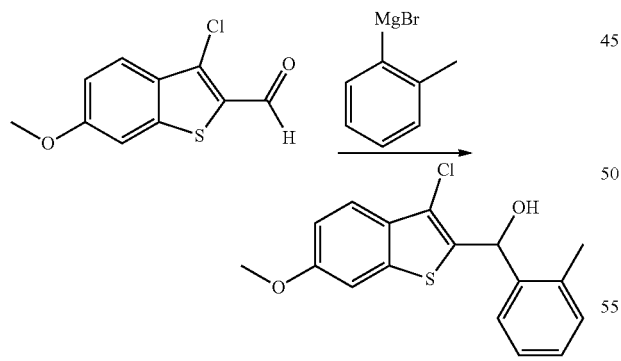

To a solution of THF (8 mL) was added (0.5 g, 2.2 mmol) 3-chloro-6-methoxybenzo[b]thiophene-2-carbaldehyde and stirred at 0° C. for 0.5 hr. o-Tolylmagnesium bromide solution (1.3 mL, 2.6 mmol, 2M in diethyl ether) was dropwise to the reaction mixture slowly at 0° C. The reaction was then stirred at room temperature for 2 hrs and monitored by TLC. Upon completion, the reaction was quenched by water and extracted by ethyl acetate, washed by water, brine and dried over $Na_2SO_4$. The organic extracts were evaporated under reduced pressure and purified by flash chromatography (10-40% ethyl acetate in hexanes) to give 0.5 g white solid (yield, 71%) H NMR (400 MHz, Acetone-d6) δ 7.71-7.69 (m, 2H), 7.46 (d, J=2.3 Hz, 1H), 7.29-7.19 (m, 2H), 7.17 (d, J=7.1 Hz, 1H), 7.11 (dd, J=8.8, 2.3 Hz, 1H), 6.46 (d, J=4.0 Hz, 1H), 5.31 (d, J=4.0 Hz, 1H), 3.88 (s, 3H), 2.32 (s, 3H). $^{13}$C NMR (101 MHz, Acetone-d6) δ 158.51, 141.11, 139.77, 138.78, 135.17, 130.24, 130.17, 127.57, 125.90, 125.82, 122.02, 116.23, 115.03, 105.38, 66.31, 55.15, 18.37.

(3-chloro-6-methoxybenzo[b]thiophen-2-yl)(o-tolyl)methanone

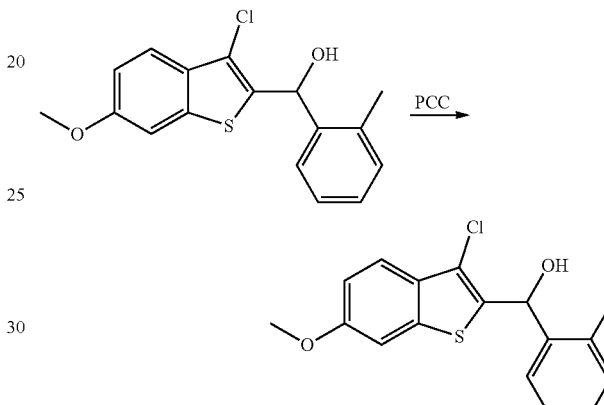

To a solution of dichloromethane (5 mL) was added (0.3 g, 0.94 mmol) (3-chloro-6-methoxybenzo[b]thiophen-2-yl)(o-tolyl)methanol, PCC (0.24 g, 1.1 mmcl) and stirred at room temperature for 3 hrs. The reaction was monitored by TLC. Upon completion, the reaction mixture was extracted by dichloromethane and washed by water, brine and dried over $Na_2SO_4$. The organic extracts were evaporated under reduced pressure and purified by flash chromatography (10-20% ethyl acetate in hexanes) to give 0.14 g yellow solid (yield, 70%). $^1$H NMR (400 MHz, $CDCl_3$) δ 7.83 (d, J=9.0 Hz, 1H), 7.47-7.39 (m, 2H), 7.33-7.29 (m, 2H), 7.27 (d, J=2.2 Hz, 1H), 7.12 (dd, J=9.0, 2.3 Hz, 1H), 3.94 (s, 3H), 2.42 (d, J=7.8 Hz, 3H). $^{13}$C NMR (101 MHz, $CDCl_3$) δ 190.94, 160.77, 141.69, 139.28, 136.09, 133.74, 131.47, 130.90, 130.60, 127.80, 126.33, 125.64, 125.20, 116.74, 104.32, 55.79, 19.58.

(3-chloro-6-hydroxybenzo[b]thiophen-2-yl)(o-tolyl)methanone

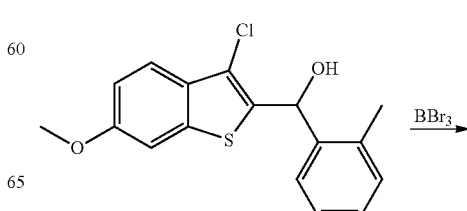

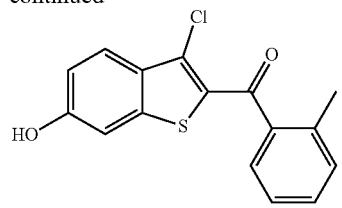

To a solution of dichloromethane (5 mL) was added (0.2 g, 0.63 mmol) (3-chloro-6-methoxybenzo[b]thiophen-2-yl)(o-tolyl)methanone and stirred at −78° C. for 0.5 hr. BBr$_3$ (0.29 mL, 3.1 mmol) was dropwise slowly to the reaction mixture. The reaction was stirred at room temperature and monitored by TLC. Upon completion, the reaction mixture was quenched by water at 0° C. and extracted by dichloromethane, washed by water, brine and dried over Na$_2$SO$_4$. The organic extracts were evaporated under reduced pressure and purified by flash chromatography (10-40% ethyl acetate in hexanes) to give 0.12 g pink solid (yield, 68%). $^1$H NMR (400 MHz, CDCl$_3$) δ 7.80 (d, J=8.9 Hz, 1H), 7.44 (t, J=7.5 Hz, 2H). 7.43 (d, J=7.5 Hz, 2H), 7.32 (d, J=7.8 Hz, 2H), 7.23 (s, 1H), 7.07 (dd, J=8.9, 0.9 Hz, 1H), 5.32 (s, 1H), 2.41 (s, 3H), $^{13}$C NMR (101 MHz, CDCl$_3$) δ 191.90, 157.45, 141.74, 139.13, 136.03, 133.28, 131.44, 130.98, 130.81, 127.76, 127.21, 125.74, 125.71, 116.62, 107.66, 19.57.

(3-chloro-6-((tetrahydro-2H-pyran-2-yl)oxy)benzo[b]thiophen-2-yl)(o-tolyl) methanone

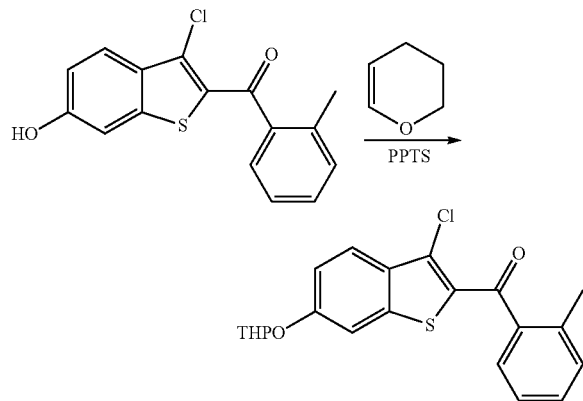

To a solution of dichloromethane (5 mL) was added (0.2 g, 0.66 mmol) (3-chloro-6-hydroxybenzo[b]thiophen-2-yl)(o-tolyl)methanone, (0.3 mL, 3.3 mmol) 3,4-Dihydropyran and (0.01 g, 0.07 mmol) Pyridinium p-toluenesulfonate. The reaction mixture was stirred at room temperature and monitored by TLC. Upon completion, the reaction was extracted by dichloromethane, washed by water, brine and dried over Na$_2$SO$_4$. The organic extracts were evaporated under reduced pressure and purified by flash chromatography (10-40% ethyl acetate in hexanes) to give 0.21 g white solid (yield, 84%), $^1$H NMR (400 MHz, Acetone-d6) δ 7.88 (d, J=9.0 Hz, 1H), 7.71 (d, J=2.1 Hz, 1H), 7.50-7.46 (m, 2H), 7.42-7.38 (m, 2H), 7.31 (dd, J=9.0, 2.2 Hz, 1H), 5.66 (t, J=3.1 Hz, 1H), 3.88-3.85 (m, 1H), 3.69-3.59 (m, 1H), 2.36 (s, 3H), 2.02-1.81 (m, 3H), 1.79-1.47 (m, 3H). $^{13}$C NMR (101 MHz, Acetone-d6) δ 190.06, 158.28, 141.01, 139.46, 135.69, 134.11, 131.60, 130.84, 130.65, 127.68, 125.77, 125.11, 124.74, 117.88, 108.44, 96.50, 61.71, 29.95, 24.92, 18.65, 18.47.

Ethylsulfonyl)oxy)methyl)azetidine-1-carboxylate

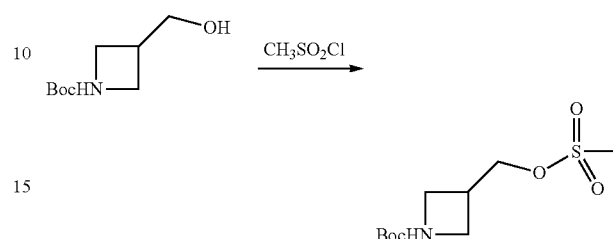

To a solution of tert-Butyl 3-(hydroxymethyl)azetidine-1-carboxylate (5 g, 26.7 mmol), triethylamine (7.4 mL, 53.4 mmol), and dichloromethane (50 mL). Methanesulfonyl chloride (32 mL, 401 mmol) was dropwise over 15 mins at 0° C. The resulting cloudy orange mixture was stirred at 0° C. for 1 h and then diluted with 10% aqueous citric acid (20 mL). The layers were separated, and the organic phase was washed by 10% aqueous citric acid, saturated NaHCO$_3$, and water. The organic phase was dried over Na$_2$SO$_4$ and concentrated to give the title compound as a dark orange oil. $^1$H NMR (400 MHz, DMSO-d$_6$): δ 4.33 (d, J=5.3 Hz, 2H), 3.91 (m, 2H), 3.61 (m, 2H), 3.21 (s, 3H), 2.89 (m, 1H), 1.37 (s, 9H).

tert-Butyl 3-(fluoromethyl)azetidine-1-carboxylate

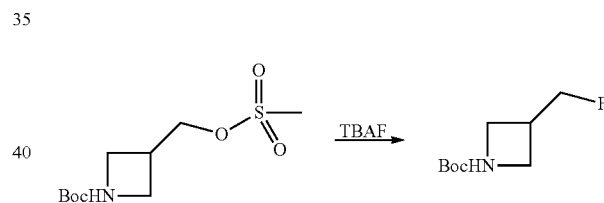

To a solution of tert-butyl 3-(((methylsulfonyl)oxy)methyl)azetidine-1-carboxylate (7 g, 26.7 mmol) and tetrabutylammonium fluoride (50) mL, 50 mmol, 1M in THF) was refluxed for 1 h and monitored by TLC stain. Upon completion, the reaction mixture was evaporated under reduced pressure to remove the solvent THF. The resulting thick oil was diluted with ethyl acetate and then washed water, brine and dried over Na$_2$SO$_4$. The organic extracts were evaporated under reduced pressure and purified by flash chromatography (10-40% ethyl acetate in hexanes) to give 4.2 g as a yellow oil (yield, 85% over two steps). $^1$H NMR (400 MHz, DMSO-d6): δ 4.52 (dd, J=47.3, 5.3 Hz, 2H), 3.94-3.83 (m, 2H), 3.66-3.52 (m, 2H), 2.94-2.77 (m, 1H), 1.37 (s, 9H).

3-(fluoromethyl)azetidine hydrochloride

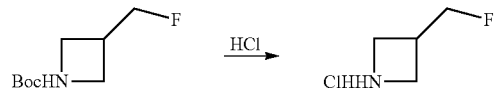

To a solution of methanol (45 mL) was added tert-butyl 3-(fluoromethyl)azetidine-1-carboxylate (4.2 g, 22.2 mmol) and aqueous HCl (6M, 11.1 mL, 66.6 mmol) was dropwised slowly to the reaction at 0° C. The reaction was stirred at room temperature and monitored by TLC stain, Upon completion, the reaction was evaporated to become solidified under high vacuum to give the title compound (2.7 g, 97%) as a hygroscopic white solid. $^1$H NMR (400 MHz, DMSO-d6): δ 9.18 (br s, 2H), 4.56 (dd, J=47.6, 5.3 Hz, 2H), 4.03-3.92 (m, 2H), 3.78-3.68 (m, 2H), 3.19-3.00 (m, 1H).

Tert-butyl (R)-3-(((methylsulfonyl)oxy)methyl)pyrrolidine-1-carboxylate

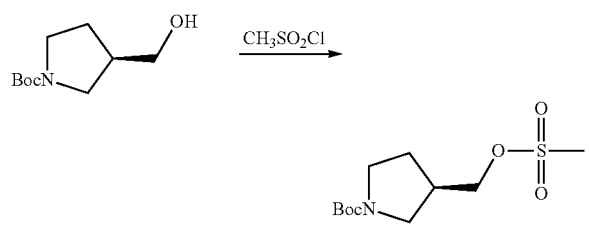

The preparation of tert-butyl (R)-3-(((methylsulfonyl)oxy)methyl)pyrrolidine-1-carboxylate was followed procedure ethylsulfonyl)oxy)methyl)azetidine-1-carboxylate. $^1$H NMR (400 MHz, DMSO-d$_6$): δ 4.26-4.11 (m, 2H), 3.44-3.28 (m, 2H), 3.26-3.14 (m, 1H), 3.18 (s, 3H), 3.05-2.93 (m, 1H), 2.62-2.49 (m, 1H), 2.00-1.87 (m, 1H), 1.72-1.56 (m, 1H). 140 (s, 9H).

(R)-tert-Butyl 3-(fluoromethyl)pyrrolidine-1-carboxylate

The preparation of tert-butyl (R)-3-(((methylsulfonyl)oxy)methyl)pyrrolidine-1-carboxylate was followed procedure of tert-Butyl 3-(fluoromethyl)azetidine-I-carboxylate. $^1$H NMR (400 MHz, DMSO-d$_6$): δ 4.49-441 (m, 1H), 4.37-4.29 (m, 1H), 3.40-3.28 (m, 2H), 3.24-3.18 (m, 1H), 3.02-2.98 (m, 1H), 2.58-2.52 (m, 1H), 1.95-1.88 (m, 1H), 1.67-1.54 (m, 1H), 1.38 (s, 9H).

(R)-3-(Fluoromethyl)pyrrolidine hydrochloride

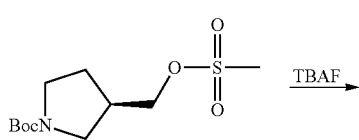

The preparation of (R)-3-(Fluoromethyl)pyrrolidine hydrochloride was followed by the procedure of 3-(fluoromethyl)azetidine hydrochloride. $^1$H NMR (400 MHz, DMSO-d$_6$, HCl salt): δ 9.35 (brs, 2H), 4.57-4.47 (m, 1H), 4.44-4.33 (m, 1H), 3.33-3.10 (m, 3H), 2.95-2.87 (m, 1H), 2.69-2.57 (m, 1H), 2.05-1.97 (m, 1H), 1.70-1.61 (m, 1H).

2-(4-(2-bromoethoxy)phenoxy)tetrahydro-2H-pyran

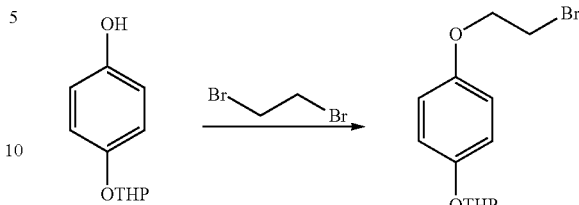

To a solution of tetrahydrofuran (30 mL) was added (2 g, 10.2 mmol) deoxyarbutin, (1.2 mL, 0.11 mol) 1,2-dibromoethane, (1.23 g, 31 mmol) NaOH. The reaction mixture was reflux for 24 hrs and monitored by TLC, The reaction mixture was evaporated under reduced pressure and diluted by ethyl acetate, washed by water, brine and dried over Na$_2$SO$_4$. The organic extracts were evaporated under reduced pressure and purified by flash chromatography (10-25% ethyl acetate in hexanes) to give 1.4 g white solid (yield, 46%). $^1$H NMR (400 MHz, Acetone-d6) δ 7.05-6.97 (m, 2H), 6.95-6.86 (m, 2H), 5.33 (t, J=3.2 Hz, 1H), 4.31 (t, J=5.7 Hz, 2H), 3.95-3.82 (m, 1H), 3.75 (t, J=5.5 Hz, 2H), 3.56-3.52 (m, 1H), 1.98-1.96 (m, 1H), 1.90-1.73 (m, 2H), 1.71-1.50 (m, 3H), $^{13}$C NMR (101 MHz, Acetone-d6) δ 153.18, 151.77, 117.74, 115.55, 96.95, 68.58, 61.50, 30.33, 30.29, 25.13, 18.79.

3-(fluoromethyl)-1-(2-(4-((tetrahydro-2H-pyran-2-yl)oxy)phenoxy) ethyl)azetidine

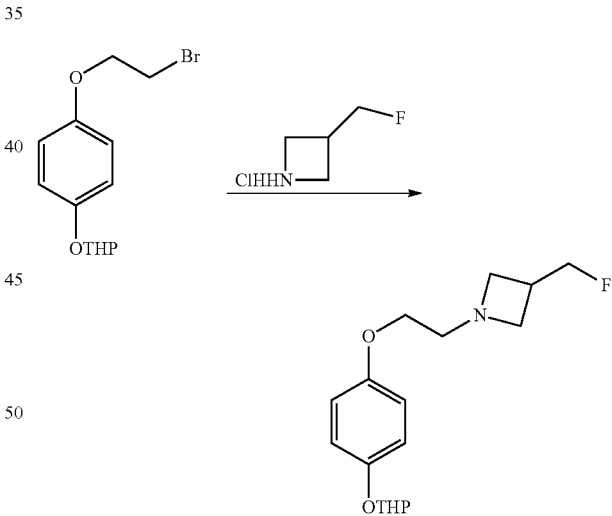

To a solution of acetonitrile (5 mL) was added (0.5 g, 1.6 mmol) 2-(4-(2-bromoethoxy)phenoxy)tetrahydro-2H-pyran, (0.4 g, 3.2 mmol) 3-(fluoromethyl)azetidine hydrochloride, (0.66 g, 4.8 mmol) potassium carbonate. The reaction mixture was stirred at 60° C. and monitored by TLC. Upon completion, the reaction was extract by ethyl acetate, washed by water, brine and dried over Na$_2$SO$_4$. The organic extracts were evaporated under reduced pressure and purified by flash chromatography (1-10% methanol in dichloromethane to give 0.45 g white solid, (yield, 88%) $^1$H NMR (400 MHz, CDCl$_3$) δ 7.04-6.96 (m, 2H), 6.87-6.79 (m, 2H), 5.31 (t, J=3.3 Hz, 1H), 4.56 (dd, J=47.6, 5.3 Hz, 2H), 3.95

(t, J=5.5 Hz, 2H), 3.72-3.48 (m, 2H), 3.20 (t, J=7.0 Hz, 2H), 2.99-2.88 (m, 1H), 2.86 (t, J=5.5 Hz, 2H), 2.08-1.93 (m, 1H), 1.86-1.83 (m, 2H), 1.75-1.56 (m, 4H). $^{13}$C NMR (101 MHz, CDCl$_3$) δ 153.67, 151.25, 117.73, 115.28, 97.31, 84.21 (d, J=167.0 Hz), 66.89, 62.10, 57.91, 56.56 (d, J=6.9 Hz), 31.50, 31.40 (d, J=20.3 Hz), 25.26, 18.94.

4-(2-(3-(fluoromethyl)azetidin-1-yl)ethoxy)phenol

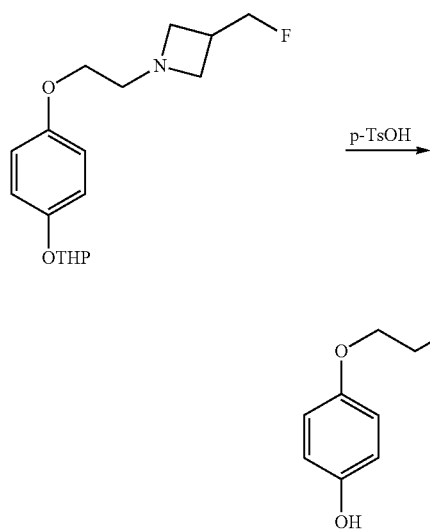

To a solution of methanol (5 mL) was added (0.2 g, 0.65 mmol) 3-(fluoromethyl)-1-(2-(4-((tetrahydro-2H-pyran-2-yl)oxy)phenoxy)ethyl)azetidine and (0.33 g, 1.95 mmol) p-toluenesulfonic acid. The reaction was stirred at room temperature and monitored by TLC. Upon completion, the reaction was extracted by ethyl acetate, washed by saturated NaHCO$_3$, water, brine and dried over Na$_2$SO$_4$. The organic extracts were evaporated under reduced pressure and purified by flash chromatography (1-10% methanol in dichloromethane to give 0.1 g white solid. (yield, 71%) $^1$H NMR (400 MHz, Acetone-d6) δ 6.76 (s, 4H), 4.55 (dd, J=47.7, 6.3 Hz, 2H), 3.89 (t, J=5.7 Hz, 2H). 3.41 (t, J=7.6 Hz, 2H). 3.13 (d, J=7.6 Hz, 2H), 2.78-2.76 (m, J=5.7 Hz, 3H). $^{13}$C NMR (101 MHz, Acetone-d6) δ 152.28, 151.34, 115.72, 115.34, 84.57 (d, J=164.9 Hz), 67.23, 57.74, 56.39 (d, J=7.7 Hz), 31.37 (d, J=20.2 Hz).

(3R)-3-(fluoromethyl)-1-(2-(4-((tetrahydro-2H-pyran-2-yl)oxy)phenoxy)ethyl) pyrrolidine

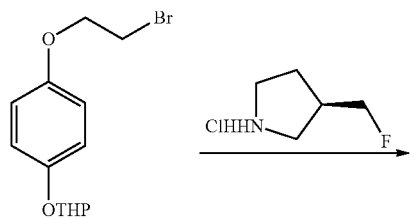

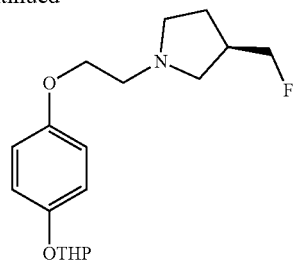

The preparation of (3R)-3-(fluoromethyl)-1-(2-(4-((tetrahydro-2H-pyran-2-yl)oxy)phenoxy)ethyl)pyrrolidine was followed by the procedure of 3-(fluoromethyl)-1-(2-(4-((tetrahydro-2H-pyran-2-yl)oxy)phenoxy)ethyl)azetidine. (Yield) $^1$H NMR (400 MHz, CDCs) δ 7.00 (d, J=8.9 Hz, 2H), 6.85 (d, J=8.9 Hz, 2H), 5.31 (t, J=3.1 Hz, 1H), 4.36 (dd, J=47.4, 6.6 Hz, 2H), 4.09 (t, J=57 Hz, 2H), 3.99-3.91 (m, 1H), 3.68-3.55 (m, 1H), 3.03-2.81 (m, 3H), 2.81-2.46 (m, 4H), 2.13-1.93 (m, 2H), 1.91-1.78 (m, 2H), 1.77-1.48 (m, 4H). $^{13}$C NMR (101 MHz, CDCl$_3$) δ 153.63, 151.29, 117.76, 115.40, 97.30, 85.80 (d, J=168.8 Hz), 67.27, 62.10, 56.65 (d, J=5.2 Hz), 54.86, 54.32, 37.71 (d, J=187 Hz), 30.50, 26.12 (d, J=6.8 Hz), 25.26, 18.94.

(R)-4-(2-(3-(fluoromethyl)pyrrolidin-1-yl)ethoxy) phenol

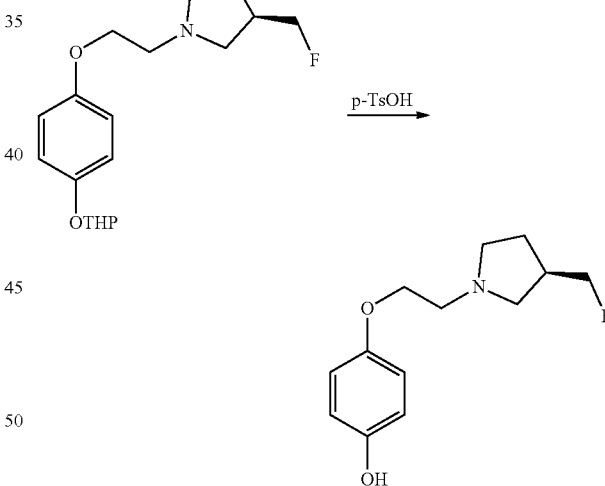

The preparation of (R)-4-(2-(3-(fluoromethyl) pyrrolidin-1-yl)ethoxy)phenol was followed by the procedure of 4-(2-(3-(fluoromethyl)azetidin-1-yl)ethoxy)phenol (Yield). $^1$H NMR (400 MHz, CDCl$_3$) δ 6.72-6.63 (m, 4H), 4.45-4.32 (m, 2H). 4.02 (t, J=5.7 Hz, 2H), 2.99-2.86 (m, 3H), 2.86-2.76 (m, 1H), 2.76-2.47 (m, 3H), 2.09-1.95 (m, 1H), 1.59 (dq, J=8.0, 6.0 Hz, 1H). $^{13}$C NMR (101 MHz, CDCl$_3$) δ 152.40, 150.22, 116.46, 115.56, 85.67 (d, J=168.8 Hz), 67.25, 56.82 (d, J=5.0 Hz), 55.01, 54.51, 37.61 (d, J=18.8 Hz). 26.04 (d, J=6.7 Hz). $^{13}$C NMR (101 MHz, CDCl$_3$) δ 152.40, 150.22, 116.46, 115.56, 85.67 (d, J=168.8 Hz), 67.25, 56.82 (d, J=5.0 Hz), 55.01, 54.51, 37.61 (d, J=18.8 Hz), 26.04 (d, J=67 Hz).

135 tert-butyl 3-(4-(benzyloxy)phenoxy)azetidine-1-carboxylate

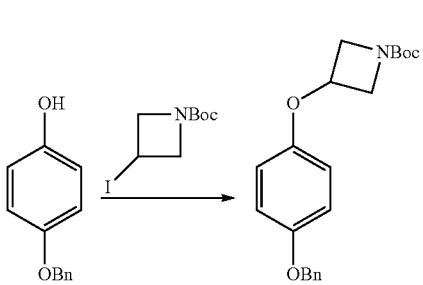

To a solution of dimethylformamide (5 mL) was added (0.3 g, 1.5 mmol) 4-(benzyloxy)phenol and (0.5 g, 1.8 mmol) tert-butyl 3-(4-(benzyloxy)phenoxy)azetidine-1-carboxylate and (1.4 g, 4.5 mmol) cesium carbonate. The reaction mixture was stirred at 140° C. for 3 hrs and monitored by TLC. Upon completion, the reaction mixture was extracted by ethyl acetate, washed by water, brine and dried over $Na_2SO_4$. The organic extracts were evaporated under reduced pressure and purified by flash chromatography (10-50% ethyl acetate in hexanes to give 0.33 g white solid (Yield, 63%). $^1$H NMR (400 MHz, $CDCl_3$) δ 7.46 7.30 (m, 5H), 6.92 (d, J=9.0 Hz, 2H), 6.70 (d, J=9.0 Hz, 2H), 5.04 (s, 2H), 4.89-4.83 (m, 1H), 4.28 (dd, J=9.6, 6.4 Hz, 2H), 4.01 (dd, J=9.7, 4.1 Hz, 2H), 1.47 (s, 9H). $^{13}$C NMR (101 MHz, $CDCl_3$) δ 156.19, 153.62, 150.87, 137.11, 128.59, 127.96, 127.47, 116.04, 115.51, 79.78, 70.65, 66.05, 56.48, 28.38.

3-(4-(benzyloxy)phenoxy)azetidine

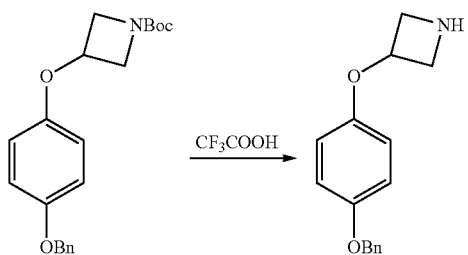 [SMILES: CC(C)(C)OC(=O)N1CC(Oc2ccc(OCc3ccccc3)cc2)C1 ; "CF3COOH" ; c1ccc(COc2ccc(OC3CNC3)cc2)cc1]

To a solution of dichloromethane (5 mL) was added (0.5 g, 1.9 mmol) 3-(4-(benzyloxy)phenoxy)azetidine followed by dropwise of (0.72 mL, 9.5 mmol) trifluoroacetic acid at 0° C. The reaction mixture then was stirred at room temperature and monitored by TLC. Upon completion, the reaction mixture was extracted by dichloromethane, washed by water, brine and dried over $Na_2SO_4$. The organic extracts were evaporated under reduced pressure and purified by flash chromatography (1-10% methanol in dichloromethane) to give 0.3 g white solid. (Yield, 85%). $^1$H NMR (400 MHz, Acetone-d6) δ 7.47 (d, J=7.6 Hz, 2H), 7.40 (dd, J=8.0, 7.0 Hz, 2H), 7.33 (t, J=6.7 Hz, 1H), 6.96 (d, J=8.9 Hz, 2H), 6.81 (d, J=8.9 Hz, 2H), 5.08 (s, 2H), 4.75 (brs, 1H), 3.99-3.69 (m, 2H), 3.54-3.44 (m, 2H). $^{13}$C NMR (101 MHz, Acetone-d6) δ 153.47, 151.28, 137.75, 128.37, 127.66, 127.46, 115.86, 115.58, 70.04, 65.29, 53.41.

136

3-(4-(benzyloxy)phenoxy)-1-(3-fluoropropyl)azetidine

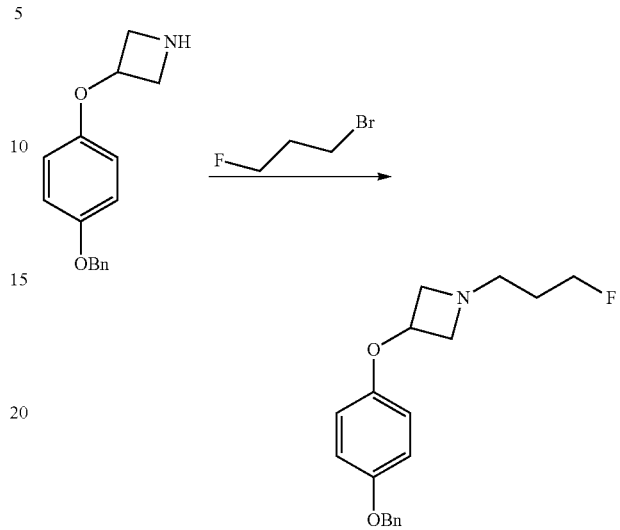

The preparation of 3-(4-(benzyloxy)phenoxy)-1-(3-fluoropropyl)azetidine was followed by the procedure of 3-(fluoromethyl)-1-(2-(4-((tetrahydro-2H-pyran-2-yl)oxy)phenoxy)ethyl)azetidine (Yield). $^1$H NMR (400 MHz, Acetone-d6) δ 7.39 (m, 5H), 7.00-6.88 (m, 3H), 6.82-6.69 (m, 1H), 5.07 (s, 2H), 4.71 (p, J=5.7 Hz, 1H), 4.49 (dt, J=47.5, 6.1 Hz, 2H), 3.82-3.72 (m, 1H), 3.02-2.94 (m, 1H), 2.90-2.64 (m, 2H), 2.65-2.54 (m, 2H), 1.94-1.61 (m, 2H). $^{13}$C NMR (101 MHz, Acetone-d6) δ 153.32, 151.56, 137.78, 128.36, 127.65, 127.47, 115.81, 115.43, 81.90 (d, J=145.1 Hz), 70.05, 66.79, 61.21, 55.16 (d, J=5.6 Hz), 27.62.

4-((1-(3-fluoropropyl)azetidin-3-yl)oxy)phenol

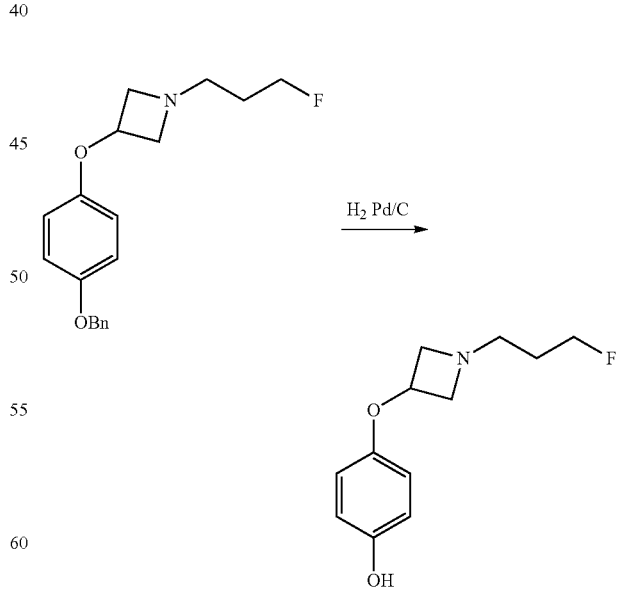

To a solution of methanol (10 mL) was added (0.5 g, 1.5 mmol) 3-(4-(benzyloxy)phenoxy)-1-(3-fluoropropyl)azetidine and (0.15 g, 0.15 mmol, 10 wt. %) palladium carbon. The reaction was degas by hydrogen for at least three times and stirred at room temperature for 5 hrs monitored by TLC. Upon completion, the reaction mixture was extracted by ethyl acetate, washed by water, brine and dried over Na$_2$SO$_4$. The organic extracts were evaporated under reduced pressure and purified by flash chromatography (1-10% methanol in dichloromethane) to give 0.3 g white solid. (Yield, 85%). $^1$H NMR (400 MHz, Acetone-d6) δ 6.79-6.71 (m, 2H), 6.71-6.62 (m, 2H), 4.70-4.60 (m, 1H), 4.49 (dt, J=47.5, 6.1 Hz, 2H), 3.78 (td, J=6.1, 1.9 Hz, 1H), 2.98 (td, J=5.7, 1.9 Hz, 2H), 2.88-2.64 (m, 1H), 2.55 (t, J=6.9 Hz, 2H), 1.91-1.64 (m, 2H). $^{13}$C NMR (101 MHz, Acetone-d6) δ 151.63, 150.53, 115.85, 115.52, 81.30 (d, J=162.4 Hz), 66.80, 61.28, 55.18 (d, J=5.5 Hz).

3-(4-(benzyloxy)phenoxy)-1-(5-fluoropentyl)azetidine

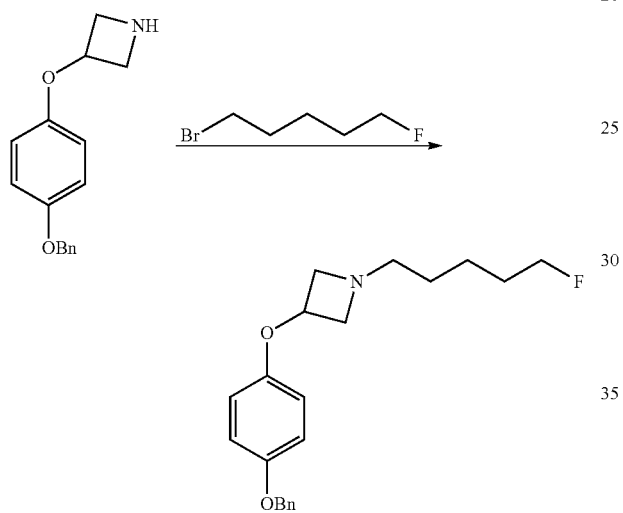

The preparation of 3-(4-(benzyloxy)phenoxy)-1-(3-fluoropropyl)azetdine was followed by the procedure of 3-(fluoromethyl)-1-(2-(4-((tetrahydro-2H-pyran-2-yl)oxy)phenoxy)ethyl)azetidine (Yield). $^1$H NMR (400 MHz, Acetone-d6) δ 7.52-7.44 (m, 2H), 7.44-7.37 (m, 2H), 7.37-7.29 (m, 1H), 7.03-6.91 (m, 2H), 6.36-6.73 (m, 2H), 5.08 (s, 2H), 4.54-4.36 (m, 2H). 4.16-3.62 (m, 2H), 3.27-3.21 (m, 2H), 2.68-2.53 (m, 3H), 1.80-1.63 (m, 2H), 1.60-1.40 (m, 4H).

(3-(4-((1-(5-fluoropentyl)azetidin-3-yl)oxy)phenoxy)-6-((tetrahydro-2H-pyran-2-yl)oxy)benzo[b]thiophen-2-yl)(o-tolyl)methanone

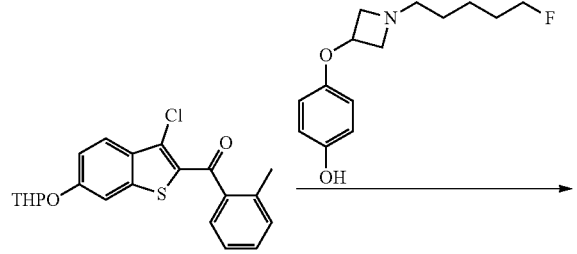

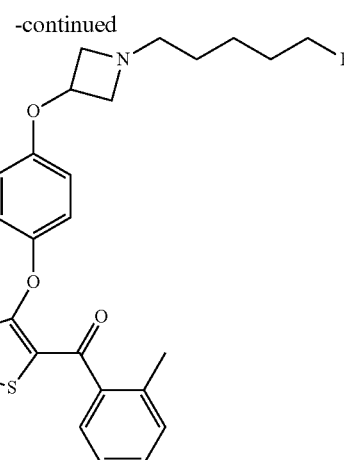

$^1$H NMR (400 MHz, Acetone-d6) δ 7.68 (d, J=2.1 Hz, 1H), 7.47 (d, J=8.9 Hz, 1H), 7.37 (d, J=7.3 Hz, 1H), 7.34-7.27 (m, 1H), 7.14-7.12 (m, 3H), 6.62 (d, J=9.1 Hz, 2H), 6.45 (d, J=9.0 Hz, 2H), 5.69-5.53 (m, 2H), 4.44 (dt, J=47.6, 6.1 Hz, 2H), 4.00-3.73 (m, 3H), 3.73-3.55 (m, 2H), 355-3.41 (m, 1H), 2.14 (s, 3H), 2.02-1.81 (m, 5H), 1.73-1.50 (m, 7H).

(3-(4-(2-(3-(fluoromethyl)azetidin-1-yl)ethoxy)phenoxy)-6-((tetrahydro-2H-pyran-2-yl)oxy)benzo[b]thiophen-2-yl)(o-tolyl)methanone

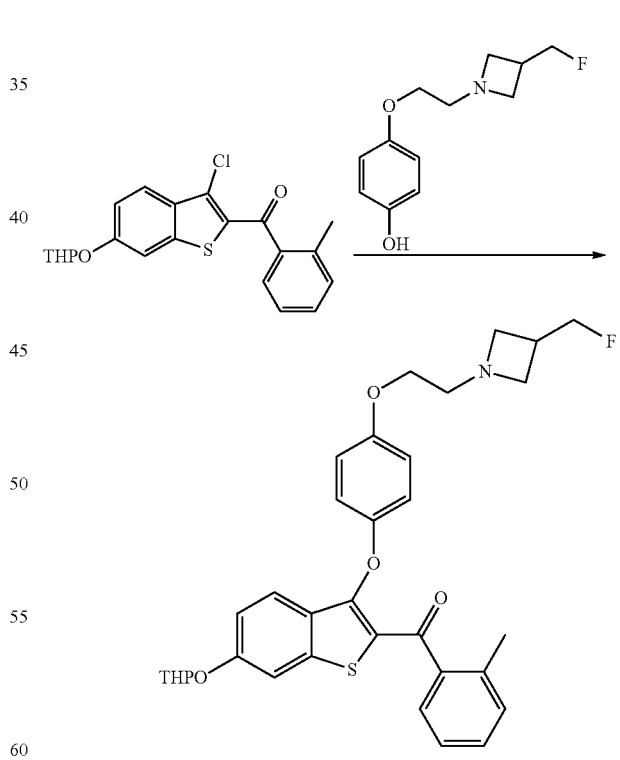

To a solution of dimethylformamide (10 mL) was added (0.5 g, 1.3 mmol) (3-chloro-6-((tetrahydro-2H-pyran-2-yl)oxy)benzo[b]thiophen-2-yl)(o-tolyl)methanone, (0.35 g, 1.6 mmol) 4-(2-(3-(fluoromethyl)azetidin-1-yl)ethoxy)phenol, and (1.26 g, 3.9 mmol) cesium carbonate. The reaction mixture was stirred at 110° C. for 5 hrs and monitored by TLC. Upon completion, the reaction mixture was extracted by ethyl acetate, washed by water, brine and dried over Na$_2$SO$_4$. The organic extracts were evaporated under reduced pressure and purified by flash chromatography (1-10% of methanol in hexanes to give 0.44 g white solid. (Yield, 62%) $^1$H NMR (400 MHz, CDCl$_3$) δ 7.51 (d, J=1.9 Hz, 1H), 7.42 (d, J=8.9 Hz, 1H), 7.29 (d, J=7.3 Hz, 1H), 7.22 (t, J=7.4 Hz, 1H), 7.07 (t, J=6.9 Hz, 2H), 7.01 (dd, J=8.9, 2.0 Hz, 1H), 6.58 (d, J=9.0 Hz, 2H), 6.35 (d, J=9.0 Hz, 2H), 5.51 (t, J=2.7 Hz, 1H), 4.50 (dd, J=47.4, 5.6 Hz, 2H), 3.91-3.31 (m, 3H), 3.64 (m, 1H), 3.50 (brs, 2H), 3.16 (brs, 2H). 2.94-2.76 (m, 3H), 2.15 (s, 3H), 2.06-1.95 (m, 1H), 1.90 (m, 2H), 1.78-1.49 (m, 4H).

(3-(4-(2-(3-(fluoromethyl)azetidin-1-yl)ethoxy)phenoxy)-6-hydroxybenzo[b]thiophen-2-yl)(o-tolyl)methanone

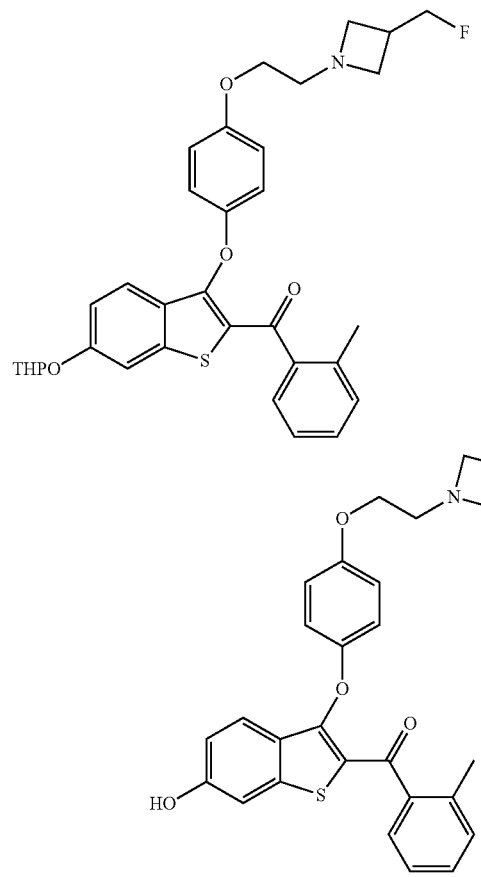

The preparation of (3-(4-(2-(3-(fluoromethyl)azetidin-1-yl)ethoxy)phenoxy)-6-hydroxybenzo[b]thiophen-2-yl)(o-tolyl)methanone was followed by the procedure of 4-(2-(3-(fluoromethyl)azetidin-1-yl)ethoxy)phenol (Yield), $^1$H NMR (400 MHz, CDCl$_3$) δ 7.37-7.15 (m, 4H), 7.08 (m, 2H), 6.81 (dd, J=3.8, 1.9 Hz, 1H), 6.50 (d, J=9.1 Hz, 2H), 6.32 (d, J=9.0 Hz, 2H), 4.46 (dd, J=47.3, 4.7 Hz), 4.10 (brs, 1H), 3.93 (d, J=4.7 Hz, 2H), 3.72 (d, J=7.7 Hz, 2H), 3.39 (t, J=7.2 Hz, 2H), 2.99 (brs, 2H), 2.16 (s, 3H). $^{13}$C NMR (101 MHz, CDCl$_3$) δ 191.02, 158.46, 153.55, 152.61, 149.90, 142.16, 139.48, 135.63, 130.35, 129.88, 127.44, 126.54, 126.29, 125.06, 125.05, 116.22, 115.87, 114.88, 108.36, 33.85 (d, J=163.2 Hz), 65.97, 57.25, 56.15 (d, J=6.2 Hz). 50.87, 31.30 (d, J=20.6 Hz), 19.25. LCMS (m/z): [M+H]$^+$ calcd. for C$_{28}$H$_{26}$FNO$_4$S, 492.58; observed, 492. HPLC purity: 98.28%

(R)-4-(2-(3-(fluoromethyl)pyrrolidin-1-yl)ethoxy)phenol

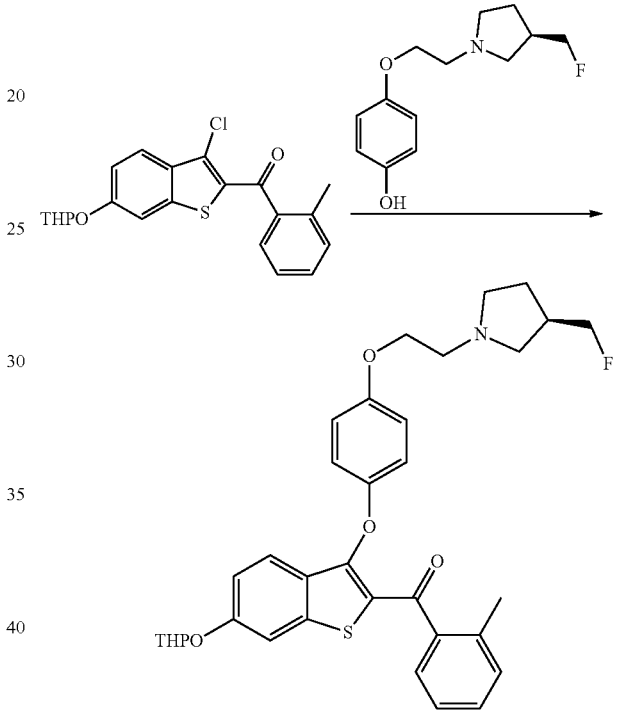

The preparation of (R)-4-(2-(3-(fluoromethyl)pyrrolidin-1-yl)ethoxy)phenol was followed by the procedure of (3-(4-(2-(3-(fluoromethyl)azetidin-1-yl)ethoxy)phenoxy)-6-((tetrahydro-2H-pyran-2-yl)oxy)benzo [b]thiophen-2-yl)(o-tolyl)methanone. (Yield)$^1$H NMR (400 MHz, Acetone-d6) δ 7.68 (d, J=2.1 Hz, 1H), 7.45 (d, J=8.9 Hz, 1H), 7.39 (d, J=5.6, 1H), 7.30 (td, J=7.6, 1.2 Hz, 1H), 7.16 (dd, J=7.2, 3.4 Hz, 2H), 7.11 (dd, J=9.0, 2.2 Hz, 1H), 6.77-6.69 (m, 2H), 6.52-6.43 (m, 2H), 5.64 (t, J=3.1 Hz, 1H), 4.31 (dd, J=47.7, 6.8 Hz, 2H), 4.03 (t, J=5.9 Hz, 2H), 3.91-3.75 (m, 1H), 3.68-3.65 (m, 1H), 2.83-2.81 (m, 2H), 2.69-2.67 (m, 2H), 2.55-2.52 (m, 3H), 2.16 (s, 3H), 2.02-1.77 (m, 4H), 1.72-1.66 (m, 4H), 1.48-1.46 (m, 1H). $^{13}$C NMR (101 MHz, Acetone) δ 189.93, 158.09, 154.50, 152.29, 149.26, 141.38, 139.63, 135.42, 130.32, 129.91, 127.52, 127.47, 125.07, 124.51, 116.95, 116.03, 115.15, 108.95, 96.42, 85.68 (d, J=167.2 Hz), 67.56, 61.71, 56.41 (d, J=5.2 Hz), 54.33, 53.82, 37.76 (d, J=18.6 Hz), 29.98, 25.84 (d, J=7.0 Hz), 24.94, 18.50.

141
(R)-(3-(4-(2-(3-(fluoromethyl)pyrrolidin-1-yl)ethoxy)phenoxy)-6-hydroxybenzo[b]thiophen-2-yl)(o-tolyl)methanone

142
(3-(4-((1-(3-fluoropropyl)azetidin-3-yl)oxy)phenoxy)-6-((tetrahydro-2H-pyran-2-yl)oxy)benzo[b]thiophen-2-yl)(o-tolyl)methanone

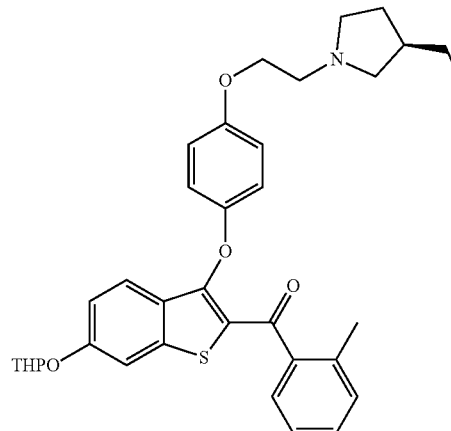

p-TsOH

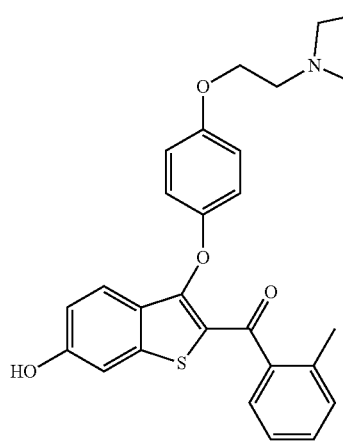

The preparation of (R)-(3-(4-(2-(3-(fluoromethyl)pyrrolidin-1-yl)ethoxy)phenoxy)-6-hydroxybenzo[b]thiophen-2-yl)(o-tolyl)methanone was followed by the procedure of (3-(4-(2-(3-(fluoromethyl)azetidin-1-yl)ethoxy)phenoxy)-6-hydroxybenzo[b]thiophen-2-yl)(o-tolyl)methanone (yield). $^1$H NMR (400 MHz, Acetone-d6) δ 7.44-7.32 (m, 3H), 7.31-7.22 (m, 1H), 7.17-7.09 (m, 2H), 6.98 (dd, J=8.8, 2.1 Hz, 1H), 6.73 (d, J=6.9 Hz, 2H), 6.45 (dJ=6.9 Hz, 2H), 4.34 (dd, J=47.6, 6.8 Hz, 2H), 4.12-4.07 (m, 2H), 2.92-2.90 (m, 2H), 2.81-2.78 (m, 2H), 2.72-2.43 (m, 3H), 2.15 (s, 3H), 2.00-1.85 (m, 1H), 1.56-1.52 (m, 1H). $^{13}$C NMR (101 MHz, Acetone-d6) δ 189.85, 158.89, 154.30, 152.37, 149.53, 141.87, 139.79, 135.31, 130.26, 129.77, 127.36, 126.41, 126.16, 125.03, 124.88, 116.03, 115.98, 115.16, 108.01, 85.46 (d, J=167.1 Hz), 67.12, 56.28 (d, J=5.1 Hz), 54.24, 53.83, 37.68 (d, J=18.7 Hz), 25.75 (d, J=6.9 Hz), 18.48. LCMS (m/z): [M+H]$^+$ calcd. for C$_{29}$H$_{28}$FNO$_4$S, 506.60; observed, 506. HPLC purity: 98.20%

The preparation of (3-(4-((1-(3-fluoropropyl)azetidin-3-yl)oxy)phenoxy)-6-((tetrahydro-2H-pyran-2-yl)oxy)benzo[b]thiophen-2-yl)(o-tolyl)methanone was followed by the procedure of (3-(4-(2-(3-(fluoromethyl)azetidin-1-yl)ethoxy)phenoxy)-6-((tetrahydro-2H-pyran-2-yl)oxy)benzo[b]thiophen-2-yl)(o-tolyl)methanone.

(3-(4-((1-(3-fluoropropyl)azetidin-3-yl)oxy)phenoxy)-6-hydroxybenzo[b]thiophen-2-yl)(o-tolyl)methanone

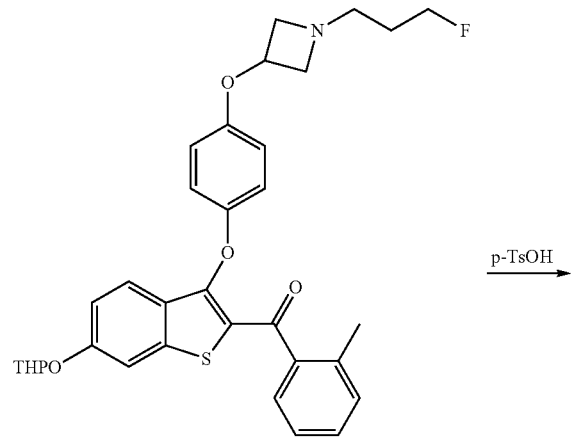

p-TsOH

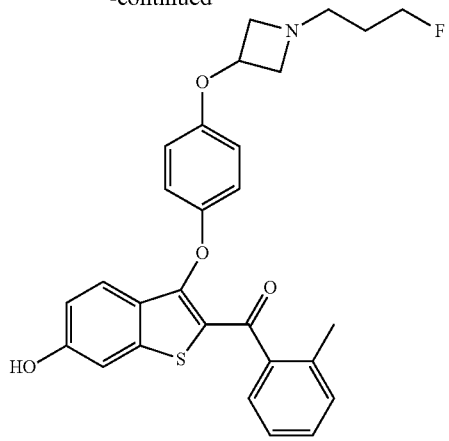

The preparation of (3-(4-((1-(3-fluoropropyl)azetidin-3-yl)oxy)phenoxy)-6-hydroxybenzo[b]thiophen-2-yl)(o-tolyl)methanone was followed by the procedure of (3-(4-(2-(3-(fluoromethyl)azetidin-1-yl)ethoxy)phenoxy)-6-hydroxybenzo[b]thiophen-2-yl)(o-tolyl)methanone (Yield). $^1$H NMR (400 MHz, Acetone-d6) δ 7.43-7.41 (m, 2H), 7.36 (d, J=7.6 Hz, 1H), 7.32-7.26 (m, 1H), 7.14 (t, J=7.7 Hz, 2H), 6.98 (dd, J=8.8, 1.9 Hz, 1H), 6.61 (d, J=9.0 Hz, 2H), 6.44 (d, J=9.0 Hz, 2H), 4.68 (dt, J=11.3, 5.7 Hz, 1H), 4.49 (dt, J=47.5, 6.1 Hz, 2H), 3.78-3.73 (m, 2H), 2.98-2.95 (m, 2H), 2.57 (t, J=6.9 Hz, 2H), 2.13 (s, 3H), 1.82-1.65 (m, 2H). $^{13}$C NMR (101 MHz, Acetone-d6) δ 189.79, 158.84, 152.67, 152.63, 149.41, 141.85, 139.71, 135.36, 130.27, 129.83, 127.41, 126.44, 126.26, 125.04, 124.82, 116.03 (2C), 115.22, 107.97, 81.79 (d, J=162.5 Hz), 66.81, 61.05, 55.13 (d, J=5.6 Hz), 18.44. LCMS (m/z): [M+H]$^+$ calcd. for C$_{28}$H$_{26}$FNO$_4$S, 492.58; observed, 492.6. HPLC purity: 98.68%

(E)-3-(4-((2-(4-chloro-2,6-dimethylbenzoyl)-6-hydroxybenzo[b]thiophen-3-yl)oxy)phenyl)-1-(3-(fluoromethyl)azetidin-1-yl)prop-2-en-1-one

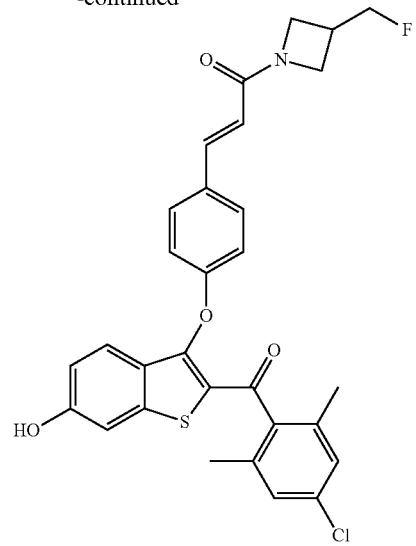

$^1$H NMR (400 MHz, DMSO-d6) δ 7.50 (d, J=8.8 Hz, 2H), 7.40 (d, J=2.1 Hz, 1H), 7.35 (d, J=15.6 Hz, 1H), 7.27 (d, J=8.8 Hz, 1H), 6.97 (s, 2H), 6.91 (dd, J=8.9, 2.1 Hz, 1H), 6.58 (d, J=15.7 Hz, 1H), 6.52 (d, J=8.5 Hz, 2H), 4.60 (dd, J=47.2, 5.6 Hz, 2H), 4.35 (t, J=8.6 Hz, 1H), 4.11-3.94 (m, 2H), 3.72 (dd, J=10.0, 5.6 Hz, 1H), 3.04-2.90 (m, 1H), 2.03 (s, 6H). $^{13}$C NMR (101 MHz, DMSO-d6) δ 190.47, 165.72, 159.96, 158.50, 149.03, 142.16, 139.60, 139.20, 136.08, 133.39, 130.00, 129.79, 127.27, 125.32, 125.10, 117.28, 116.17, 115.26, 108.80, 84.63 (d, J=164.3 Hz), 55.38, 51.74 (d, J=7.6 Hz), 49.46 (d, J=8.5 Hz), 28.69 (d, J=20.0 Hz), 18.96.

(3-chloro-6-((tetrahydro-2H-pyran-2-yl)oxy)benzo[b]thiophen-2-yl)(phenyl)methanone

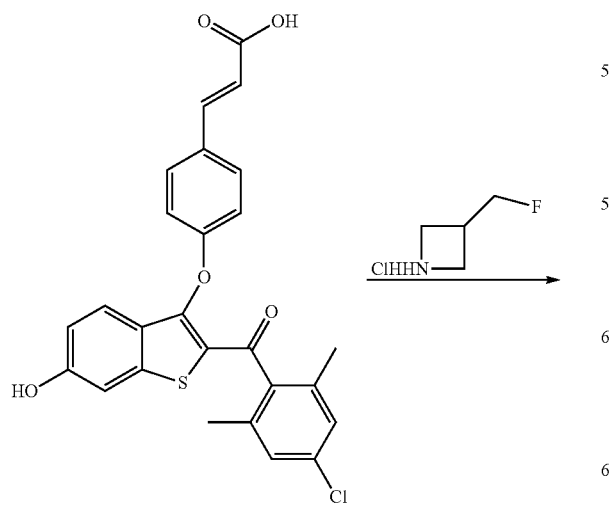

$^1$H NMR (400 MHz, Acetone-d6) δ 7.91 (d, J=8.4 Hz, 3H), 7.75-7.69 (m, 2H), 7.60 (t, J=7.7 Hz, 2H), 7.37-7.32 (m, 1H), 5.66 (t, J=3.1 Hz, 1H), 4.92 (t, J=3.6 Hz, 1H), 4.82 (t, J=3.4 Hz, 1H), 3.96-3.80 (m, 1H), 3.91-3.76 (m, 2H), 3.70-3.60 (m, 1H), 3.46-3.42 (m, 2H), 2.04-1.78 (m, 2H), 1.78-1.60 (m, 2H), 1.60-1.36 (m, 3H).

145
(4-fluoro-2,6-dimethylphenyl)(3-(4-(2-(3-(fluoromethyl)azetidin-1-yl)ethoxy)phenoxy)-6-hydroxybenzo[b]thiophen-2-yl)methanone

146
(3-(4-(2-(3-(fluoromethyl)azetidin-1-yl)ethoxy)phenoxy)-6-hydroxybenzo[b]thiophen-2-yl)(phenyl)methanone

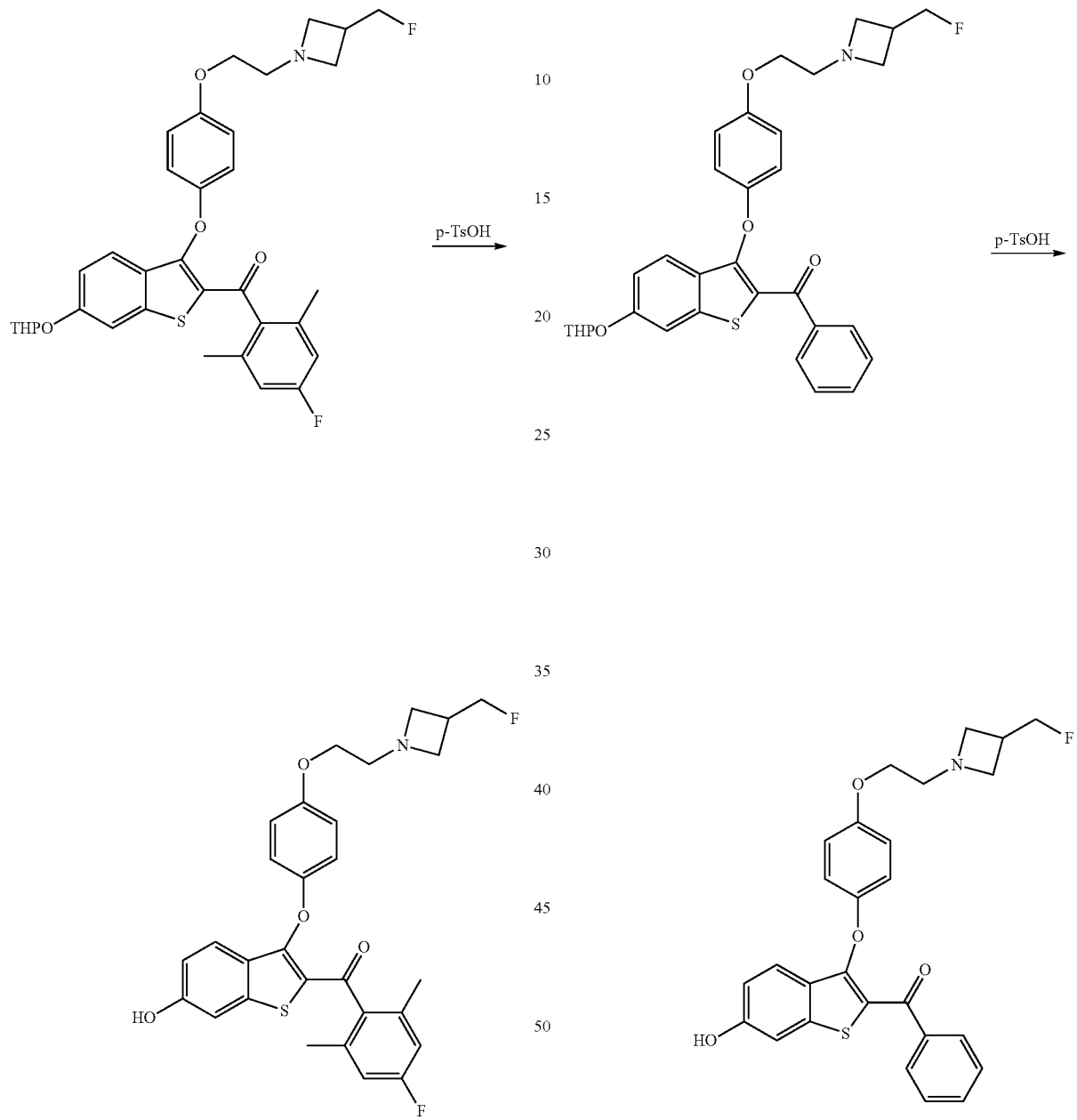

¹H NMR (400 MHz, Acetone-d6) δ 7.42 (d, J=2.0 Hz, 1H), 7.31 (d, J=8.8 Hz, 1H), 6.96 (dd, J=8.8, 2.1 Hz, 1H), 6.75-6.66 (m, 4H), 6.52-6.45 (m, 2H), 4.54 (dd, J=47.7, 6.3 Hz, 2H), 3.90 (d, J=5.6 Hz, 2H), 3.41 (t, J=7.5 Hz, 2H), 3.12 (t, J=6.5 Hz, 2H), 2.77 (m, 3H), 2.12 (s, 6H), ¹³C NMR (101 MHz, Acetone-d6) δ 190.40, 162.21 (d, J=244.4 Hz), 159.13, 154.52, 151.82, 149.70, 142.20, 137.06, 136.61 (d, J=8.6 Hz), 127.30, 125.91, 125.20, 117.70, 116.17, 115.52, 114.94, 113.64 (d, J=21.5 Hz), 108.18, 84.52 (d, J=165.1 Hz), 67.25, 57.56, 56.38 (d, J=7.7 Hz), 31.36 (d, J=20.2 Hz), 18.45.

¹H NMR (400 MHz, Acetone-d6) δ 7.72-7.66 (m, 2H), 7.51 (t, J=7.4 Hz, 1H), 7.37 (m, 2H), 7.33 (d, J=2.0 Hz, 2H), 6.93 (dd, J=8.8, 2.1 Hz, 1H), 6.73-6.67 (m, 2H), 6.62-6.52 (m, 2H), 4.52 (dd, J=47.7, 6.3 Hz, 2H), 3.85 (t, J=5.6 Hz, 2H), 3.34 (t, J=7.6 Hz, 2H), 3.09-3.02 (m, 2H), 2.71 (M, 3H). ¹³C NMR (101 MHz, Acetone-d6) δ 188.10, 154.42, 152.19, 148.90, 141.88, 139.09, 131.73, 128.55, 127.79, 124.73, 124.57, 123.72, 116.76, 116.45, 115.07, 107.98, 84.62 (d, J=165.0 Hz), 67.21, 57.64, 56.39 (d, J=7.7 Hz), 31.37 (d, J=20.1 Hz).

147

(4-fluoro-2-methylphenyl)(3-(4-(2-(3-(fluoromethyl)azetidin-1-yl)ethoxy)phenoxy)-6-hydroxybenzo[b]thiophen-2-yl)methanone

148

(3-(4-(2-(3-(fluoromethyl)azetidin-1-yl)ethoxy)phenoxy)-6-hydroxybenzo[b]thiophen-2-yl)(4-hydroxyphenyl)methanone

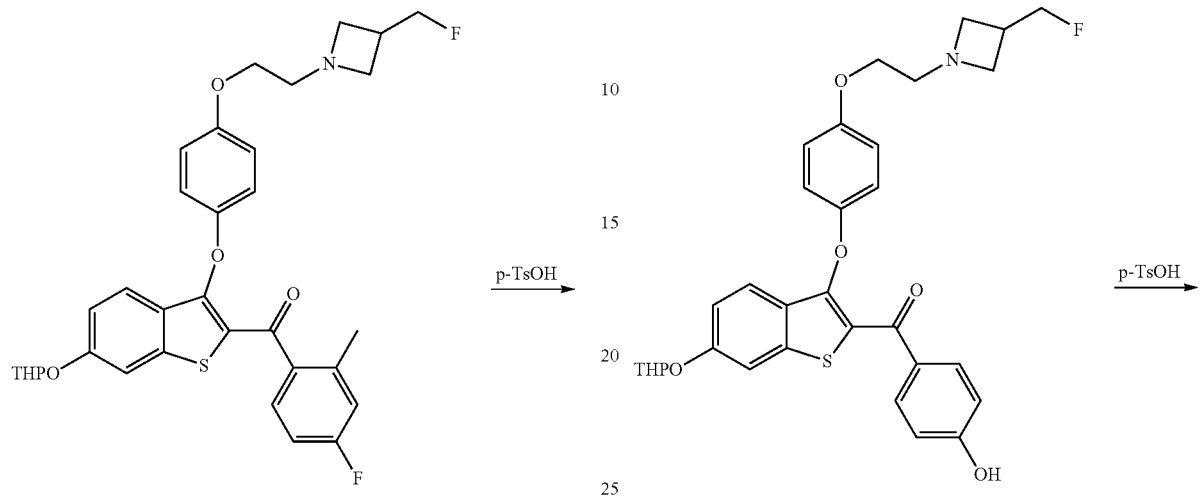

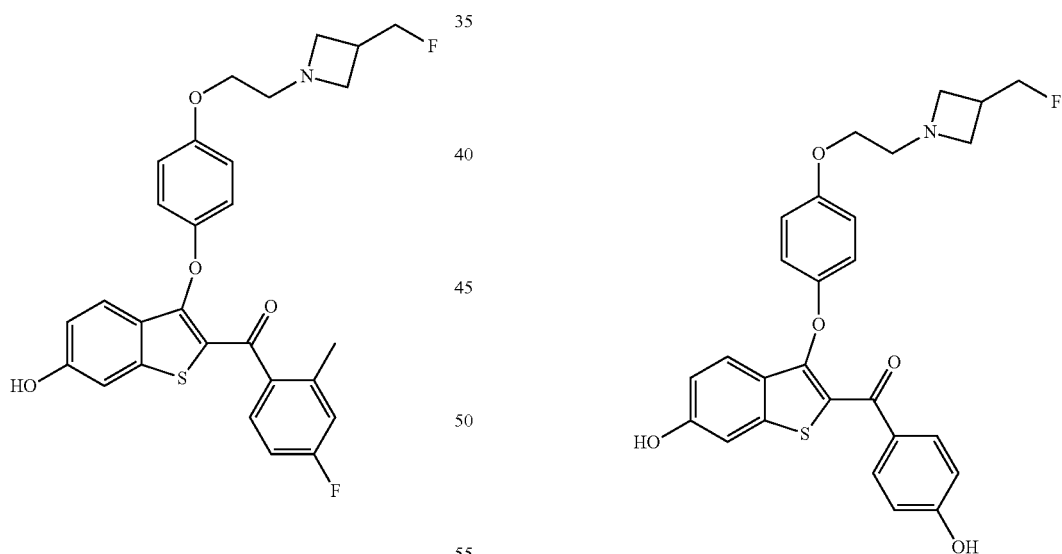

$^1$H NMR (400 MHz, Acetone-d6) δ 7.48-7.42 (m, 1H), 7.40 (d, J=9.2 Hz, 2H), 6.98 (dd, J=8.8, 2.1 Hz, 1H), 6.92 (d, J=9.2 Hz, 2H), 6.72 (d, J=9.1 Hz, 2H), 6.49 (d, J=9.1 Hz, 2H), 4.54 (dd, J=47.7, 6.3 Hz, 2H), 3.90 (t, J=5.6 Hz, 2H), 3.40 (t, J=7.2 Hz, 2H), 3.15 (t, J=6.4 Hz, 2H), 2.76 (m, 3H), 2.17 (s, 3H). $^{13}$C NMR (101 MHz, Acetone-d6) δ 188.72, 163.26 (d, J=247.5 Hz), 159.11, 154.47, 152.30, 149.52, 141.96, 139.11 (d, J=8.6 Hz), 136.03, 130.05 (d, J=9.1 Hz). 126.13 (d, J=18.6 Hz). 124.88, 116.96, 116.85 (d, J=21.6 Hz), 115.82, 115.10, 111.79 (d, J=21.6 Hz), 108.02, 84.45 (d, J=165.0 Hz), 67.16, 59.66, 57.48, 56.35 (d, J=7.6 Hz), 31.34 (d, J=20.2 Hz), 18.55.

$^1$H NMR (400 MHz, Acetone-d6) δ 7.78-7.66 (m, 2H), 7.43 (d, J=8.8 Hz, 1H), 7.39 (d, J=2.1 Hz, 1H), 6.98 (dd, J=3.6, 2.2 Hz, 1H), 6.90-6.83 (m, 2H), 6.79-6.69 (m, 2H), 6.69-6.60 (m, 2H), 4.53 (dd, J=47.7, 6.3 Hz, 2H), 3.88 (t, J=5.6 Hz, 2H), 3.39 (d, J=4.4 Hz, 2H). 3.10 (t, J=6.6 Hz, 2H), 2.88-2.61 (m, 3H). $^{13}$C NMR (101 MHz, Acetone-d6) δ 186.50, 161.77, 158.18, 154.43, 152.24, 147.16, 140.87, 131.75, 129.97, 126.01, 124.86, 124.34, 116.56, 115.77, 115.10, 114.72, 107.81, 84.51 (d, J=165.0 Hz), 67.10, 57.57, 56.34 (d, J=7.7 Hz), 31.34 (d, J=20.2 Hz). (YL-02-114)

(3-(4-(2-(3-(fluoromethyl)azetidin-1-yl)ethoxy)phenoxy)-6-hydroxybenzo[b]thiophen-2-yl)(4-hydroxy-2-methylphenyl)methanone

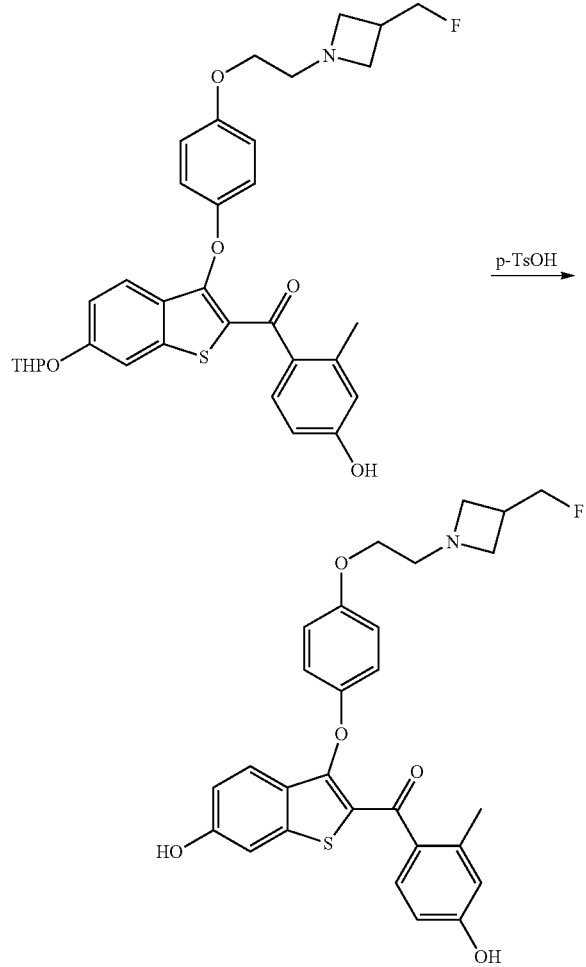

¹H NMR (400 MHz, Acetone-d6) δ 7.32 (d, J=8.5 Hz, 2H), 7.22 (d, J=1.9 Hz, 1H), 6.90 (dd, J=8.9, 2.0 Hz, 1H), 6.67 (d, J=9.1 Hz, 2H), 6.61 (dd, J=8.4, 24 Hz, 1H), 6.57 (d, J=2.1 Hz, 1H), 6.49 (d, J=9.1 Hz, 2H), 4.53 (dd, J=47.7, 6.4 Hz, 2H), 3.86 (t, J=5.6 Hz, 2H), 3.37 (dd, J=7.6, 6.3 Hz, 2H), 3.13-3.04 (t, J=6.2 Hz, 2H), 2.72 (m, 3H). ¹³C NMR (101 MHz, Acetone-d6) δ 188.39, 163.61, 160.93, 154.18, 152.73, 143.74, 141.68, 138.99, 131.47, 130.01, 124.31, 123.98, 123.77, 117.79, 117.71, 116.09, 114.92, 112.00, 108.22, 84.64 (d, J=164.9 Hz), 67.25, 57.63, 56.37 (d, J=7.7 Hz), 31.37 (d, J=20.1 Hz), 19.24, (CR-28)

Tert-butyl (R)-3-(((methylsulfonyl)oxy)methyl)pyrrolidine-1-carboxylate

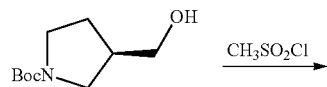 $\xrightarrow{\text{CH}_3\text{SO}_2\text{Cl}}$

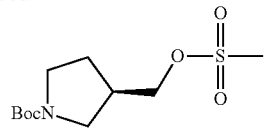

The preparation of tert-butyl (R)-3-(((methylsulfonyl)oxy)methyl)pyrrolidine-1-carboxylate was followed procedure ethylsulfonyl)oxy)methyl)azetidine-4-carboxylate. ¹H NMR (400 MHz, DMSO-d₆): δ 4.26-4.11 (m, 2H), 3.44-3.28 (m, 2H), 3.26-3.14 (m, 1H), 3.18 (s, 3H), 3.05-2.93 (m, 1H), 2.62-2.49 (m, 1H), 2.00-1.87 (m, 1H), 1.72-1.56 (m, 1H), 1.40 (s, 9H).

(R)-tert-Butyl 3-(fluoromethyl)pyrrolidine-1-carboxylate

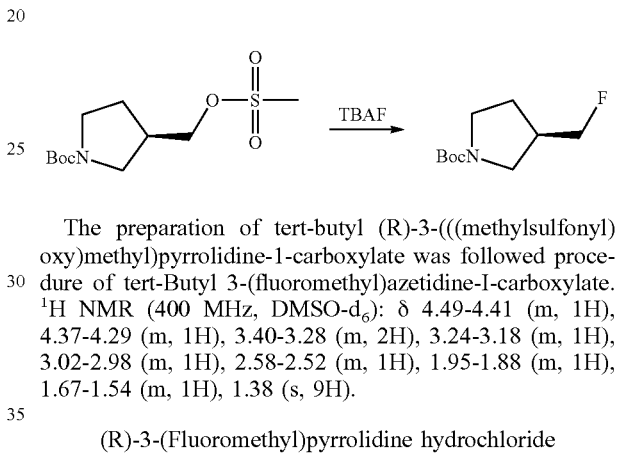

The preparation of tert-butyl (R)-3-(((methylsulfonyl)oxy)methyl)pyrrolidine-1-carboxylate was followed procedure of tert-Butyl 3-(fluoromethyl)azetidine-I-carboxylate. ¹H NMR (400 MHz, DMSO-d₆): δ 4.49-4.41 (m, 1H), 4.37-4.29 (m, 1H), 3.40-3.28 (m, 2H), 3.24-3.18 (m, 1H), 3.02-2.98 (m, 1H), 2.58-2.52 (m, 1H), 1.95-1.88 (m, 1H), 1.67-1.54 (m, 1H), 1.38 (s, 9H).

(R)-3-(Fluoromethyl)pyrrolidine hydrochloride

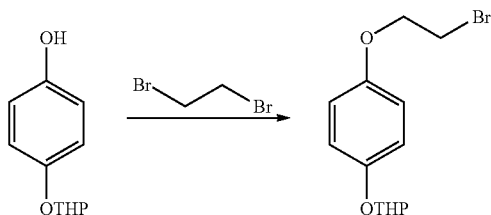

The preparation of (R)-3-(Fluoromethyl)pyrrolidine hydrochloride was followed by the procedure of 3-(fluoromethyl)azetidine hydrochloride. ¹H NMR (400 MHz, DMSO-d₆, HCl salt): δ 9.35 (brs, 2H), 4.57-4.47 (m, 1H), 4.44-4.33 (m, 1H), 3.33-3.10 (m, 3H), 2.95-2.87 (m, 1H), 2.69-2.57 (m, 1H), 205-1.97 (m, 1H), 1.70-1.81 (m, 1H).

2-(4-(2-bromoethoxy)phenoxy)tetrahydro-2H-pyran

To a solution of tetrahydrofuran (30 mL) was added (2 g, 10.2 mmol) deoxyarbutin, (1.2 mL, 0.11 mol) 1,2-dibromoethane, (1.23 g. 31 mmd) NaOH. The reaction mixture was reflux for 24 hrs and monitored by TLC. The reaction mixture was evaporated under reduced pressure and diluted by ethyl acetate, washed by water, brine and dried over Na₂SO₄. The organic extracts were evaporated under reduced pressure and purified by flash chromatography (10-25% ethyl acetate in hexanes) to give 1.4 g white solid (yield, 46%). ¹H NMR (400 MHz. Acetone-d6) δ 7.05-6.97 (m, 2H), 6.95-8.36 (m, 2H), 5.33 (t, J=3.2 Hz, 1H), 4.31 (t, J=5.7 Hz, 2H), 3.95-3.32 (m, 1H), 3.75 (t, J=5.5 Hz, 2H). 3.56-3.52 (m, 1H), 1.98-1.96 (m, 1H), 1.90-1.73 (m, 2H), 1.71-1.50 (m, 3H), ¹³C NMR (101 MHz, Acetone-d6) δ 153.18, 151.77, 117.74, 115.55, 96.95, 68.58, 61.50, 30.33, 30.29, 25.13, 18.79. (YL-02-47)

(3R)-3-(fluoromethyl)-1-(2-(4-((tetrahydro-2H-pyran-2-yl)oxy)phenoxy)ethyl) pyrrolidine

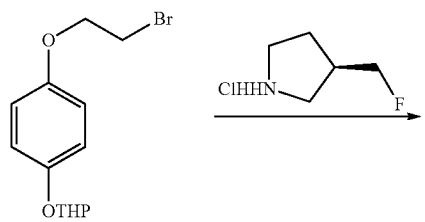

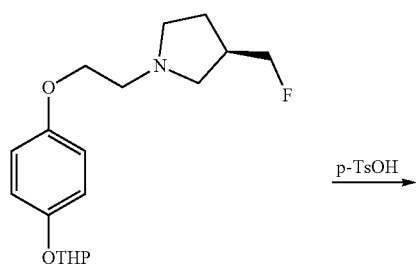

The preparation of (3R)-3-(fluoromethyl)-1-(2-(4-((tetrahydro-2H-pyran-2-yl)oxy)phenoxy)ethyl)pyrrolidine was followed by the procedure of 3-(fluoromethyl)-1-(2-(4-((tetrahydro-2H-pyran-2-yl)oxy)phenoxy)ethyl)azetidine. (Yield)¹H NMR (400 MHz, CDCl₃) δ 7.00 (d, J=3.9 Hz, 2H), 6.85 (d, J=8.9 Hz, 2H), 5.31 (t, J=3.1 Hz, 1H), 4.36 (dd, J=47.4, 6.6 Hz, 2H), 4.09 (t, J=5.7 Hz, 2H), 3.99-3.91 (m, 1H), 3.68-3.55 (m, 1H), 3.03-2.81 (m, 3H), 2.81-2.46 (m, 4H), 2.13-1.93 (m, 2H), 1.91-1.78 (m, 2H), 1.77-1.48 (m, 4H). ¹³C NMR (101 MHz, CDCl₃) δ 153.63, 151.29, 117.76, 115.40, 97.30, 85.80 (d, J=168.8 Hz), 67.27, 62.10, 56.65 (d, J=5.2 Hz), 54.86, 54.32, 37.71 (d, J=18.7 Hz), 30.50, 26.12 (d, J=6.8 Hz), 25.26, 18.94. (YL-02-67)

(R)-4-(2-(3-(fluoroethyl)pyrrolidin-1-yl)ethoxy)phenol

The preparation of (R)-4-(2-(3-(fluoromethyl) pyrrolidin-1-yl)ethoxy)phenol was followed by the procedure of 4-(2-(3-(fluoromethyl)azetidin-1-yl)ethoxy)phenol. H NMR (400 MHz, CDCl₃) δ 6.72-6.63 (m, 4H), 4.45-4.32 (m, 2H), 4.02 (t, J=5.7 Hz, 2H), 2.99-286 (m, 3H), 2.86-2.76 (m, 1H), 2.76-2.47 (m, 3H), 2.09-1.95 (m, 1H), 1.59 (dq, J=8.0, 6.0 Hz, 1H). ¹³C NMR (101 MHz, CDCl₃) δ 152.40, 150.22, 116.46, 115.56, 85.67 (d, J=168.8 Hz), 67.25, 56.82 (d, J=5.0 Hz), 55.01, 54.51, 37.61 (d, J=18.8 Hz), 26.04 (d, J=6.7 Hz). ¹³C NMR (101 MHz, CDCl₃) δ 152.40, 150.22, 116.46, 115.56, 85.67 (d, J 168.8 Hz), 67.25, 56.82 (d, J=5.0 Hz), 55.01, 54.51, 37.61 (d, J=18.8 Hz), 26.04 (d, J=6.7 Hz). (YL-02-83)

(3-chloro-6-methoxybenzo[b]thiophen-2-yl)(4-fluoro-2,6-dimethylphenyl) methanone

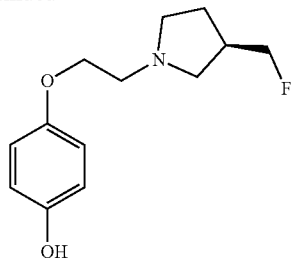

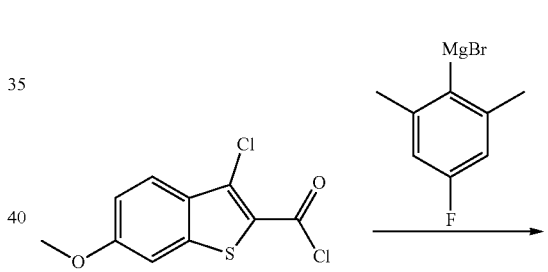

¹H NMR (400 MHz, CDCl₃) δ 7.79 (d, J=9.0 Hz, 1H), 7.25 (d, J=2.0 Hz, 1H), 7.09 (dd, J=9.0, 2.1 Hz, 1H), 6.80 (d, J=9.5 Hz, 2H), 3.91 (s, 3H), 2.21 (s, 6H). ¹³C NMR (100 MHz, CDCl3) δ 191.75, 162.97 (d, J=247.5 Hz), 161.25, 142.26, 137.08 (d, J=8.6 Hz), 136.28 (d, J=3.0 Hz), 134.27, 131.68, 126.98, 125.60, 117.02, 114.67 (d, J=21.3 Hz), 104.51, 55.92, 19.43, 19.42.

153

(3-chloro-6-hydroxybenzo[b]thiophen-2-yl)(4-fluor-2,6-dimethylphenyl) methanone

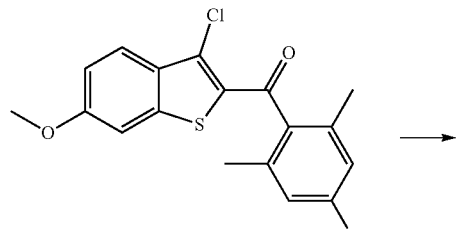

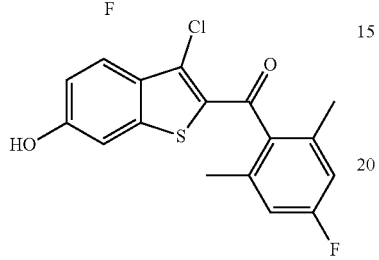

$^1$H NMR (400 MHz, Acetone-d6) δ 9.40 (s, 1H), 7.83 (d, J=3.9 Hz, 1H), 7.45 (d, J=2.1 Hz, 1H). 7.17 (dd, J=8.9, 2.2 Hz, 1H). 6.97 (d, J=9.7 Hz, 2H), 2.22 (s, 6H). $^{13}$C NMR (101 MHz, Acetone-d6) δ 190.54, 162.78 (d, J=245.6 Hz), 159.41, 141.93, 137.03 (d, J=8.7 Hz), 136.72 (d, J=2.7 Hz), 133.47, 130.57, 126.02, 125.54, 117.05, 114.28 (d, J=21.7 Hz), 107.62, 18.34. (YL-02-36)

(3-chloro-6-((tetrahydro-2H-pyran-2-yl)oxy)benzo[b]thiophen-2-yl)(4-fluoro-2,6-dimethylphenyl)-methanone

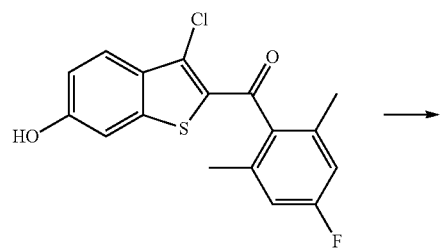

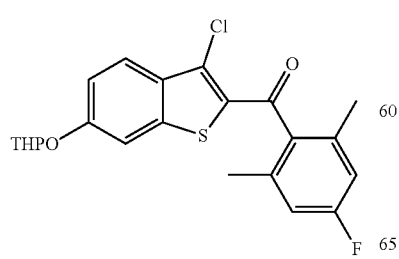

154

$^1$H NMR (400 MHz, Acetone-d6) δ 7.89 (d, J=9.0 Hz, 1H), 7.73 (d, J=2.1 Hz, 1H), 7.31 (dd, J=9.0, 2.2 Hz, 1H), 6.98 (d, J=98 Hz, 2H), 5.67 (t, J=3.1 Hz, 1H), 3.88-3.78 (m, 1H), 3.70-3.57 (m, 1H), 2.23 (s, 6H), 1.91-1.89 (m, 2H), 1.68-1.64 (m, 4H). $^{13}$C NMR (101 MHz, Acetone-d6) δ 190.66, δ 161.47 (d, J=242.4 Hz), 158.63, 141.48, 137.07 (d, J=8.3 Hz), 136.12, 133.19, 131.75, 125.12, 118.02, 116.59, 114.32 (d, J=21.6 Hz), 108.54, 96.46, 61.69, 29.91, 24.90, 18.42, 18.34. (YL-03-105) (YL-02-62)

(4-fluoro-2,6-dimethylphenyl)(3-(4-(2-((R)-3-(fluoromethyl)pyrrolidin-1-yl)ethoxy)phenoxy)-6-(tetrahydro-2H-pyran-2-yl)benzo[b]thiophen-2-yl)methanone

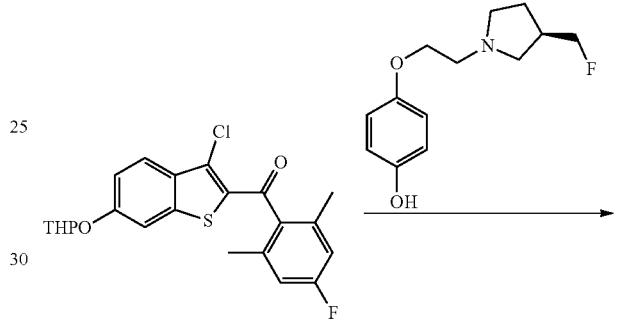

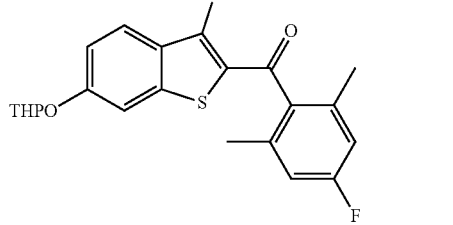

$^1$H NMR (400 MHz, Acetone-d6) δ 7.69 (d, J=2.0 Hz, 1H), 7.37 (d, J=3.9 Hz, 1H), 7.09 (dd, J=8.9, 2.1 Hz, 1H), 6.80-6.73 (m, 2H), 6.70 (d, J=9.7 Hz, 2H), 6.55-6.44 (m, 2H), 5.64 (t, J=2.9 Hz, 1H). 4.31 (dd, J=47.7, 6.7 Hz, 2H), 4.04 (t, J=5.9 Hz, 2H), 3.90-3.76 (m, 1H), 3.70-3.54 (m, 1H), 2.62 (d, J=5.3 Hz, 2H), 2.72-2.62 (m, 2H), 2.59-2.45 (m, 2H), 2.13 (s, 6H), 1.90-1.83 (m, 4H), 1.78-1.52 (m, 4H), 1.52-1.35 (m, 1H). $^{13}$C NMR (101 MHz, Acetone-d6) δ 190.55, 162.26 (d, J=244.5 Hz), 158.28, 154.58, 151.32, 149.44, 141.73, 136.95, 136.65 (d, J=8.6 Hz), 128.41, 127.28, 124.82, 117.08, 115.58, 115.08, 113.69 (d, J=21.5 Hz), 109.10, 96.40, 85.68 (d, J=167.2 Hz), 67.58, 61.70, 56.42 (d, J=5.2 Hz), 54.33, 53.83, 37.76 (d, J=13.6 Hz), 29.94, 25.85 (d, J=6.9 Hz), 24.92, 18.47. (YL-03-125)

(R)-(4-fluoro-2,6-dimethylphenyl)(3-(4-(2-(3-(fluoromethyl)pyrrolidin-1-yl) ethoxy)phenoxy)-6-hydroxybenzo[b]thiophen-2-yl)methanone

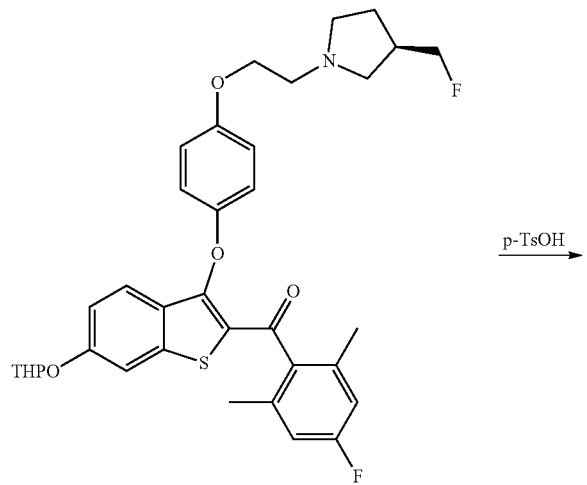

$\xrightarrow{\text{p-TsOH}}$

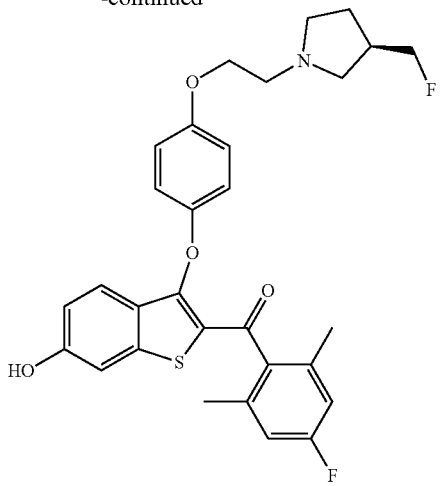

$^1$H NMR (400 MHz, Acetone-d6) δ 7.45 (d, J=1.8 Hz, 1H), 7.30 (d, J=8.8 Hz, 1H), 6.98 (dd, J=8.8, 2.0 Hz, 1H), 6.78-6.73 (m, 2H), 6.68 (d, J=9.8 Hz, 2H), 6.48 (d, J=9.0 Hz, 2H), 4.34 (dd, J=47.6, 6.8 Hz, 2H), 4.08 (t, J=5.7 Hz, 2H), 2.92 (t, J=5.7 Hz, 2H), 2.79-2.76 (m, 2H), 2.75-2.65 (m, 1H), 2.65-2.47 (m, 2H), 2.12 (s, 6H), 2.01-1.89 (m, 1H), 1.52-1.49 (m, 1H). $^{13}$C NMR (101 MHz, Acetone-d6) δ 190.39, 162.21 (d, J=244.4 Hz), 159.47, 154.37, 151.93, 149.75, 142.19, 137.07, 136.62 (d, J=8.6 Hz), 127.15, 125.74, 125.10, 116.33, 115.54, 115.07, 113.64 (d, J=21.5 Hz), 108.23, 85.47 (d, J=167.2 Hz), 67.14, 5630 (d, J=5.3 Hz), 54.27, 53.86, 37.69 (d, J=18.7 Hz), 25.78 (d, J=6.9 Hz), 18.48. LC-MS: M+H=538.6

TABLE 1

| Compound No. | Structure | Chemical name | Characterization |
|---|---|---|---|
| 1 | 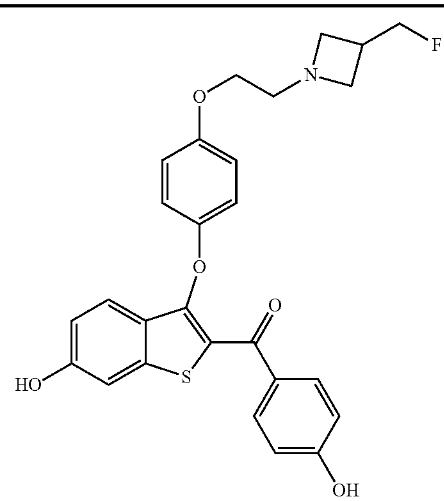 | (3-(4-(2-(3-(fluoromethyl) azetidin-1-yl)ethoxy)phenoxy)-6-hydroxybenzo[b] thiophen-2-yl)(4-hydroxyphenyl) methanone | M + H = 494.5 $^1$H NMR (400 MHz, Acetone-d6) δ 7.78-7.66 (m, 2H), 7.43 (d, J = 8.8 Hz, 1H), 7.39 (d, J = 2.1 Hz, 1H), 6.98 (dd, J = 8.8, 2.2 Hz, 1H), 6.90-6.83 (m, 2H), 6.79-6.69 (m, 2H), 6.69-6.60 (m, 2H), 4.53 (dd, J = 47.7, 6.3 Hz, 2H), 3.88 (t, J = 5.6 Hz, 2H), 3.39 (d, J = 4.4 Hz, 2H), 3.10 (t, J = 6.6 Hz, 2H), 2.88-2.61 (m, 3H). |

TABLE 1-continued

| Compound No. | Structure | Chemical name | Characterization |
|---|---|---|---|
| 2 | 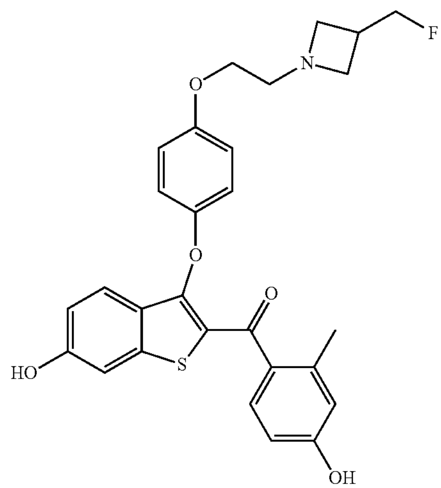 [SMILES: Cc1cc(O)ccc1C(=O)c1sc2cc(O)ccc2c1Oc1ccc(OCCN2CC(CF)C2)cc1] | (3-(4-(2-(3-(fluoromethyl)azetidin-1-yl)ethoxy)phenoxy)-6-hydroxybenzo[b]thiophen-2-yl)(4-hydroxy-2-methylphenyl)methanone | M + H = 508.6<br>$^1$H NMR (400 MHz, Acetone-d6) δ 7.32 (d, J = 8.5 Hz, 2H), 7.22 (d, J = 1.9 Hz, 1H), 6.90 (dd, J = 8.9, 2.0 Hz, 1H), 6.67 (d, J = 9.1 Hz, 2H), 6.61 (dd, J = 8.4, 2.4 Hz, 1H), 6.57 (d, J = 2.1 Hz, 1H), 6.49 (d, J = 9.1 Hz, 2H), 4.53 (dd, J = 47.7, 6.4 Hz, 2H), 3.86 (t, J = 5.6 Hz, 2H), 3.37 (dd, J = 7.6, 6.3 Hz, 2H), 3.13-3.04 (t, J = 6.2 Hz, 2H), 2.72-2.69 (m, 3H), 2.09 (s, 3H). |
| 3 | 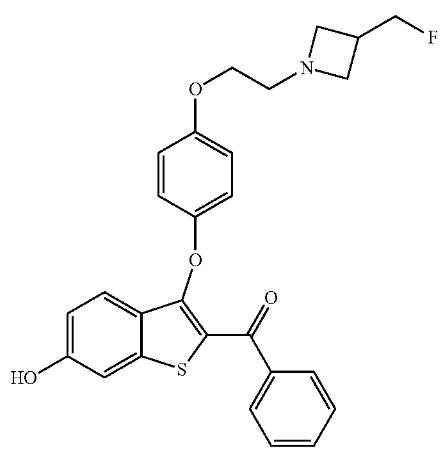 [SMILES: O=C(c1ccccc1)c1sc2cc(O)ccc2c1Oc1ccc(OCCN2CC(CF)C2)cc1] | (3-(4-(2-(3-(fluoromethyl)azetidin-1-yl)ethoxy)phenoxy)-6-hydroxybenzo[b]thiophen-2-yl)(phenyl)methanone | M + H = 478.6<br>$^1$H NMR (400 MHz, Acetone-d6) δ 7.72-7.66 (m, 2H), 7.51 (t, J = 7.4 Hz, 1H), 7.37-7.34 (m, 2H), 7.33 (d, J = 2.0 Hz, 2H), 6.93 (dd, J = 8.8, 2.1 Hz, 1H), 6.73-6.67 (m, 2H), 6.62-6.52 (m, 2H), 4.52 (dd, J = 47.7, 6.3 Hz, 2H), 3.85 (t, J = 5.6 Hz, 2H), 3.34 (t, J = 7.6 Hz, 2H), 3.09-3.02 (m, 2H), 2.71-2.69 (m, 3H). |
| 4 | 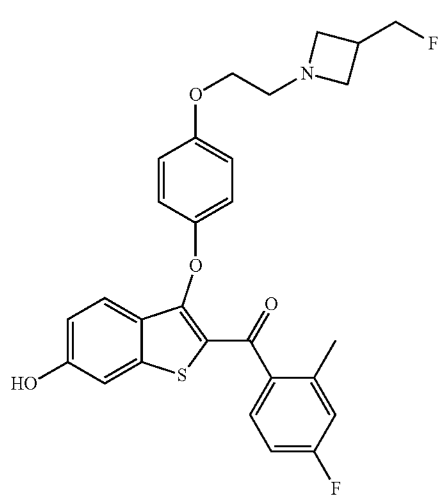 [SMILES: Cc1cc(F)ccc1C(=O)c1sc2cc(O)ccc2c1Oc1ccc(OCCN2CC(CF)C2)cc1] | (4-fluoro-2-methylphenyl)(3-(4-(2-(3-(fluoromethyl)azetidin-1-yl)ethoxy)phenoxy)-6-hydroxybenzo[b]thiophen-2-yl)methanone | M + H = 510.16<br>$^1$H NMR (400 MHz, Acetone-d6) δ 7.48-7.42 (m, 1H), 7.40 (d, J = 9.2 Hz, 2H), 6.98 (dd, J = 8.8, 2.1 Hz, 1H), 6.92 (d, J = 9.2 Hz, 2H), 6.72 (d, J = 9.1 Hz, 2H), 6.49 (d, J = 9.1 Hz, 2H), 4.54 (dd, J = 47.7, 6.3 Hz, 2H), 3.90 (t, J = 5.6 Hz, 2H), 3.40 (t, J = 7.2 Hz, 2H), 3.15 (t, J = 6.4 Hz, 2H), 2.76-2.74 (m, 3H), 2.17 (s, 3H). |

TABLE 1-continued

| Compound No. | Structure | Chemical name | Characterization |
|---|---|---|---|
| 5 | 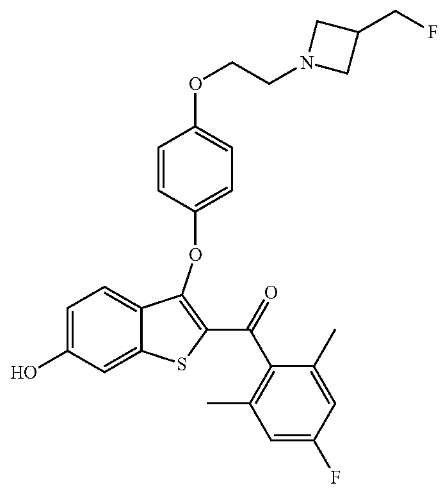 [SMILES: Cc1cc(F)cc(C)c1C(=O)c1sc2cc(O)ccc2c1Oc1ccc(OCCN2CC(CF)C2)cc1] | (4-fluoro-2,6-dimethylphenyl)(3-(4-(2-(3-(fluoromethyl)azetidin-1-yl)ethoxy)phenoxy)-6-hydroxybenzo[b]thiophen-2-yl)methanone | M + H = 524.6<br>$^1$H NMR (400 MHz, Acetone-d6) δ 7.42 (d, J = 2.0 Hz, 1H), 7.31 (d, J = 8.8 Hz, 1H), 6.96 (dd, J = 8.8, 2.1 Hz, 1H), 6.75-6.66 (m, 4H), 6.52-6.45 (m, 2H), 4.54 (dd, J = 47.7, 6.3 Hz, 2H), 3.90 (d, J = 5.6 Hz, 2H), 3.41 (t, J = 7.5 Hz, 2H), 3.12 (t, J = 6.5 Hz, 2H), 2.77-2.75 (m, 3H), 2.12 (s, 6H). |
| 6 | 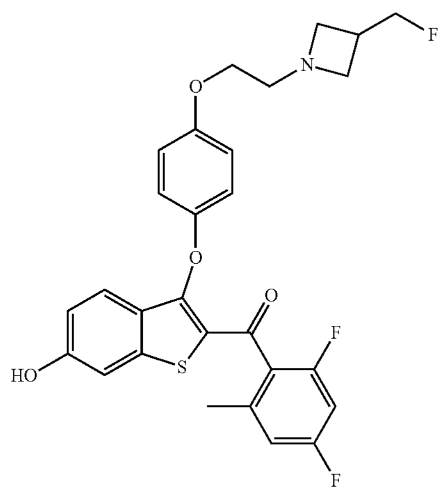 | (2,4-difluoro-6-methylphenyl)(3-(4-(2-(3-(fluoromethyl)azetidin-1-yl)ethoxy)phenoxy)-6-hydroxybenzo[b]thiophen-2-yl)methanone | M + H = 528.3 |
| 7 | 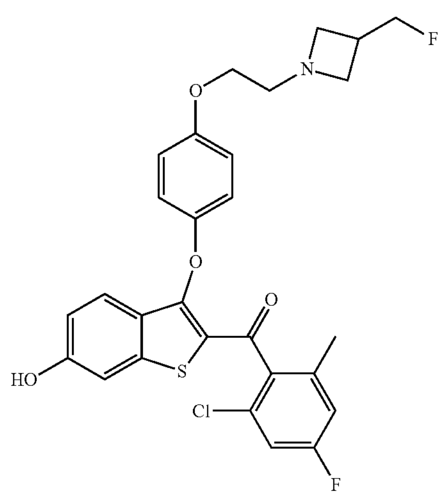 [SMILES: Cc1cc(F)cc(Cl)c1C(=O)c1sc2cc(O)ccc2c1Oc1ccc(OCCN2CC(CF)C2)cc1] | (2-chloro-4-fluoro-6-methylphenyl)(3-(4-(2-(3-(fluoromethyl)azetidin-1-yl)ethoxy)phenoxy)-6-hydroxybenzo[b]thiophen-2-yl)methanone | M + H = 544.1 |

TABLE 1-continued

| Compound No. | Structure | Chemical name | Characterization |
|---|---|---|---|
| 8 | 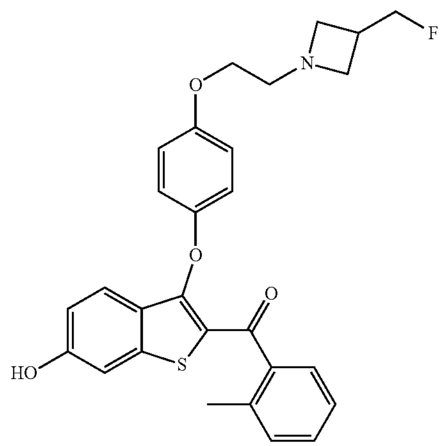 [SMILES: Cc1ccccc1C(=O)c1sc2cc(O)ccc2c1Oc1ccc(OCCN2CC(CF)C2)cc1] | (3-(4-(2-(3-(fluoromethyl)azetidin-1-yl)ethoxy)phenoxy)-6-hydroxybenzo[b]thiophen-2-yl)(o-tolyl)methanone | M + H = 492.1<br>$^1$H NMR (400 MHz, CDCl$_3$) δ 7.37-7.15 (m, 4H), 7.08-7.06 (m, 2H), 6.81 (dd, J = 8.8, 1.9 Hz, 1H), 6.50 (d, J = 9.1 Hz, 2H), 6.32 (d, J = 9.0 Hz, 2H), 4.46 (dd, J = 47.3, 4.7 Hz), 4.10 (brs, 1H), 3.93 (d, J = 4.7 Hz, 2H), 3.72 (d, J = 7.7 Hz, 2H), 3.39 (t, J = 7.2 Hz, 2H), 2.99 (brs, 2H), 2.16 (s, 3H). |
| 9 | 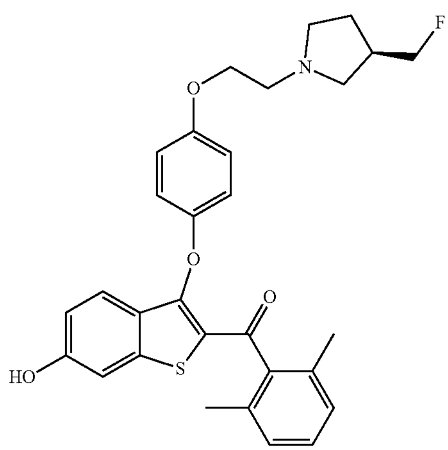 | (R)-(2,6-dimethylphenyl)(3-(4-(2-(3-(fluoromethyl)pyrrolidin-1-yl)ethoxy)phenoxy)-6-hydroxybenzo[b]thiophen-2-yl)methanone | M + H = 523.6 |
| 10 | 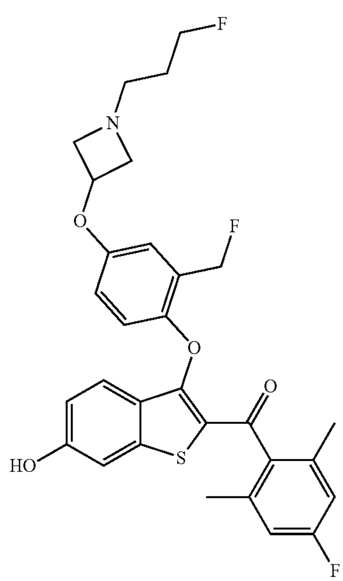 [SMILES: Cc1cc(F)cc(C)c1C(=O)c1sc2cc(O)ccc2c1Oc1ccc(OC2CN(CCCF)C2)cc1CF] | (4-fluoro-2,6-dimethylphenyl)(3-(2-(fluoromethyl)-4-((1-(3-fluoropropyl)azetidin-3-yl)oxy)phenoxy)-6-hydroxybenzo[b]thiophen-2-yl)methanone | M + H = 556.1 |

| Compound No. | Structure | Chemical name | Characterization |
|---|---|---|---|
| 11 | 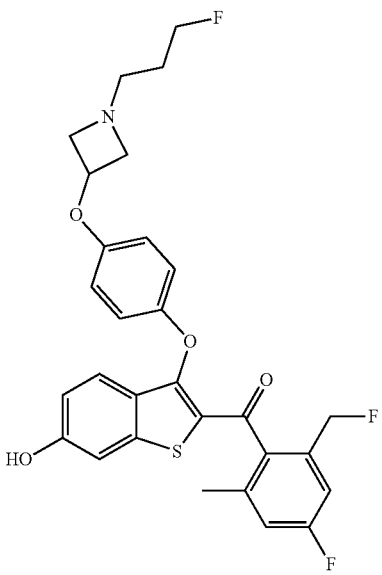 [SMILES: Cc1cc(F)cc(CF)c1C(=O)c1sc2cc(O)ccc2c1Oc1ccc(OC2CN(CCCF)C2)cc1] | (4-fluoro-2-(fluoromethyl)-6-methylphenyl)(3-(4-((1-(3-fluoropropyl)azetidin-3-yl)oxy)phenoxy)-6-hydroxybenzo[b]thiophen-2-yl)methanone | M + H = 542.1 |
| 12 | 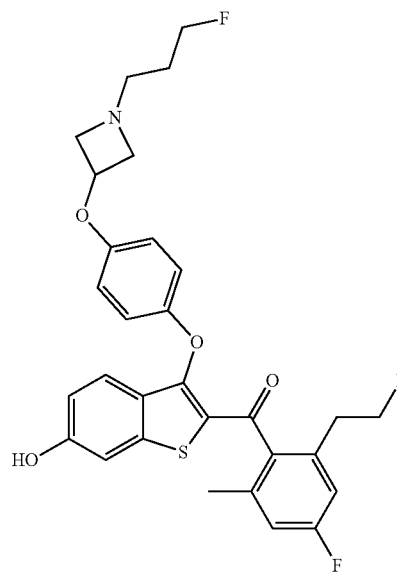 | (4-fluoro-2-(2-fluoroethyl)-6-methylphenyl)(3-(4-((1-(3-fluoropropyl)azetidin-3-yl)oxy)phenoxy)-6-hydroxybenzo[b]thiophen-2-yl)methanone | M + H = 556.2 |

TABLE 1-continued

| Compound No. | Structure | Chemical name | Characterization |
|---|---|---|---|
| 13 | 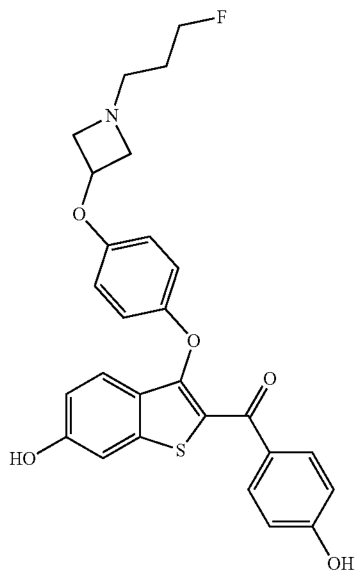 [SMILES: O=C(c1ccc(O)cc1)c1sc2cc(O)ccc2c1Oc1ccc(OC2CN(CCCF)C2)cc1] | (3-(4-((1-(3-fluoropropyl)azetidin-3-yl)oxy)phenoxy)-6-hydroxybenzo[b]thiophen-2-yl)(4-hydroxyphenyl)methanone | M + H = 494.2 |
| 14 | 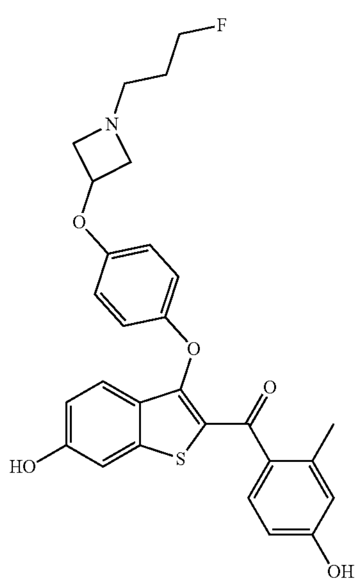 [SMILES: Cc1cc(O)ccc1C(=O)c1sc2cc(O)ccc2c1Oc1ccc(OC2CN(CCCF)C2)cc1] | (3-(4-((1-(3-fluoropropyl)azetidin-3-yl)oxy)phenoxy)-6-hydroxybenzo[b]thiophen-2-yl)(4-hydroxy-2-methylphenyl)methanone | M + H = 508.15 |

TABLE 1-continued

| Compound No. | Structure | Chemical name | Characterization |
|---|---|---|---|
| 15 | 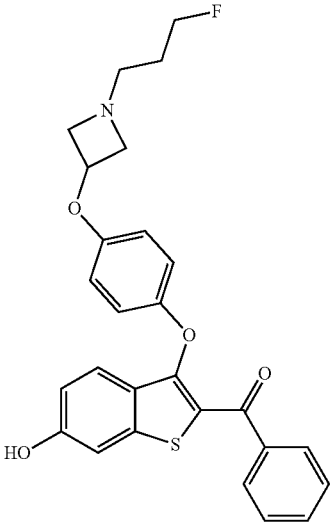 [SMILES: O=C(c1ccccc1)c1sc2cc(O)ccc2c1Oc1ccc(OC2CN(CCCF)C2)cc1] | (3-(4-((1-(3-fluoropropyl)azetidin-3-yl)oxy)phenoxy)-6-hydroxybenzo[b]thiophen-2-yl)(phenyl)methanone | M + H = 478.14<br>$^1$H NMR (400 MHz, Acetone-d6) δ 7.73-7.69 (m, 2H), 7.57-7.51 (m, 1H), 7.45-7.37 (m, 4H), 6.99 (dd, J = 8.9, 2.1 Hz, 1H), 6.66-6.53 (m, 4H), 4.67 (p, J = 5.7 Hz, 1H), 4.48 (dt, J = 47.5, 6.1 Hz, 2H), 3.80-3.68 (m, 2H), 3.05-2.89 (m, 2H), 2.58 (t, J = 7.0 Hz, 2H), 1.82-1.63 (m, 2H). |
| 16 | 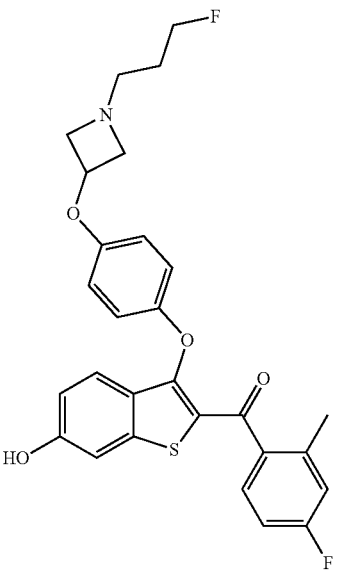 [SMILES: Cc1cc(F)ccc1C(=O)c1sc2cc(O)ccc2c1Oc1ccc(OC2CN(CCCF)C2)cc1] | (4-fluoro-2-methylphenyl)(3-(4-((1-(3-fluoropropyl)azetidin-3-yl)oxy)phenoxy)-6-hydroxybenzo[b]thiophen-2-yl)methanone | M + H = 510.15<br>$^1$H NMR (400 MHz, Acetone-d6) δ 7.47-7.39 (m, 3H), 6.98 (dd, J = 8.8, 2.2 Hz, 1H), 6.94-6.86 (m, 2H), 6.63 (d, J = 9.1 Hz, 2H), 6.47 (d, J = 9.1 Hz, 2H), 4.77-4.64 (m, 1H), 4.49 (dt, J = 47.5, 6.1 Hz, 2H), 3.77 (t, J = 7.0 Hz, 2H), 3.06-2.96 (m, 2H), 2.59 (t, J = 6.9 Hz, 2H), 2.14 (s, 3H), 1.83-1.65 (m, 2H). |

TABLE 1-continued

| Compound No. | Structure | Chemical name | Characterization |
|---|---|---|---|
| 17 | 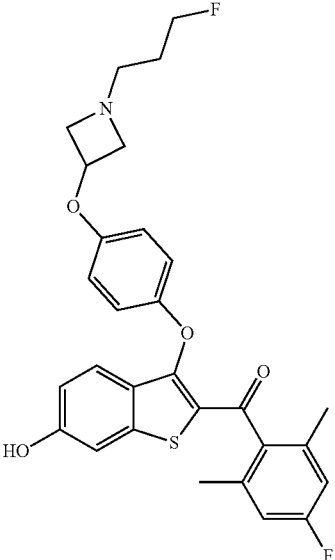 | (4-fluoro-2,6-dimethylphenyl)(3-(4-((1-(3-fluoropropyl)azetidin-3-yl)oxy)phenoxy)-6-hydroxybenzo[b]thiophen-2-yl)methanone | M + H = 524.16<br>$^1$H NMR (400 MHz, Acetone) δ 7.42 (d, J = 2.0 Hz, 1H), 7.34 (d, J = 8.8 Hz, 1H), 6.97 (dd, J = 8.8, 2.1 Hz, 1H), 6.75-6.59 (m, 4H), 6.54-6.39 (m, 2H), 4.77-4.65 (m, 1H), 4.55 (t, J = 6.0 Hz, 1H), 4.43 (t, J = 6.1 Hz, 1H), 3.77-3.75 (m, 2H), 3.10-2.92 (m, 2H), 2.60 (t, J = 6.9 Hz, 2H), 2.11 (s, 6H), 1.75-1.65 (m, 2H). |
| 18 | 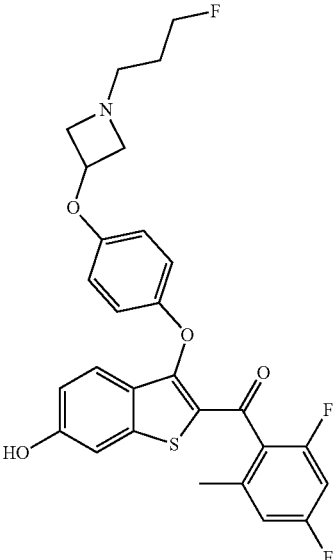 | (2,4-difluoro-6-methylphenyl)(3-(4-((1-(3-fluoropropyl)azetidin-3-yl)oxy)phenoxy)-6-hydroxybenzo[b]thiophen-2-yl)methanone | M + H = 528.15 |

TABLE 1-continued

| Compound No. | Structure | Chemical name | Characterization |
|---|---|---|---|
| 19 | 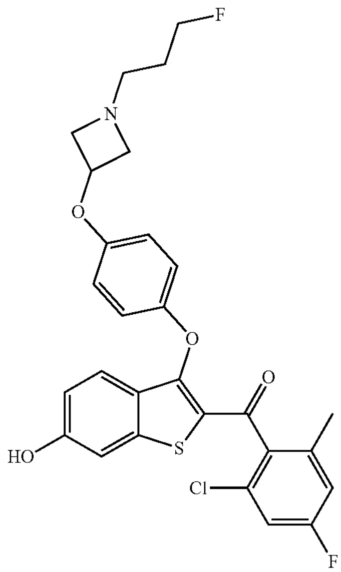 [SMILES: Cc1cc(F)cc(Cl)c1C(=O)c1sc2cc(O)ccc2c1Oc1ccc(OC2CN(CCCF)C2)cc1] | (2-chloro-4-fluoro-6-methylphenyl)(3-(4-((1-(3-fluoropropyl)azetidin-3-yl)oxy)phenoxy)-6-hydroxybenzo[b]thiophen-2-yl)methanone | M + H = 544.11 |
| 20 | 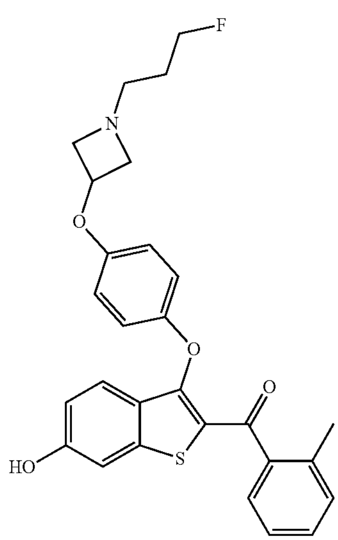 [SMILES: Cc1ccccc1C(=O)c1sc2cc(O)ccc2c1Oc1ccc(OC2CN(CCCF)C2)cc1] | (3-(4-((1-(3-fluoropropyl)azetidin-3-yl)oxy)phenoxy)-6-hydroxybenzo[b]thiophen-2-yl)(o-tolyl)methanone | M + H = 492.16<br>$^1$H NMR (400 MHz, Acetone-d6) δ 7.43-7.41 (m, 2H), 7.36 (d, J = 7.6 Hz, 1H), 7.32-7.26 (m, 1H), 7.14 (t, J = 7.7 Hz, 2H), 6.98 (dd, J = 8.8, 1.9 Hz, 1H), 6.61 (d, J = 9.0 Hz, 2H), 6.44 (d, J = 9.0 Hz, 2H), 4.68 (dt, J = 11.3, 5.7 Hz, 1H), 4.49 (dt, J = 47.5, 6.1 Hz, 2H), 3.78-3.73 (m, 2H), 2.98-2.95 (m, 2H), 2.57 (t, J = 6.9 Hz, 2H), 2.13 (s, 3H), 1.82-1.65 (m, 2H). |

TABLE 1-continued
| Compound No. | Structure | Chemical name | Characterization |
|---|---|---|---|
| 21 | 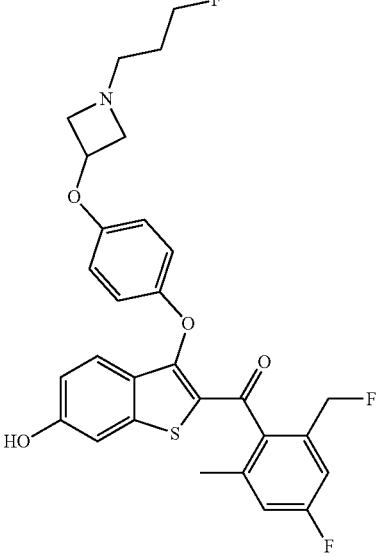 | (4-fluoro-2-(fluoromethyl)-6-methylphenyl)(3-(4-((1-(3-fluoropropyl)azetidin-3-yl)oxy)phenoxy)-6-hydroxybenzo[b]thiophen-2-yl)methanone | M + H = 542.15 |
| 22 | 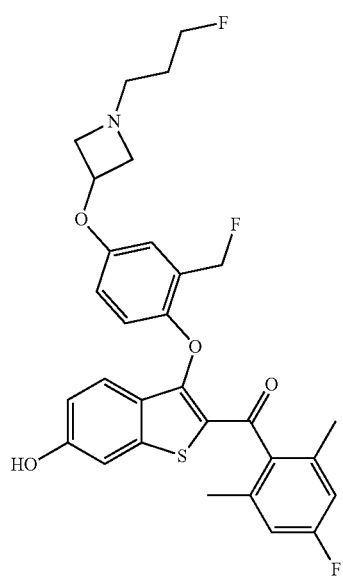 [SMILES: Cc1cc(F)cc(C)c1C(=O)c1sc2cc(O)ccc2c1Oc1ccc(OC2CN(CCCF)C2)cc1CF] | (4-fluoro-2,6-dimethylphenyl)(3-(2-(fluoromethyl)-4-((1-(3-fluoropropyl)azetidin-3-yl)oxy)phenoxy)-6-hydroxybenzo[b]thiophen-2-yl)methanone | M + H = 556.17 |

TABLE 1-continued
| Compound No. | Structure | Chemical name | Characterization |
|---|---|---|---|
| 23 | 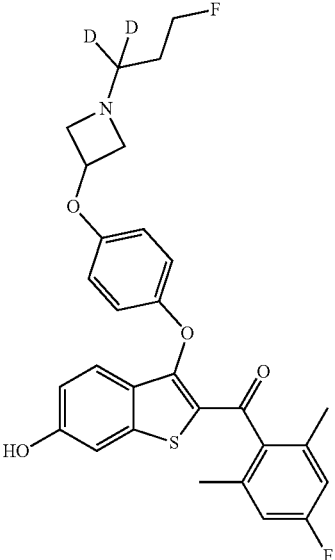 | (4-fluoro-2,6-dimethylphenyl)(3-(4-((1-(3-fluoropropyl-1,1-d2)azetidin-3-yl)oxy)phenoxy)-6-hydroxybenzo[b]thiophen-2-yl)methanone | M + H = 526.18 |
| 24 | 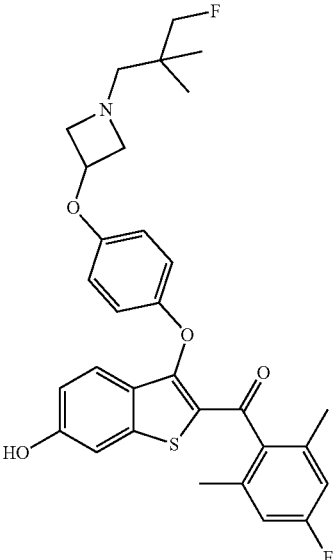 | (3-(4-((1-(3-fluoro-2,2-dimethylpropyl)azetidin-3-yl)oxy)phenoxy)-6-hydroxybenzo[b]thiophen-2-yl)(4-fluoro-2,6-dimethylphenyl)methanone | M + H = 552.19 |

TABLE 1-continued
| Compound No. | Structure | Chemical name | Characterization |
|---|---|---|---|
| 25 | 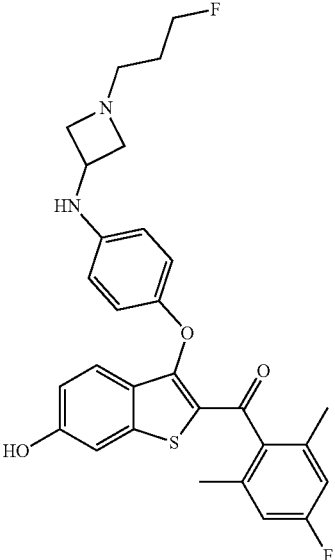 [SMILES: Cc1cc(F)cc(C)c1C(=O)c1sc2cc(O)ccc2c1Oc1ccc(NC2CN(CCCF)C2)cc1] | (4-fluoro-2,6-dimethylphenyl)(3-(4-((1-(3-fluoropropyl)azetidin-3-yl)amino)phenoxy)-6-hydroxybenzo[b]thiophen-2-yl)methanone | M + H = 523.18 |
| 26 | 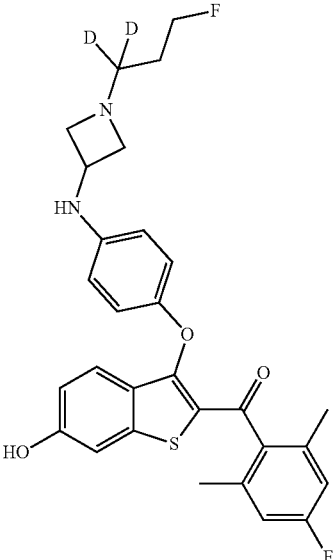 | (4-fluoro-2,6-dimethylphenyl)(3-(4-((1-(3-fluoropropyl-1,1-d2)azetidin-3-yl)amino)phenoxy)-6-hydroxybenzo[b]thiophen-2-yl)methanone | M + H = 525.19 |

TABLE 1-continued
| Compound No. | Structure | Chemical name | Characterization |
|---|---|---|---|
| 27 | 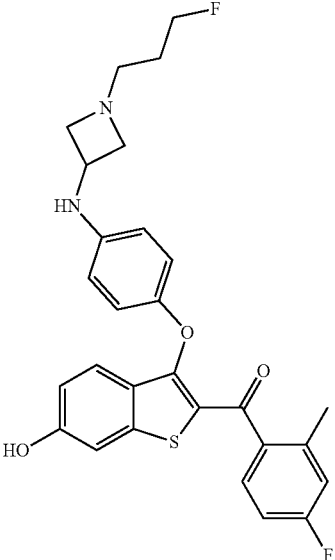 | (4-fluoro-2-methylphenyl)(3-(4-((1-(3-fluoropropyl)azetidin-3-yl)amino)phenoxy)-6-hydroxybenzo[b]thiophen-2-yl)methanone | M + H = 509.16 |
| 28 | 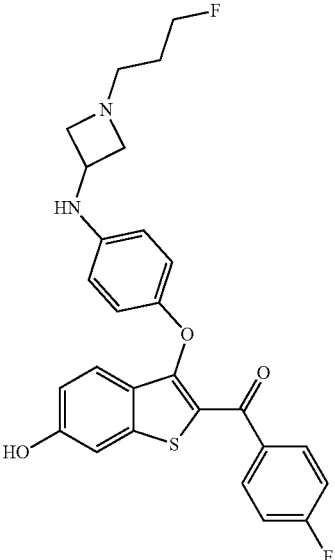 | (4-fluorophenyl)(3-(4-((1-(3-fluoropropyl)azetidin-3-yl)amino)phenoxy)-6-hydroxybenzo[b]thiophen-2-yl)methanone | M + H = 495.15 |

TABLE 1-continued

| Compound No. | Structure | Chemical name | Characterization |
|---|---|---|---|
| 29 | 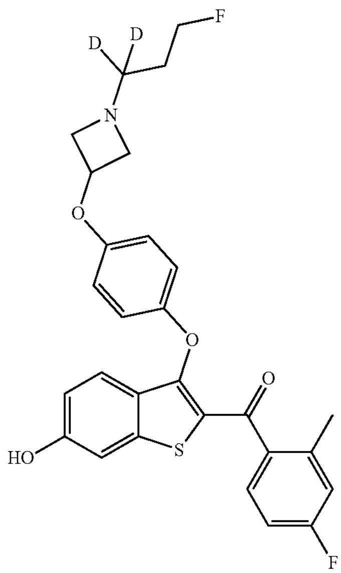 [SMILES: [2H]C([2H])(CCF)N1CC(Oc2ccc(Oc3c(C(=O)c4ccc(F)cc4C)sc4cc(O)ccc34)cc2)C1] | (4-fluoro-2-methylphenyl)(3-(4-((1-(3-fluoropropyl-1,1-d2)azetidin-3-yl)oxy)phenoxy)-6-hydroxybenzo[b]thiophen-2-yl)methanone | M + H = 512.16 |
| 30 | 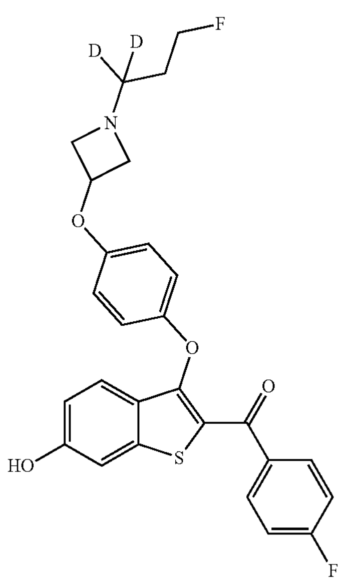 [SMILES: [2H]C([2H])(CCF)N1CC(Oc2ccc(Oc3c(C(=O)c4ccc(F)cc4)sc4cc(O)ccc34)cc2)C1] | (4-fluorophenyl)(3-(4-((1-(3-fluoropropyl-1,1-d2)azetidin-3-yl)oxy)phenoxy)-6-hydroxybenzo[b]thiophen-2-yl)methanone | M + H = 498.14 |

TABLE 1-continued

| Compound No. | Structure | Chemical name | Characterization |
|---|---|---|---|
| 31 | 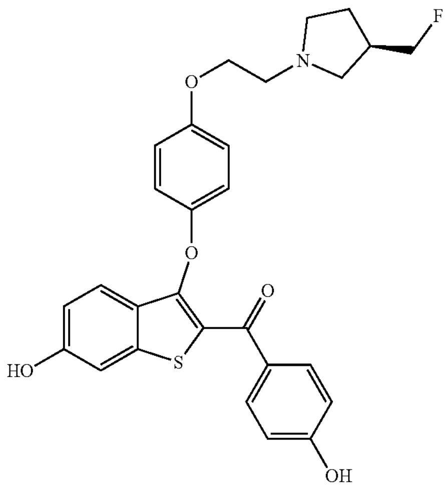 [SMILES: O=C(c1ccc(O)cc1)c1sc2cc(O)ccc2c1Oc1ccc(OCCN2CC[C@@H](CF)C2)cc1] | (R)-(3-(4-(2-(3-(fluoromethyl)pyrrolidin-1-yl)ethoxy)phenoxy)-6-hydroxybenzo[b]thiophen-2-yl)(4-hydroxyphenyl)methanone | M + H = 508.15 |
| 32 | 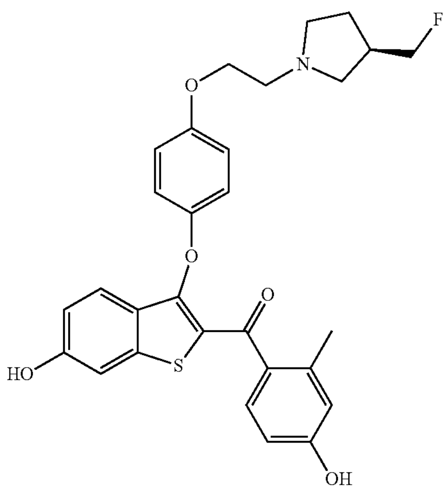 [SMILES: Cc1cc(O)ccc1C(=O)c1sc2cc(O)ccc2c1Oc1ccc(OCCN2CC[C@@H](CF)C2)cc1] | (R)-(3-(4-(2-(3-(fluoromethyl)pyrrolidin-1-yl)ethoxy)phenoxy)-6-hydroxybenzo[b]thiophen-2-yl)(4-hydroxy-2-methylphenyl)methanone | M + H = 522.17 |
| 33 | 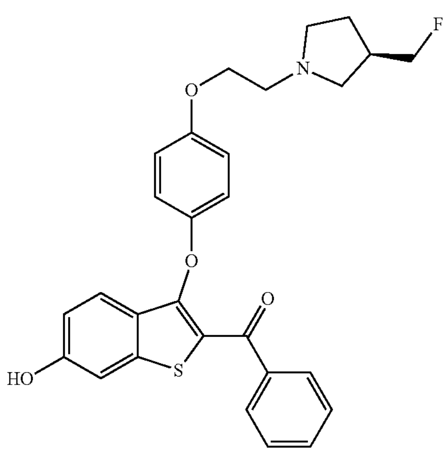 [SMILES: O=C(c1ccccc1)c1sc2cc(O)ccc2c1Oc1ccc(OCCN2CC[C@@H](CF)C2)cc1] | (R)-(3-(4-(2-(3-(fluoromethyl)pyrrolidin-1-yl)ethoxy)phenoxy)-6-hydroxybenzo[b]thiophen-2-yl)(phenyl)methanone | M + H = 492.16 |

TABLE 1-continued

| Compound No. | Structure | Chemical name | Characterization |
|---|---|---|---|
| 34 | 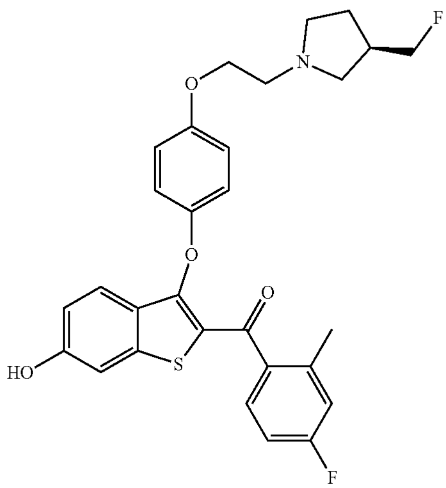 [SMILES: Cc1cc(F)ccc1C(=O)c1sc2cc(O)ccc2c1Oc1ccc(OCCN2CC[C@@H](CF)C2)cc1] | (R)-(4-fluoro-2-methylphenyl)(3-(4-(2-(3-(fluoromethyl)pyrrolidin-1-yl)ethoxy)phenoxy)-6-hydroxybenzo[b]thiophen-2-yl)methanone | M + H = 524.16 |
| 35 | 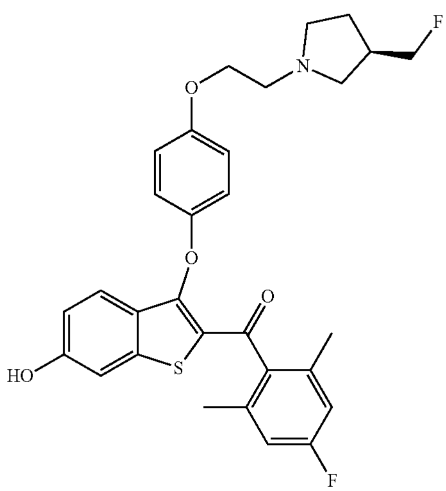 [SMILES: Cc1cc(F)cc(C)c1C(=O)c1sc2cc(O)ccc2c1Oc1ccc(OCCN2CC[C@@H](CF)C2)cc1] | (R)-(4-fluoro-2,6-dimethylphenyl)(3-(4-(2-(3-(fluoromethyl)pyrrolidin-1-yl)ethoxy)phenoxy)-6-hydroxybenzo[b]thiophen-2-yl)methanone | M + H = 538.18<br>$^1$H NMR (400 MHz, Acetone-d6) δ 7.45 (d, J = 1.8 Hz, 1H), 7.30 (d, J = 8.8 Hz, 1H), 6.98 (dd, J = 8.8, 2.0 Hz, 1H), 6.78-6.73 (m, 2H), 6.68 (d, J = 9.8 Hz, 2H), 6.48 (d, J = 9.0 Hz, 2H), 4.34 (dd, J = 47.6, 6.8 Hz, 2H), 4.08 (t, J = 5.7 Hz, 2H), 2.92 (t, J = 5.7 Hz, 2H), 2.79-2.76 (m, 2H), 2.75-2.65 (m, 1H), 2.65-2.47 (m, 2H), 2.12 (s, 6H), 2.01-1.89 (m, 1H), 1.52-1.49 (m, 1H). |
| 36 | 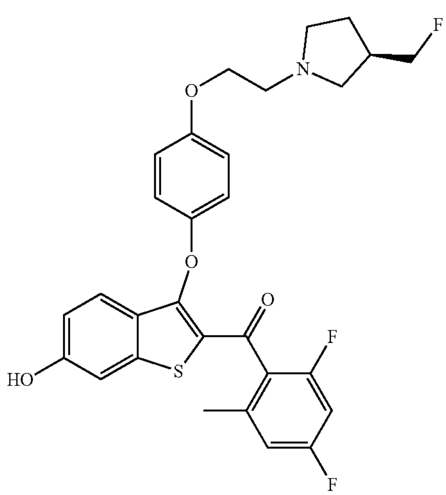 | (R)-(2,4-difluoro-6-methylphenyl)(3-(4-(2-(3-(fluoromethyl)pyrrolidin-1-yl)ethoxy)phenoxy)-6-hydroxybenzo[b]thiophen-2-yl)methanone | M + H = 542.15 |

TABLE 1-continued

| Compound No. | Structure | Chemical name | Characterization |
|---|---|---|---|
| 37 | 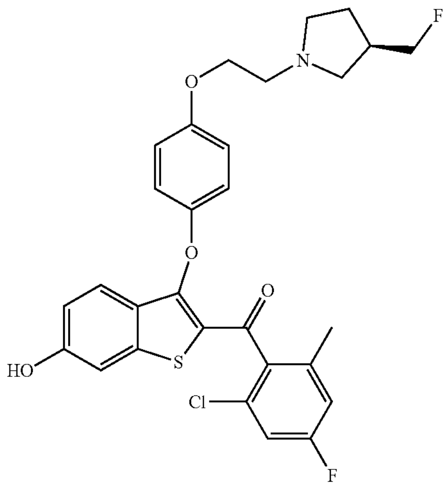 [SMILES: Cc1cc(F)cc(Cl)c1C(=O)c1sc2cc(O)ccc2c1Oc1ccc(OCCN2CC[C@@H](CF)C2)cc1] | (R)-(2-chloro-4-fluoro-6-methylphenyl)(3-(4-(2-(3-(fluoromethyl)pyrrolidin-1-yl)ethoxy)phenoxy)-6-hydroxybenzo[b]thiophen-2-yl)methanone | M + H = 558.12 |
| 38 | 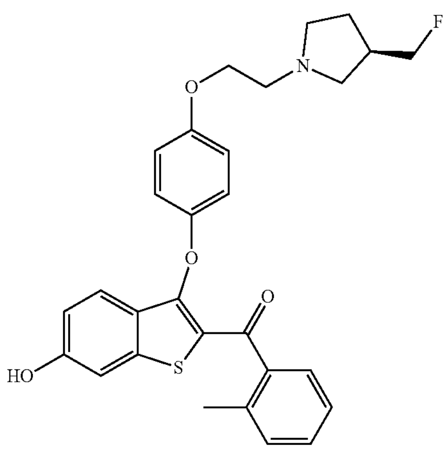 [SMILES: Cc1ccccc1C(=O)c1sc2cc(O)ccc2c1Oc1ccc(OCCN2CC[C@@H](CF)C2)cc1] | (R)-(3-(4-(2-(3-(fluoromethyl)pyrrolidin-1-yl)ethoxy)phenoxy)-6-hydroxybenzo[b]thiophen-2-yl)(o-tolyl)methanone | M + H = 506.18<br>$^1$H NMR (400 MHz, Acetone-d6) δ 7.44-7.32 (m, 3H), 7.31-7.22 (m, 1H), 7.17-7.09 (m, 2H), 6.98 (dd, J = 8.8, 2.1 Hz, 1H), 6.73 (d, J = 6.9 Hz, 2H), 6.45 (d J = 6.9 Hz, 2H), 4.34 (dd, J = 47.6, 6.8 Hz, 2H), 4.12-4.07 (m, 2H), 2.92-2.90 (m, 2H), 2.81-2.78 (m, 2H), 2.72-2.43 (m, 3H), 2.15 (s, 3H), 2.00-1.85 (m, 1H), 1.56-1.52 (m, 1H). |
| 39 | 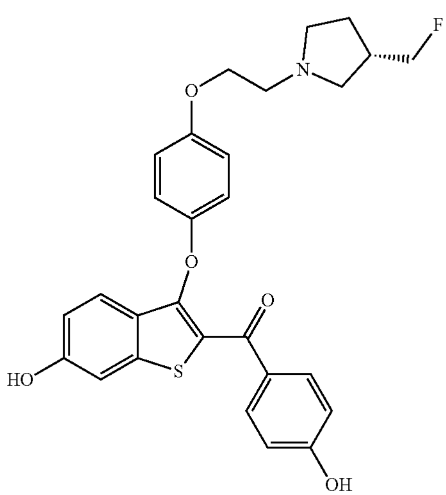 [SMILES: O=C(c1ccc(O)cc1)c1sc2cc(O)ccc2c1Oc1ccc(OCCN2CC[C@H](CF)C2)cc1] | (S)-(3-(4-(2-(3-(fluoromethyl)pyrrolidin-1-yl)ethoxy)phenoxy)-6-hydroxybenzo[b]thiophen-2-yl)(4-hydroxyphenyl)methanone | M + H = 508.15 |

TABLE 1-continued

| Compound No. | Structure | Chemical name | Characterization |
|---|---|---|---|
| 40 | 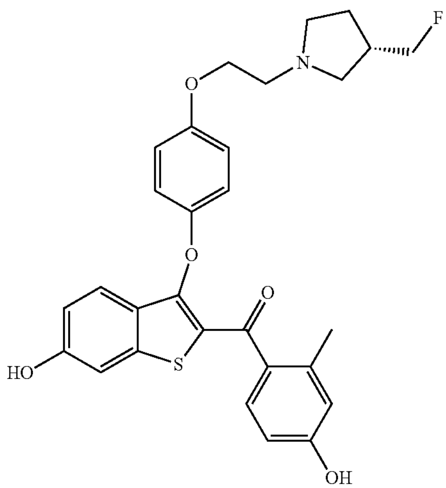 [SMILES: Cc1cc(O)ccc1C(=O)c1sc2cc(O)ccc2c1Oc1ccc(OCCN2CC[C@H](CF)C2)cc1] | (S)-(3-(4-(2-(3-(fluoromethyl)pyrrolidin-1-yl)ethoxy)phenoxy)-6-hydroxybenzo[b]thiophen-2-yl)(4-hydroxy-2-methylphenyl)methanone | M + H = 522.18 |
| 41 | 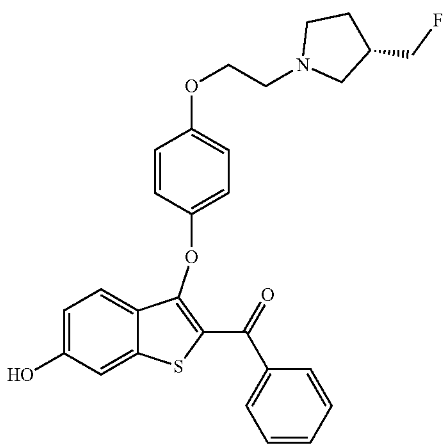 | (S)-(3-(4-(2-(3-(fluoromethyl)pyrrolidin-1-yl)ethoxy)phenoxy)-6-hydroxybenzo[b]thiophen-2-yl)(phenyl)methanone | M + H = 492.16 |
| 42 | 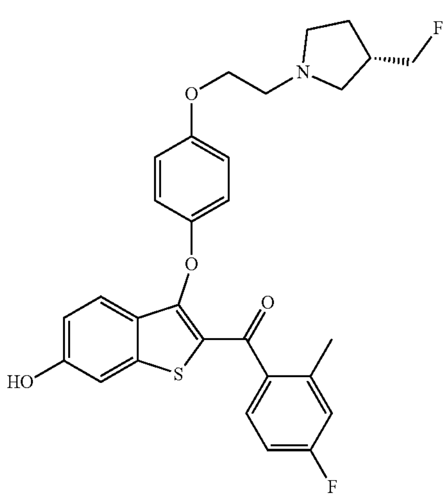 [SMILES: Cc1cc(F)ccc1C(=O)c1sc2cc(O)ccc2c1Oc1ccc(OCCN2CC[C@H](CF)C2)cc1] | (S)-(4-fluoro-2-methylphenyl)(3-(4-(2-(3-(fluoromethyl)pyrrolidin-1-yl)ethoxy)phenoxy)-6-hydroxybenzo[b]thiophen-2-yl)methanone | M + H = 524.16 |

TABLE 1-continued

| Compound No. | Structure | Chemical name | Characterization |
|---|---|---|---|
| 43 | 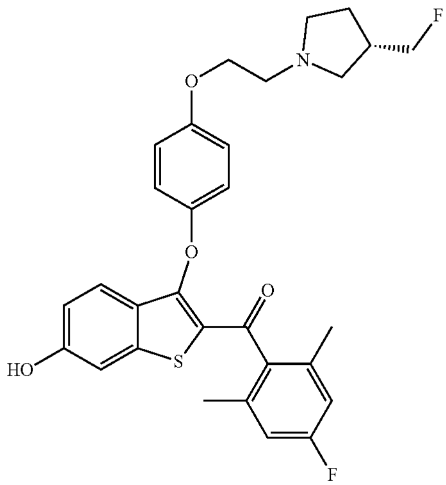 [SMILES: Cc1cc(F)cc(C)c1C(=O)c1sc2cc(O)ccc2c1Oc1ccc(OCCN2CC[C@H](CF)C2)cc1] | (S)-(4-fluoro-2,6-dimethylphenyl)(3-(4-(2-(3-(fluoromethyl)pyrrolidin-1-yl)ethoxy)phenoxy)-6-hydroxybenzo[b]thiophen-2-yl)methanone | M + H = 538.18<br>$^1$H NMR (400 MHz, Acetone-d6) δ 7.41 (d, J = 1.9 Hz, 1H), 7.31 (d, J = 8.8 Hz, 1H), 6.95 (dd, J = 8.8, 2.1 Hz, 1H), 6.75 (d, J = 9.1 Hz, 2H), 6.70 (s, 1H), 6.67 (s, 1H), 6.48 (d, J = 9.1 Hz, 2H), 4.32 (dd, J = 47.7, 6.8 Hz, 2H), 4.05 (t, J = 5.7 Hz, 2H), 2.84 (t, J = 5.7 Hz, 2H), 2.76-2.66 (m, 2H), 2.62-2.46 (m, 3H), 2.12 (s, 6H), 1.92-1.85 (m, 1H), 1.48-1.45 (m, 1H). |
| 44 | 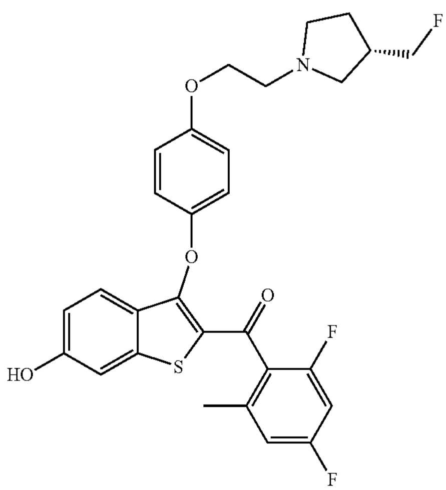 [SMILES: Cc1cc(F)cc(F)c1C(=O)c1sc2cc(O)ccc2c1Oc1ccc(OCCN2CC[C@H](CF)C2)cc1] | (S)-(2,4-difluoro-6-methylphenyl)(3-(4-(2-(3-(fluoromethyl)pyrrolidin-1-yl)ethoxy)phenoxy)-6-hydroxybenzo[b]thiophen-2-yl)methanone | M + H = 542.15 |
| 45 | 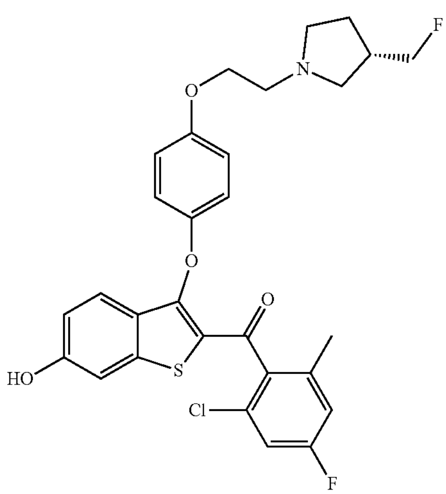 [SMILES: Cc1cc(F)cc(Cl)c1C(=O)c1sc2cc(O)ccc2c1Oc1ccc(OCCN2CC[C@H](CF)C2)cc1] | (S)-(2-chloro-4-fluoro-6-methylphenyl)(3-(4-(2-(3-(fluoromethyl)pyrrolidin-1-yl)ethoxy)phenoxy)-6-hydroxybenzo[b]thiophen-2-yl)methanone | M + H = 559.05 |

TABLE 1-continued

| Compound No. | Structure | Chemical name | Characterization |
|---|---|---|---|
| 46 | 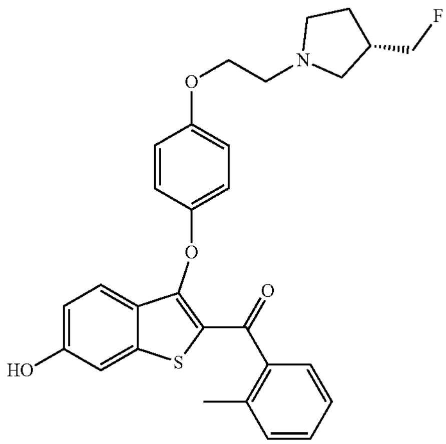 [SMILES: Cc1ccccc1C(=O)c1sc2cc(O)ccc2c1Oc1ccc(OCCN2CC[C@H](CF)C2)cc1] | (S)-(3-(4-(2-(3-(fluoromethyl)pyrrolidin-1-yl)ethoxy)phenoxy)-6-hydroxybenzo[b]thiophen-2-yl)(o-tolyl)methanone | M + H = 506.17 |
| 47 | 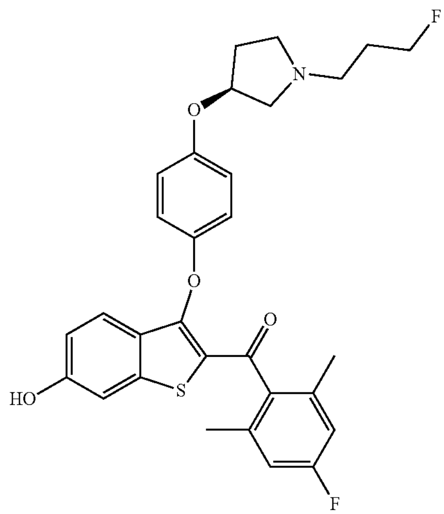 [SMILES: Cc1cc(F)cc(C)c1C(=O)c1sc2cc(O)ccc2c1Oc1ccc(O[C@H]2CCN(CCCF)C2)cc1] | (S)-(4-fluoro-2,6-dimethylphenyl)(3-(4-((1-(3-fluoropropyl)pyrrolidin-3-yl)oxy)phenoxy)-6-hydroxybenzo[b]thiophen-2-yl)methanone | M + H = 538.6 |
| 48 | 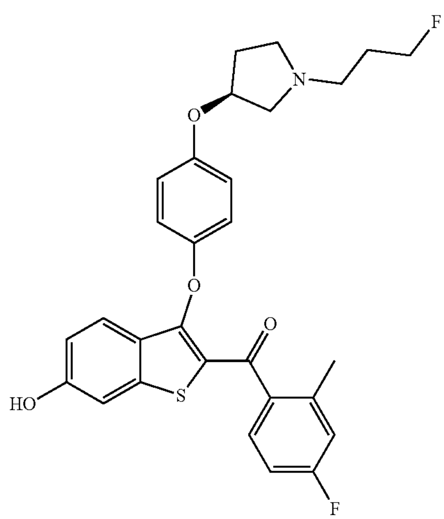 | (S)-(4-fluoro-2-methylphenyl)(3-(4-((1-(3-fluoropropyl)pyrrolidin-3-yl)oxy)phenoxy)-6-hydroxybenzo[b]thiophen-2-yl)methanone | M + H = 545.0 |

TABLE 1-continued

| Compound No. | Structure | Chemical name | Characterization |
|---|---|---|---|
| 49 | 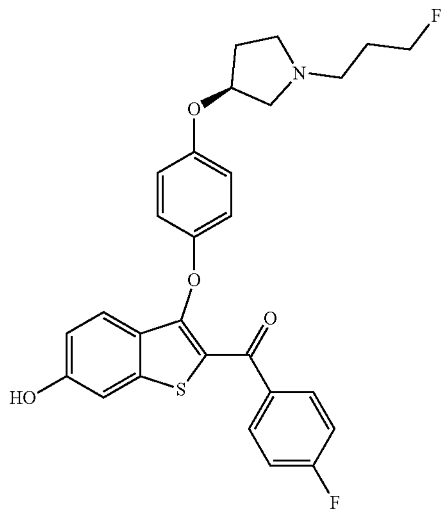 [SMILES: O=C(c1ccc(F)cc1)c1sc2cc(O)ccc2c1Oc1ccc(O[C@H]2CCN(CCCF)C2)cc1] | (S)-(4-fluorophenyl)(3-(4-((1-(3-fluoropropyl)pyrrolidin-3-yl)oxy)phenoxy)-6-hydroxybenzo[b]thiophen-2-yl)methanone | M + H = 510.6 |
| 50 | 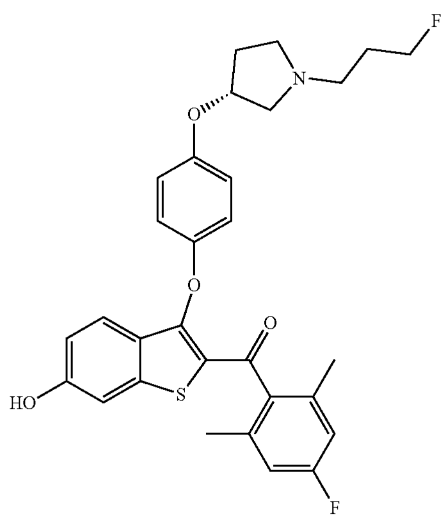 [SMILES: Cc1cc(F)cc(C)c1C(=O)c1sc2cc(O)ccc2c1Oc1ccc(O[C@@H]2CCN(CCCF)C2)cc1] | (R)-(4-fluoro-2,6-dimethylphenyl)(3-(4-((1-(3-fluoropropyl)pyrrolidin-3-yl)oxy)phenoxy)-6-hydroxybenzo[b]thiophen-2-yl)methanone | M + H = 538.6 |
| 51 | 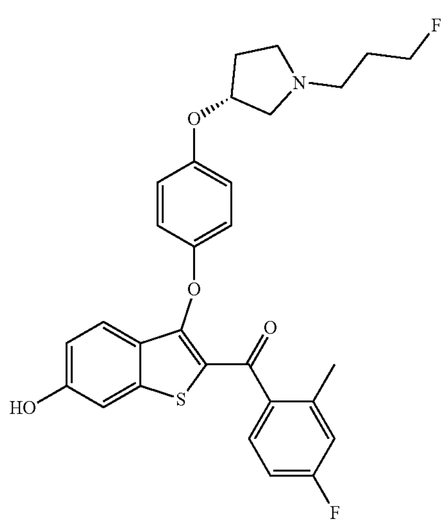 [SMILES: Cc1cc(F)ccc1C(=O)c1sc2cc(O)ccc2c1Oc1ccc(O[C@@H]2CCN(CCCF)C2)cc1] | (R)-(4-fluoro-2-methylphenyl)(3-(4-((1-(3-fluoropropyl)pyrrolidin-3-yl)oxy)phenoxy)-6-hydroxybenzo[b]thiophen-2-yl)methanone | M + H = 525.0 |

TABLE 1-continued

| Compound No. | Structure | Chemical name | Characterization |
|---|---|---|---|
| 52 | 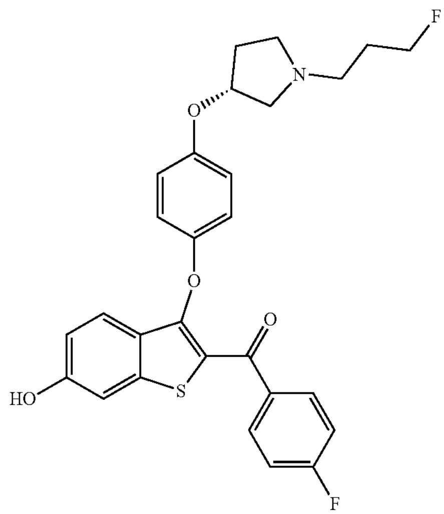 [SMILES: O=C(c1ccc(F)cc1)c1sc2cc(O)ccc2c1Oc1ccc(O[C@@H]2CCN(CCCF)C2)cc1] | (R)-(4-fluorophenyl)(3-(4-((1-(3-fluoropropyl)pyrrolidin-3-yl)oxy)phenoxy)-6-hydroxybenzo[b]thiophen-2-yl)methanone | M + H = 510.6 |
| 53 | 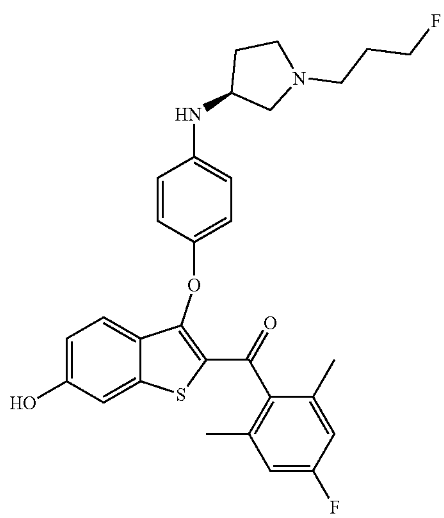 [SMILES: Cc1cc(F)cc(C)c1C(=O)c1sc2cc(O)ccc2c1Oc1ccc(N[C@H]2CCN(CCCF)C2)cc1] | (S)-(4-fluoro-2,6-dimethylphenyl)(3-(4-((1-(3-fluoropropyl)pyrrolidin-3-yl)amino)phenoxy)-6-hydroxybenzo[b]thiophen-2-yl)methanone | M + H = 537.6 |
| 54 | 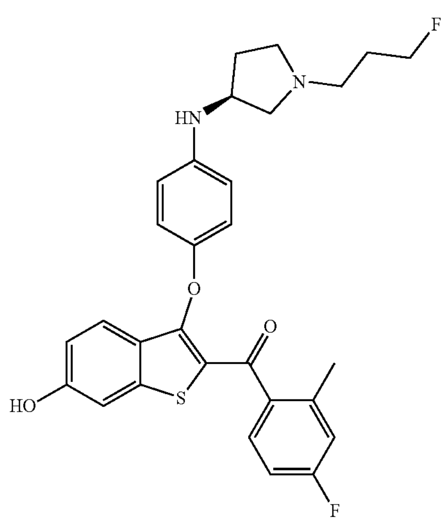 [SMILES: Cc1cc(F)ccc1C(=O)c1sc2cc(O)ccc2c1Oc1ccc(N[C@H]2CCN(CCCF)C2)cc1] | (S)-(4-fluoro-2-methylphenyl)(3-(4-((1-(3-fluoropropyl)pyrrolidin-3-yl)amino)phenoxy)-6-hydroxybenzo[b]thiophen-2-yl)methanone | M + H = 523.6 |

TABLE 1-continued

| Compound No. | Structure | Chemical name | Characterization |
|---|---|---|---|
| 55 | 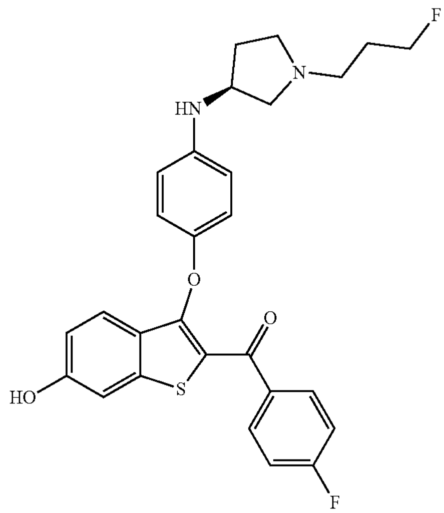 [SMILES: O=C(c1ccc(F)cc1)c1sc2cc(O)ccc2c1Oc1ccc(N[C@H]2CCN(CCCF)C2)cc1] | (S)-(4-fluorophenyl)(3-(4-((1-(3-fluoropropyl)pyrrolidin-3-yl)amino)phenoxy)-6-hydroxybenzo[b]thiophen-2-yl)methanone | M + H = 509.6 |
| 56 | 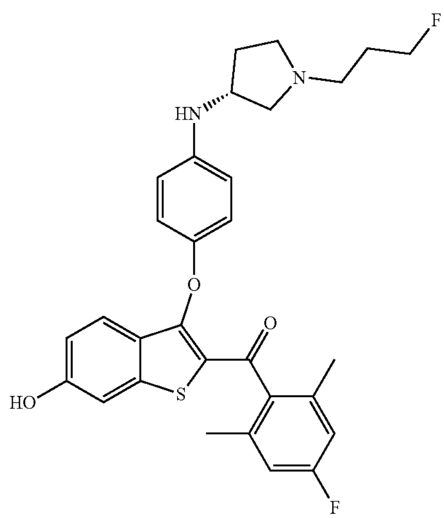 [SMILES: Cc1cc(F)cc(C)c1C(=O)c1sc2cc(O)ccc2c1Oc1ccc(N[C@@H]2CCN(CCCF)C2)cc1] | (R)-(4-fluoro-2,6-dimethylphenyl)(3-(4-((1-(3-fluoropropyl)pyrrolidin-3-yl)amino)phenoxy)-6-hydroxybenzo[b]thiophen-2-yl)methanone | M + H = 537.6 |
| 57 | 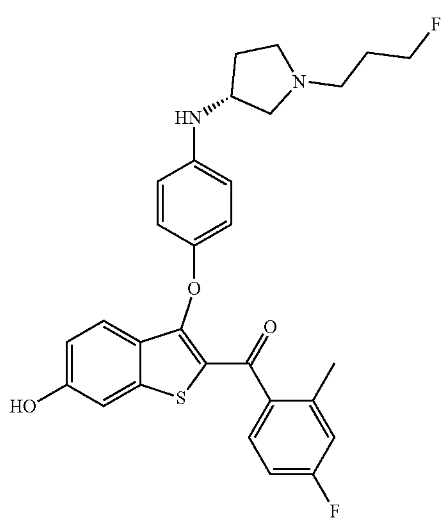 [SMILES: Cc1cc(F)ccc1C(=O)c1sc2cc(O)ccc2c1Oc1ccc(N[C@@H]2CCN(CCCF)C2)cc1] | (R)-(4-fluoro-2-methylphenyl)(3-(4-((1-(3-fluoropropyl)pyrrolidin-3-yl)amino)phenoxy)-6-hydroxybenzo[b]thiophen-2-yl)methanone | M + H = 523.6 |

| Compound No. | Structure | Chemical name | Characterization |
|---|---|---|---|
| 58 | 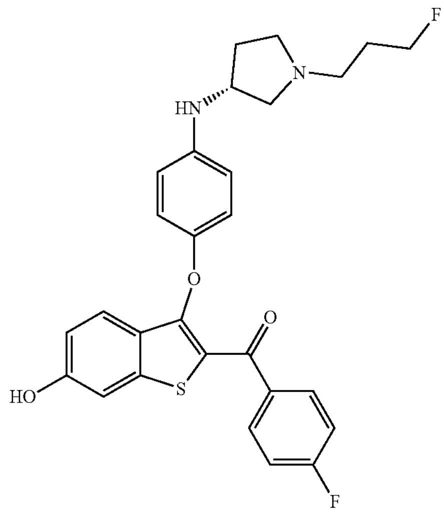 [SMILES: O=C(c1ccc(F)cc1)c1sc2cc(O)ccc2c1Oc1ccc(N[C@@H]2CCN(CCCF)C2)cc1] | (R)-(4-fluorophenyl)(3-(4-((1-(3-fluoropropyl)pyrrolidin-3-yl)amino)phenoxy)-6-hydroxybenzo[b]thiophen-2-yl)methanone | M + H = 509.6 |
| 59 | 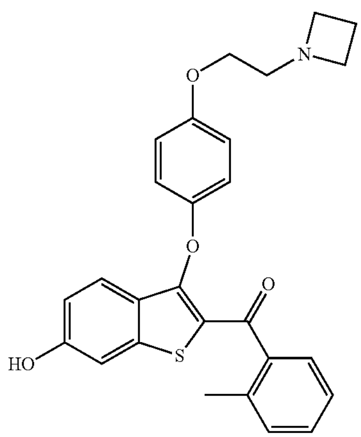 [SMILES: Cc1ccccc1C(=O)c1sc2cc(O)ccc2c1Oc1ccc(OCCN2CCC2)cc1] | (3-(4-(2-(azetidin-1-yl)ethoxy)phenoxy)-6-hydroxybenzo[b]thiophen-2-yl)(o-tolyl)methanone | M + H = 460.15<br>$^1$H NMR (400 MHz, Acetone-d6) δ 7.43-7.32 (m, 3H), 7.26-7.23 (m, 1H), 7.15-7.07 (m, 2H), 6.96 (dd, J = 8.8, 2.1 Hz, 1H), 6.67 (d, J = 9.1 Hz, 2H), 6.43 (d, J = 9.1 Hz, 2H), 3.89 (t, J = 5.6 Hz, 2H), 3.33 (t, J = 7.0 Hz, 4H), 2.79 (t, J = 5.6 Hz, 2H), 2.14 (s, 3H), 2.05-2.02 (m, 2H). |
| 60 | 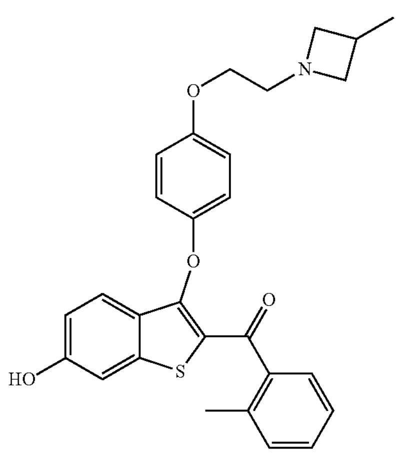 [SMILES: Cc1ccccc1C(=O)c1sc2cc(O)ccc2c1Oc1ccc(OCCN2CC(C)C2)cc1] | (6-hydroxy-3-(4-(2-(3-methylazetidin-1-yl)ethoxy)phenoxy)benzo[b]thiophen-2-yl)(o-tolyl)methanone | M + H = 474.17<br>$^1$H NMR (400 MHz, Acetone-d6) δ 7.42 (d, J = 2.1 Hz, 1H), 7.37 (t, J = 8.4 Hz, 2H), 7.28 (t, J = 7.5 Hz, 1H), 7.14-7.12 (m, 2H), 6.98 (dd, J = 8.8, 2.1 Hz, 1H), 6.72-6.66 (m, 2H), 6.47-6.41 (m, 2H), 3.89 (t, J = 5.7 Hz, 2H), 3.51 (t, J = 7.3 Hz, 2H), 2.85 (t, J = 6.8 Hz, 2H), 2.75-2.73 (m, 4H), 2.52-2.50 (m, 1H), 2.15 (s, 3H). |

TABLE 1-continued

| Compound No. | Structure | Chemical name | Characterization |
|---|---|---|---|
| 61 | 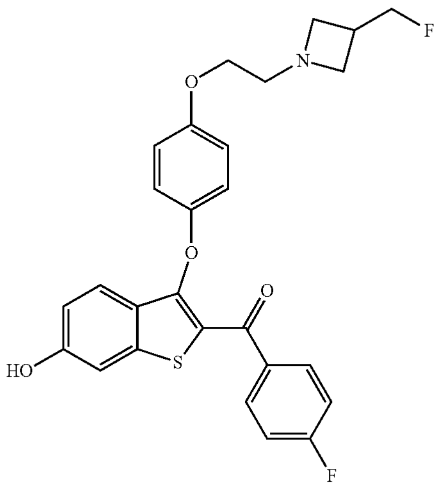 [SMILES: O=C(c1ccc(F)cc1)c1sc2cc(O)ccc2c1Oc1ccc(OCCN2CC(CF)C2)cc1] | (3-(4-(2-(3-(fluoromethyl) azetidin-1-yl)ethoxy)phenoxy)-6-hydroxybenzo[b]thiophen-2-yl)(4-fluorophenyl) methanone | M + H = 496.14<br>$^1$H NMR (400 MHz, Acetone-d6) δ 7.91-7.71 (m, 2H), 7.42-7.39 (m, 2H), 7.18 (t, J = 8.8 Hz, 2H), 7.00 (dd, J = 8.9, 2.0 Hz, 1H), 6.74 (d, J = 9.1 Hz, 2H), 6.64 (d, J = 9.1 Hz, 2H), 4.54 (dd, J = 47.7, 6.3 Hz, 2H), 3.89 (t, J = 5.6 Hz, 2H), 3.39 (t, J = 7.2 Hz, 2H), 3.10 (t, J = 6.5 Hz, 2H), 2.76-2.74 (m, 1H), 2.75 (t, J = 5.5 Hz, 2H). |
| 62 | 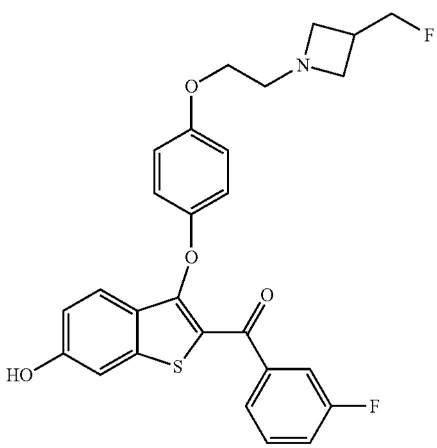 [SMILES: O=C(c1cccc(F)c1)c1sc2cc(O)ccc2c1Oc1ccc(OCCN2CC(CF)C2)cc1] | (3-(4-(2-(3-(fluoromethyl) azetidin-1-yl)ethoxy)phenoxy)-6-hydroxybenzo[b]thiophen-2-yl)(3-fluorophenyl) methanone | M + H = 496.14<br>$^1$H NMR (400 MHz, Acetone-d6) δ 7.55 (dt, J = 7.6, 1.1 Hz, 1H), 7.49-7.38 (m, 4H), 7.36-7.26 (m, 1H), 6.98 (dd, J = 8.9, 2.1 Hz, 1H), 6.74 (d, J = 9.2 Hz, 2H), 6.63 (d, J = 9.2 Hz, 2H), 4.54 (dd, J = 47.7, 6.3 Hz, 2H), 3.89 (t, J = 5.6 Hz, 2H), 3.39 (td, J = 7.7, 1.3 Hz, 2H), 3.13-3.05 (m, 2H), 2.84-2.68 (m, 3H). |
| 63 | 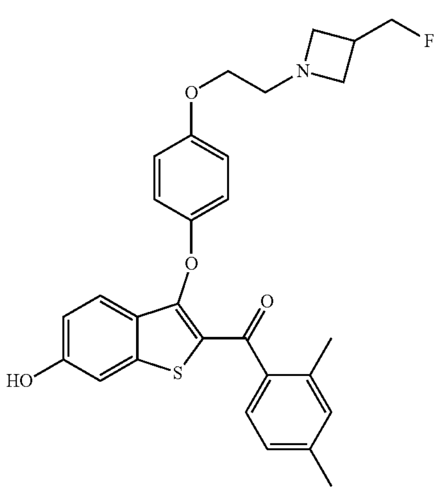 [SMILES: Cc1ccc(C(=O)c2sc3cc(O)ccc3c2Oc2ccc(OCCN3CC(CF)C3)cc2)c(C)c1] | (2,4-dimethylphenyl)(3-(4-(2-(3-(fluoromethyl) azetidin-1-yl)ethoxy)phenoxy)-6-hydroxybenzo[b]thiophen-2-yl)methanone | M + H = 506.17<br>$^1$H NMR (400 MHz, Acetone-d6) δ 7.42-7.38 (m, 2H), 7.28 (d, J = 7.5 Hz, 1H), 6.98 (dd, J = 8.8, 2.1 Hz, 1H), 6.95 (s, 2H), 6.70 (d, J = 9.1 Hz, 2H), 6.46 (d, J = 9.1 Hz, 2H), 4.54 (dd, J = 47.7, 6.3 Hz, 2H), 3.89 (t, J = 5.6 Hz, 2H), 3.40 (t, J = 7.6 Hz, 2H), 3.11 (t, J = 6.5 Hz, 2H), 2.85-2.68 (m, 3H), 2.31 (s, 3H), 2.12 (s, 3H). |

TABLE 1-continued

| Compound No. | Structure | Chemical name | Characterization |
|---|---|---|---|
| 64 | 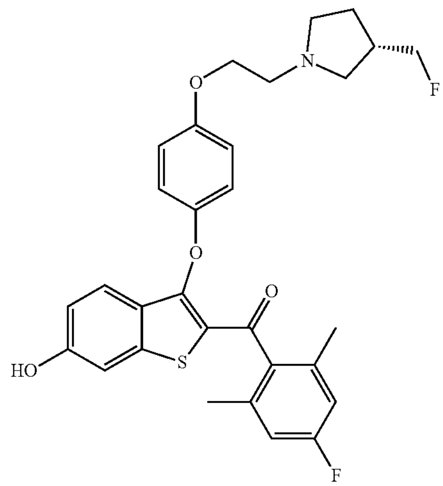 [SMILES: Cc1cc(F)cc(C)c1C(=O)c1sc2cc(O)ccc2c1Oc1ccc(OCCN2CC[C@H](CF)C2)cc1] | (S)-(4-fluoro-2,6-dimethylphenyl)(3-(4-(2-(3-(fluoromethyl)pyrrolidin-1-yl)ethoxy)phenoxy)-6-hydroxybenzo[b]thiophen-2-yl)methanone | M + H = 538.18<br>$^1$H NMR (400 MHz, Acetone-d6) δ 7.41 (d, J = 1.9 Hz, 1H), 7.31 (d, J = 8.8 Hz, 1H), 6.95 (dd, J = 8.8, 2.1 Hz, 1H), 6.75 (d, J = 9.1 Hz, 2H), 6.70 (s, 1H), 6.67 (s, 1H), 6.48 (d, J = 9.1 Hz, 2H), 4.32 (dd, J = 47.7, 6.8 Hz, 2H), 4.05 (t, J = 5.7 Hz, 2H), 2.84 (t, J = 5.7 Hz, 2H), 2.76-2.66 (m, 2H), 2.62-2.46 (m, 3H), 2.12 (s, 6H), 1.92-1.85 (m, 1H), 1.48-1.45 (m, 1H). |
| 65 | 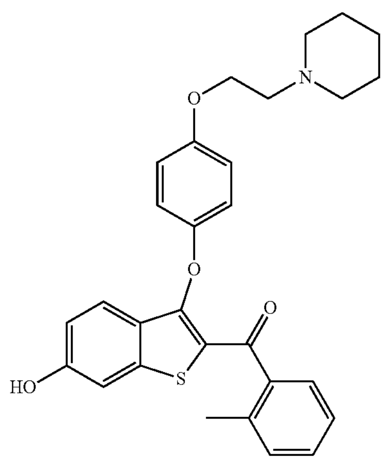 [SMILES: Cc1ccccc1C(=O)c1sc2cc(O)ccc2c1Oc1ccc(OCCN2CCCCC2)cc1] | (6-hydroxy-3-(4-(2-(piperidin-1-yl)ethoxy)phenoxy)benzo[b]thiophen-2-yl)(o-tolyl)methanone | M + H = 488.18<br>$^1$H NMR (400 MHz, Acetone-d6) δ 7.43 (d, J = 2.1 Hz, 1H), 7.37 (t, J = 8.3 Hz, 2H), 7.28 (td, J = 7.5, 1.3 Hz, 1H), 7.14-7.12 (m, 2H), 6.98 (dd, J = 8.8, 2.2 Hz, 1H), 6.71 (d, J = 9.1 Hz, 2H), 6.45 (d, J = 9.1 Hz, 2H), 4.02 (t, J = 6.0 Hz, 2H), 2.69 (t, J = 6.0 Hz, 2H), 2.50-2.49 (m, 4H), 2.15 (s, 3H), 1.55-1.53 (m, 4H), 1.46-1.36 (m, 2H). |
| 66 | 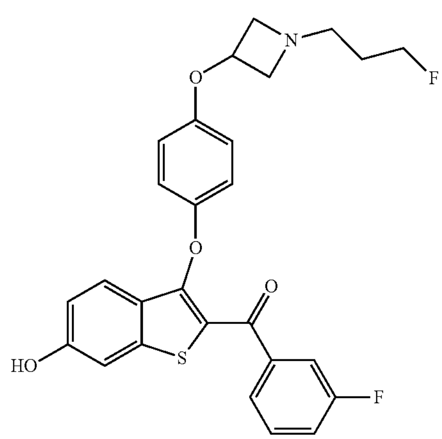 [SMILES: O=C(c1cccc(F)c1)c1sc2cc(O)ccc2c1Oc1ccc(OC2CN(CCCF)C2)cc1] | (3-fluorophenyl)(3-(4-((1-(3-fluoropropyl)azetidin-3-yl)oxy)phenoxy)-6-hydroxybenzo[b]thiophen-2-yl)methanone | M + H = 496.13<br>$^1$H NMR (400 MHz, Acetone-d6) δ 7.53 (d, J = 7.6 Hz, 1H), 7.50-7.35 (m, 4H), 7.30 (td, J = 8.4, 1.8 Hz, 1H), 7.00 (dd, J = 8.8, 2.0 Hz, 1H), 6.63 (q, J = 9.3 Hz, 4H), 4.68 (p, J = 5.7 Hz, 1H), 4.48 (dt, J = 47.5, 6.1 Hz, 2H), 3.75 (t, J = 7.2 Hz, 2H), 3.05-2.91 (m, 2H), 2.58 (t, J = 6.9 Hz, 2H), 1.83-1.63 (m, 2H). |

TABLE 1-continued

| Compound No. | Structure | Chemical name | Characterization |
|---|---|---|---|
| 67 | 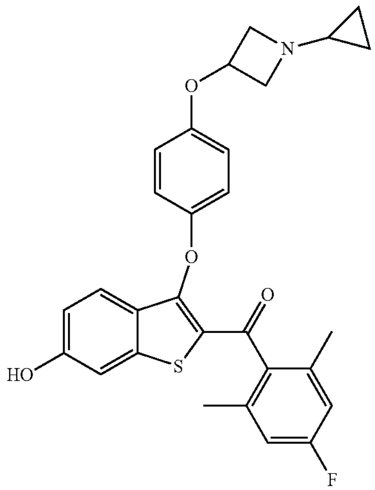 [SMILES: Cc1cc(F)cc(C)c1C(=O)c1sc2cc(O)ccc2c1Oc1ccc(OC2CN(C3CC3)C2)cc1] | (3-(4-((1-cyclopropylazetidin-3-yl)oxy)phenoxy)-6-hydroxybenzo[b]thiophen-2-yl)(4-fluoro-2,6-dimethylphenyl)methanone | M + H = 504.16. $^1$H NMR (400 MHz, Acetone-d6) δ 7.44 (d, J = 2.1 Hz, 1H), 7.32 (d, J = 8.8 Hz, 1H), 6.98 (dd, J = 8.8, 2.1 Hz, 1H), 6.69 (s, 1H), 6.66 (s, 1H), 6.64 (d, J = 9.1 Hz, 2H), 6.46 (d, J = 9.1 Hz, 2H), 4.64-4.61 (m, 1H), 3.79-3.69 (m, 2H), 3.20-3.10 (m, 2H), 1.90-1.88 (m, 1H), 0.36-0.34 (m, 2H), 0.30-0.22 (m, 2H). |

Example compounds numbers 1-56 were assayed in ER+ breast cancer cells from 0.01 nM to 1 uM and the $IC_{50}$ for growth inhibition determined. The data were obtained, as shown in Table 2, using tamoxifen-sensitive ER+ MCF-7:WS8 and tamoxifen-resistant MCF-7:5C breast cancer cells.

TABLE 2

| Compound No. | MCF7:WS8 $IC_{50}$ (nM) | Max efficacy (%) | MCF7:5C $IC_{50}$ (nM) | Max efficacy (%) |
|---|---|---|---|---|
| Vehicle | NI | 0 | NI | 0 |
| Fulvestrant | 0.48 ± 0.03 | 75 | 1.9 ± 0.01 | 55 |
| 59 | 0.50 ± 0.05 | 70 | 0.31 ± 0.07 | 35 |
| 60 | 0.02 ± 0.004 | 75 | 0.65 ± 0.01 | 55 |
| 3 | 0.55 ± 0.01 | 65 | 15 ± 4 | 60 |
| 8 | 0.73 ± 0.02 | 70 | 0.65 ± 0.03 | 40 |
| 4 | 0.30 ± 0.02 | 75 | 0.20 ± 0.02 | 50 |
| 5 | 0.41 ± 0.01 | 70 | 3.4 ± 0.5 | 55 |
| 1 | 1.1 ± 0.1 | 75 | 1.2 ± 0.3 | 30 |
| 2 | 0.50 ± 0.05 | 80 | 7.9 ± 0.15 | 45 |
| 61 | 1.3 ± 0.1 | 70 | 0.58 ± 0.04 | 55 |
| 62 | 0.28 ± 0.03 | 75 | 1.4 ± 0.2 | 60 |
| 63 | 0.47 ± 0.009 | 65 | 0.56 ± 0.005 | 50 |
| 9 | 0.10 ± 0.01 | 85 | 0.23 ± 0.06 | 25 |
| 35 | 0.56 ± 0.01 | 65 | 0.28 ± 0.07 | 40 |
| 64 | 0.36 ± 0.001 | 70 | 0.16 ± 0.1 | 50 |
| 65 | 0.39 ± 0.05 | 65 | NI | NI |
| 15 | 0.15 ± 0.02 | 60 | 0.12 ± 0.02 | 40 |
| 20 | 0.04 ± 0.006 | 75 | 4.9 ± 0.2 | 70 |
| 16 | 0.15 ± 0.02 | 70 | 0.95 ± 0.04 | 50 |
| 17 | 0.55 ± 0.01 | 75 | 0.15 ± 0.06 | 70 |
| 66 | 0.27 ± 0.006 | 70 | 0.12 ± 0.03 | 35 |
| 67 | 0.42 ± 0.04 | 65 | 1.0 ± 0.8 | 20 |

Example compounds were assayed to determine ER downregulation, relative binding affinity, and ER antagonism. The data are shown in Table 3.

TABLE 3

| Example compound | $IC_{50}$ (nM) | RBA (%) | ERE IC50 |
|---|---|---|---|
| Fulvestrant | 1.6 ± 0.1 | 17.7 | 11.1 ± 0.1 |
| 60 | 0.53 ± 0.01 | | 1.9 ± 0.06 |
| 3 | 1.3 ± 0.6 | 30.7 ± 7 | 4.3 ± 0.1 |
| 8 | 0.73 ± 0.04 | 46.5 ± 7 | 1.5 ± 0.09 |
| 4 | 3.9 ± 0.1 | | 2.7 ± 0.09 |
| 5 | 0.75 ± 0.05 | 59.6 ± 3 | 3.5 ± 0.06 |
| 1 | 6.0 ± 0.1 | 57.0 ± 14 | 6.4 ± 0.4 |
| 2 | 4.9 ± 0.03 | 21.9 ± 3 | |
| 61 | 1.3 ± 0.08 | 9.15 ± 0.9 | 2.8 ± 0.1 |
| 62 | | 120 ± 13 | |
| 63 | 1.1 ± 0.4 | | 7.4 ± 0.3 |
| 9 | 7.7 ± 0.06 | | 45 ± 15 |
| 35 | 2.3 ± 0.5 | 32.6 ± 6 | 12 ± 2 |
| 64 | 0.49 ± 0.04 | | 0.05 ± 0.001 |
| 65 | 2.5 ± 0.3 | 91.8 ± 6 | 2.1 ± 0.06 |
| 15 | 8.3 ± 0.04 | | 5.2 ± 0.06 |
| 20 | 1.1 ± 0.1 | 27.8 ± 8 | 5.3 ± 0.08 |
| 16 | 11.8 ± 1.3 | 38.1 ± 9 | 11 ± 0.5 |

It will be apparent to those skilled in the art that various modifications and variations can be made in the present disclosure without departing from the scope or spirit of the disclosure. Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A method for the treatment of breast cancer in a mammal comprising the step of administering to the mammal a therapeutically effective amount of a compound having a structure represented by a formula:

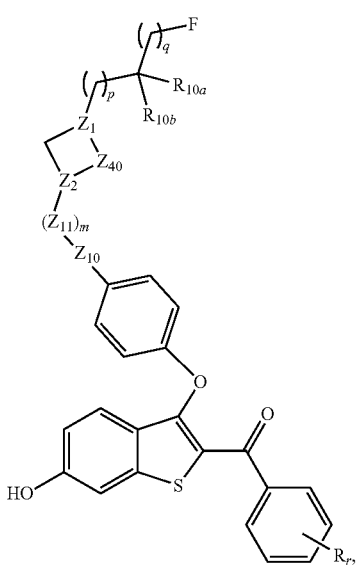

wherein m is selected from 0 and 1;
wherein p is selected from 0, 1, and 2;
wherein q is selected from 0, 1, and 2;
wherein each of $Z_1$ and $Z_2$ is independently selected from —CH— or —N—; provided $Z_1$ and $Z_2$ are not simultaneously —CH— or —N—; and provided when $Z_1$ is —CH— and m is 1, that p and q are not both 0;
wherein $Z_{10}$ is selected from —O— or —NH;
wherein $Z_{11}$ is, when present, —CH$_2$CH$_2$;
wherein $Z_{40}$ is —(CH$_2$)$_n$—, wherein n is selected from 1, 2, 3, or 4;
wherein each of $R_{10a}$ and $R_{10b}$ are independently selected from hydrogen, deuterium, halogen, and C1-C3 methyl;
wherein R is C1-C6 alkyl, C1-C6 haloalkyl, halogen, or hydroxy; and
r is 0, 1, 2, 3, or 4;
or a pharmaceutically acceptable salt thereof.

2. The method of claim 1, wherein the breast cancer is selected from the group consisting of hormone receptor positive metastatic breast cancer, tamoxifen resistant breast cancer, aromatase inhibitor resistant breast cancer, CDK4/6 inhibitor resistant breast cancer breast cancer, a triple negative breast cancer, and combinations thereof.

3. The method of claim 2, further comprising co-administering a hormone therapy agent.

4. The method of claim 3, wherein the hormone therapy agent is selected an antibody that specifically binds bicalutamide, flutamide, fulvestrant, leuprolide acetate, megestrol acetate, tamoxifen, raloxifene, anastrozole, exemestane, letrozole, and combinations thereof.

5. The method of claim 2, further comprising co-administering a therapeutic antibody selected from the group consisting of an antibody that binds EGFR, an antibody that binds PD-1, an antibody that binds PD-L1, an antibody that binds VEGF, an antibody that binds HER2, and combinations of the foregoing antibodies thereof.

6. The method of claim 5, wherein the therapeutic antibody is selected from the group consisting of panitumumab, bevacizumab, cetuximab, trastuzumab, and combinations thereof.

7. The method of claim 2, further comprising co-administering a therapeutic agent selected from the group consisting of a chemotherapeutic agent, a radioisotope, an antihormonal agent, a cytotoxic agent, an immunotherapeutic agent, a targeted cancer therapeutic agent, and combinations thereof.

8. The method of claim 7, wherein the chemotherapeutic agent is selected from the group consisting of folate antagonists, purine antagonists, pyrimidine antagonists, DNA alkylating agents, DNA cross-linking drugs, antibiotics, platinum complexes, and combinations thereof.

9. The method of claim 7, wherein the targeted cancer therapeutic agent is selected from the group consisting of proteosome inhibitors, mitotic spindle poisons, topoisomerase inhibitors, tyrosine kinase inhibitors, CDK4/6 inhibitors, mTOR inhibitors, PI3K inhibitors, BET (Bromodomain and Extra-Terminal motif proteins) inhibitors, and combinations thereof.

10. The method of claim 1, wherein $Z_{10}$ is —O—.

11. The method of claim 1 wherein —$Z_1$— is N and $Z_2$ is —CH—.

12. The method of claim 1 wherein —$Z_1$— is —CH— and $Z_2$ is —N—.

13. The method of claim 1, having a structure represented by a formula:

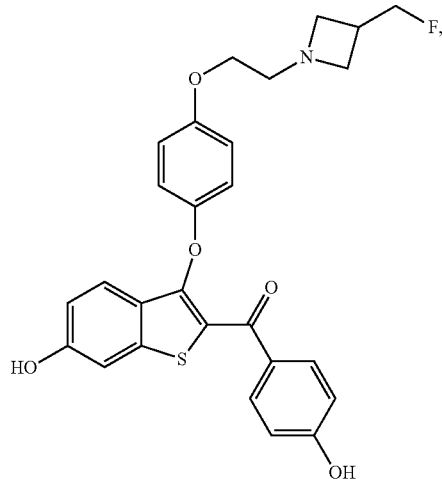

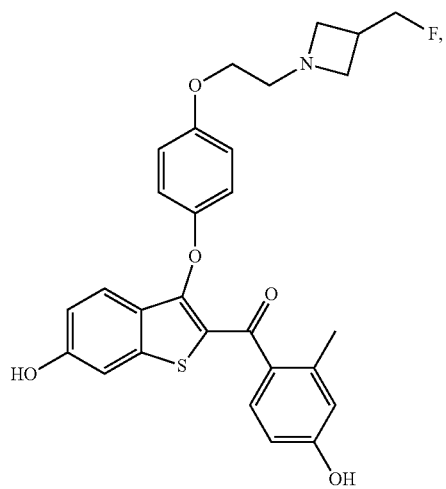

211
-continued
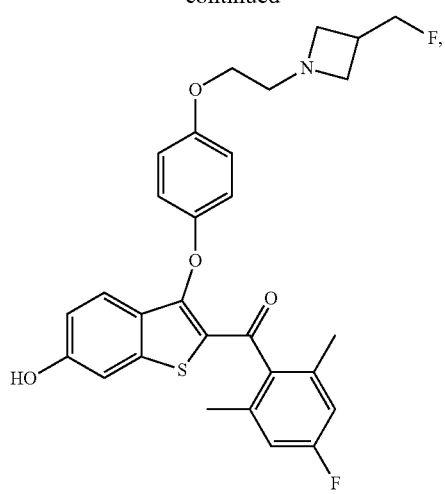
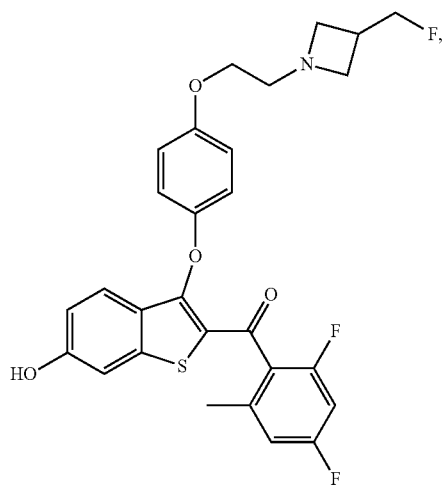
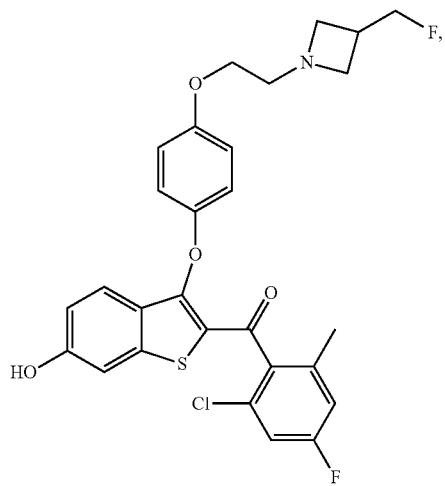
212
-continued
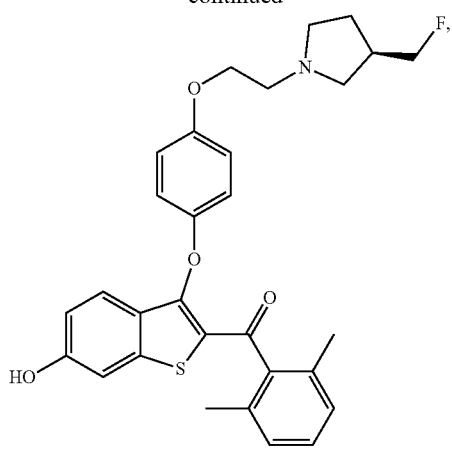
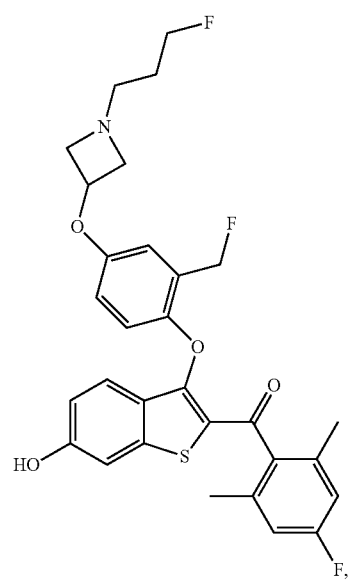
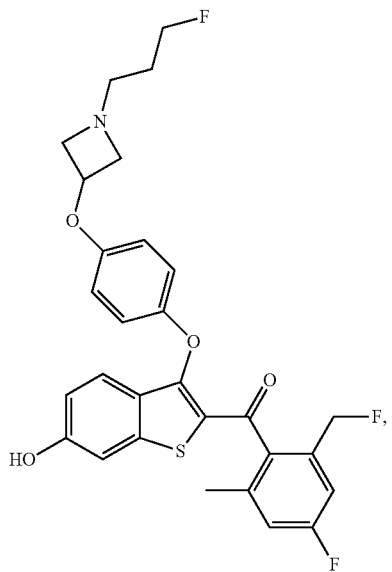

-continued
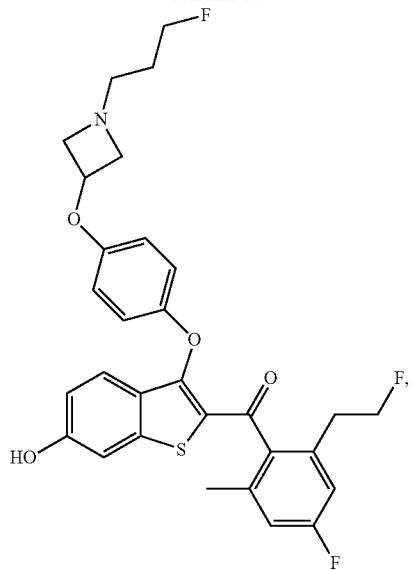
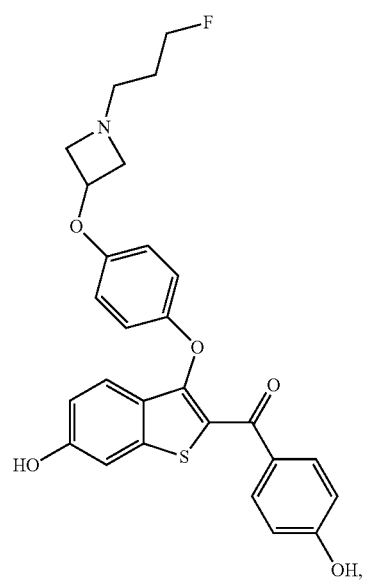
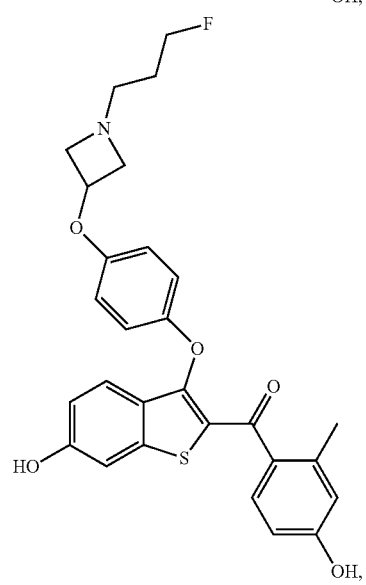
-continued
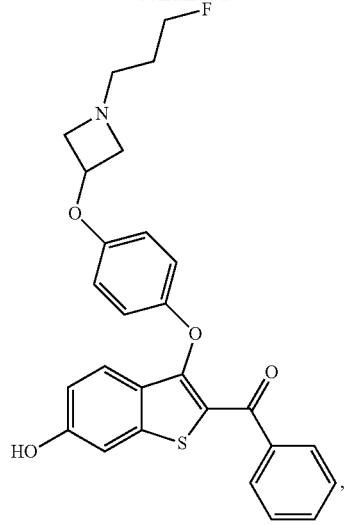
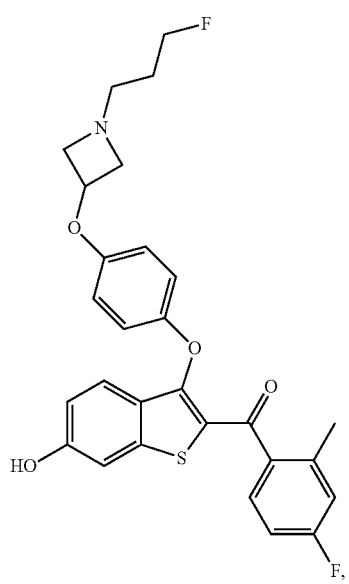
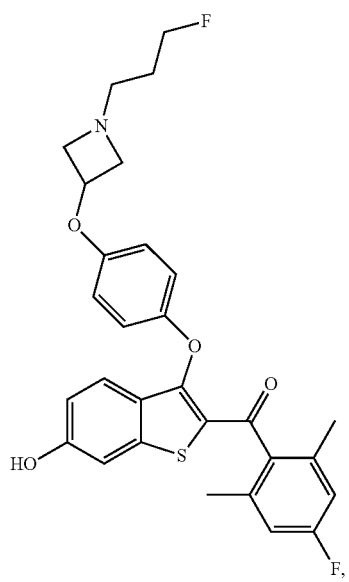

215
-continued
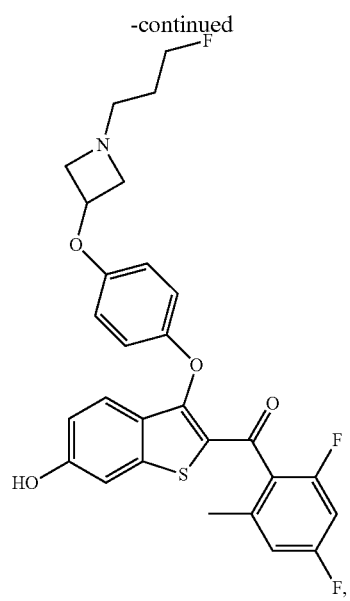
216
-continued
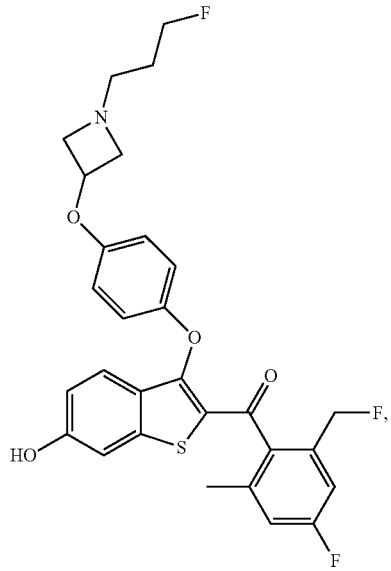
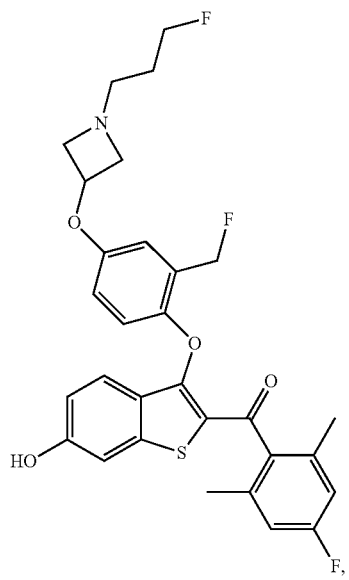
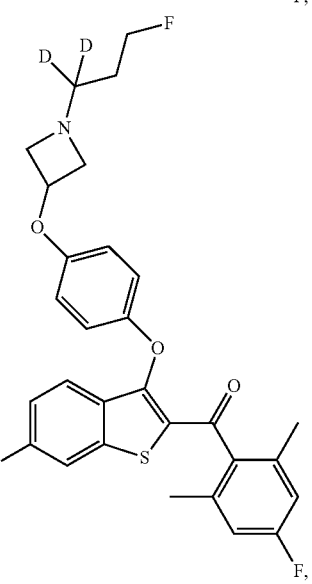

217
-continued
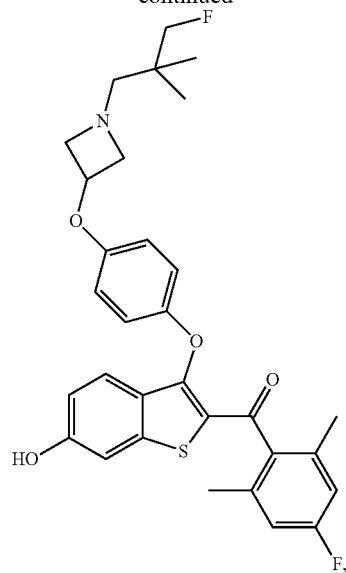
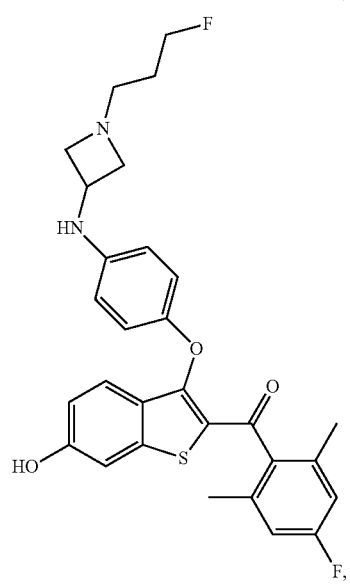
218
-continued
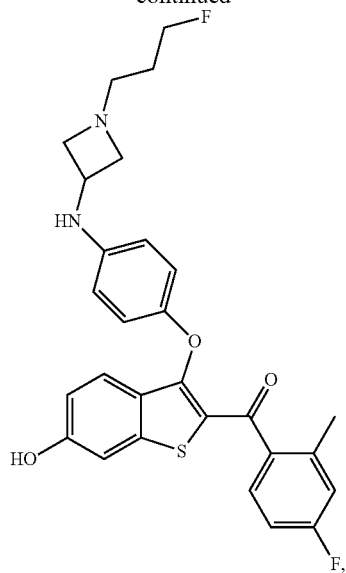
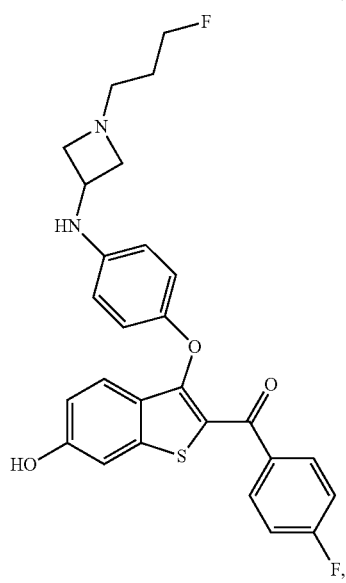
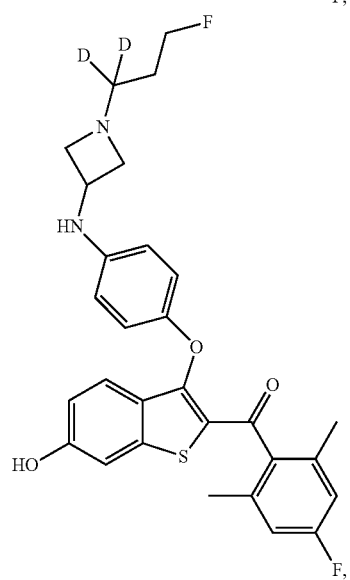
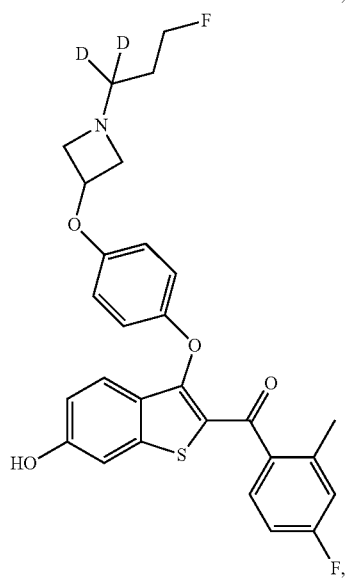

219
-continued
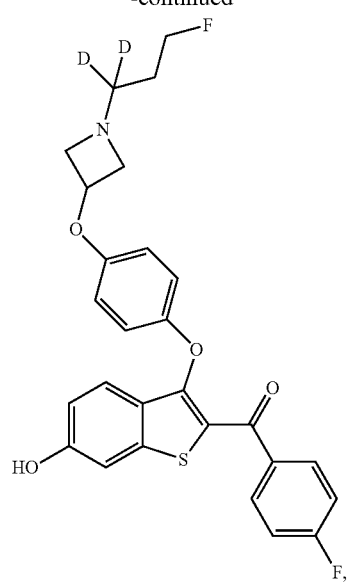
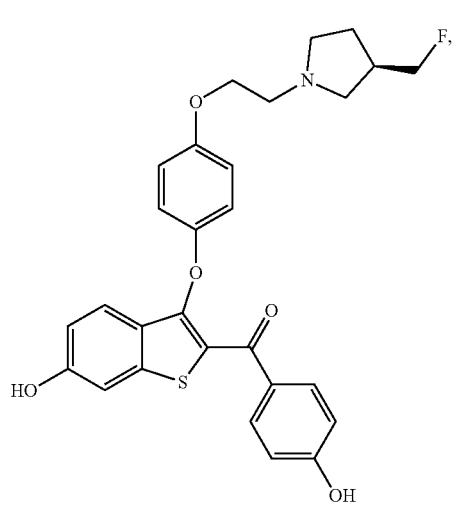
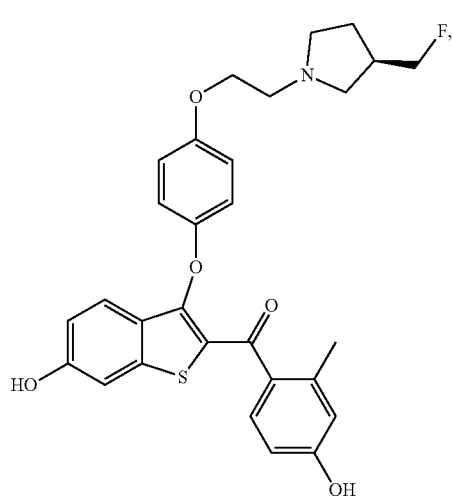
220
-continued
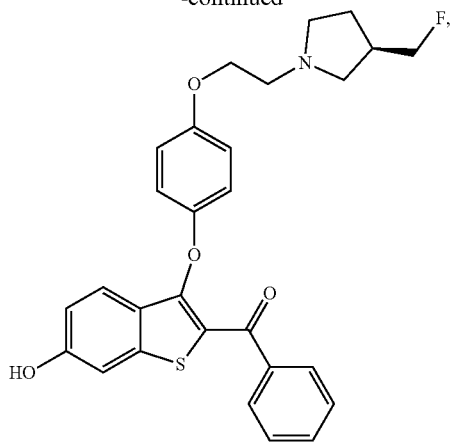
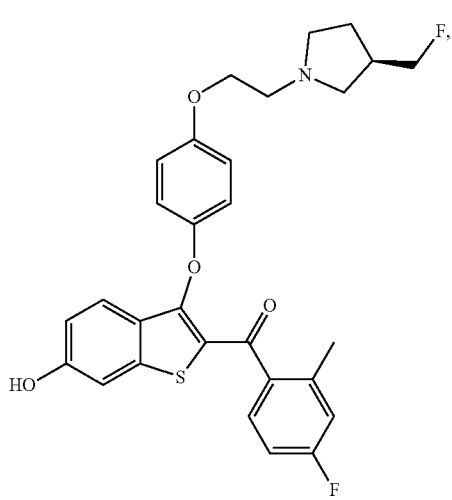
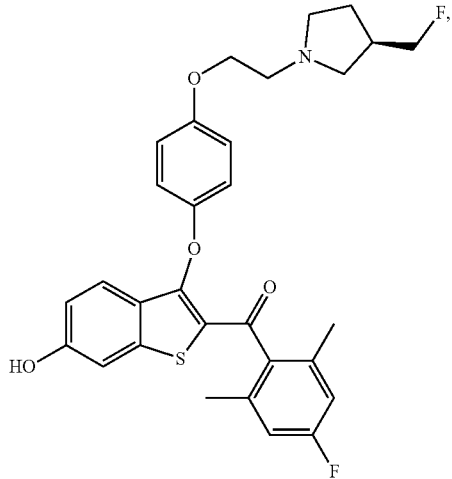

221
-continued
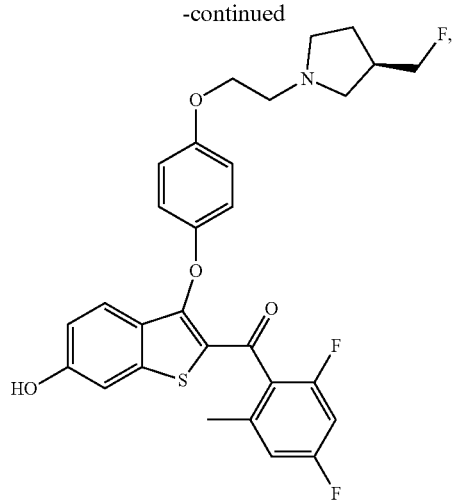
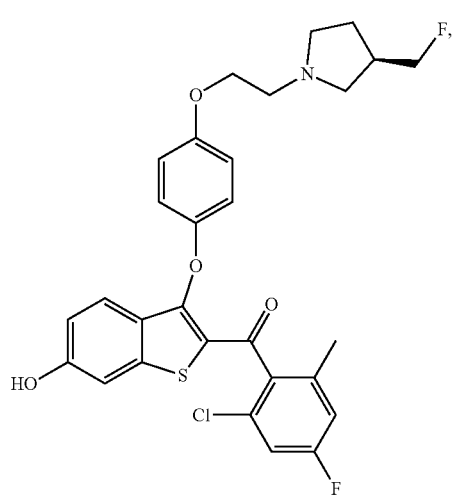
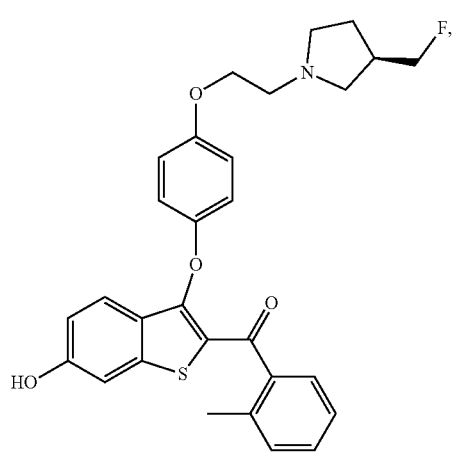
222
-continued
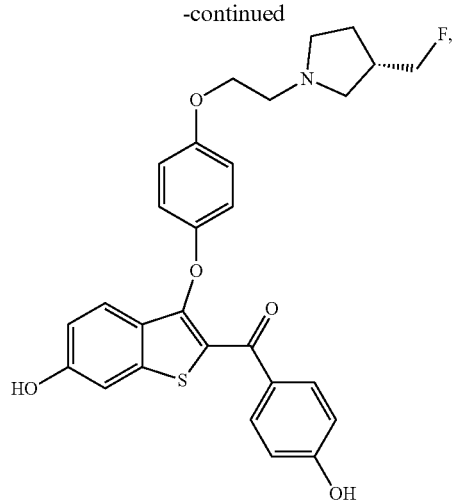
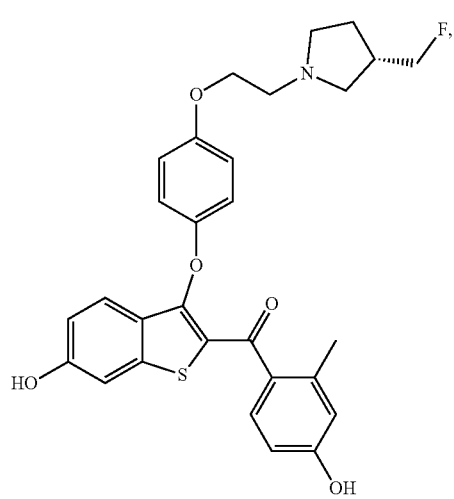
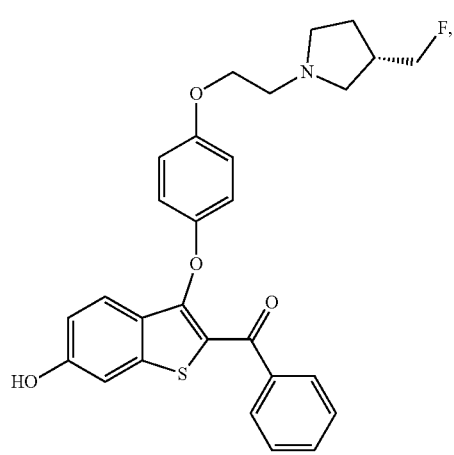

223
-continued
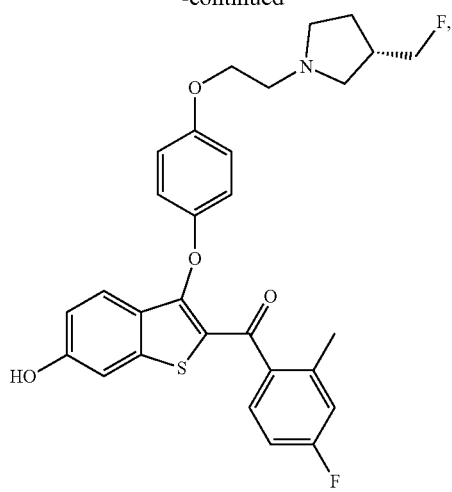
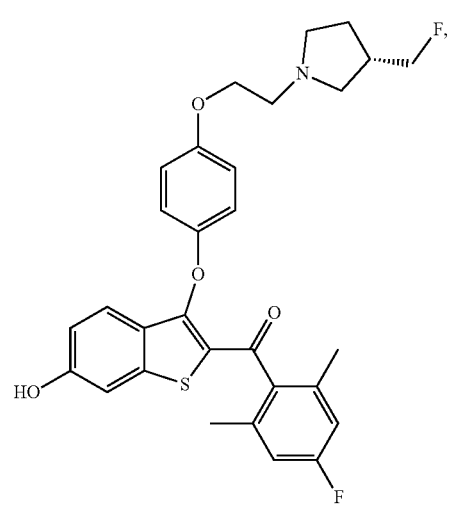
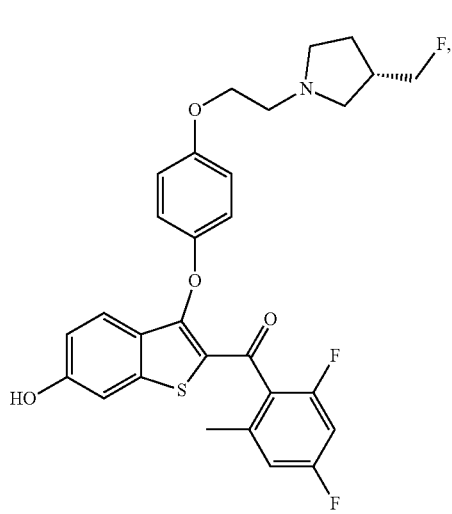
224
-continued
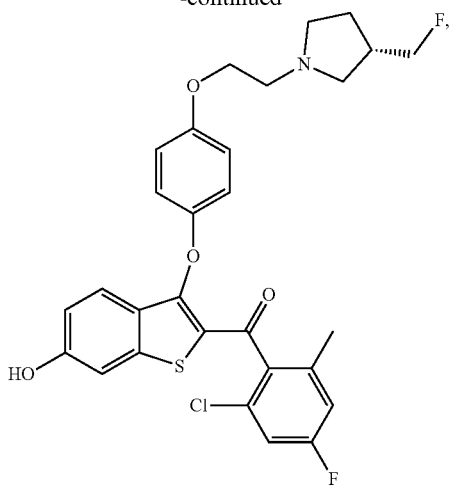
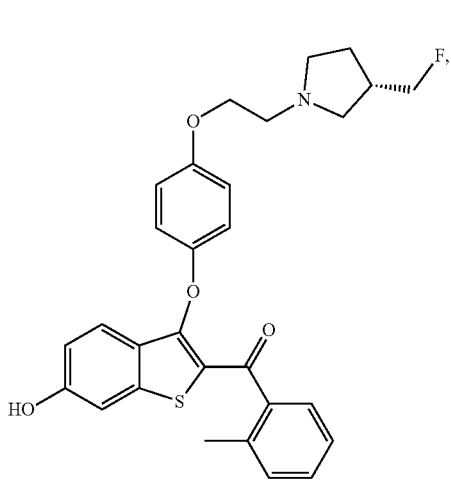
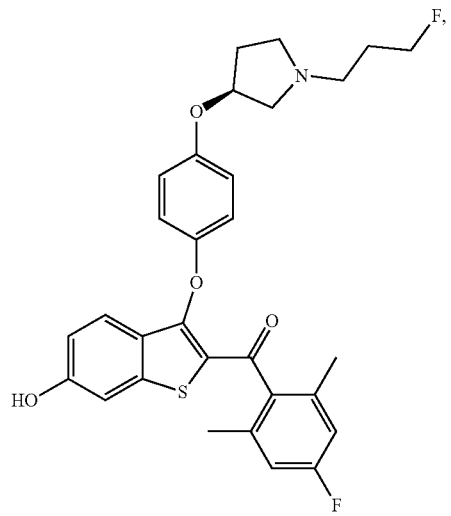

225
-continued
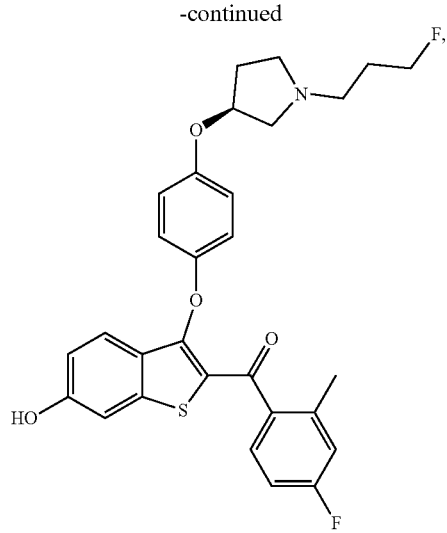
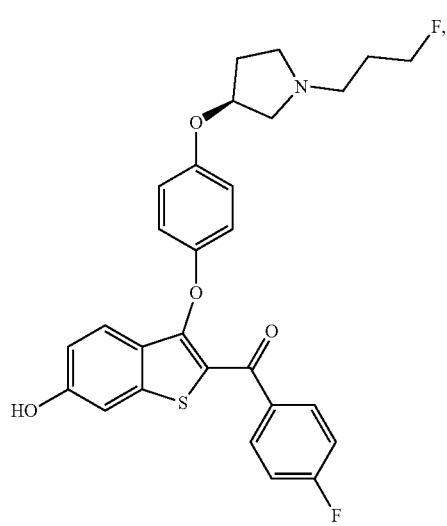
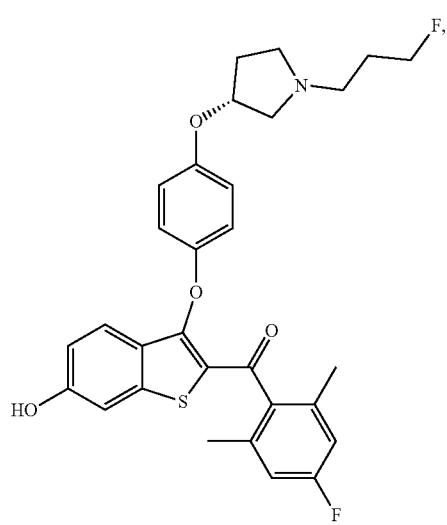
226
-continued
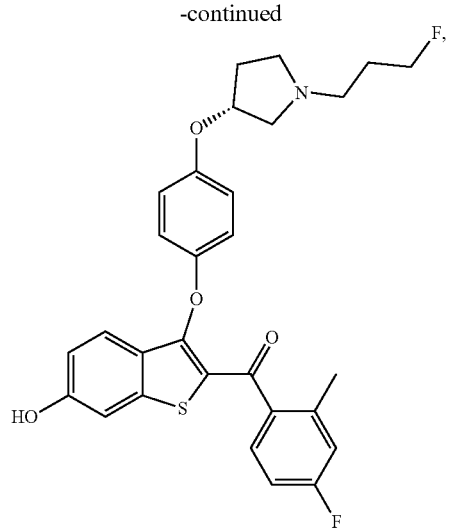
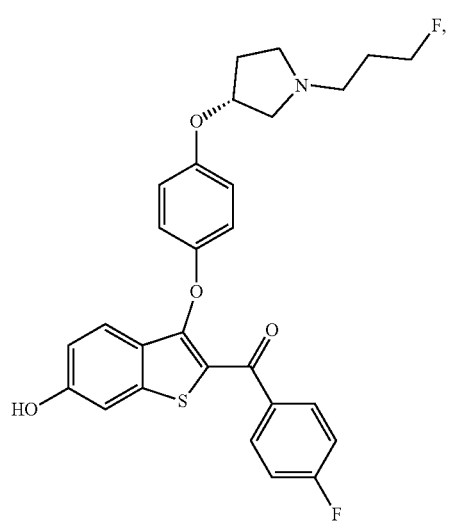
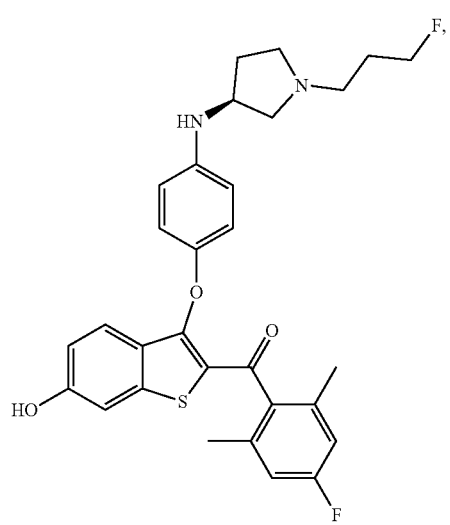

227
-continued
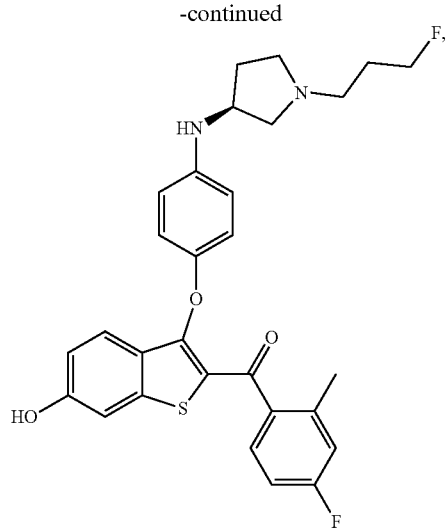
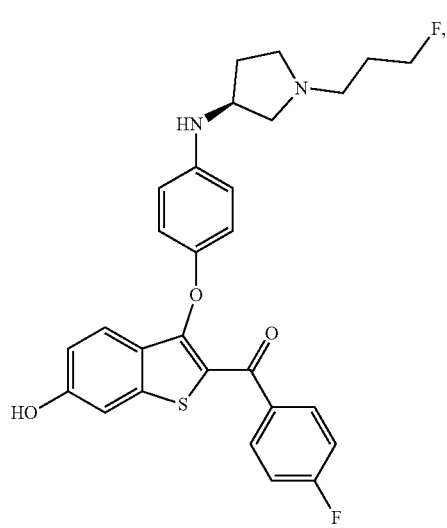 [SMILES: O=C(c1ccc(F)cc1)c1sc2cc(O)ccc2c1Oc1ccc(N[C@@H]2CCN(CCCF)C2)cc1]
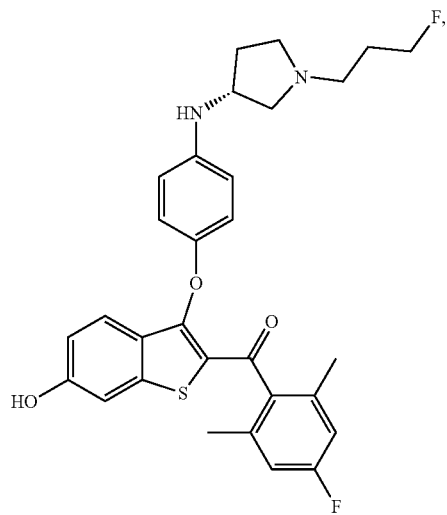
228
-continued
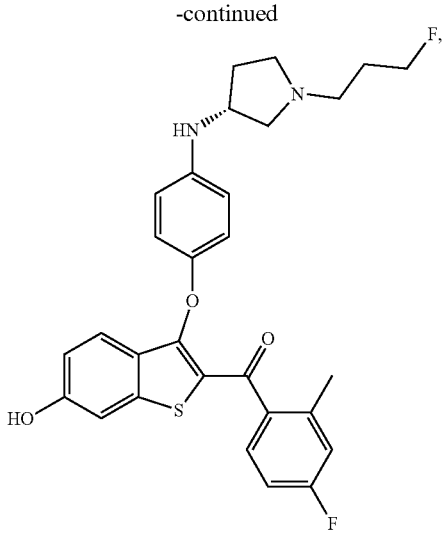
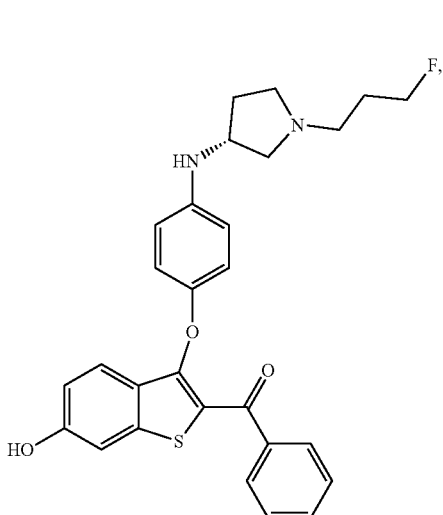
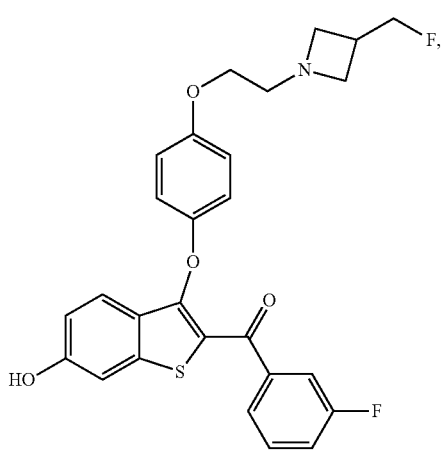

-continued
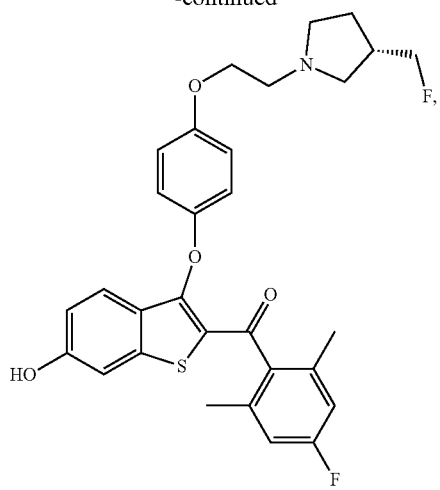
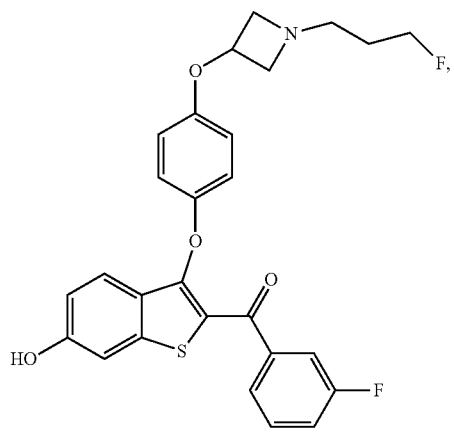 [SMILES: O=C(c1cccc(F)c1)c1sc2cc(O)ccc2c1Oc1ccc(OC2CN(CCCF)C2)cc1]
or a subgroup thereof.
14. The method of claim 1, having a structure represented by a formula:
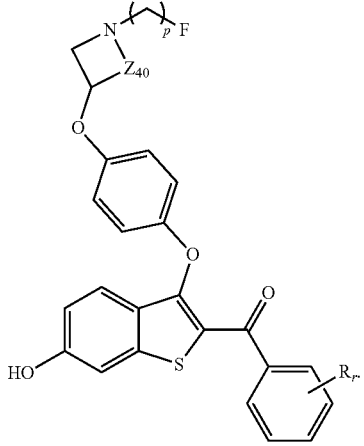
15. The method of claim 1, having a structure represented by a formula:
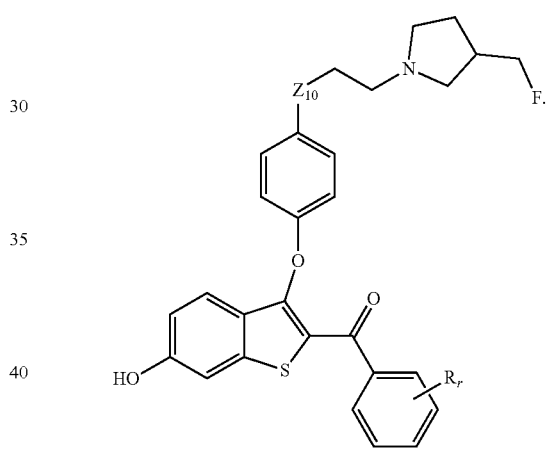
* * * * *